(12) United States Patent
Osborne et al.

(10) Patent No.: US 6,658,680 B2
(45) Date of Patent: Dec. 9, 2003

(54) HOSPITAL BED

(75) Inventors: Eugene E. Osborne, Hebron, KY (US); John W. Koenig, Cincinnati, OH (US); Glenn C. Suttman, Batesville, IN (US); Matthew Visca, Fairfield, OH (US); Jack Wilker, Jr., Shelbyville, IN (US); Jeffrey R. Welling, Batesville, IN (US); Gregory W. Branson, Batesville, IN (US); Kenneth L. Kramer, Greensburg, IN (US); Bruce E. Dickman, Jr., Batesville, IN (US); Dean M. Valvano, Cincinnati, OH (US); Robert A. Kinker, Jr., Greensburg, IN (US); William L. Jacques, II, Batesville, IN (US); James K. Findlay, Fishers, IN (US); Francis C. Ganance, Batesville, IN (US)

(73) Assignee: Hill-Rom Services, Inc., Wilmington, DE (US)

(*) Notice: Subject to any disclaimer, the term of this patent is extended or adjusted under 35 U.S.C. 154(b) by 5 days.

(21) Appl. No.: 09/750,741

(22) Filed: Dec. 29, 2000

(65) Prior Publication Data

US 2002/0066142 A1 Jun. 6, 2002

Related U.S. Application Data

(60) Provisional application No. 60/173,428, filed on Dec. 29, 1999.

(51) Int. Cl.[7] .......................... A61G 7/05; A47C 21/08
(52) U.S. Cl. ................................. 5/600; 5/425
(58) Field of Search ................. 5/600, 616, 424, 5/425, 658, 662, 503.1

(56) References Cited

U.S. PATENT DOCUMENTS

| | | | |
|---|---|---|---|
| 3,977,664 A | * 8/1976 | Mitchell et al. ............... 5/614 |
| 4,038,709 A | * 8/1977 | Kerwit ........................... 5/601 |
| 4,183,015 A | * 1/1980 | Drew et al. ............. 340/825.19 |
| 4,195,829 A | * 4/1980 | Reser ............................. 5/614 |
| 4,484,367 A | 11/1984 | Jenkins ......................... 5/425 |
| 4,612,679 A | 9/1986 | Mitchell ........................ 5/425 |
| 4,680,790 A | 7/1987 | Packard et al. ............. 379/432 |
| 5,097,550 A | 3/1992 | Marra, Jr. ...................... 5/424 |
| 5,175,897 A | * 1/1993 | Marra, Jr. ...................... 5/425 |
| 5,191,663 A | 3/1993 | Holder et al. .................. 5/424 |
| 5,222,132 A | 6/1993 | Rioux, Jr. .................... 379/455 |
| 5,235,258 A | 8/1993 | Schuerch ..................... 318/16 |
| 5,255,403 A | 10/1993 | Ortiz ........................ 5/503.1 |
| 5,279,010 A | * 1/1994 | Ferrand et al. ................ 5/600 |
| 5,542,136 A | 8/1996 | Tappel ........................... 5/710 |
| 5,715,548 A | 2/1998 | Weismiller et al. ............ 5/624 |
| 5,732,423 A | * 3/1998 | Weismiller et al. ............ 5/425 |
| 5,737,781 A | 4/1998 | Votel ....................... 5/81.1 HS |
| 5,802,640 A | 9/1998 | Ferrand et al. ................ 5/617 |
| 5,878,452 A | 3/1999 | Brooke et al. ................ 5/428 |
| 5,906,016 A | * 5/1999 | Ferrand et al. ................ 5/600 |
| 5,906,017 A | * 5/1999 | Ferrand et al. ................ 5/617 |
| 6,008,598 A | 12/1999 | Luff et al. .................... 318/16 |
| 6,163,903 A | * 12/2000 | Weismiller et al. ............ 5/610 |
| 6,182,310 B1 | * 2/2001 | Weismiller et al. ............ 5/425 |
| 6,185,767 B1 | * 2/2001 | Brooke et al. ................ 5/600 |
| 6,208,250 B1 | * 3/2001 | Dixon et al. ............. 340/573.1 |
| 6,320,510 B2 | * 11/2001 | Menkedick et al. ...... 340/573.1 |
| 6,336,235 B1 | * 1/2002 | Ruehl ............................ 5/610 |
| 6,438,776 B2 | * 8/2002 | Ferrand et al. ................ 5/600 |
| 6,473,921 B2 | * 11/2002 | Brooke et al. ................ 5/600 |
| 6,481,688 B1 | * 11/2002 | Welling et al. ............. 5/600 X |
| 6,486,792 B1 | * 11/2002 | Moster et al. .............. 5/425 X |

(List continued on next page.)

FOREIGN PATENT DOCUMENTS

WO  WO 00/69386  11/2000

*Primary Examiner*—Robert G. Santos
(74) *Attorney, Agent, or Firm*—Bose McKinney & Evans LLP

(57) ABSTRACT

A bed for a person is provided. The bed includes a frame, a deck, a mattress, a pair of head end siderails, and a pair of foot end siderails. The bed further includes a controller configured to be coupled to the head and foot end siderails.

85 Claims, 84 Drawing Sheets

U.S. PATENT DOCUMENTS

| | | | |
|---|---|---|---|
| 2001/0011393 A1 * | 8/2001 | Brooke et al. | 5/600 |
| 2001/0027578 A1 * | 10/2001 | Brooke et al. | 5/662 |
| 2001/0029628 A1 * | 10/2001 | Ferrand et al. | 5/600 |
| 2001/0032362 A1 * | 10/2001 | Welling et al. | 5/600 |
| 2002/0002742 A1 * | 1/2002 | Osborne et al. | 5/600 |
| 2002/0059679 A1 * | 5/2002 | Weismiller et al. | 5/610 |
| 2002/0066142 A1 * | 6/2002 | Osborne et al. | 5/600 |
| 2002/0080037 A1 * | 6/2002 | Dixon et al. | 340/573.1 |
| 2002/0144348 A1 * | 10/2002 | Ganance | 5/600 |
| 2003/0009952 A1 * | 1/2003 | Gallant et al. | 5/658 X |
| 2003/0019038 A1 * | 1/2003 | Welling et al. | 5/503.1 |
| 2003/0051291 A1 * | 3/2003 | Brooke et al. | 5/425 X |
| 2003/0051292 A1 * | 3/2003 | Ferrand et al. | 5/600 |
| 2003/0056293 A1 * | 3/2003 | Brooke et al. | 5/662 |

* cited by examiner

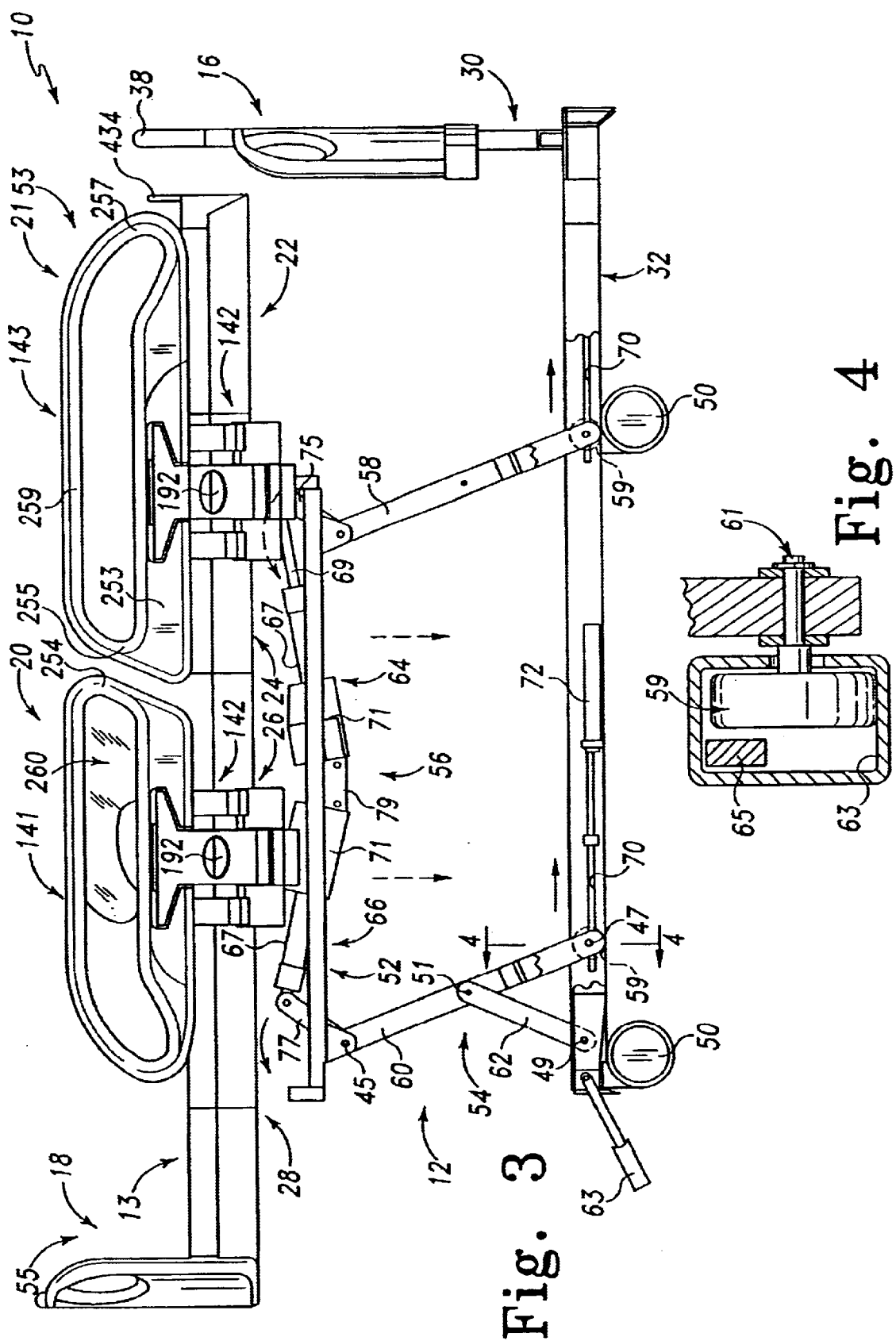

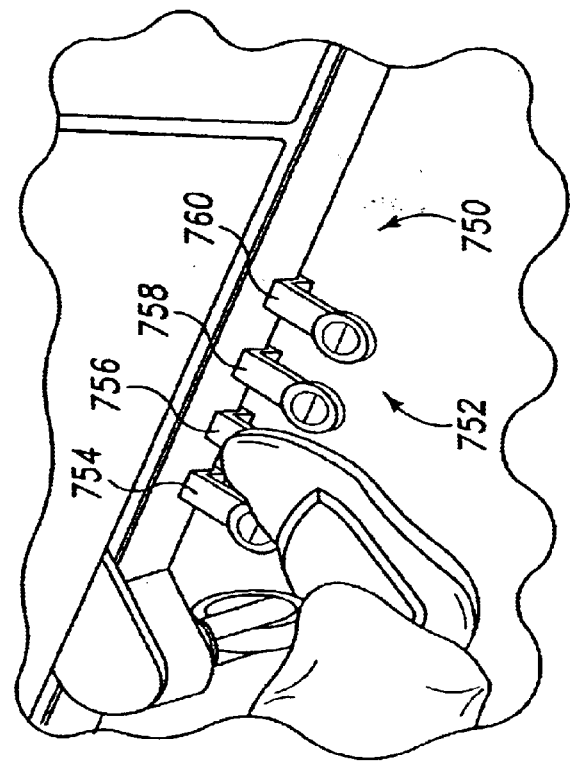
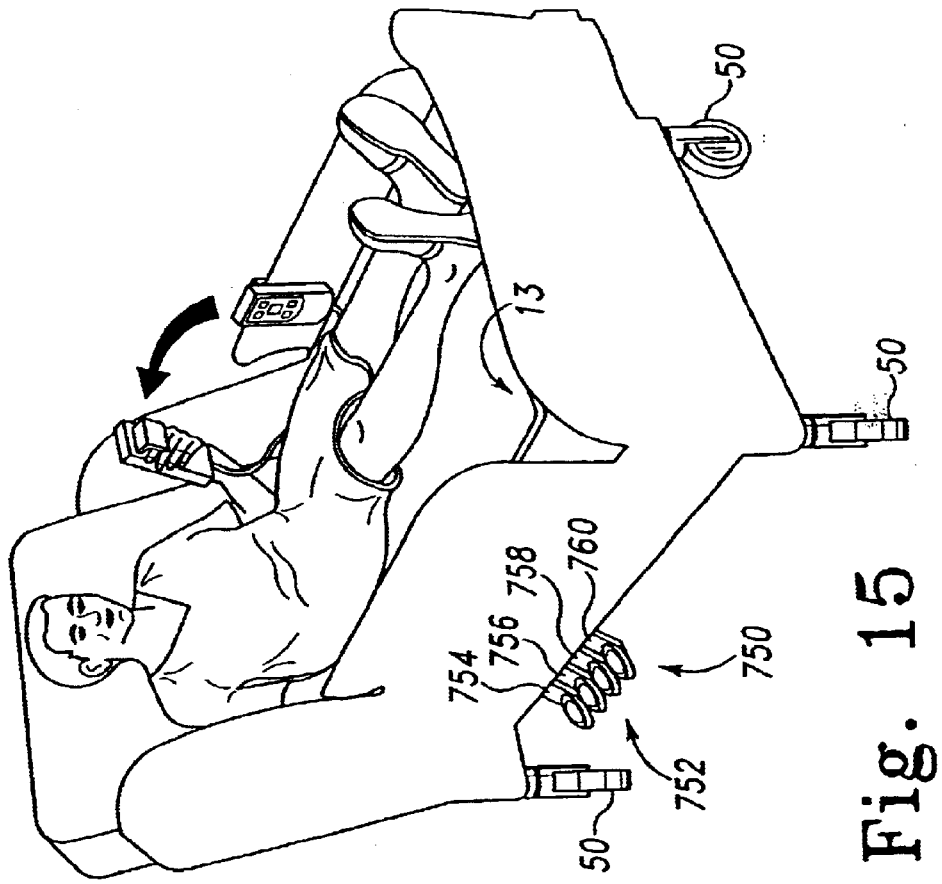
Fig. 16
Fig. 15

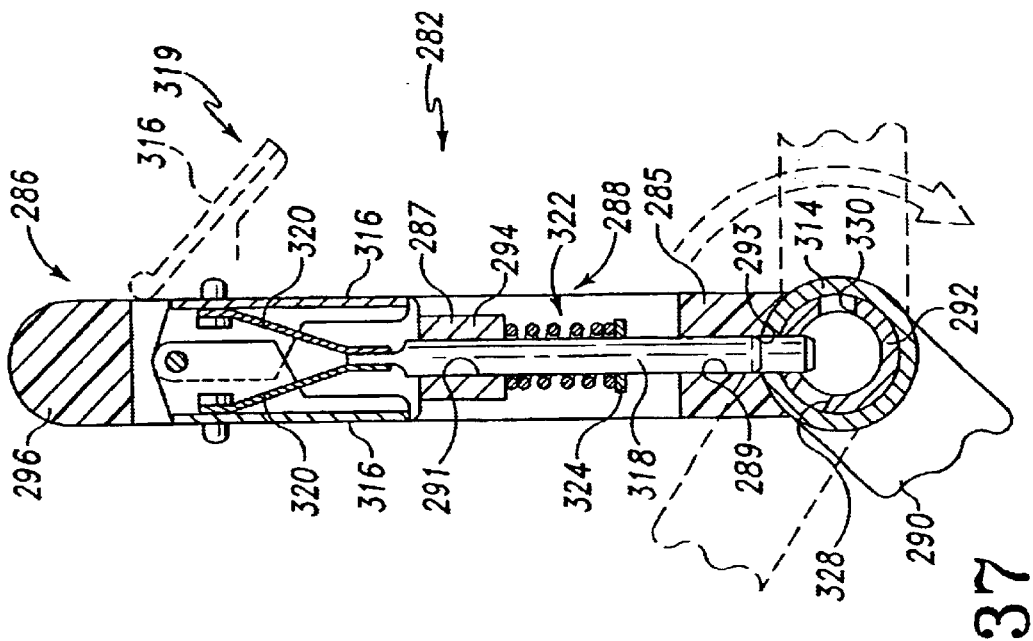
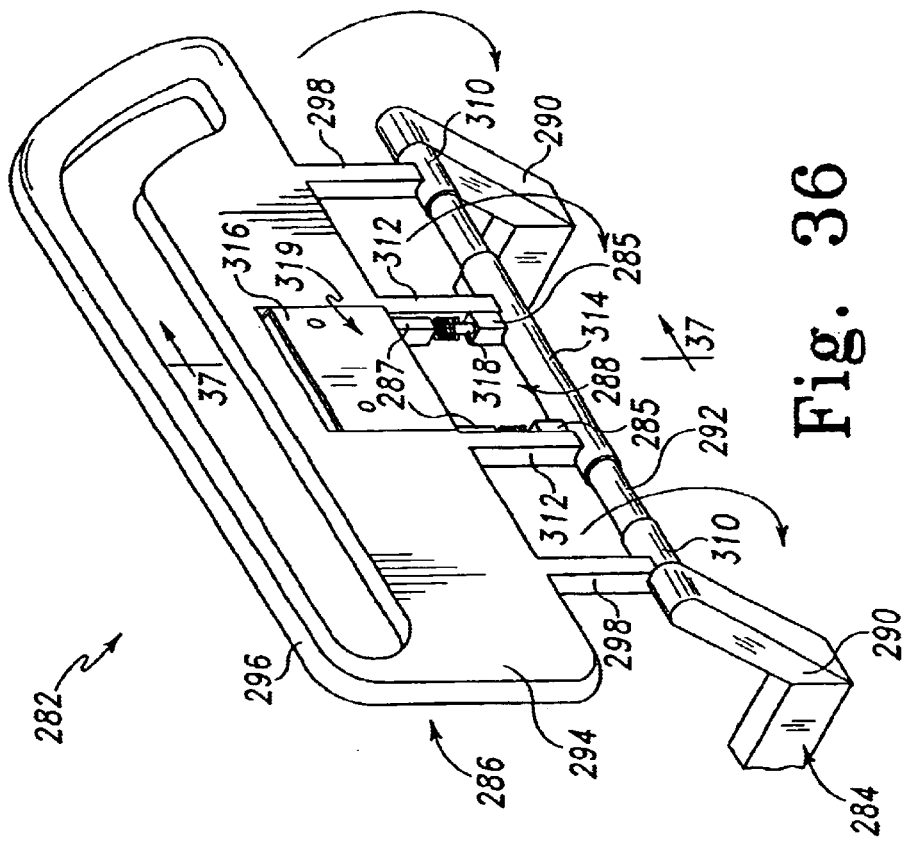

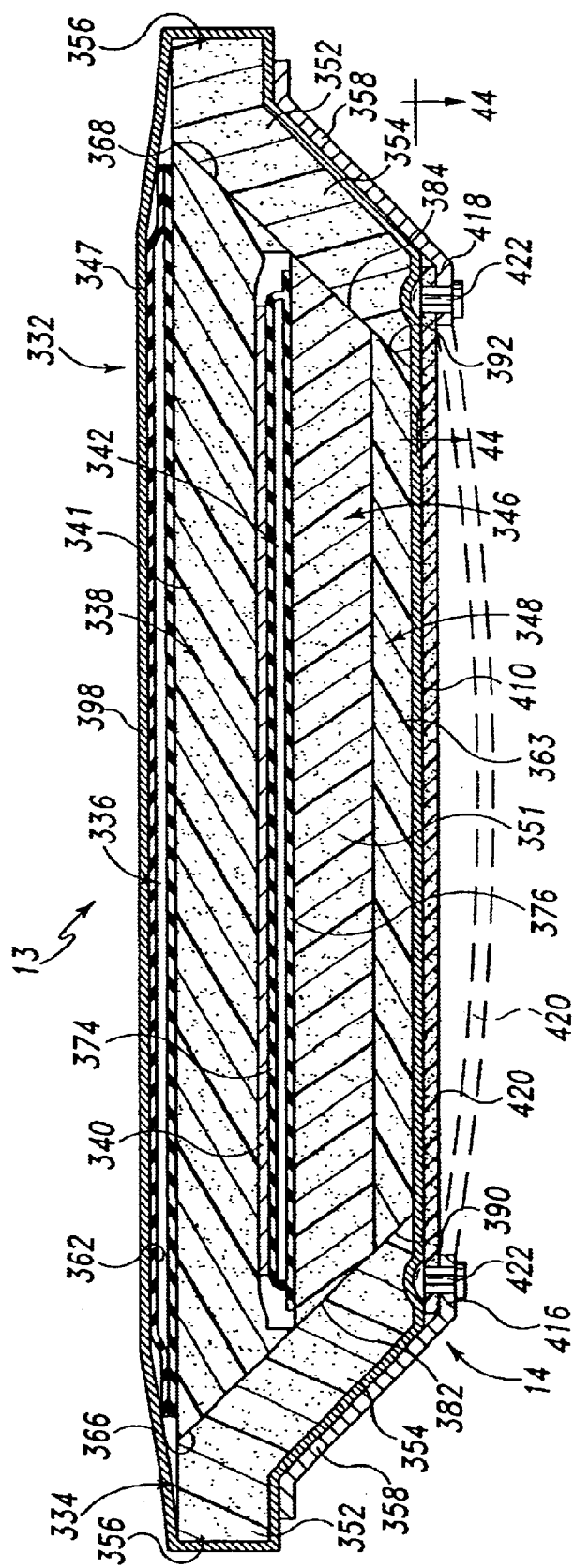
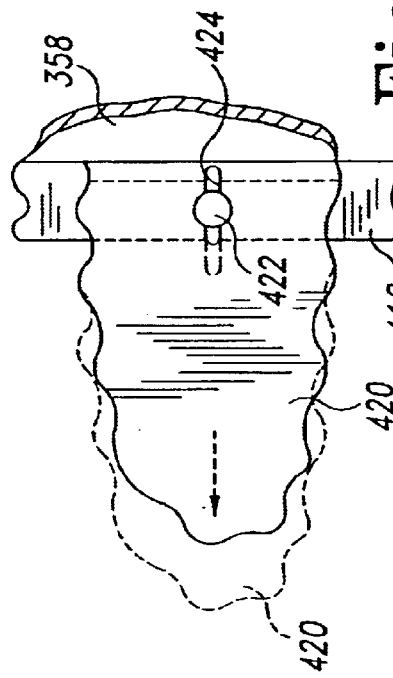
Fig. 43
Fig. 44

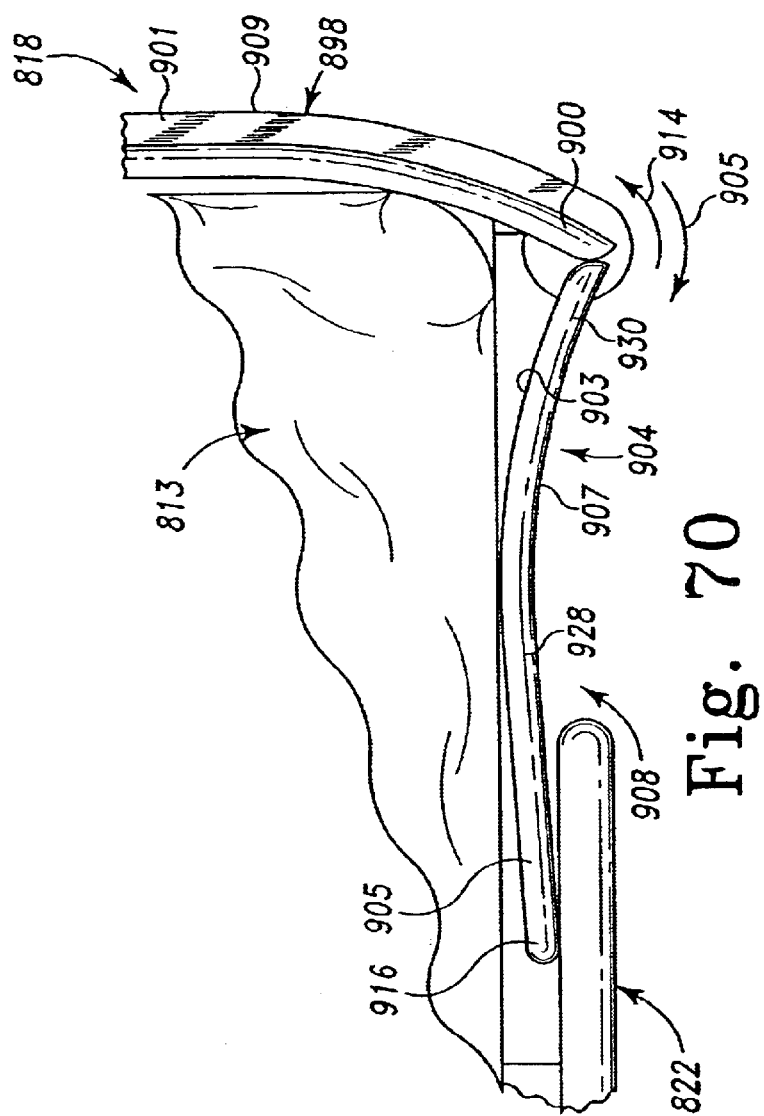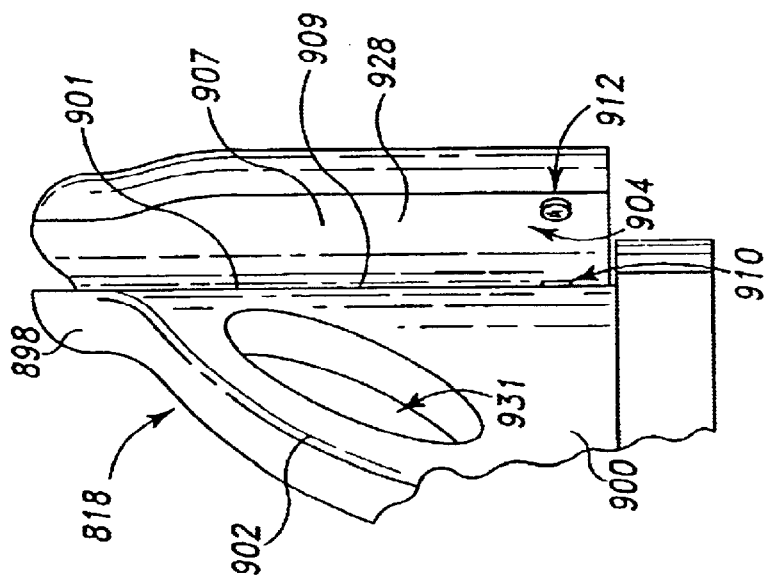

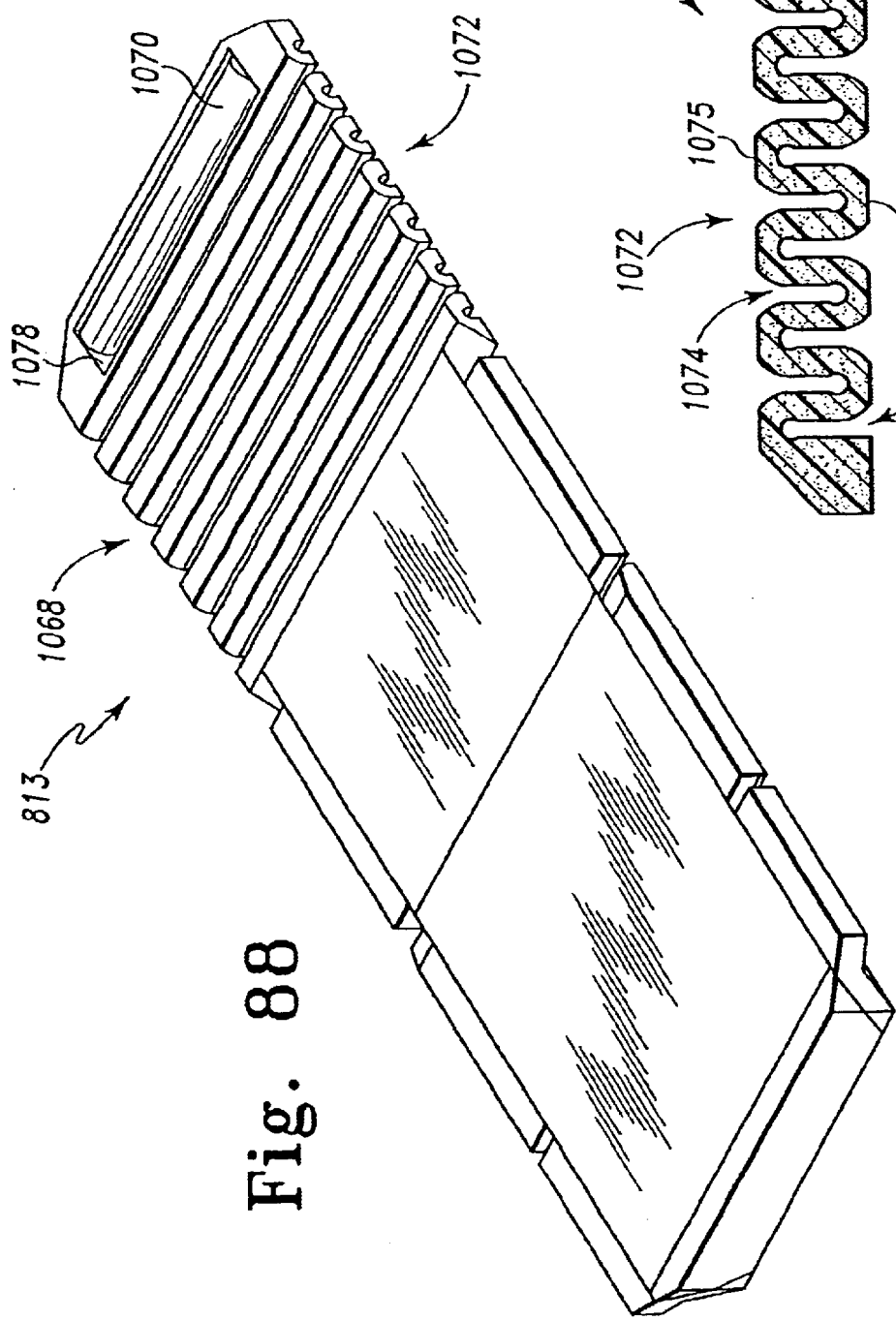
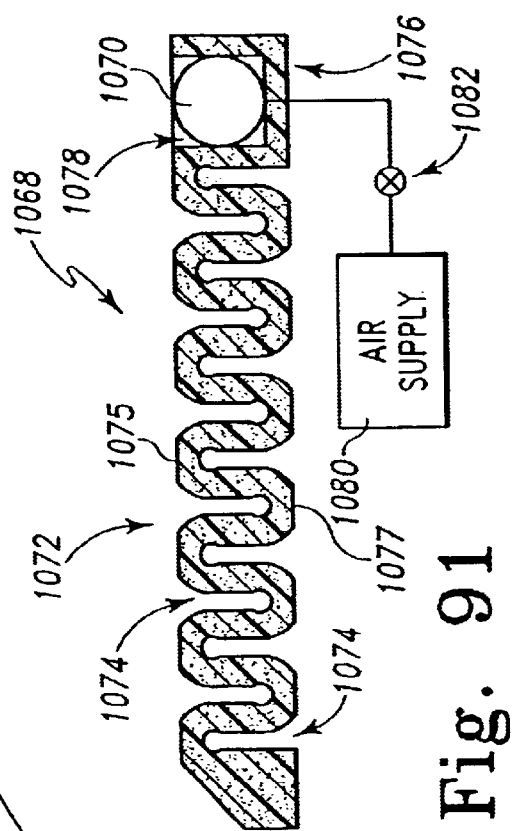

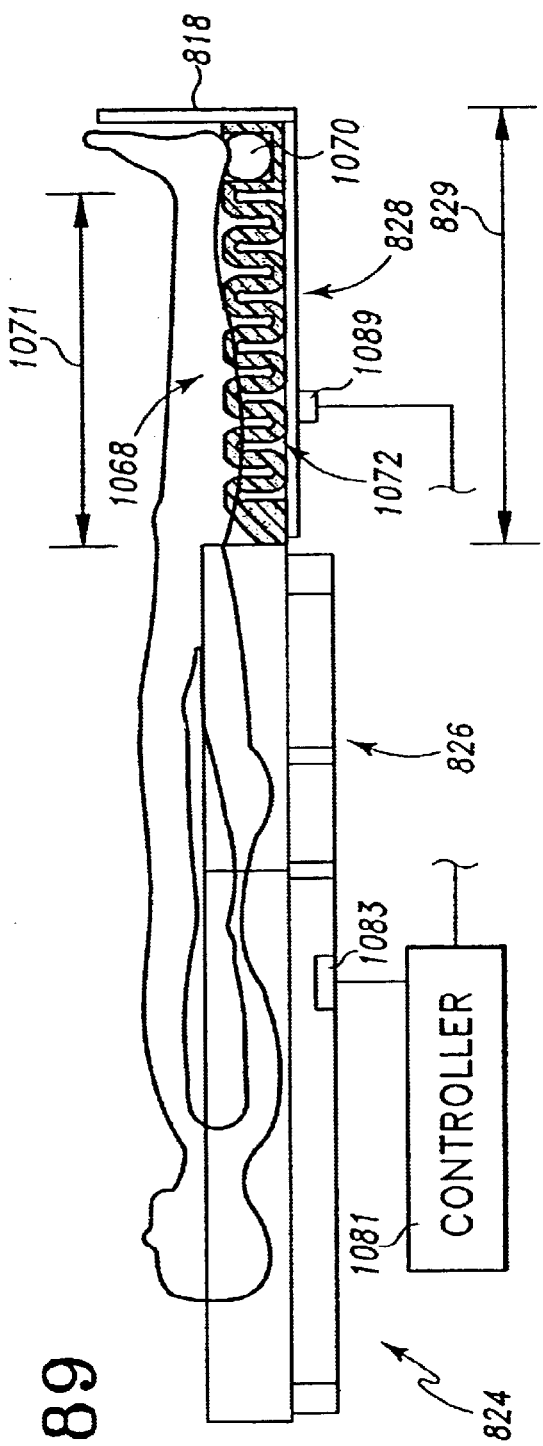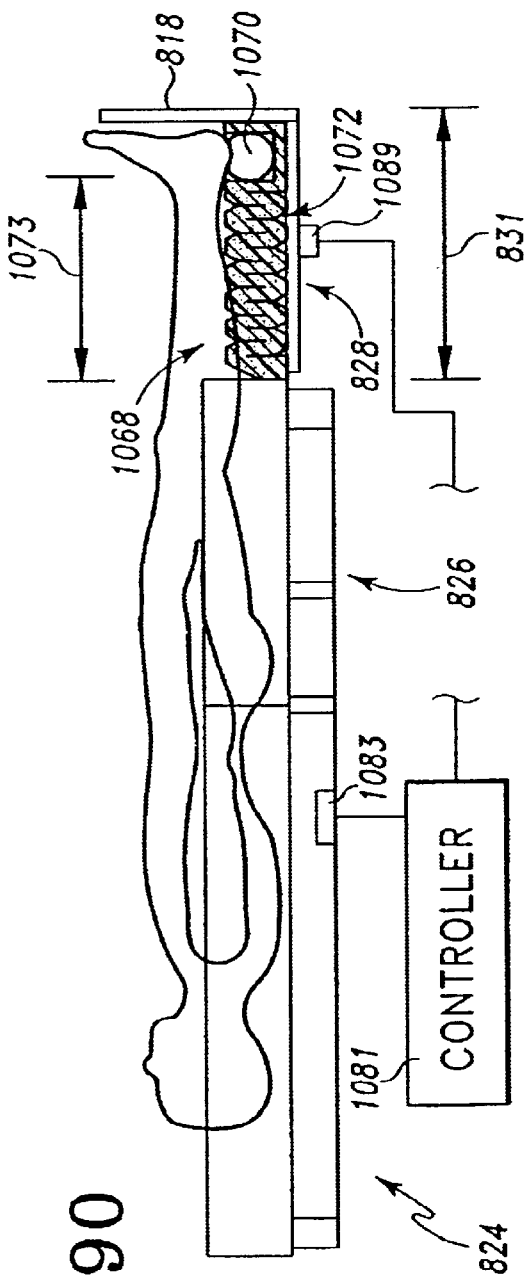

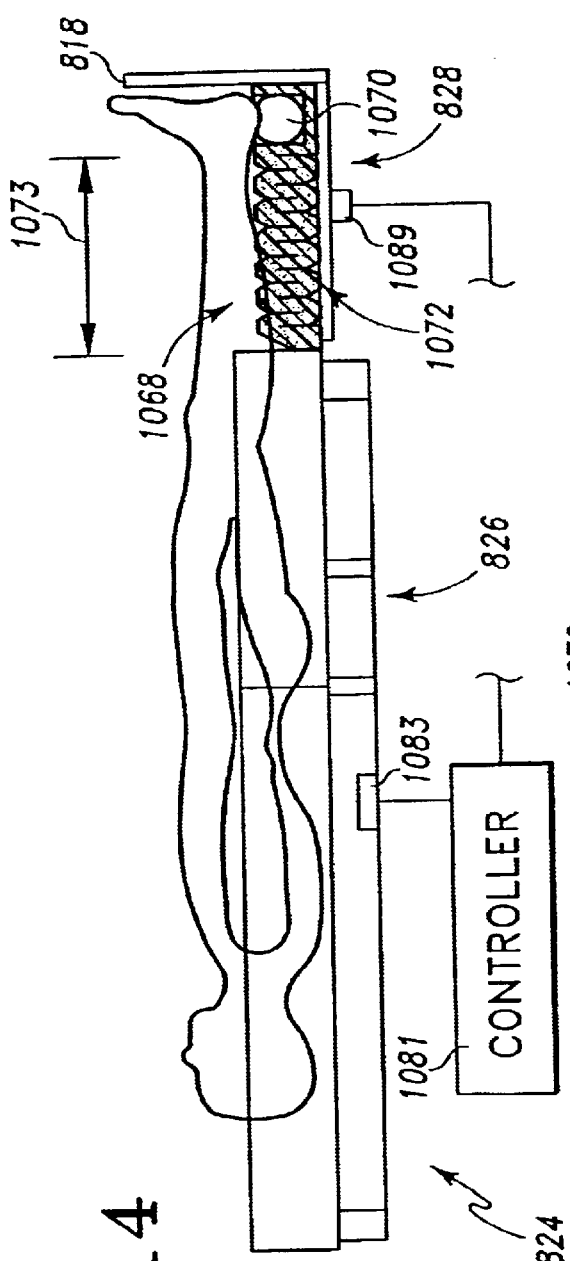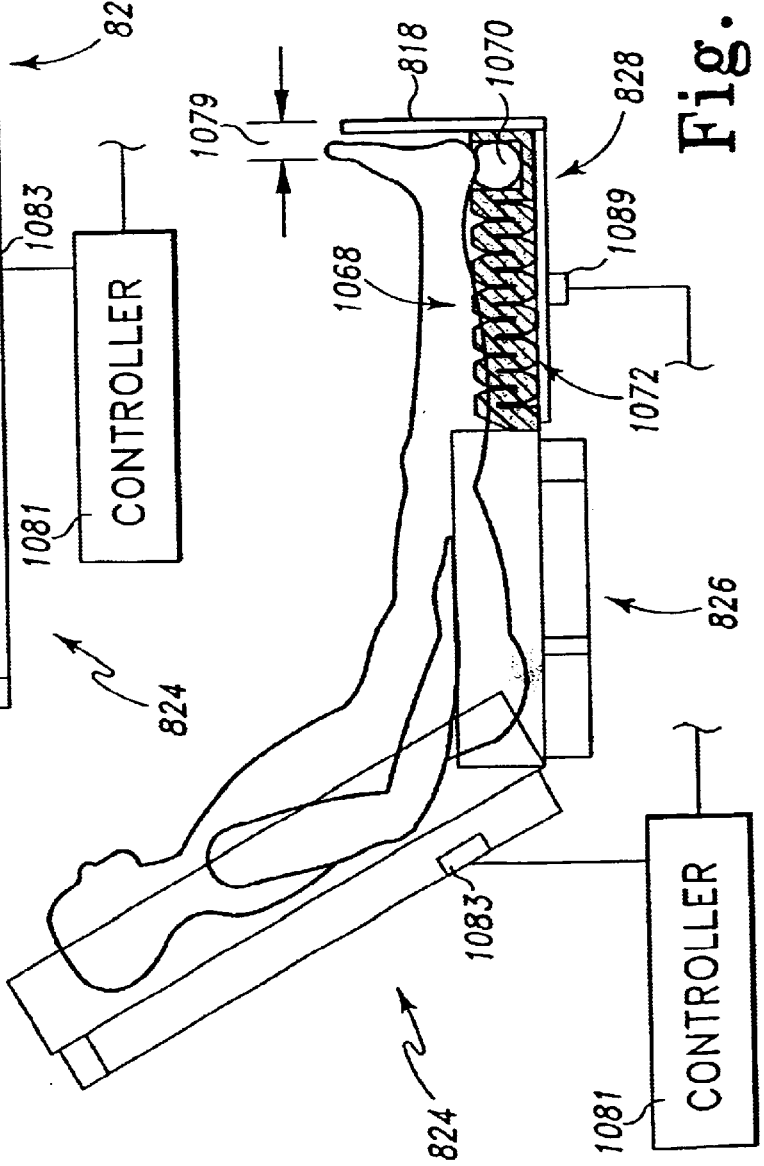

HOSPITAL BED

This application claims benefit of U.S. Provisional Application Serial No. 60/173,428, filed Dec. 29, 1999, titled Hospital Bed, the disclosure of which is expressly incorporated by reference herein. The disclosures of PCT application PCT/US98/20002, titled Hospital Bed Having a Retracting Foot Section, filed Sep. 23, 1998, to Allen et al.; U.S. Utility patent application Ser. No. unknown, titled Mattress Having a Retractable Foot Section, filed herewith, to Welling et al.; U.S. Utility patent application Ser. No. unknown, titled Foot Controls for a Bed, filed herewith, to Osborne et al.; and PCT application Ser. No. unknown, titled Hospital Bed, filed herewith, to Hill-Rom Services, Inc. and naming Osborne et al. are expressly incorporated by reference herein.

BACKGROUND AND SUMMARY OF THE INVENTION

The present invention relates to a hospital bed. More particularly, the present invention relates to a hospital bed siderails and a controller coupled to one of the siderail.

Hospital bed and other patient supports are known. Typically, such patient supports are used to provide a support surface for patients or other individuals for treatment, recuperation, or rest. Many such patient supports include a frame, a deck supported by the frame, a mattress, siderails configured to block egress of a patient from the mattress, and a controller configured to control one or more features of the bed.

According to the present invention, a patient support is provided. The patient support includes a frame, a mattress supported by the frame, a barrier positioned to block egress of a patient from the mattress, and a controller. The barrier includes first and second spaced-apart rails and the controller is positioned to slide along the first and second rails.

According to another embodiment of the present invention, a patient support is provided that includes a frame, a mattress supported by the frame, a barrier positioned to block egress of a patient from the mattress, and a controller. The barrier includes upper and lower surfaces that cooperate to define an opening. The controller is positioned to slide along the lower surface defining the opening in the barrier.

According to another embodiment of the present invention, a patient support is provided that includes a frame, a mattress supported by the frame, a barrier positioned to block egress of a patient from the mattress, and a controller. The barrier includes a curved opening and the controller is positioned in the curved opening to move along the barrier.

According to another embodiment of the present invention, a patient support is provided that includes a frame, a mattress supported by the frame, a barrier positioned to block egress of a patient from the mattress, and a controller. The barrier includes a surface defining an opening in the barrier. The controller includes a housing and a retainer coupled to the housing. The retainer is configured to contact the surface of the barrier to removable couple the housing to the barrier.

According to another embodiment of the present invention, a patient support is provided that includes a frame, a mattress supported by the frame, a barrier positioned to block egress of a patient from the mattress, and a controller. The controller is removably coupled to the barrier and is movable from a first position spaced apart from the barrier to a second position coupled to the barrier. The controller is movable along a path having a horizontal component from the first position to the second position to couple the controller to the barrier. The controller is movable along the barrier when in the second position.

According to another embodiment of the present invention, a patient support is provided that includes a frame and a mattress supported by the frame. The mattress has a first side and a second side transversely spaced-apart from the first side. The patient support further includes a first barrier positioned to block egress of a patient from the first side of the mattress, a second barrier positioned to block egress of a patient from the second side of the mattress, and a controller. The first barrier includes a first opening formed therein and the second barrier includes a second opening formed therein. The controller is configured to be removably received in the first opening of the first barrier and removably received in the second opening of the second barrier.

According to another embodiment of the present invention, a patient support is provided that includes a frame, a mattress supported by the frame, a barrier positioned to block egress of a patient from the mattress, and a controller. The barrier has a longitudinal axis. The barrier includes a guide configured to direct movement of the controller along the barrier in a path having longitudinal and transverse components.

According to another embodiment of the present invention, a patient support is provided that includes a frame, a mattress supported by the frame, a pair of spaced-apart barriers positioned to block egress of a patient from the mattress, and a controller removably coupled to the barrier. The controller includes a housing, a cord coupled to the housing, and a first connector coupled to the cord. The patient support further includes a second connector supported by the frame. The first connector is configured to couple to the second connector to provide communication for the controller through the first and second connectors when the first connector is coupled to the second connector. The patient support further includes a third connector supported by the frame. The first connector is configured to couple to the third connector to provide communication for the controller through the first and third connectors when the first connector is coupled to the third connector.

Additional features of the present invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which:

FIG. 3 is a side elevation view of the hospital bed showing the frame in an upper position supporting the deck in an upper position;

FIG. 4 is a cross-sectional view taken along line 4—4 of FIG. 3 showing a roller and caster-brake linkage positioned in a hollow base frame;

FIG. 15 is a perspective view of an alternative embodiment control system including four foot pedals configured to control the various functions of the hospital bed;

FIG. 16 is a perspective view of the control system of FIG. 15 showing a caregiver depressing one of the foot pedals to lower a back section of the hospital bed;

FIG. 36 is a perspective view of an alternative embodiment siderail showing the siderail in an upper position;

FIG. 37 is a cross-sectional view taken along lines 37—37 of FIG. 36 showing the siderail of FIG. 36 including a vertical rail member pivotably coupled about a tubular support member, a pair of handles pivotably coupled to the vertical rail member, a retainer including a vertical pin engaging an aperture formed in the tubular support member, and a pair of cables coupling the vertical pin to the handles, one of said handles (in phantom) in an actuated position pulling the vertical pin from locking engagement with the tubular support member to permit pivoting of the rail member in a counterclockwise (in phantom) or clockwise (in phantom) direction relative to the tubular support member;

FIG. 43 is a cross-sectional view taken along line 43—43 of FIG. 40 showing the mattress including another crowning bladder in a deflated position and the deck including a flexible deck panel in an un-flexed position and a flexed position (in phantom);

FIG. 44 is a cross-sectional view taken along line 44—44 of FIG. 43, with portions broken away, showing one portion of the flexible panel including an elongated slot and a fastener positioned in the elongated slot to permit the flexible panel to slide relative to the fastener to permit the flexible panel to bow downwardly when weight is applied to the flexible panel (in phantom);

FIG. 69 is a side elevation view of the footboard and one of the gap fillers of FIG. 61 showing the footboard including a first fastener and the gap filler including a second fastener aligned with the first fastener to couple the gap filler to the footboard;

FIG. 70 is a top plan view of the footboard, one of the foot end siderails, and one of the gap filler of FIG. 61 showing the gap filler positioned between the foot end siderail and the mattress;

FIG. 88 is a perspective view of the mattress of FIG. 61, with a protective cover removed, showing the mattress including a foot section including a retractable foam portion and a heel-pressure relief bladder positioned in a cavity formed in the retractable foot section;

FIG. 89 is a side elevation view of the deck and mattress showing a tall person positioned on the mattress and the foot section of the deck in an extended position with the heel of the tall person positioned over the heel-pressure relief bladder;

FIG. 90 is a view similar to FIG. 89 showing a short person positioned on the mattress and the foot section in a retracted position with the heel of the short person positioned over the heel-pressure relief bladder;

FIG. 91 is a cross-sectional view taken along line 91—91 of FIG. 90 showing the heel-pressure relief bladder positioned in the cavity formed in the retractable foam portion;

FIG. 114 is a view identical to FIG. 90 showing a deck in a substantially flat bed position; and FIG. 115 is a view similar to FIG. 90 showing a head section of the deck raised to a tilted position and the foot section of the deck extended in response to the head section of the deck being raised.

DETAILED DESCRIPTION OF THE DRAWINGS

Figure 1:
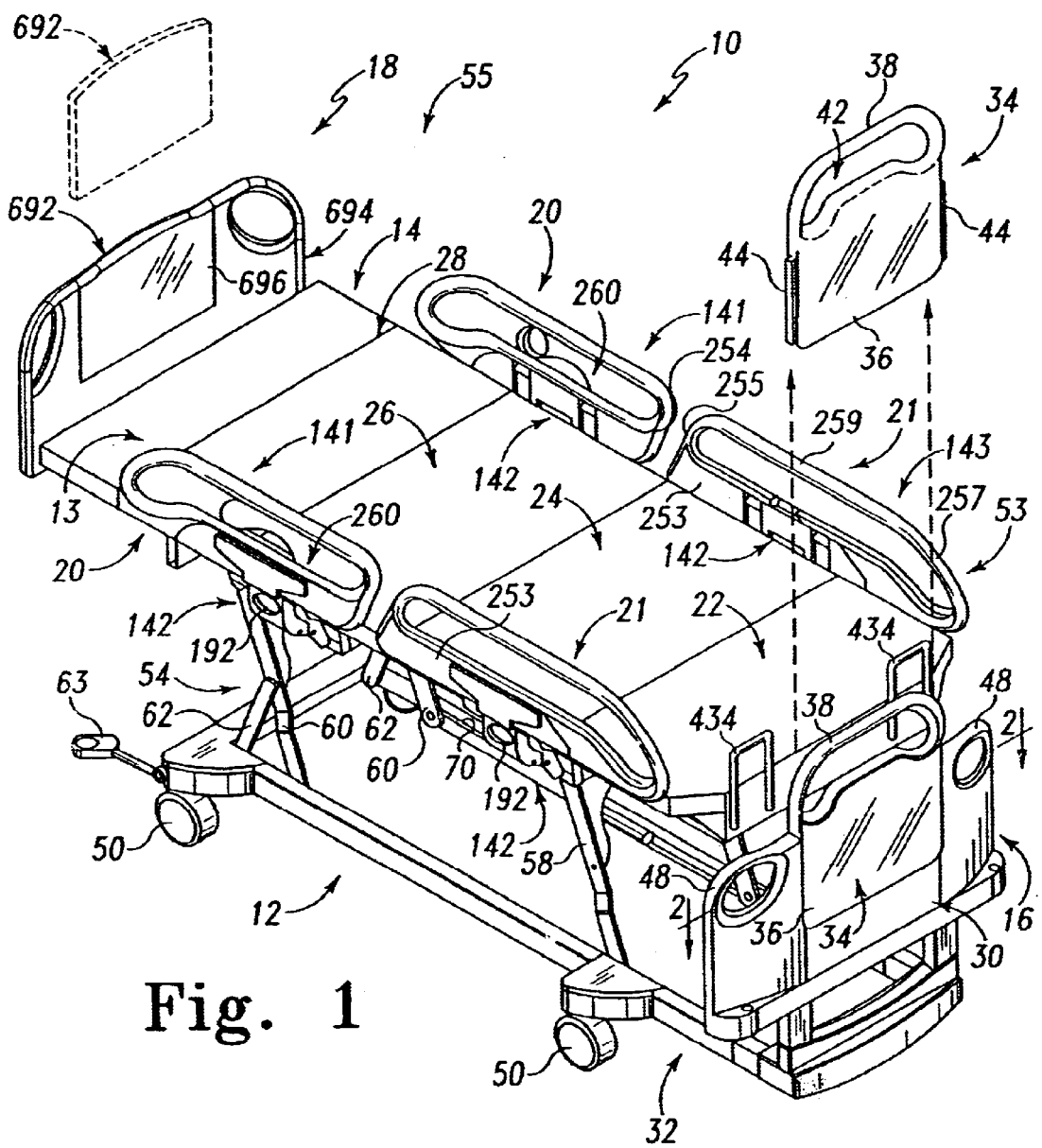
FIG. 1 is a perspective view of a hospital bed showing the hospital bed including a frame, a deck coupled to and positioned above the frame, a headboard coupled to the frame, a footboard coupled to the deck, and two pair of split siderails coupled to the frame.

As shown in FIG. 1, a hospital bed 10 is provided including a frame 12 positioned on the floor, a deck 14 coupled to frame 12, a mattress 13 positioned on deck 14, a headboard 16 coupled to frame 12, a footboard 18 coupled to deck 14, and a pair of split siderails 20, 21 coupled to frame 12. Frame 12 is configured to raise and lower deck 14 relative to the floor and to move deck 14 to the Trendelenburg position and the Reverse Trendelenburg position.

As shown in FIG. 1, headboard or first barrier 16 includes a curved base 30 coupled to frame 12 and a center panel 34 removably coupled to base 30. Base 30 includes a pair of handles 48 to facilitate pushing hospital bed 10 about a care facility.

When necessary a caregiver removes center panel 34 from base 30 and positions center panel 34 under a patient's torso to assist the caregiver in administering CPR to the patient. The removability of center panel 34 also permits access to the patient during such a procedure from a head end of hospital bed 10 to allow the caregiver to more easily administer the CPR procedure.

Figure 2:
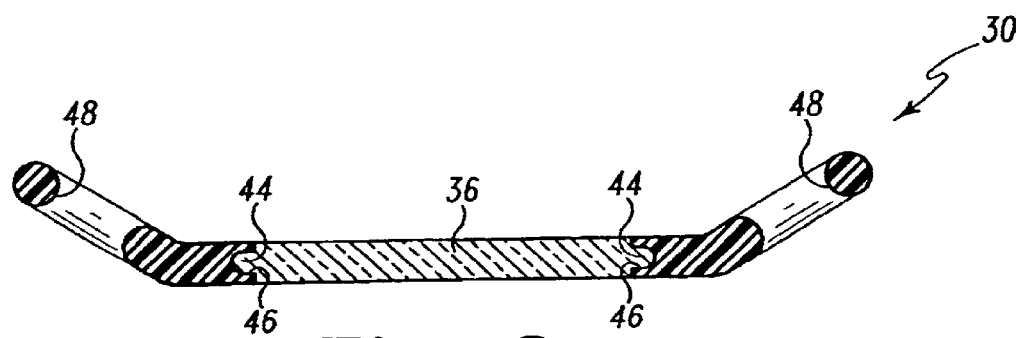
FIG. 2 is a cross-sectional view taken along line 2—2 of FIG. 1 showing the headboard including a base and a removable center panel slidably coupled to the base.

Center panel 34 includes a body portion 36, a handle portion 38 coupled to body portion 36 to define an opening 42 therebetween, and a pair of tongues 44 configured to mate with base 30 and provide sliding movement therebetween. The preferred embodiment of center panel 34 is made of a clear plastics material such as acrylic or clarified polyethylene (PETG) so that a caregiver may view a patient positioned on hospital bed 10 through headboard 16. According to alternative embodiments of the present disclosure, the center panel is made of other materials known to those of ordinary skill in the art that have transparent, translucent, or non-opaque properties so that visible light passes therethrough. According to another alternative embodiment of the present disclosure, portions or all of the center panel is made of an opaque material. As shown in FIG. 2, base 30 is formed to include a pair of grooves 46 configured to receive tongues 44 of center panel 34 so that center panel 34 is slidably coupled to base 30.

As shown in FIGS. 1 and 3, frame 12 includes a rectangular lower frame member or base frame 32, a plurality of casters 50 coupled to base frame 32 to permit hospital bed 10 to be rolled about a care facility, a rectangular upper frame member or intermediate frame 52, a linkage system 54 coupled to intermediate and base frames 52, 32 to permit relative motion therebetween, and an actuator system 56 providing power to actuate linkage system 54 and move upper member 52 relative to base frame 32. Linkage system 54 includes a pair of head links 58 pivotably coupled to a head end 53 of intermediate frame 52 and slidably coupled to base frame 32, a pair of foot links 60 pivotably coupled to a foot end 55 of intermediate frame 52 and slidably coupled to base frame 32, and a pair of guide links 62 pivotably coupled to respective foot links 60 and pivotably coupled to base frame 32 at a fixed pivot point.

As shown in FIGS. 3 and 4, linkage system 54 further includes rollers 59 that ride in hollow base frame 32 and pins 61 extending through elongated slots 70 formed in inner side walls of base frame 32 to rotatably couple rollers 59 to the lower ends of head and foot links 58, 60. Rollers 59 ride over a lower wall 63 of base frame 32 to provide smooth rolling movement between head and foot links 58, 60 and base frame 32 to facilitate the sliding movement of head and foot links 58, 60 in base frame 32.

Hospital bed 10 further includes a caster braking system including a caster-brake link 65 extending through hollow base frame 32 adjacent to roller 59 as shown in FIG. 4. The caster braking system interconnects each caster 50 to provide simultaneous braking of casters 50. To simultaneously brake casters 50, the caregiver steps on one of foot brake pedals 63 and the caster braking system locks casters 50 against rolling. A caster braking system similar to the caster braking system of the present disclosure is more fully disclosed in U.S. patent application Ser. No. 09/263,039, filed Mar. 5, 1999, to Mobley et al., entitled Caster and Braking System, which is expressly incorporated by reference herein.

Guide links 62 restrict the motion of foot links 60 such that the pivot point between foot links 60 and intermediate frame 52 is restrained to move vertically without moving horizontally. This restriction prevents horizontal movement of intermediate frame 52 relative to base frame 32 during raising and lowering of intermediate frame 52. This restrained movement prevents intermediate frame 52 from moving through an arch while moving between the upper and lower positions so that intermediate frame 52 can be raised and lowered without requiring additional hospital room for clearance.

It will be appreciated that, in order for guide links 62 to perform the restriction function, the distance between pivot points 49, 51 of guide links 62 is one half the distance between axis 47 of rollers 59 and pivot points 45 of the upper ends of foot links 60 and that each guide link 62 is pivotably coupled to the respective foot link 60 at pivot point 51 that is one half the distance between axis 47 of the associated roller 59 and pivot point 45 of the upper end of the respective foot link 60. Thus, the distance between upper pivot point 51 of each guide link 62 and the lower pivot point 49 of each guide link 62 is equal to the distance between upper pivot point 51 of each guide link 62 and upper pivot point 45 of each foot link 60. As a result of this link geometry, upper pivot points 45 of foot links 60 are maintained in vertical alignment with lower pivot point 49 of guide links 62 during raising and lower of frame members 52 relative to frame member 32.

Actuator system 56 provides the force and power necessary to raise and lower intermediate frame 52. Actuator system 56 includes a head link actuator 64 coupled to head links 58 and intermediate frame 52 and a foot link actuator 66 coupled to foot links 60 and intermediate frame 52. Actuator 64 is coupled to head links 58 through an extension link 75 that is rigidly coupled to a cross strut (not shown) which extends between and is rigidly coupled to each of head links 58. Similarly, actuator 66 is coupled to foot links 60 through an extension link 77 that is rigidly coupled to a cross strut (not shown) which extends between and which is rigidly coupled to each of foot links 60. The cross strut coupled to head links 58 coordinates the simultaneous movement thereof, whereas the cross strut coupled to foot links 60 coordinates simultaneous movement thereof.

Actuators 64, 66 have expandable lengths to adjust the angular position of head and foot links 58, 60 relative to intermediate frame 52 so that head and foot ends 53, 55 of intermediate frame 52 can be raised or lowered. Each of actuators 64, 66 is preferably an electric linear actuator having respective cylinder bodies 67, cylinder rods 69, and motors 71 that operate to extend and retract cylinder rods 69 relative to cylinder bodies 67. Cylinder rods 69 are each pivotably coupled to respective pivot links 75, 77 and motors 71 are each pivotably coupled to a bracket 79 included in intermediate frame 52 as shown, for example, in FIG. 3.

Figure 5:
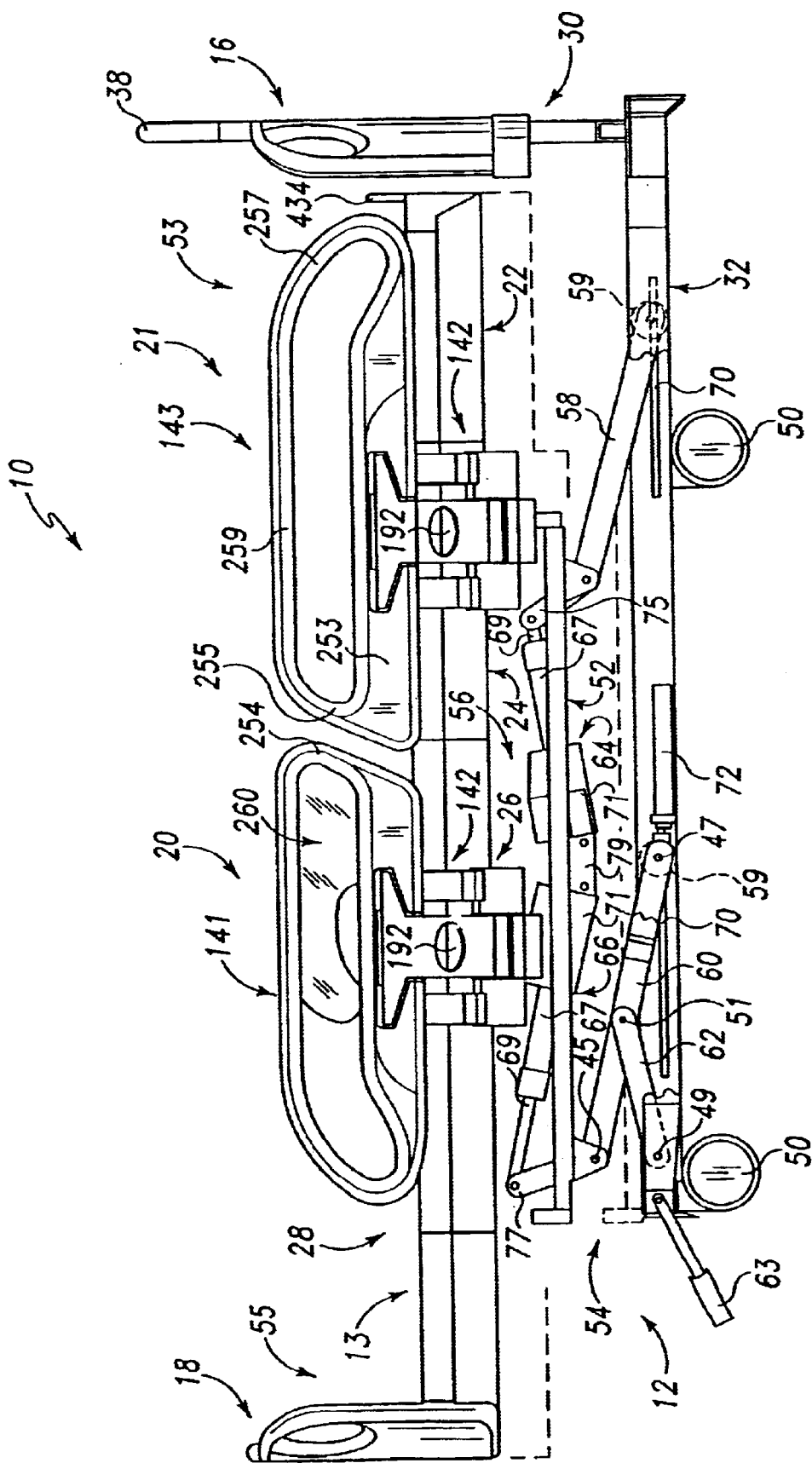
FIG. 5 is a side elevation view of the hospital bed similar to FIG. 3 showing the frame in an intermediate position supporting the deck in an intermediate position and showing the frame (in phantom) in a lower position supporting the deck in a lower position.

When head and foot link actuators 64, 66 are actuated simultaneously, such that one of actuators 64, 66 extends while the other actuator 66, 64 retracts, intermediate frame 52 either raises away from or lowers toward base frame 32 so that intermediate frame 52 is maintained in a horizontal position and does not "swing" outwardly or inwardly relative to base frame 32. When head link actuator 64 is activated and foot link actuator 66 is maintained at a constant length, intermediate frame 52 moves to the Trendelenburg position as shown in FIG. 5 so that head end 53 of intermediate frame 52 is lowered and foot end 55 of intermediate frame 52 is slightly raised. When the foot link actuator 66 is activated and head link actuator 64 is maintained at a constant length, intermediate frame 52 moves to the Reverse Trendelenburg position so that foot end 55 of intermediate frame 52 lowers and head end 53 of intermediate frame 52 slightly raises as shown in FIG. 6.

As shown in FIGS. 3 and 5, deck 14 is lowered by activating both head and foot link actuators 64, 66. As the length of foot link actuator 66 increases, the angle between foot links 60 and intermediate frame 52 decreases and foot end 55 of intermediate frame 52 lowers. As the length of head link actuator 64 decreases, the angle between head links 58 and intermediate frame 52 increases and head end 53 of intermediate frame 52 lowers as shown, for example, in FIG. 5. As the length of foot link actuator 66 continues to increase and the length of head link actuator 64 continues to decrease, intermediate frame 52 continues to lower from the upper position to a lower position as shown in FIG. 5 (in phantom). Because head and foot link actuators 64, 66 decrease and increase their respective lengths at substantially the same rate, intermediate frame 52 remains substantially horizontal while moving from the upper position, shown in FIG. 3, to the lower position shown in phantom in FIG. 5 (in phantom). To position upper frame 52 back in the upper position, link actuator 64 is lengthened and foot link actuator 66 is simultaneously shortened until each actuator 64, 66 returns to its original length as shown in FIG. 3.

Figure 6:
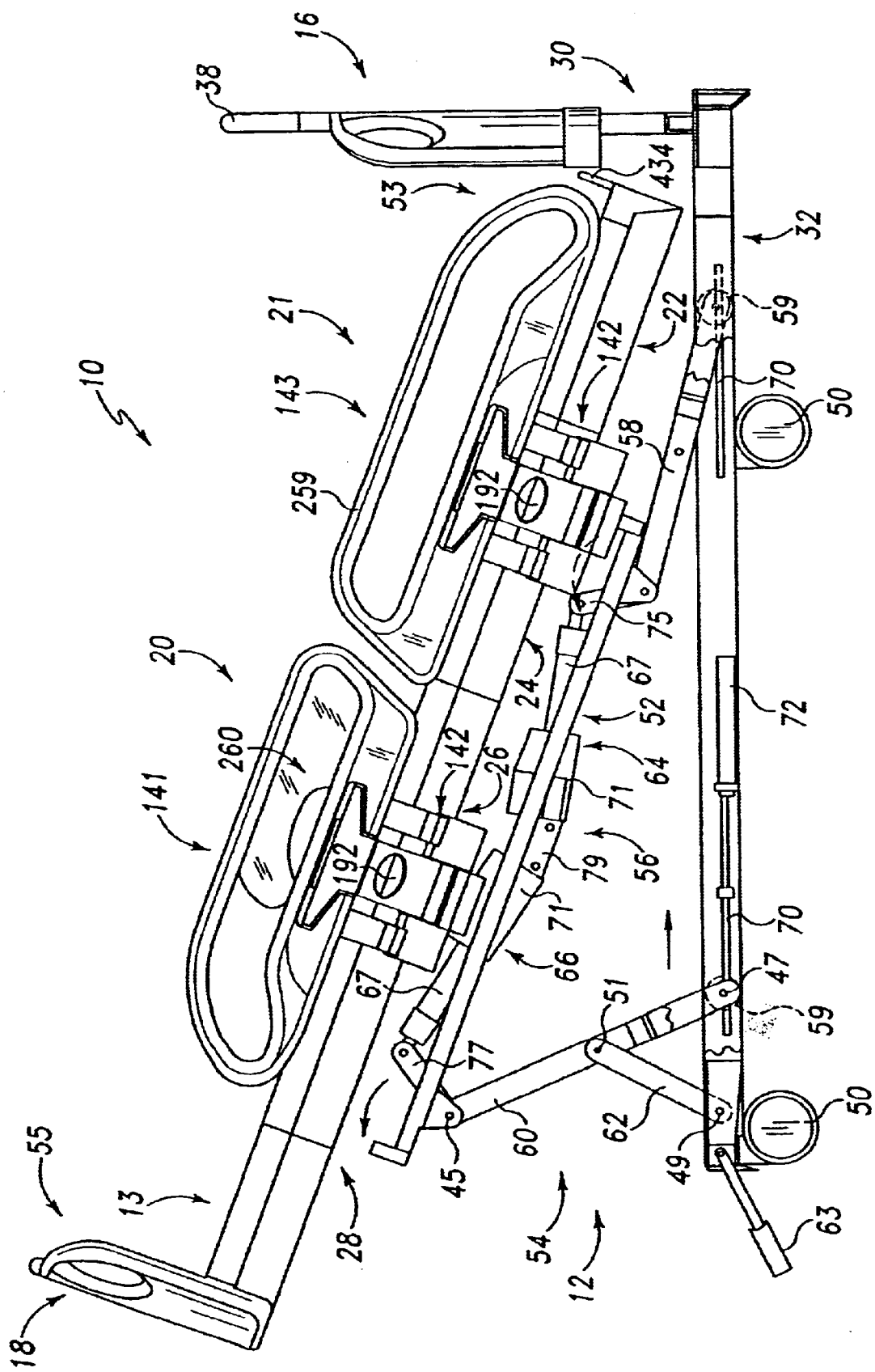
FIG. 6 is a side elevation view of the hospital bed similar to FIG. 3 showing the frame in the Trendelenburg position supporting the deck with a head section of the deck positioned lower than a foot section of the deck.

Linkage system 54 and actuator system 56 also cooperate to move intermediate frame 52 to the Trendelenburg position as shown in FIG. 6. To move intermediate frame 52 to the Trendelenburg position, head link actuator 64 decreases its length such that the angle between intermediate frame 52 and head links 58 increases. Head end 53 of intermediate frame 52 lowers and the length of foot link actuator 66 remains substantially constant to provide a pivot point about which intermediate frame 52 rotates. As intermediate frame 52 rotates, foot end 55 of intermediate frame 52 is slightly raised as shown in FIG. 6. To reposition intermediate frame 52 in the upper horizontal position, the length of head link actuator 64 is increased until it is returned to its previous length.

Figure 7:
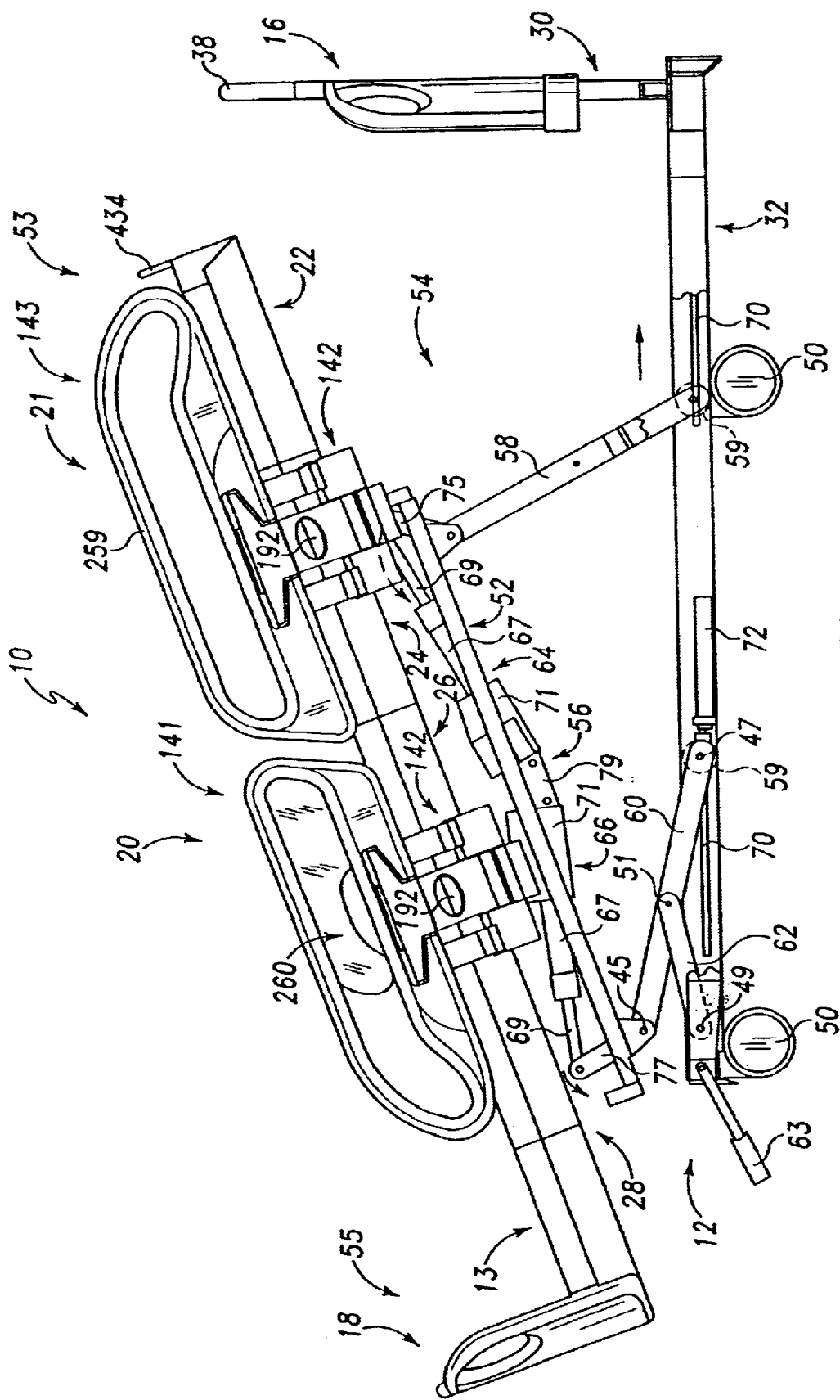
FIG. 7 is a side elevation view of the hospital bed similar to FIG. 3 showing the frame in the Reverse Trendelenburg position supporting the deck with the head section of the deck positioned higher than the foot section of the deck.

Actuator system 56 and linkage system 54 also cooperate to position intermediate frame 52 in the Reverse Trendelenburg position as shown in FIG. 7. To move intermediate frame 52 to the reserve-Trendelenburg position, the length of foot link actuator 66 is increased so that the angle between foot links 60 and intermediate frame 52 is decreased and foot end 55 of intermediate frame 52 lowers. The overall length of head link actuator 64 remains substantially constant so that intermediate frame 52 pivots about head links 58. As intermediate frame 52 pivots, head end 53 of intermediate frame 52 is slightly raised as foot end 55 of intermediate frame 52 lowers. To reposition upper frame 52 in the upper horizontal position, the length of foot link actuator 66 is decreased until it is returned to its previous length.

Hospital bed 10 further includes two dampers 72 coupled to the inner walls of base frame 32 to engage the lower ends of foot links 60. Dampers 72 aid in raising intermediate frame 52 and deck 14 from the lower and Reverse Trendelenburg positions. During lowering of foot end 55 of intermediate frame 52, dampers 72 resist movement of the foot links 60 and store potential energy as a result of the lowering of foot end 55 of intermediate frame 52. For example, as shown in FIG. 5, as foot links 60 move along slot 70, damper 72 is compressed so that potential energy is stored. As intermediate frame 52 is moved from the lower position, as shown in FIG. 5, to the upper position as shown in FIG. 3, dampers 72 aid foot link actuators 66 in raising foot end 55 of intermediate frame 52 by pushing lower ends of foot links 60 in the direction that raises foot end 55 of intermediate frame 52 to the upper position. Because dampers 72 store potential energy during lowering of foot end 55 of intermediate frame 52, foot link actuator 66 does not need to be as powerful to raise foot end 55 of intermediate frame 52 from the lower position to the upper position. According to an alternative embodiment frame, a more powerful foot link actuator is provided and dampers are not provided.

Figure 8:
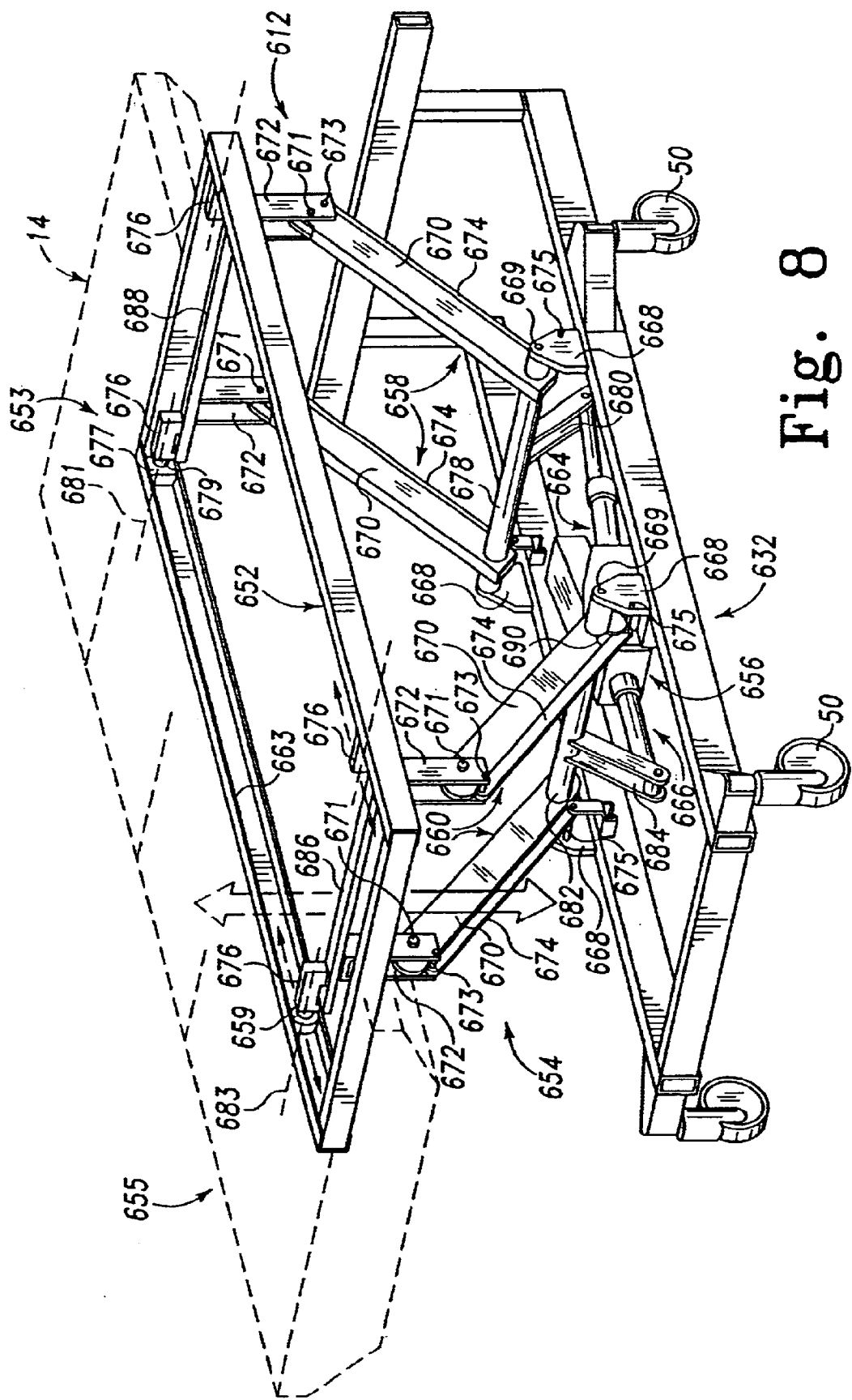
FIG. 8 is a perspective view of an alternative embodiment hospital bed frame having four linkage assemblies supporting an intermediate frame and a deck (in phantom)

An alternative embodiment frame 612 is shown in FIGS. 8–13. As shown in FIG. 8, frame 612 includes a lower frame member or base frame 632, plurality of casters 50 coupled to base frame 632 to permit the hospital bed to be rolled about a care facility, an upper frame member or intermediate frame 652, a linkage system 654 coupled to intermediate and base frames 652, 632 to permit relative motion therebetween, and an actuator system 656 providing power and force to actuate linkage system 654 and move intermediate frame 652 relative to base frame 632. Linkage system 654 includes a pair of head link assemblies 658 pivotably coupled to intermediate frame 652 near a head end 653 of intermediate frame 652 and rigidly coupled to base frame 632 and a pair of foot link assemblies 660 slidably coupled to intermediate frame 652 near a foot end 655 of intermediate frame 652 and rigidly coupled to base frame 632.

Figure 9:
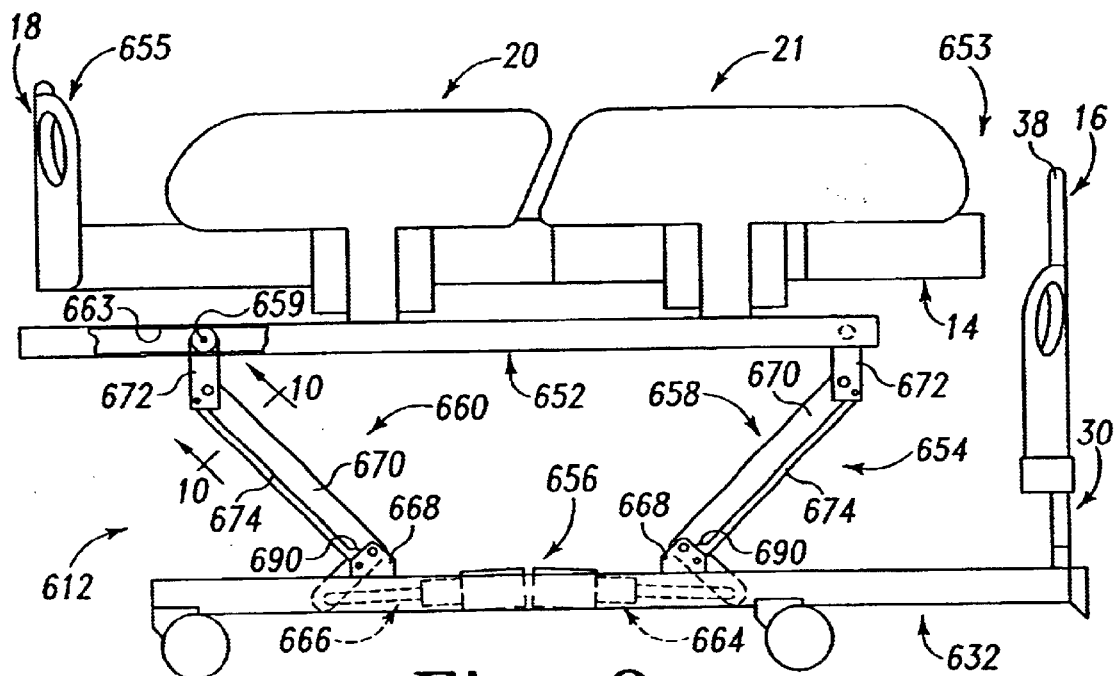
FIG. 9 is a side elevation view of the hospital bed of FIG. 8 showing the frame in an upper position supporting the intermediate frame and the deck in an upper position.

As shown in FIGS. 8 and 9, foot link assembly 660 further includes rollers 659 that ride in hollow intermediate frame 652. Rollers 659 are coupled to the upper ends of foot link assemblies 660 to facilitate the sliding of foot link assemblies 660 relative to intermediate frame 652. Rollers 659 ride under an upper wall 663 of intermediate frame 652 to provide smooth rolling movement between foot link assemblies 660 and intermediate frame 652.

Actuator system 656 provides the power and force necessary to raise and lower upper frame assembly 652. Actuator system 656 includes a head link actuator 664 coupled to head link assemblies 658 and base frame 632 and a foot link actuator 666 coupled to foot link assemblies 660 and base frame 632. Actuators 664, 666 are similar to actuators 64, 66 and have expandable lengths to adjust the angular position of head and foot link assemblies 658, 660 relative to base frame 632 so that head and foot ends 653, 655 of intermediate frame 652 can be raised or lowered.

Figure 12:
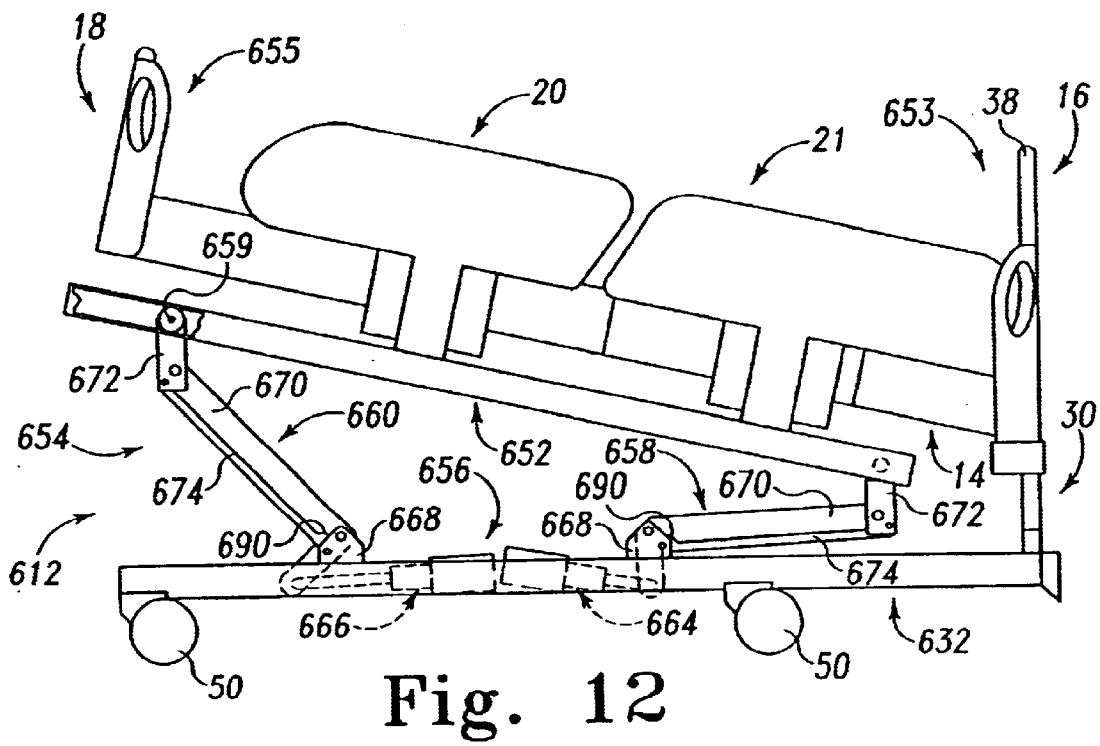
FIG. 12 is a side elevation view of the hospital bed similar to FIG. 9 showing the frame in the Trendelenburg position supporting the deck with a head section of the deck positioned lower than a foot section of the deck.

When head and foot link actuators 664, 666 are actuated simultaneously such that both actuators 664, 666 retract or extend, intermediate frame 652 either raises away from or lowers toward base frame 632 so that intermediate frame 652 is maintained in a horizontal position. When head link actuator 664 is activated and foot link actuator 666 is maintained at a constant length, intermediate frame 652 moves to the Trendelenburg position, as shown in FIG. 12, so that head end 653 of intermediate frame 652 is lowered and foot end 655 of intermediate frame 652 is raised. When the foot link actuator 666 is activated and head link actuator 664 is maintained at a constant length, intermediate frame 652 moves to the Reverse Trendelenburg position so that foot end 655 of intermediate frame 652 lowers and head end 653 of intermediate frame 652 raises as shown in FIG. 13.

Figure 11:
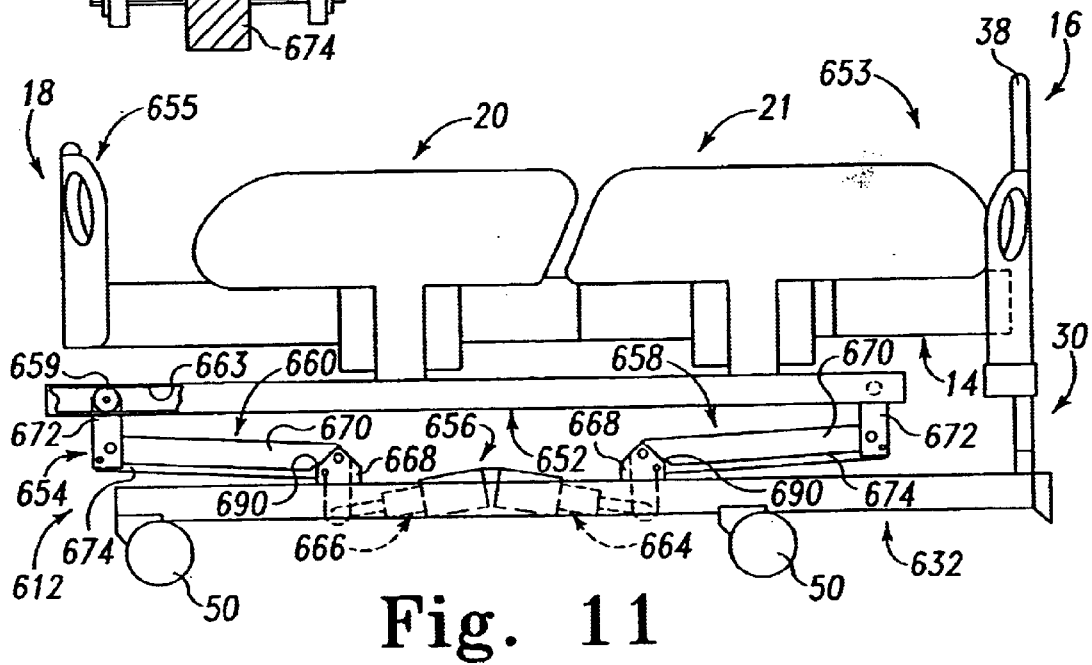
FIG. 11 is a side elevation view of the hospital bed similar to FIG. 9 showing the frame in a lower position supporting the deck in a lower position.

As shown in FIGS. 9 and 11, intermediate frame 652 is lowered by activating both head and foot link actuators 664, 666. As the length of foot link actuator 666 decreases, the angle between foot link assemblies 660 and intermediate frame 652 decreases and foot end 655 of intermediate frame 652 lowers. As the length of head link actuator 664 decreases, the angle between head link assemblies 658 and intermediate frame 652 decreases and head end 653 of intermediate frame 652 lowers as shown, for example, in FIG. 11. As the length of foot and head link actuators 666, 664 continue to decrease, intermediate frame 652 continues to lower from the upper position to a lower position as shown in FIG. 11. Because head and foot link actuators 664, 666 decrease their respective lengths at substantially the same rate, intermediate frame 652 remains substantially horizontal while moving from the upper position shown in FIG. 9 to the lower position shown in FIG. 11 (in phantom). To reposition intermediate frame 652 back in the upper position, head and foot link actuators 664, 666 are simultaneously lengthened until each actuator 664, 666 is returned to its original length.

As previously mentioned, linkage system 654 and actuator system 656 cooperate to move intermediate frame 652 to the Trendelenburg position as shown in FIG. 12. To move intermediate frame 652 from the position shown in FIG. 9 to the Trendelenburg position shown in FIG. 12, head link actuator 664 decreases its length such that the angle between intermediate frame 652 and head link assemblies 658 decreases and head end 653 of intermediate frame 652 lowers and the length of foot link actuator 666 remains substantially constant to provide a pivot point about which intermediate frame 652 rotates such that foot end 655 of intermediate frame 652 is slightly raised. To reposition intermediate frame 652 to the horizontal upper position, the length of head link actuator 664 is increased until it is returned to its original length as shown in FIG. 9.

Figure 13:
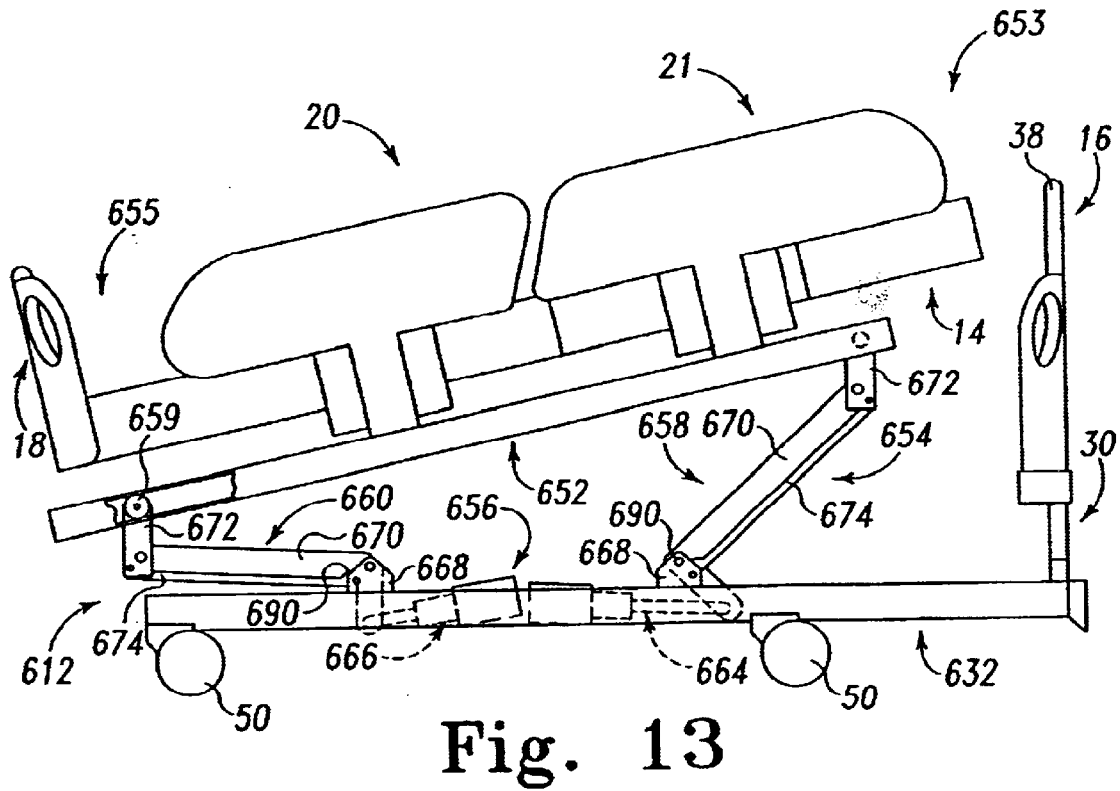
FIG. 13 is a side elevation view of the hospital bed similar to FIG. 9 showing the frame in the Reverse Trendelenburg position supporting the deck with the head section of the deck positioned higher than the foot section of the deck.

Actuator system 656 and linkage system 654 also cooperate to position intermediate frame 652 in the Reverse Trendelenburg position as shown in FIG. 13. To move intermediate frame 652 from the position shown in FIG. 9 to the Reverse Trendelenburg position shown in FIG. 13, the length of foot link actuator 666 is decreased so that the angle between foot link assemblies 660 and intermediate frame 652 is decreased and foot end 655 of intermediate frame 652 lowers. The overall length of head link actuator 664 remains substantially constant so that intermediate frame 652 pivots about head link assemblies 658. As intermediate frame 652 pivots, head end 653 is slightly raised as foot end 655 lowers. To reposition intermediate frame 652 to the horizontal upper position, the length of foot link actuator 666 is increased until it is returned to its original length as shown in FIG. 9.

As shown in FIGS. 9, 12, 13, head and foot link assemblies 658, 660 are configured to maintain a vertical orientation of the upper end thereof during movement of upper frame 652 between the various positions. Each head and foot link assembly 658, 660 includes first, second, third, and fourth links 668, 670, 672, 674 that cooperate to maintain third link 672 in said vertical position. Each head and foot link assembly 658, 660 further includes a load cell 676 positioned between respective blocks 677 and rollers 659 and respective third links 672 that measure the respective weight applied to each third link 672. Because third links 672 remain vertical, no trigonometric calculations must be made to correct the weight measurement due to the orientation of load cell 676 relative to the floor.

As shown in FIG. 8, first links 668 comprise a series of brackets that are rigidly coupled to lower frame 632. Second links 670 are C-shaped and are pivotably coupled to the respective first links 668 by pins 669. A strut 678 extends between the respective second links 670 of foot link assemblies 660 to provide a rigid connection therebetween to coordinate simultaneous movement of foot link assemblies 660 during actuation by foot link actuator 666. An extension 680 is rigidly coupled to strut 678 to provide a moment arm through which the linear force provided by foot link actuator 666 is converted to torque for rotating second links 670 of foot link assemblies 660.

Similarly, a strut 682 extends between the respective second links 670 of head link assemblies 658 to provide a rigid connection therebetween to coordinate simultaneous movement of head link assemblies 658 during actuation by head link actuator 664. An extension 684 is rigidly coupled to strut 682 to provide a moment arm through which the linear force provided by head link actuator 664 is converted to torque for rotating second links 670 of head link assemblies 658.

Third links 672 comprise a series of C-shaped brackets pivotably coupled to respective second links 670 by pins 671. A strut 686 extends between respective third links 672 of foot link assemblies 660 to provide a rigid connection therebetween to coordinate simultaneous movement of foot link assemblies 660 during actuation by foot link actuator 666. Similarly, a strut 688 extends between the respective third links 672 of head link assemblies 658 to provide a rigid connection therebetween to coordinate simultaneous movement of head link assemblies 658 during actuation by head link actuator 664. Load cells 676 are rigidly coupled to respective struts 686, 688 as shown in FIG. 8.

Figure 10:
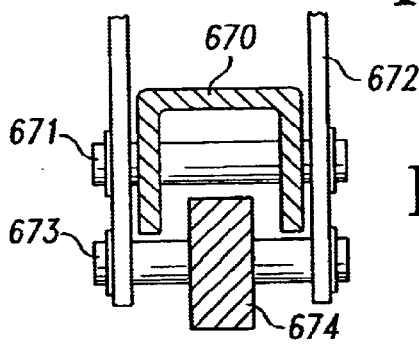
FIG. 10 is a cross-sectional view taken along line 10—10 of FIG. 9 showing one of the linkage assemblies including a C-shaped link and a rectangle-shaped link partially positioned in the C-shaped link.

Fourth links 674 comprise flat elongated bars pivotably coupled to respective third links 672 by pins 673 and first links 668 by pins 675 to provide a complete four bar linkage for each head and foot link assembly 658, 660. As shown in FIG. 10, each respective fourth link 674 is positioned partially within the respective C-shaped second link 670 to block insertion of objects between the respective second and fourth links 670, 674 to prevent pinching. As shown in FIG. 8, each respective second link 670 is formed to include a notch 690 positioned to provide clearance for pin 675 while each foot and head link assemblies 658, 660 is in the lower position.

As shown in FIGS. 8–13, third link 672 remains substantially vertical during movement of intermediate frame 652 through the various positions. As second links 670 are turned by respective head and foot link actuators 664, 666, third link 672 directs the horizontal and vertical movement of pin 673 so that pin 673 remains in substantially the same vertical and horizontal position relative to pin 671. By maintaining this relationship, third link 672 remains substantially vertical regardless of the vertical positions of head and foot ends 653, 655 of intermediate frame 652.

Because third links 672 remain substantially vertical, load cells 676 also remain in a substantially vertical orientation simplifying the overall calculation necessary for determining the weight of the patient. To determine the total weight of the patient, the weights measured by load cells 676 are totaled and the predetermined weight of the components of the hospital bed supported by load cells 676 are subtracted from this total resulting in the weight of the patient. The weights measured from load cells 676 do not need adjusted for the angular position of upper frame 652 because load cells 676 remain vertically oriented.

Pair of coupling blocks 677 are fixed to intermediate frame 652 adjacent to head end 653 thereof and load cells 676 associated with head link assemblies 658 each include a cylindrical stud 679 extending transversely therefrom into a bore formed in the respective block 677. As intermediate frame 652 tilts relative to base frame 632, blocks 677 tilt along with frame member 652 while pivoting relative to the associated load cells 676 on cylindrical stud 679 about pivot axis 681. In addition, as intermediate frame 652 tilts relative to base frame 632, rollers 659 rotate about pivot axis 683 relative to the associated load cells 676 while also rolling either toward or away from blocks 677 depending upon the direction that intermediate frame 652 tilts.

Figure 14:
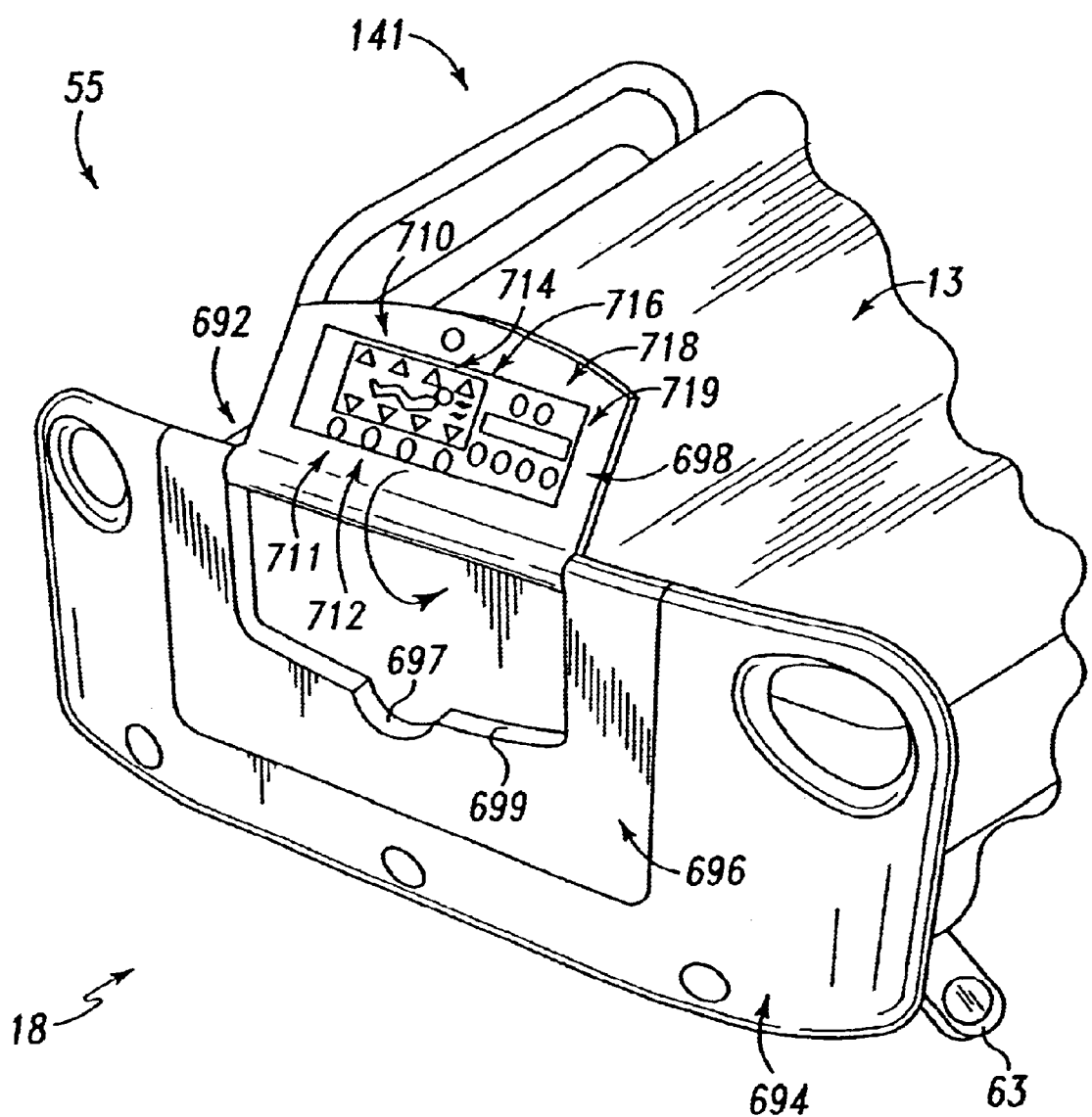
FIG. 14 is a perspective view of a control panel pivotably coupled to the footboard and including a plurality of control buttons for operating various functions of the hospital bed.

As shown in FIG. 14, footboard or second barrier 18 includes a modular control unit 692 for controlling the automated features of hospital bed 10. Footboard 18 further includes a base 694 and modular control unit 692 includes a support panel 696 slidably coupled to base 694 and a control panel 698 pivotably coupled to support panel 696. Control panel 698 is rotatable between a use position, as shown in FIG. 14, and a storage position in a recess 699 formed in support panel 696. Support panel 696 is also formed to include a notch 697 in which a caregiver can grab a distal end of control panel 698 to rotate it back to the use position.

As shown in FIG. 1 in phantom, control unit 692 is removable from base 694 to permit replacement of control unit 692 for repairs or upgrading. According to the presently preferred embodiment of the hospital bed, multiple configurations of modular control units are provided at the manufacturing facility. Depending on the specific configuration of the hospital bed, a different control unit will be provided with the respective hospital bed by sliding the respective control unit into standard base 694.

Control panel 698 includes a series of buttons 710 for controlling the various functions of hospital bed 10. Deck 14 includes head, back, seat, and foot portions or sections 22, 24, 26, 28 that can be tilted relative to intermediate frame 52 and several mechanisms configured to adjust the angular position of these deck sections 22, 24, 26, 28. As will be described in greater detail below, foot section 28 of deck 14 is extendable, seat section 26 of deck 14 can be tilted relative to intermediate frame 52, back section 24 of deck 14 can be tilted relative to intermediate frame 52, and head section 22 of deck 14 can also be tilted relative to intermediate frame 52.

Series of buttons 710 includes a first pair of buttons 711 for raising and lowering intermediate frame 52 and a second pair of buttons 712 for raising and lowering seat section 26. Series of buttons 710 also includes a third pair of buttons 714 for raising and lowering back section 24 relative to intermediate frame 52 and a fourth pair of buttons 716 for simultaneously raising and lowering seat and back sections 26, 24. Another set of buttons 718 is provided for controlling the various functions of the mattress as will be described in greater detail below. Control panel 698 further includes a display 719 for monitoring the status of the various functions of hospital bed 10. According to an alternative embodiment, the series of buttons also includes a pair of buttons for moving the intermediate frame between the Trendelenburg and Reverse Trendelenburg positions, extending and retracting the foot section of the deck, and any other function of the bed. Control panel 698 preferably also includes buttons and a display associated with a bed exit and weighing system of bed 10.

An alternative embodiment control system 750 is shown in FIGS. 15 and 16. Control system 750 includes a plurality of pedals 752 pivotably coupled to the base frame. Each pedal 752 interacts with a three-position, dual contact switch that is activated by upward or downward movement of said pedal 752 from a middle, neutral position to operate a specific function of the hospital bed. For example, a first pedal 754 is pivoted upwardly to raise the intermediate frame and stepped on to lower the intermediate frame. A second pedal 756 is provided for tilting and untilting back section 24 relative to intermediate frame 52. Series of pedals 752 also includes a third pedal 758 for moving intermediate frame 52 between the Trendelenburg and Reverse Trendelenburg positions and a fourth pedal for 760 for tilting and untilting seat section 26 relative to intermediate frame 52. According to an alternative embodiment the plurality of pedals also includes a pedal for extending and retracting foot section 28 of the hospital bed. Each of pedals 752, therefore, is operated in an intuitive manner to control the various functions of the hospital bed. That is, pedals 752 are stepped on to perform a "down" function and are lifted upwardly with the top of a user's foot to perform an "up" function.

Figure 17:
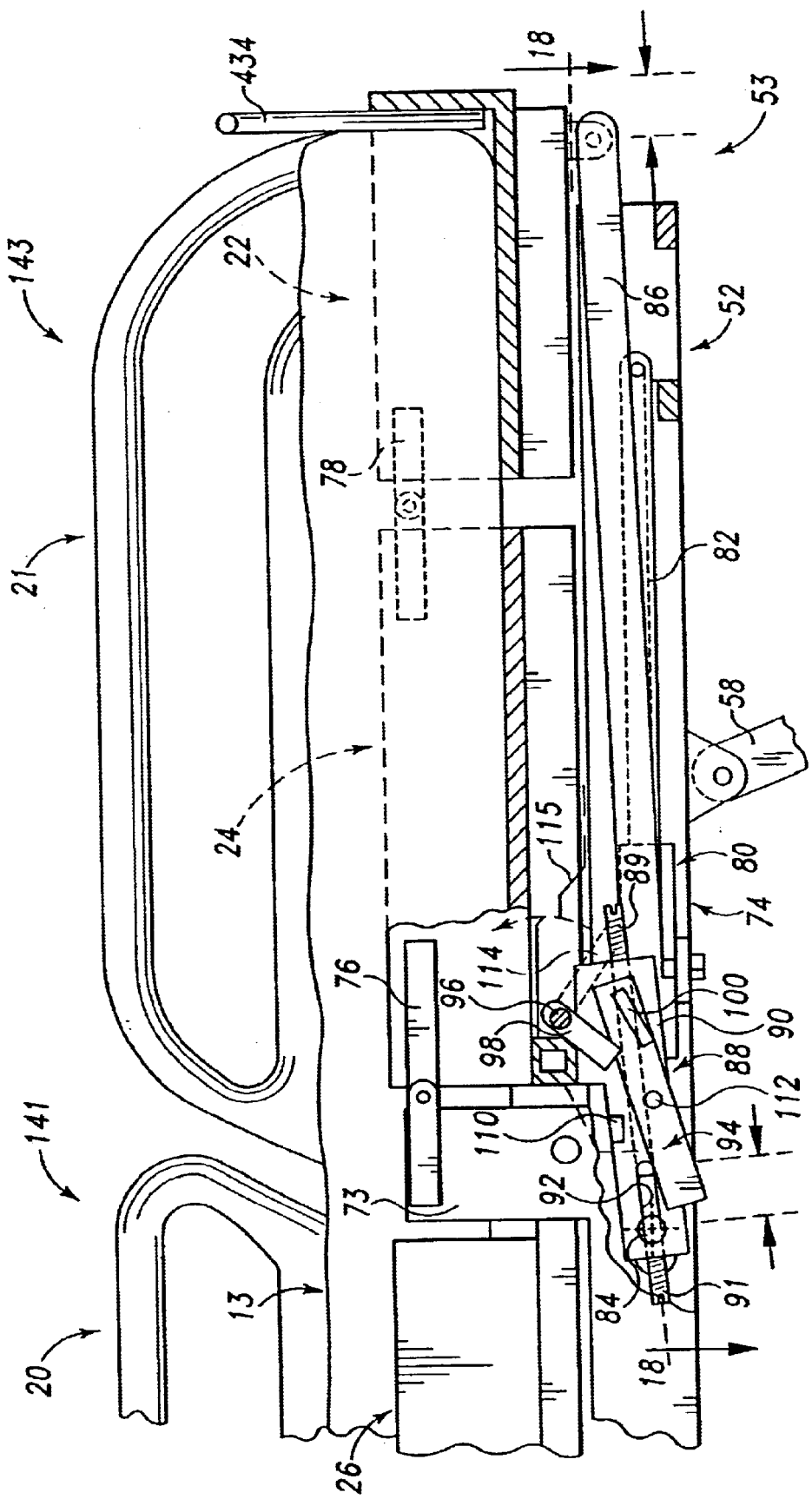
FIG. 17 is a side elevation view of a head end of the hospital bed of FIG. 1 with portions cut away (in partial phantom) showing the deck including the head section (in partial phantom), the back section (in partial phantom) pivotably coupled to the head section, and a tilt mechanism coupled to an intermediate frame of the frame, the back section of the deck, and to the head section of the deck.

As previously mentioned, deck 14 includes several sections 22, 24, 26, 28 that can be tilted relative to intermediate frame 52. Head section 22 is positioned adjacent to headboard 16 and is pivotably coupled to back section 24 by a hinge 78 as shown in FIG. 17. Back section 24 is pivotally coupled to upwardly extending flanges 73 of intermediate frame 52 by a hinge 76. Seat section 26 is pivotally coupled to upwardly extending flanges 73 of intermediate frame 52 by a hinge 116 as shown in FIGS. 22–25. Foot section 28 is pivotally coupled to seat section 26 by a hinge 118. Footboard 18 is coupled to foot section 28. Seat and foot sections 26, 28 have tapered ends 25, 27 providing clearance therebetween during titling of foot section 28 relative to seat section 26 as shown in FIG. 25. Thus, all sections 22, 24, 26, 28 are pivotable relative to intermediate frame 52.

Figure 18:
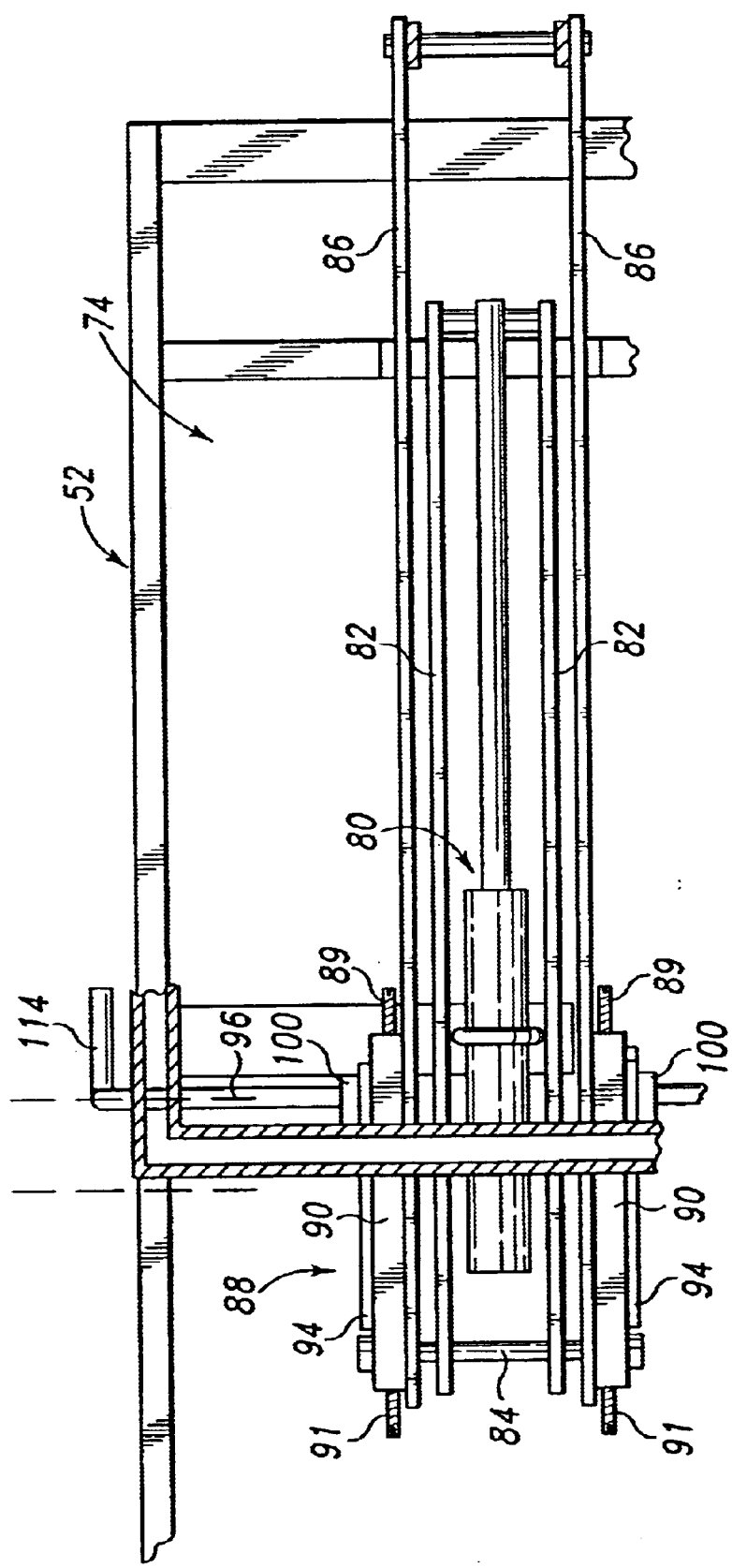
FIG. 18 is a top view of the tilt mechanism taking along lines 18—18 of FIG. 17.
Figure 19:
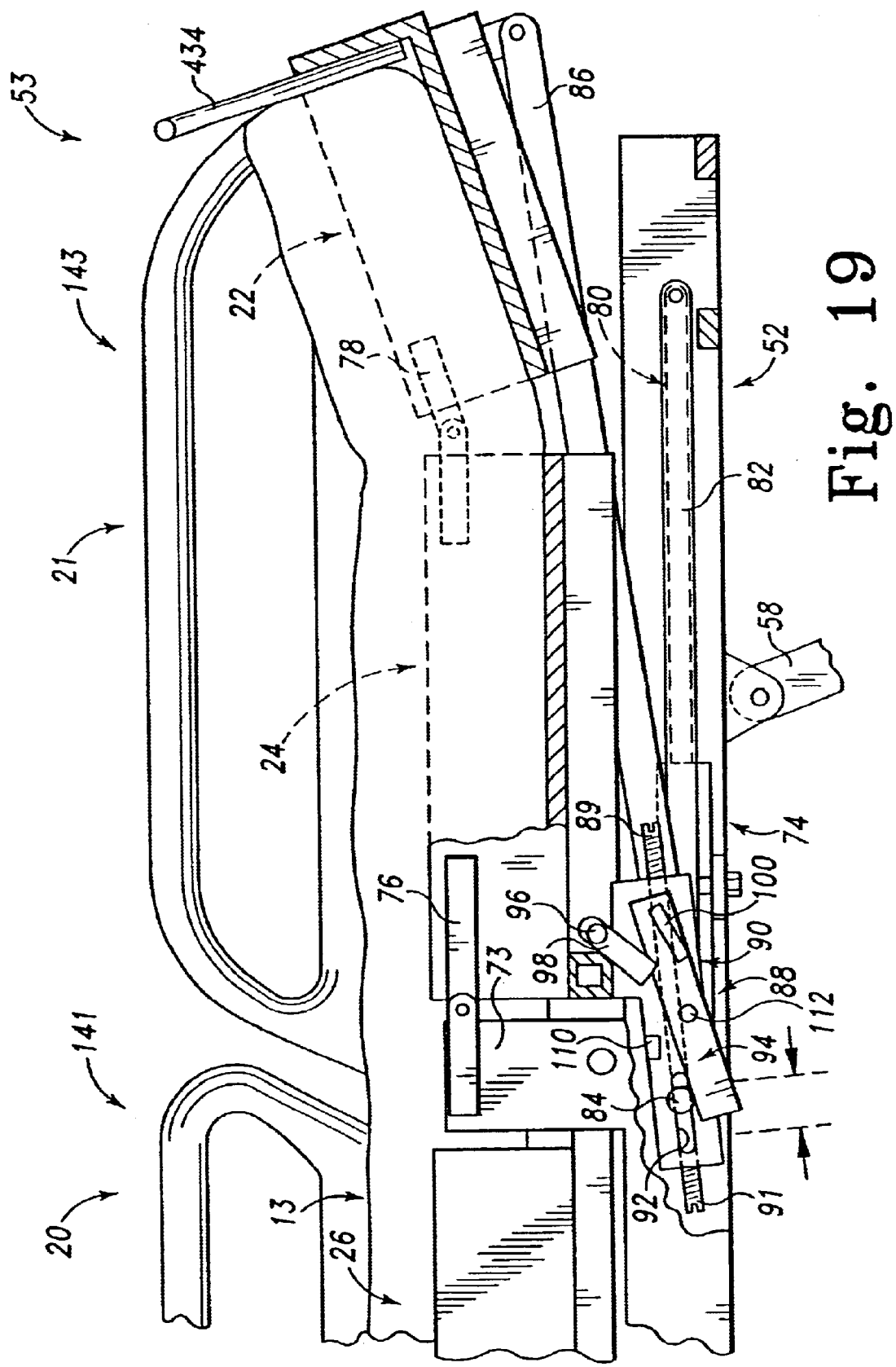
FIG. 19 is a side elevation view similar to FIG. 17 showing the tilt mechanism tilting the head section of the deck relative to the back section of the deck.
Figure 20:
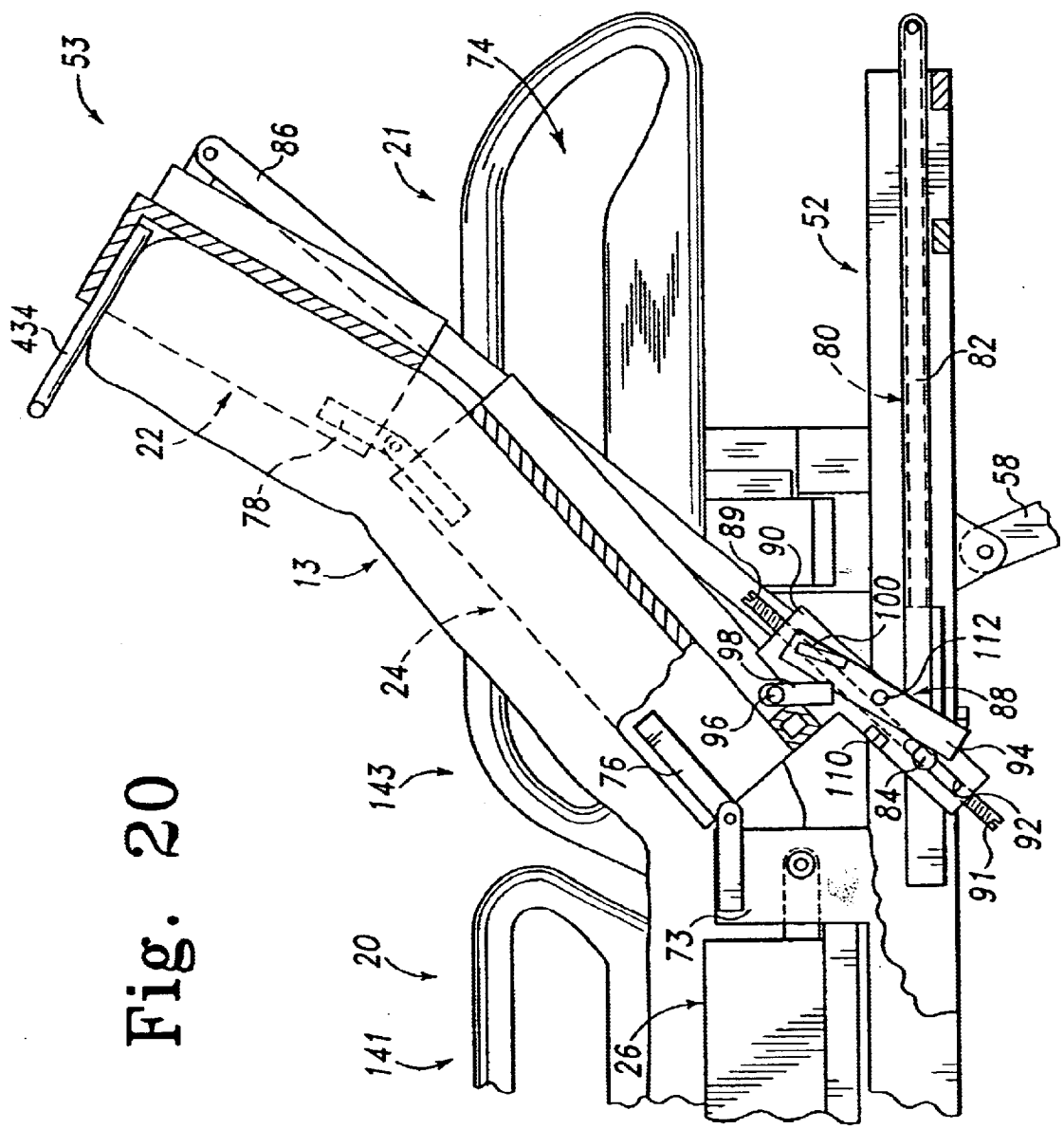
FIG. 20 is a side elevation view similar to FIG. 17 showing the tilt mechanism tilting the head section relative to the back section and tilting the back section relative to the intermediate frame.

Hospital bed 10 includes a tilt mechanism 74 that enables head and back sections 22, 24 to be moved automatically relative to intermediate frame 52 (see FIGS. 20 and 21) and head section 22 to be movable automatically relative to back section 24 (see FIGS. 19 and 20). As shown in FIGS. 17 and 18, tilt mechanism 74 includes a tilt actuator 80 coupled to intermediate frame 52, a pair of transfer linkages 82 pivotably coupled to tilt actuator 80, a transfer shaft 84 coupled to transfer linkages 82, a head-tilt linkage 86 pivotably coupled to head section 22 and transfer shaft 84, and a back-tilt linkage assembly 88 pivotably and slidably coupled to transfer shaft 84 and rigidly coupled to back section 24. As shown in FIG. 17, back-tilt linkage assembly 88 includes a pair of links 90 rigidly coupled to back section 24 of deck 14. Links 90 include slots 92 sized to receive transfer shaft 84.

To tilt head section 22 relative to back section 24, tilt actuator 80 is activated to push transfer linkage 82 to the right, as shown in FIG. 18, which pulls head tilt linkage 86 to the right to slide transfer shaft 84 in slots 92 as shown in FIG. 19. This relative movement of transfer shaft 84 relative to link 90 pivots head section 22 relative to back section 24. Because head-tilt linkage 86 pushes the lower right hand corner of head section 22 outwardly and hinge 78 continues to pivotably couple head section 22 to back section 24, head section 22 tilts relative to back section 24 as shown in FIG. 19.

As tilt actuator 80 continues to push transfer linkage 82 to the right, transfer shaft 84 reaches the right-hand ends of slots 92 and engages links 90. Transfer shaft 84 then pushes links 90 to the right to pivot back section 24 relative to intermediate frame 52 as shown in FIG. 20. Because first hinge 76 pivotably couples back section 24 to intermediate frame 52 and links 90 are coupled to a lower left hand corner of back section 24 that is actuated to the right by tilt actuator 80, back section 24 tilts relative to intermediate frame 52. Furthermore, the additional actuation of tilt actuator 80 continues the movement of head section 22 relative to intermediate frame 52 so that the degree of tilt between head section 22 and back section 24 is maintained as back section 24 is tilted relative to intermediate frame 52 as shown in FIG. 20. To return head and back sections 22, 24 to the horizontal position, the length of tilt actuator is shortened until it reaches its original length.

Back-tilt linkage assembly 88 is configured to enable restriction of the relative movement of head and back section 22 during actuation of tilt actuator 80. Back-tilt linkage assembly 88 further includes a pair of blockers 94 pivotably coupled to link 90 to move between an unblocking position (see FIG. 17) permitting movement of head section 22 relative to back section 24 and a blocking position (see FIG. 21) restraining movement of head section 22 relative to back section 24. While in the unblocking position, transfer shaft 84 is free to move in slots 92 permitting movement of link 90 relative to head tilt linkage 86 so that head section 22 can tilt relative to back section 24.

Figure 21:
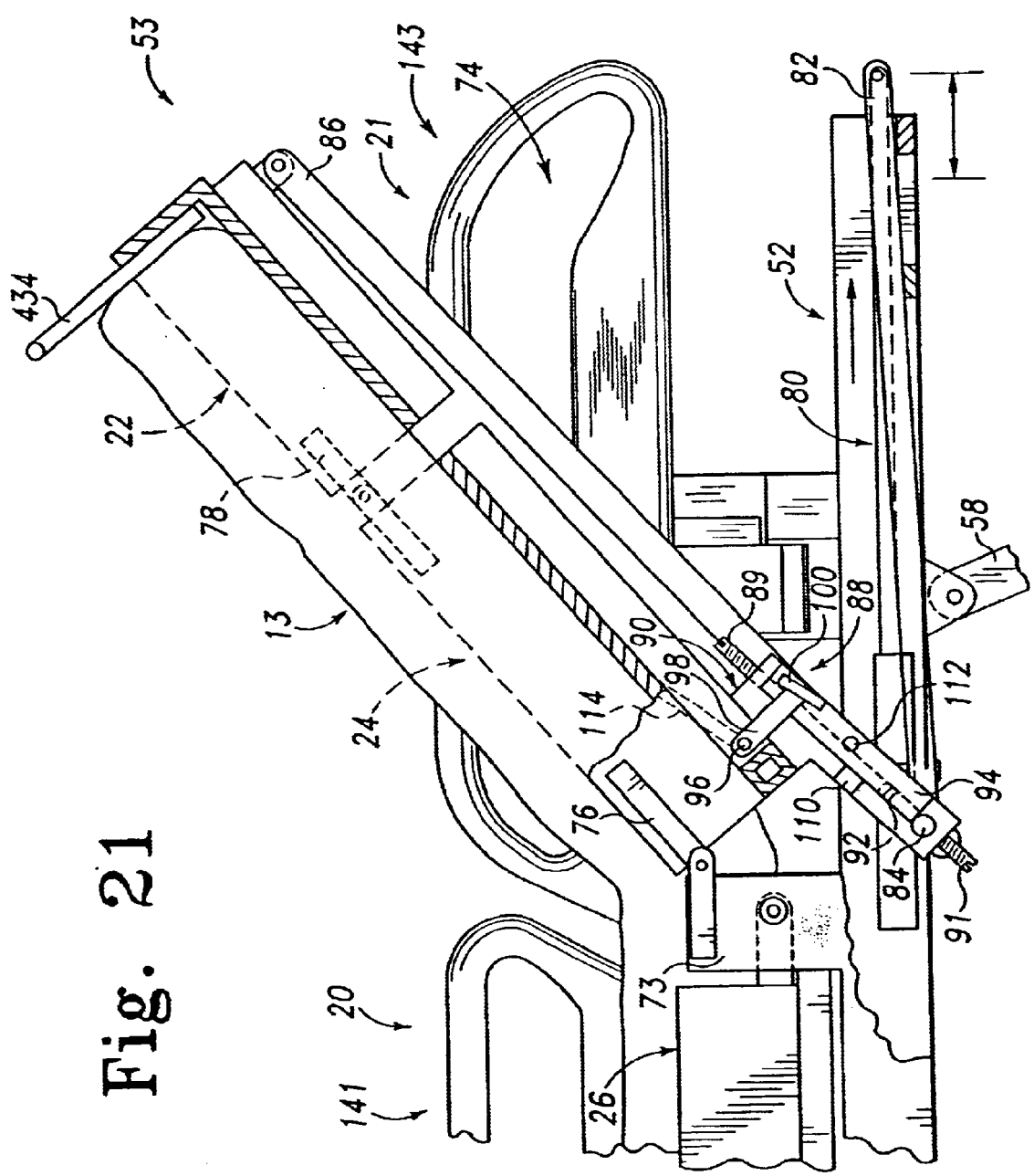
FIG. 21 is a side elevation view similar to FIG. 17 showing the tilt mechanism tilting the head and back sections of the deck relative to the intermediate frame while maintaining a coplanar relationship between the head and back sections.
Figure 22:
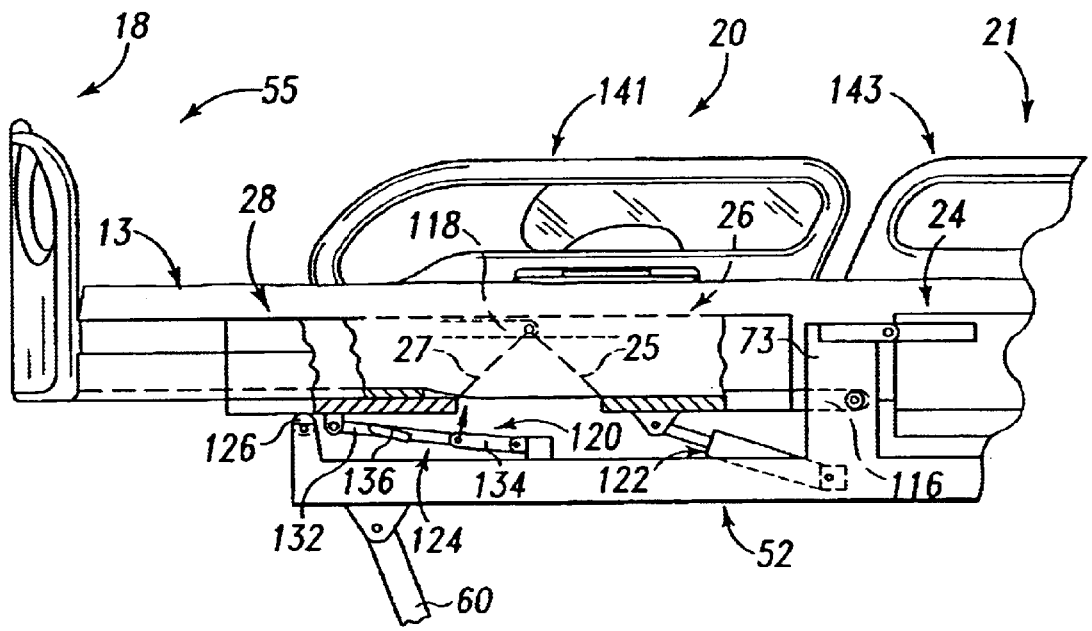
FIG. 22 is a side elevation view of a foot end of the hospital bed showing the deck including a foot section with the footboard coupled thereto and a seat section pivotably coupled to the foot section and the intermediate frame, and a tilt mechanism positioned between the foot and seat sections of the deck and the intermediate frame.

When blockers 94 are moved to the blocking position, as shown in FIG. 21, transfer shaft 84 is prevented from moving in slots 92 so that the initial movement of tilt actuator 80 not only moves head-tilt linkage 86 and head section 22 but also moves links 90 of back-tilt linkage assembly 88 and back section 24. This causes head section 22 to tilt relative to intermediate frame 52 and back section 24 to simultaneously tilt relative to intermediate frame 52 so that head and back sections 22, 24 remain substantially coplanar to one another as shown in FIG. 21.

Back-tilt linkage assembly 88 further includes a pair of adjustment screws 89, 91 extending into links 90 for adjusting the effective length of slots 92. As shown in FIG. 17, screw 89 extends into the right end of link 90. If screw 89 is turned further into link 90, the effective length of the right end of slot 92 decreases to shorten the travel range of transfer shaft 84 in the right end of slot 92. By decreasing the effective length of the right end of slots 92, the degree of maximum tilt between head and back sections 22, 24 is reduced.

As shown in FIG. 17, screw 91 extends into the left end of link 90. As screw 91 is turned into link 90, the effective length of the left end of slot 92 decreases to shorten the travel range of transfer shaft 84 in the left end of slot 92. By decreasing the effective length of the left end of slots 92, the degree of minimum tilt between head and back sections 22, 24 is increased.

To facilitate movement of blocker 94 between the unblocking and blocking positions, back-tilt linkage assembly 88 includes a blocker lever 96 pivotably coupled to back section 24, cams 98 rigidly coupled to blocker lever 96, cam followers 100 rigidly coupled to blockers 94, and stops 110 rigidly coupled to links 90. Blocker lever 96 and cams 98 are movable between a disengaged position, as shown in FIG. 17, and an engaged position as shown in FIG. 21. When in the disengaged position, cams 98 are spaced apart from cam followers 100 and blockers 94 are in the unblocking position so that transfer shaft 84 is capable of moving in slots 92. When blocker lever 96 and cams 98 are moved to the engaged position, blockers 94 pivot about pins 112 so that blockers 94 cover slots 92 and transfer shaft 84 is blocked from moving in slots 92.

To move blocker lever 96 to the engaged position, handle 114 is gripped and turned counter-clockwise in the direction of phantom arrow 115, shown in FIG. 17, so that cams 98 engage cam followers 100. Cam followers 100 have a slight angle relative to the length of blockers 94 so that cams 98 ride up cam followers 100 to rotate blockers 94 relative to links 90. Blockers 94 continue to rotate about pins 112 until blockers 94 engage stops 110 preventing blockers 94 from rotating past the desired position. Thus, tilt mechanism 74 has a first configuration, corresponding to blockers 94 being in the unblocking position, in which head section 22 automatically tilts relative to back section 24 during raising of head and back sections 22, 24 from a lowered, horizontal position by actuator 80 and tilt mechanism 74 has a second configuration, corresponding to blockers 94 being in the blocking position, in which head and back sections 22, 24 are maintained in coplanar relation during raising of head and back sections 22, 24 from the lowered, horizontal position by actuator 80.

As shown in FIGS. 22–25, hospital bed 10 further includes a tilt mechanism 120 facilitating automatic tilting of foot and seat sections 28, 26 relative to intermediate frame 52 and foot section 28 relative to seat section 26. Tilt mechanism 120 includes a tilt actuator 122 coupled to intermediate frame 52 and seat section 26 and a foot-tilt linkage assembly 124 pivotably coupled to foot section 28 and intermediate frame 52. Foot-tilt linkage assembly 124 is movable between a locked position, shown in FIGS. 22 and 23, and an unlocked position, shown in FIGS. 24 and 25, to provide two modes of titling between seat section 26 and foot section 28.

Figure 23:
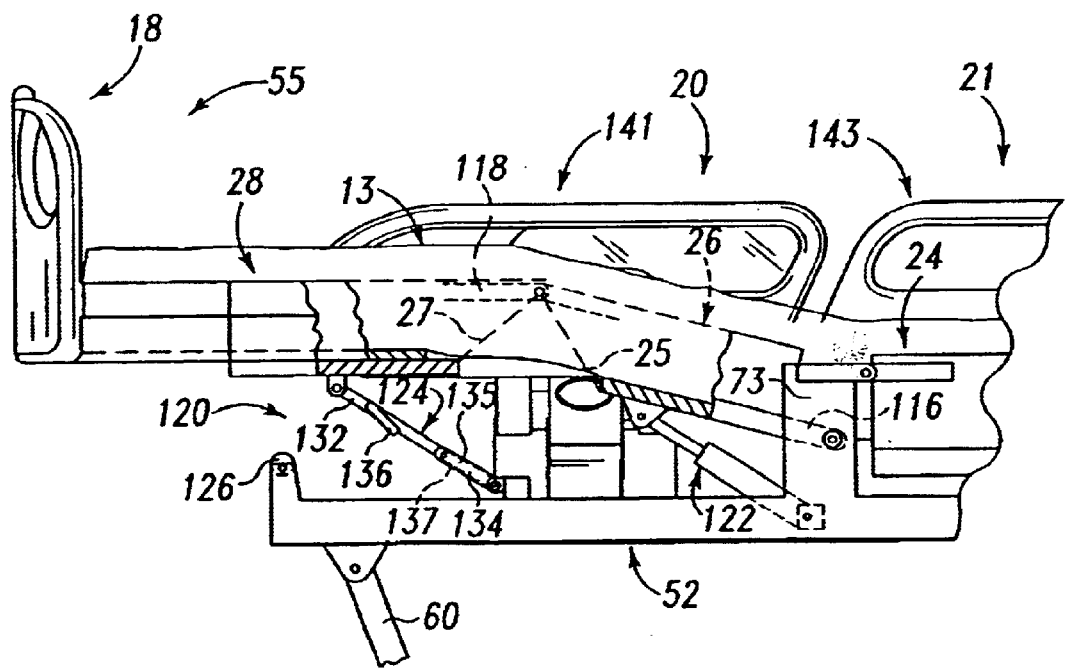
FIG. 23 is a side elevation view similar to FIG. 22 showing the tilt mechanism including an actuator lifting the seat section of the deck to an upper position and a pair of links in a locked position elevating the foot section of the deck in response to the movement of the seat section.

When in the locked position, foot-tilt linkage assembly 124 provides a rigid link between intermediate frame 52 and foot section 28. As tilt actuator 122 is lengthened, seat section 26 pivots relative to intermediate frame 52 as shown in FIGS. 23 and 25. When foot-tilt linkage assembly 124 is in the locked position and tilt actuator 122 is activated, foot section 28 moves upwardly relative to intermediate frame 52 as shown in FIG. 23 while maintaining a substantially horizontal orientation.

Figure 24:
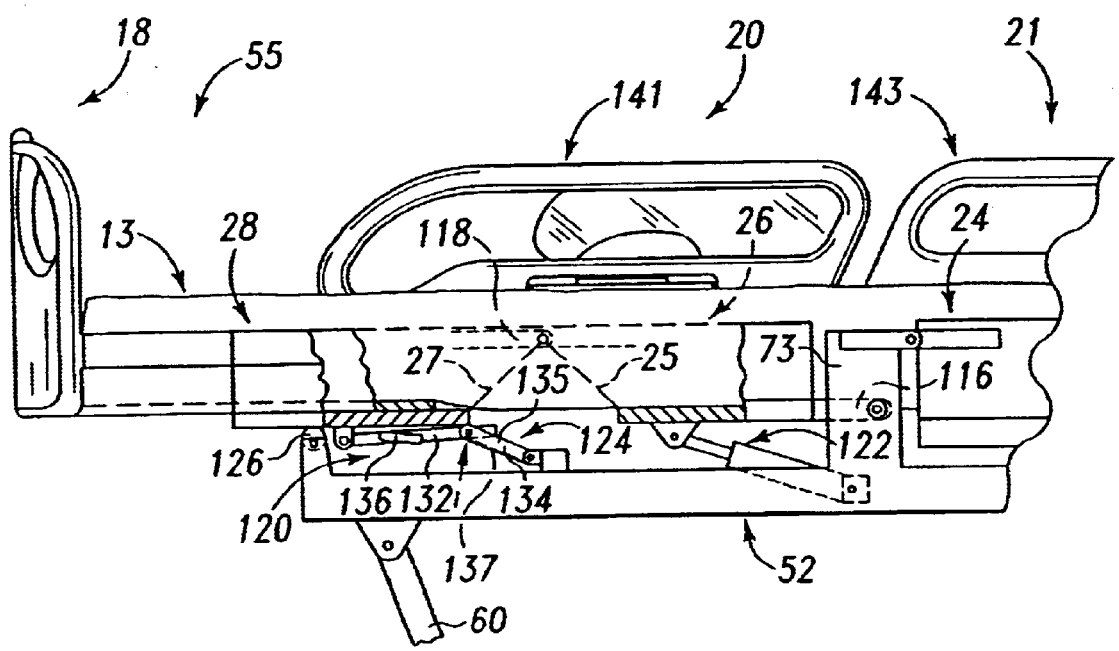
FIG. 24 is a side elevation similar to FIG. 22 showing the actuator in a retracted position and the links of the tilt mechanism in an unlocked position.
Figure 25:
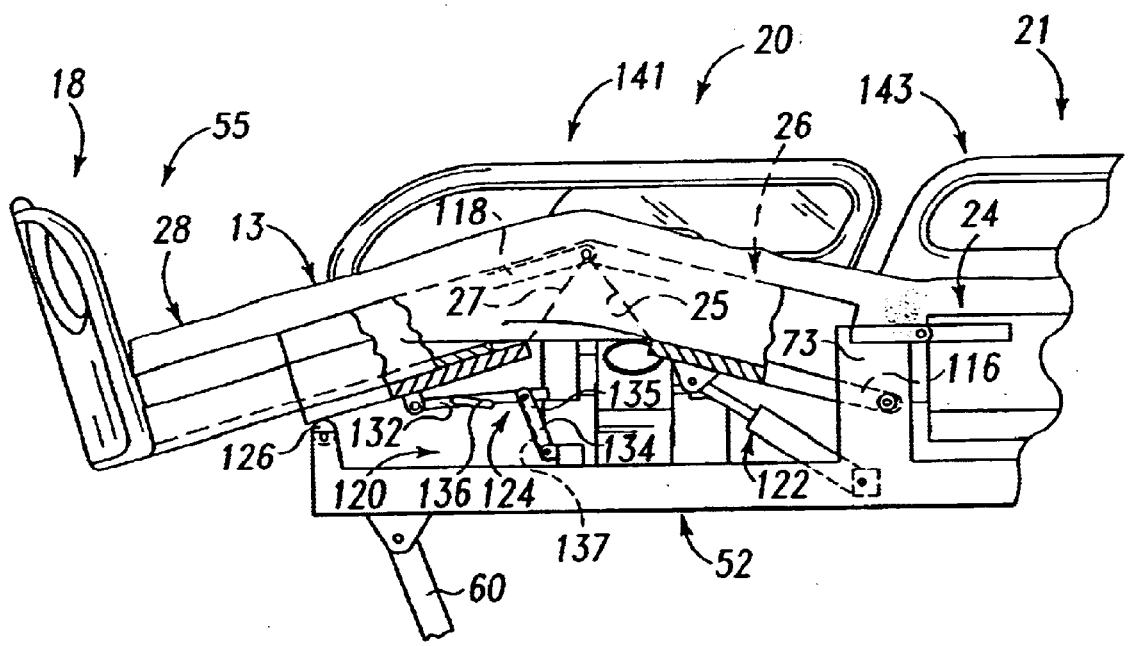
FIG. 25 is a side elevation view similar to FIG. 22 showing the actuator lifting the seat section of the deck, the links in the unlocked position, and the foot section of the deck tilting relative to the seat section as the actuator lifts the seat section.

When foot-tilt linkage assembly 124 is "broken", as shown in FIG. 24, and tilt actuator 122 is activated, as shown in FIG. 25, foot section 28 rotates about a roller 126 coupled to intermediate frame 52 so that a proximal end of foot section 28 is raised and a distal end of foot section 28 lowers. Thus, foot section 28 is movable relative to seat section 26 to maintain a substantially horizontal position, as shown in FIG. 23, when foot-tilt linkage assembly 124 is in the locked position and a tilted position, as shown in FIG. 25, relative to intermediate frame 52 when foot-tilt linkage assembly 124 is in the unlocked position.

Figure 26:
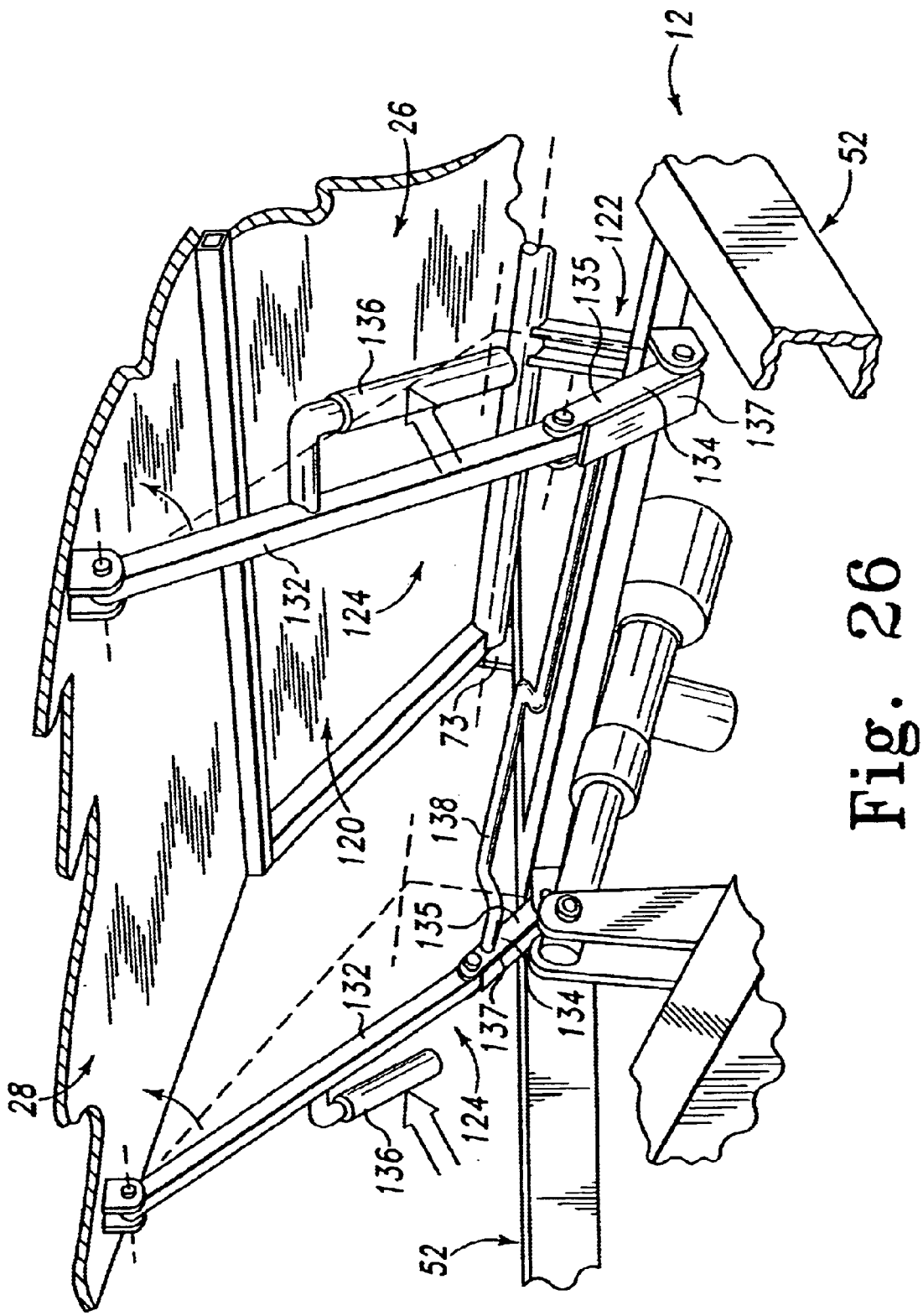
FIG. 26 is a perspective view of the underside of the foot and seat sections of the deck showing the links in the locked position and the tilt mechanism further including a connector link interconnecting the right and left links for simultaneous movement therebetween.

To facilitate movement between the locked and unlocked positions, foot-tilt linkage assembly 124 includes a pair of first links 132 pivotably coupled to foot section 28 and a pair of second links 134 pivotably coupled to respective first links 132 and intermediate frame 52 as shown in FIGS. 23 and 26. Foot-tilt linkage assembly 124 also includes a pair of handles 136 coupled to second links 134 to facilitate movement of second links 134 relative to first links 132 to position foot-tilt linkage assembly 124 in either the locked or unlocked position.

Second link 134 is U-shaped having a pair of parallel side walls 135 and a bottom plate 137. As shown in FIG. 23, the end of first link 132 coupled to second link 134 engages bottom plate 137 when first and second links 132, 134 are in the locked position to prevent first and second links 132, 134 from going over center.

As shown in FIG. 26, foot-tilt linkage assembly 124 further includes a connector link 138 extending between right and left first links 132. Connector link 138 coordinates the movement of the respective pairs of links 132, 134 so that each pair of links 132, 134 is locked and unlocked simultaneously.

Figure 28:
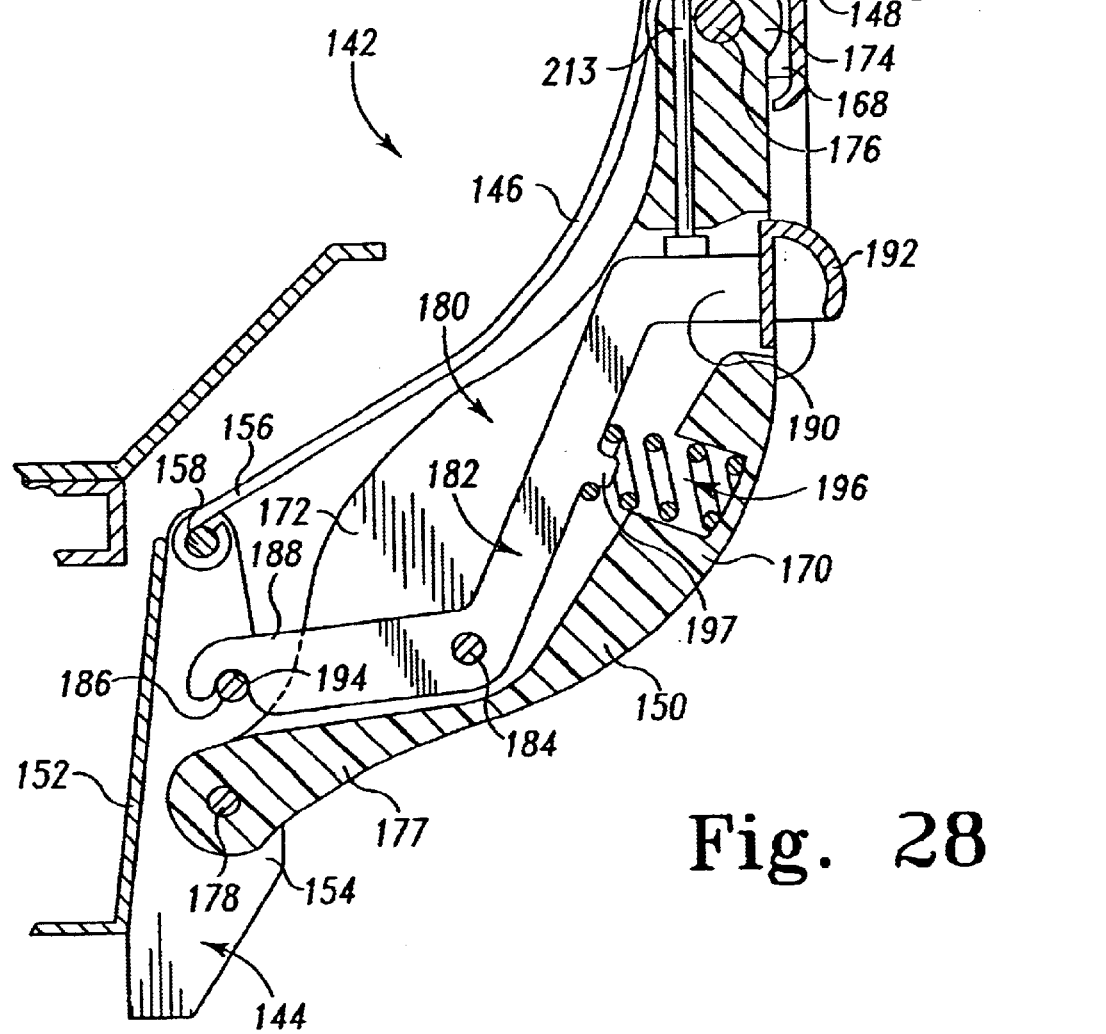
FIG. 28 is a cross-sectional view taken along line 28—28 of FIG. 27 showing the linkage assembly including a retainer including a Z-shaped latch coupled to a catch rod, a lower release handle coupled to the Z-shaped latch, and a patient-accessible upper release handle interacting with the Z-shaped latch through a pair of vertical transfer rods.
Figure 30:
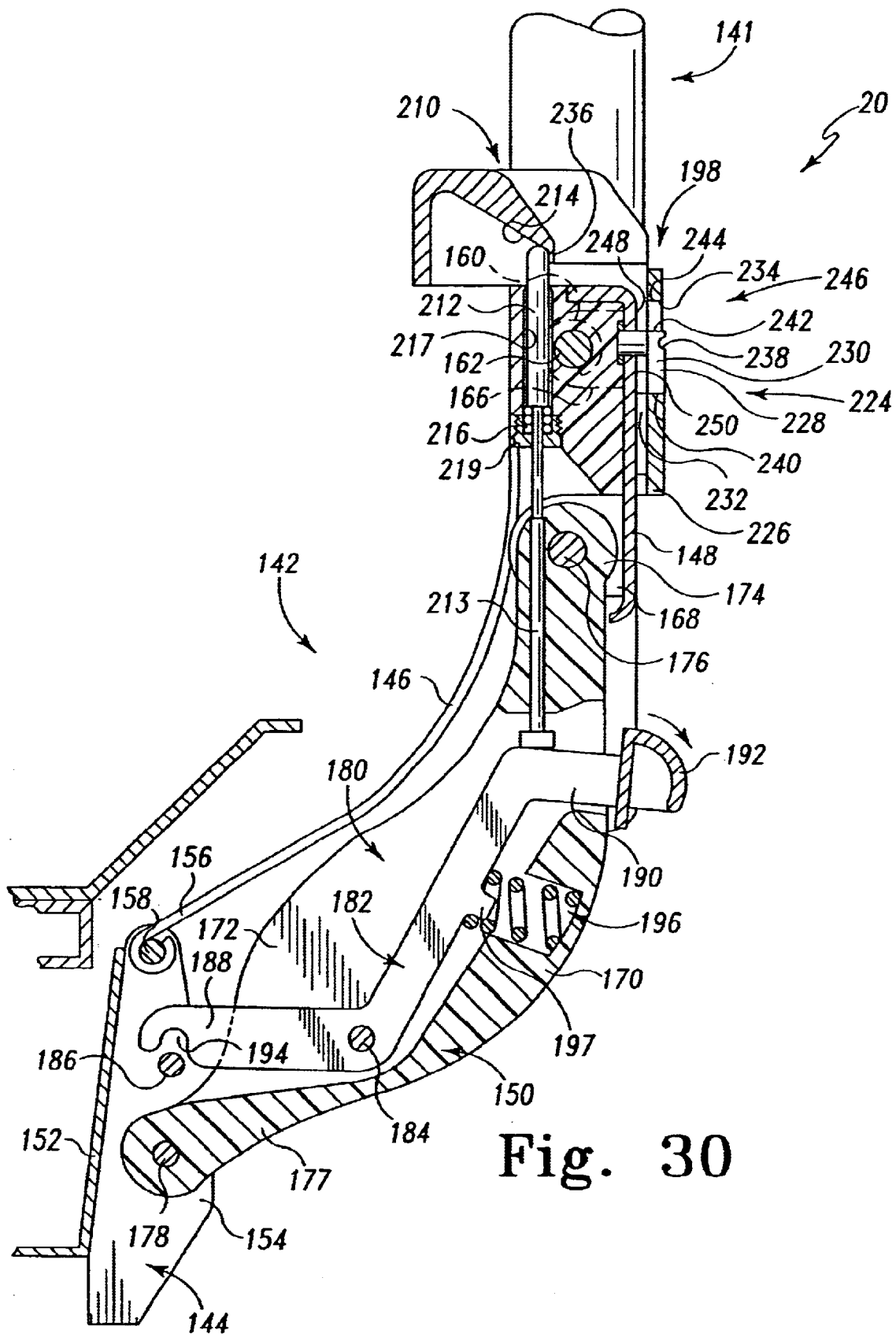
FIG. 30 is a cross-sectional view similar to FIG. 28 showing the patient-accessible upper release handle pivoted inwardly to push the vertical transfer rods downwardly so that the Z-shaped latch is rotated away from the catch rod to permit the siderail to be lowered.
Figure 31:
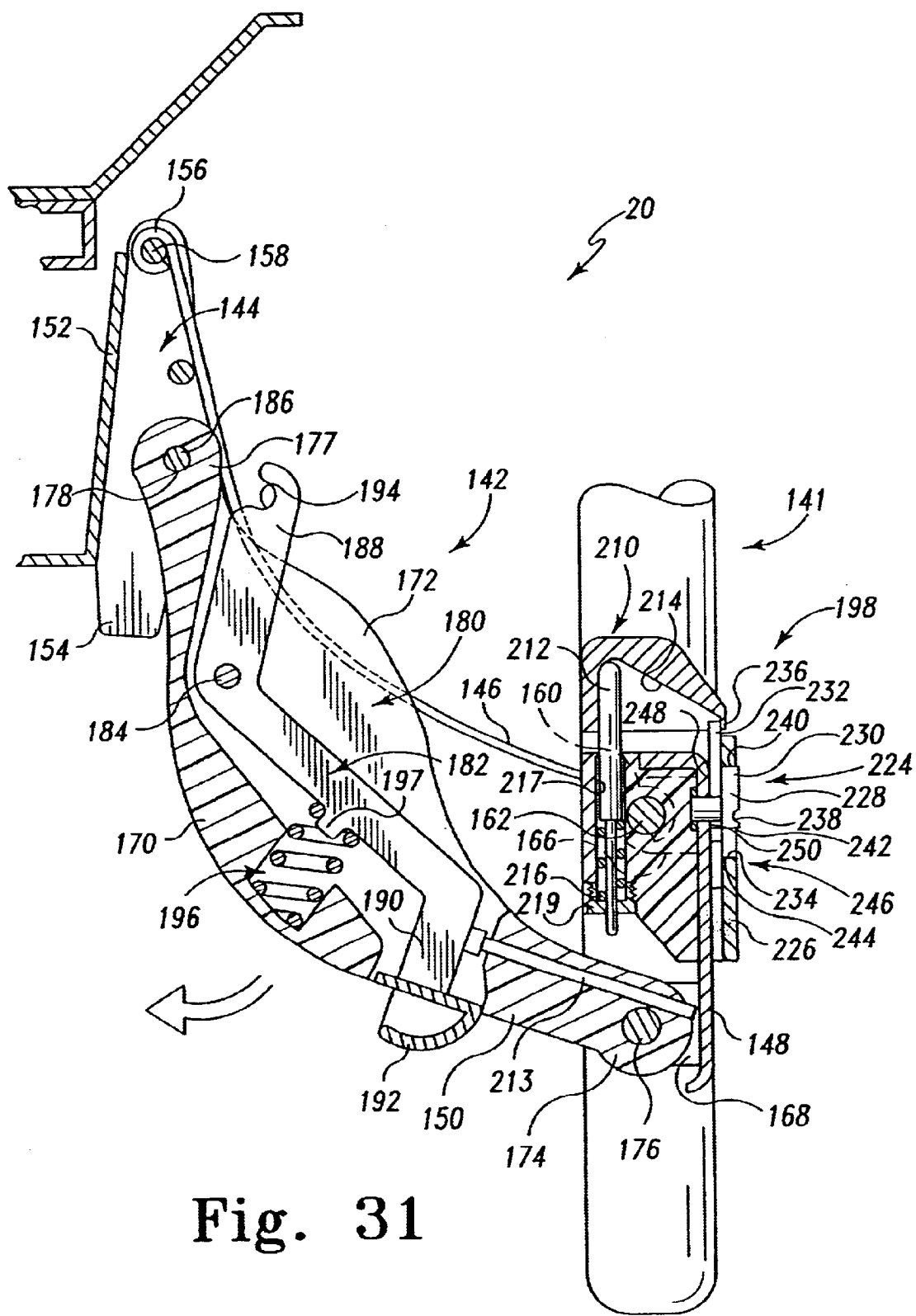
FIG. 31 is a cross-sectional view similar to FIG. 28 showing the siderail in an intermediate lower position.

Split siderails or third and fourth barriers 20, 21 are pivotably coupled to frame 12 and configured to move between upper positions, as shown in FIGS. 1, 28 and 30, and lower positions, as shown in FIG. 31, to permit entry and egress of patients into and out of hospital bed 10. Split siderails 20, 21 are configured to be movable between the upper and lower positions by a caregiver or by a patient positioned in hospital bed 10 by releasing split siderails 20, 21 to move. Furthermore split siderails 20, 21 are provided with locks that prevent a patient positioned in hospital bed 10 from lowering siderails 20 as will be discussed in greater detail below.

Each siderail 20, 21 is coupled to intermediate frame 52 by a pair of fasteners 140. Thus, as each section 22, 24, 26, 28 of deck 14 is tilted relative to intermediate frame 52 as previously described, siderails 20, 21 do not move relative to intermediate frame 52 as shown in FIGS. 19–21, 23, and 25.

Each siderail 20, 21 includes a respective clear rail member 141, 143 and a linkage assembly 142 coupled between respective clear rail member 141, 143 and intermediate frame 52 that permits rail member 141, 143 to be moved between upper and lower positions as shown in FIGS. 30 and 31. The preferred embodiment of rail members 141, 143 are made of a clear plastics material such as acrylic or clarified polyethylene (PETG). According to alternative embodiments of the present disclosure, the rail members are made of other materials known to those of ordinary skill in the art that have transparent, translucent, or other non-opaque properties so that visible light can pass through the rail members.

According to an alternative embodiment clear siderails, light is "piped" through clear siderail members to provide illumination of the clear siderail member. Such illumination provides an indication to caregivers of the location of the hospital bed when the hospital room is dark because the siderails are illuminated. Such illumination also may serve as a nightlight for the patient supported on bed 10. Those skilled in the art will appreciate that appropriate circuitry may be fashioned so that the clear siderails become illuminated only when in the lowered position to light up the floor adjacent bed 10, thereby facilitating a patient getting into or out of bed when the hospital room is dark. The light source may be fiber optic, high intensity LED's, light bulbs or an Indiglo™-brand illuminating material coupled to the respective rail member 141, 143 to illuminate all or a portion of said rail member 141, 143.

It is within the scope of the disclosure as presently perceived for a first portion of the clear siderail to be piped with light of a first color and for a second portion of the clear siderail to be piped with light of a second color. In such an embodiment, an opaque, dividing material is provided between the first and second portions of the siderail to prevent light from being piped therebetween. Optionally, multiple colors of light may illuminate multiple portions of the clear siderail if desired. According to alternative embodiments, the rail members are colored and/or translucent.

Figure 27:
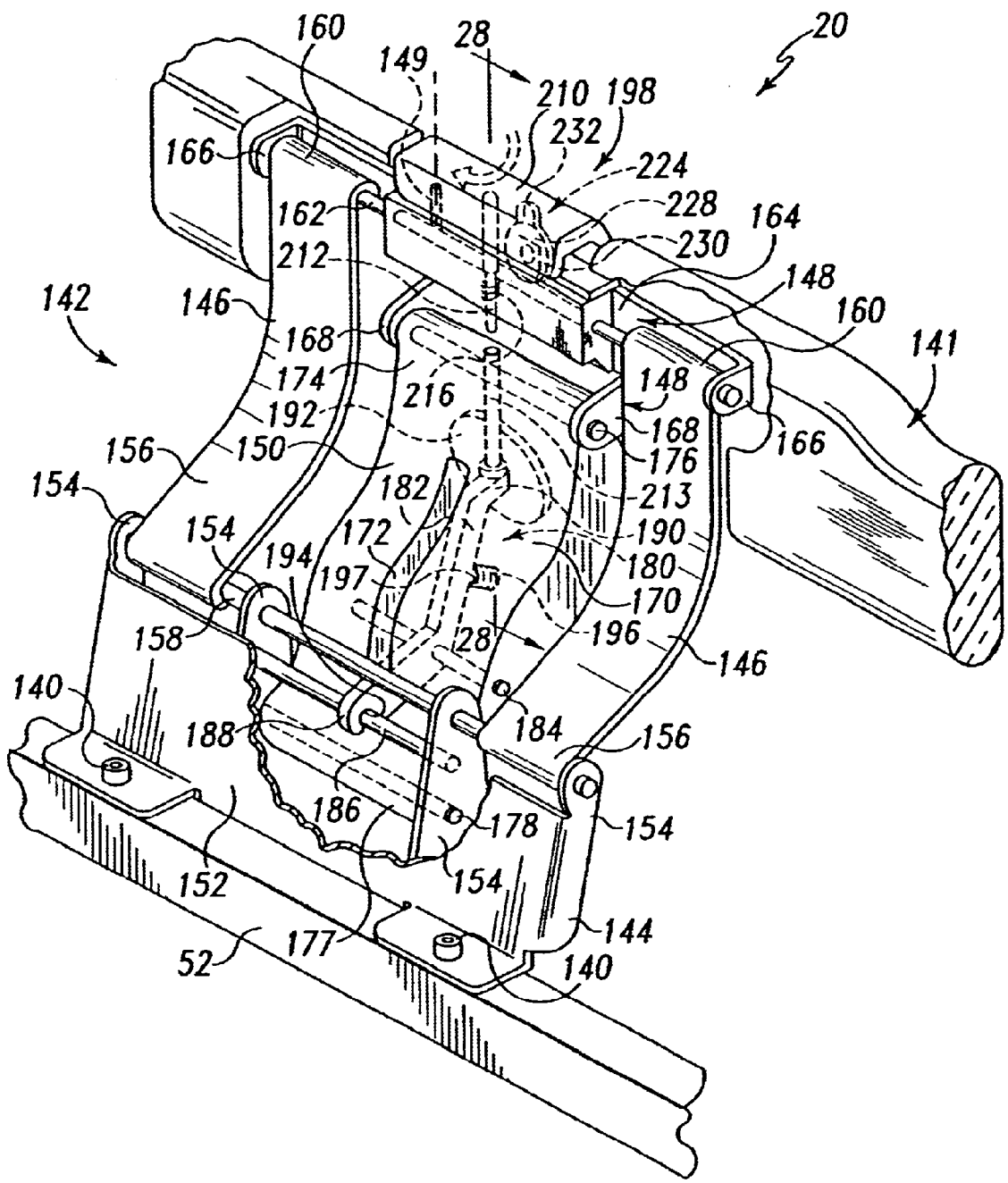
FIG. 27 is a perspective view of one of the siderails including a linkage assembly coupled to the intermediate frame and a clear rail member, with portions broken away, coupled to the linkage assembly.

Linkage assembly 142 includes a first link 144 rigidly coupled to intermediate frame 52, a pair of curved second links 146 pivotably coupled to first link 144, a third link 148 pivotably coupled to second links 146, and a curved fourth link 150 pivotably coupled to third and first links 144, 148. First link 144 includes a base 152 coupled to intermediate frame 52 by fasteners 140 and four upwardly extending flanges 154 rigidly coupled to base 152 as shown in FIG. 27. Each second link 146 includes a looped first end 156 pivotably coupled to flanges 154 by a rod 158 and a looped second end 160 pivotably coupled to third link 148 by a rod 162 as shown in FIGS. 27 and 28.

Third link 148 includes a base plate 164, a first pair of inwardly extending flanges 166 coupled to base plate 164, and a second pair of inwardly extending flanges 168 also coupled to base plate 164 as shown in FIG. 27. Rod 162 extends between flanges 166 and through second ends 160 of second link 146 to provide the pivotable connection therebetween.

As shown in FIG. 27, fourth link 150 includes a base 170 and a latch-receiving slot 172 formed in base 170. A first end 174 of base is pivotably coupled to second pair of flanges 168 of third link 148 by a rod 176. Similarly, a second end 177 of base 170 is pivotably coupled to the lower ends of flanges 154 of first link 144 by a rod 178. Thus, linkage assembly 142 provides a four bar linkage permitting siderails 20, 21 to swing between the upper and lower positions.

Each siderail 20, 21 further includes a retainer 180 configured to "bind" the four bar linkage to prevent siderails 20, 21 from moving from the upper position to the lower position. As shown in FIG. 28, retainer 180 includes a Z-shaped latch member 182 positioned in latch-receiving slot 172 and pivotably coupled to fourth link 150 by rod 184 to move between a latched position, as shown in FIG. 28, and an unlatched position, as shown in FIG. 30, and a catch rod 186 coupled to first link 144. Rod 186 extends between flanges 154 of first links 144 as shown in FIG. 27. Latch member 182 includes a first end 188 that engages catch rod 186 and a second end 190. A patient-inaccessible release or handle 192 is provided that is coupled to second end 190. First end 188 includes a notch 194 configured to receive catch rod 186 therein to secure latch member 182 in the latched position as shown in FIG. 28.

When first end 188 is latched onto catch rod 186, a three bar linkage is established between first link 144, latch member 182, and fourth link 150. This arrangement of linkages binds first link 144 relative to fourth link 150 so that linkage assembly 142 is also bound from moving while latch member 182 is in the latched position to prevent siderails 20, 21 from swinging to the lower position.

To unbind linkage assembly 142 and permit siderails 20, 21 to swing to the down position, latch member 182 must be moved from the latched position to the unlatched position as shown in FIG. 30. A caregiver can unlatch latch member 182 by pulling downwardly and outwardly on handle 192 to pivot latch member 182 in the clockwise direction as shown in FIG. 30. This movement pulls first end 188 of latch member 182 away from catch rod 186 so that latch member 182 no longer binds first and fourth links 144, 150. Because first and fourth links 144, 150 are free to pivot relative to one another, linkage assembly 142 is also unbound and free to permit siderails 20, 21 to swing between the upper and lower positions. A spring 196 is provided between a middle portion of fourth link 150 and a spring mount 197 coupled to a middle portion of latch member 182 to bias latch member 182 toward the latched position. According to alternative embodiments of the present disclosure, other retainers are provided to hold the siderails in the upper position such as clasps, catches, locks, other latches, clamps, pins, bolts, bars, hasp, hooks, or other retainers known to those of ordinary skill in the art.

Handle 192 is positioned to be inaccessible by a person lying, sitting or otherwise normally positioned on mattress 13 so that only a caregiver can easily reach handle 192 to remove the hold of latch member 182 to permit lowering of siderail 20. Therefore, handle 192 is remote to or out of reach of a person positioned on mattress 13 so that such a person cannot readily use handle 192 to lower siderail 20 while lying or sitting on mattress 13.

Siderails 20 further include a patient-accessible release 198 to permit a patient lying or sitting in hospital bed 10 to release latch member 182. Release 198 includes a handle 210 pivotably coupled to third link 148 by a pin 149 and upper and lower transfer rods 212, 213 extending between handle 210 and latch member 182 as shown in FIG. 28. Handle 210 includes a cam surface 214 configured to engage the upper end of upper transfer rod 212. As handle 210 is pivoted inwardly by the patient, as shown in FIG. 30, the upper end of transfer rod 212 is pushed downwardly to engage an upper end of lower transfer rod 213 and push lower transfer rod 213 downwardly. This downward movement of lower transfer rod 213 rotates latch member 182 in the clockwise direction to unlatch latch member 182 from catch rod 186 as shown in FIG. 30. Thus, a patient positioned in hospital bed 10 may reach handle 210 and release latch member 182 to lower either of siderails 20 and leave hospital bed 10.

Release 198 further includes a spring 216 positioned to bias upper transfer rod 212 upwardly. Upper transfer rod 212 has a stepped configuration as shown in FIG. 28 and rail member 141 is formed to include a bore 217 sized to receive upper transfer rod 212. Spring 216 is trapped between the step of upper transfer rod 212 and a plug 219 screwed into a lower end of bore 217. As upper transfer rod 212 is moved downwardly by handle 210, spring 216 is compressed. After handle 210 is released, this compression forces upper transfer rod 212 back upwardly and the engagement of upper transfer rod 212 with handle 210 rotates handle 210 back to the position shown in FIGS. 27 and 28. According to alternative embodiments of the present disclosure, other configurations of releases known to those of ordinary skill in the art are provided that release the retainer from holding the siderails in the up position.

As shown in FIG. 31, when siderail 20 is moved to the down position, upper transfer rod 212 is spaced apart from and misaligned with lower transfer rod 213. Thus, a two-piece transfer rod 212, 213 is provided that transmits motion from handle 210 to latch member 182 when siderail 20 is in the up position, as shown in FIG. 30, and is "broken" when siderail 20 is in the lowered position as shown in FIG. 31.

Figure 29:
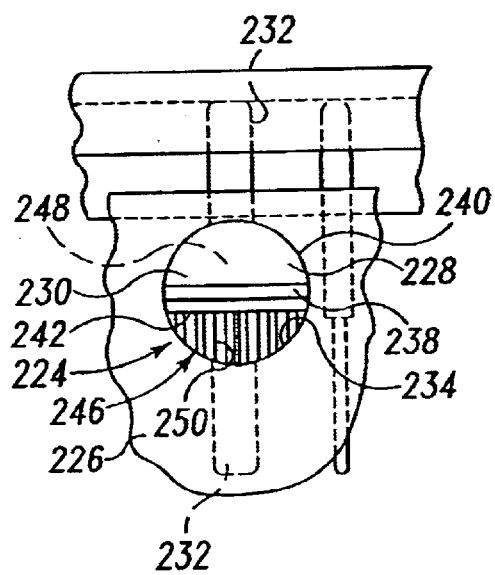
FIG. 29 is a side view of a lockout mechanism configured to block movement of the patient-accessible upper release handle.

Patient-accessible release 198 further includes a lock 224 that locks handle 210 to prevent the patient from lowering siderails 20. As shown in FIG. 29, lock 224 includes a lock member 228 pivotably coupled to third link 148. Lock member 228 includes a core 230 and a finger 232 coupled to core 230. A base plate 226 is coupled to rail member 141 and is formed to include a core-receiving aperture 234 sized to receive core 230 of lock member 228. Handle 210 includes a ledge 236 positioned to engage finger 232 of lock member 228. Core 230 is formed to include a slot 238 sized to receive a key such as a coin, screw driver, or other flat object therein.

Core 230 is rotatably received in core-receiving aperture 234 so that finger 232 can rotate between an upright locked position, as shown in FIG. 28, and a downwardly extending unlocked position as shown in FIG. 30. To turn finger 232 between the locked and unlocked position, a caregiver positions a coin, screw driver, or other flat object in slot 238 and turns lock member 228 in the clockwise direction to move finger 232 to the locked position from the unlocked position and in the counter-clockwise direction to move finger 232 to the unlocked position. While in the locked position, finger 232 is positioned adjacent ledge 236 and blocks pivoting of handle 210 so that upper transfer rod 212 cannot be pushed downwardly. While in the unlocked position, finger 232 is positioned away from ledge 236 so that handle 210 is free to pivot and a patient may unlock latch member 182 and lower siderail 20.

Lock mechanism 224 is configured to provide an indication of whether lock member 228 is in the locked or unlocked position. Core 230 is somewhat cylinder-shaped having a curved side wall 240 and a flat side wall 242. Curved side wall 240 permits core 230 to rotate in core-receiving aperture 234. Flat side wall 242 and an edge 244 of base plate 226 that defines core-receiving aperture 234 cooperate to define a rotating window 246 therebetween. As core 230 is rotated, window 246 rotates from being located above core 230, as shown in FIG. 30, to below core 230 as shown in FIG. 28. Third link 148 includes a portion positioned behind core 230. An upper half 248 of the portion is painted white and a lower half 250 is painted red.

Painted upper and lower halves 248, 250 and window 246 cooperate to provide an indication as to when lock member 228 is in the locked or unlocked positions. When lock member 228 is in the locked position, as shown in FIG. 28, the red surface of lower half 250 is exposed through window 246 to indicate that lock 224 is locked to prevent lowering of siderail 20 by the patient. As core 230 is rotated, the white surface of upper half 248 is exposed through window 246 to indicate that lock 224 is unlocked so that a patient can lower siderail 20.

According to alternative embodiments of the present disclosure, other configurations of locks are provided such as latches, bolts, pins, clasps, hooks, clamps, keyed locks, unkeyed locks, or other devices known to those of ordinary skill in the art that prevent or avoid movement of the retainer from holding the siderails in the upper position. For example, according to one embodiment of the present disclosure, a lock configuration is provided so that when the lock configuration is in a first position a release is moved to release the hold of the retainer on the siderail and in a second position the release is moved, but the motion is "lost" and the retainer continues to hold the siderail in the upper position.

According to alternative embodiments of the present disclosure, other configurations of siderails that also include patient-accessible release assemblies are provided such as clocking siderails that rotate about a transverse and horizontal axis, dropping siderails the move in a substantially vertical plane, or any other configuration of siderails known to those of ordinary skill in the art. According to alternative embodiments of the present disclosure, other configurations of rail members with patient-accessible release assemblies are provided. For example, rail members including tubes, bars, solid panels, panels with openings, or other configurations of rail members known to those of ordinary skill in the art are provided with patient-accessible unlatching assemblies. According to an alternative embodiment of the present disclosure, a mechanical damper, dashpot, or gas spring is provided to prevent rapid movement of the siderail from the up position to the down position. Additional description of such a device is provided in U.S. Pat. No. 5,715,548, entitled Chair Bed, to Weismiller et al., the disclosure of which is expressly incorporated by reference herein.

As shown in FIG. 1, when siderails 20, 21 are in upper position, rail members 141, 143 block a patient's egress from hospital bed 10. Rail member 141 includes a bottom portion 252 coupled to third link 148 of linkage assembly 142, an angled end portion 254 extending from bottom portion 252, a curved end portion 256 extending up from bottom portion 252 and spaced apart from angled end portion 254, and a top rail portion 258 coupled to and extending between angled and curved end portions 254, 256. Rail member 143 includes a bottom portion 253 coupled to linkage assembly 142, an angled end portion 255 extending from bottom portion 253 at an angle complementary to angled end portion 254 of rail member 141, a curved end portion 257 extending up from bottom portion 253 and spaced apart from angled end portion 255, and a top rail portion 259 coupled to and extending between angled and curved end portions 255, 257. Thus, each rail member 141, 143 provides a barrier to a patient positioned in hospital bed 10 so that the patient is restrained from exiting hospital bed 10 when siderails 20, 21 are in the upper positions.

Figure 32:
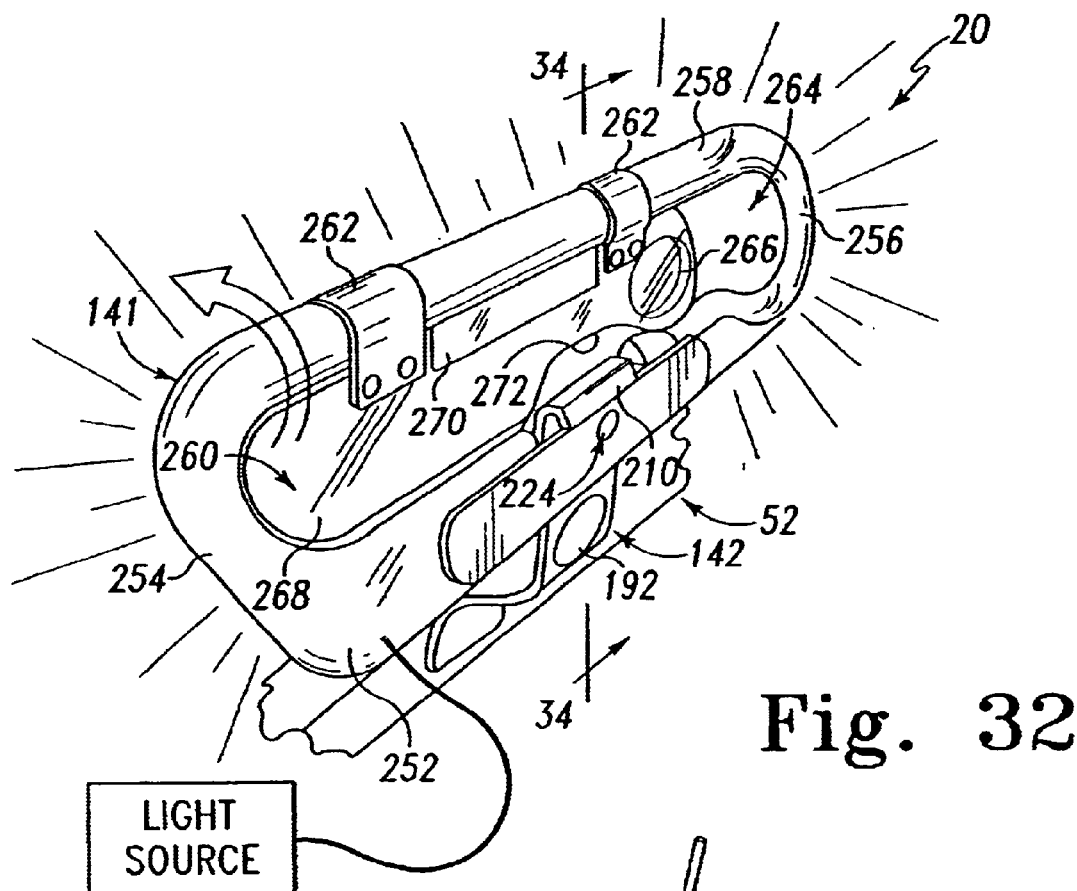
FIG. 32 is a perspective view of the siderail showing the clear rail member coupled to the linkage assembly and a clear armrest pivotably coupled to the clear rail member in a storage position.
Figure 33:
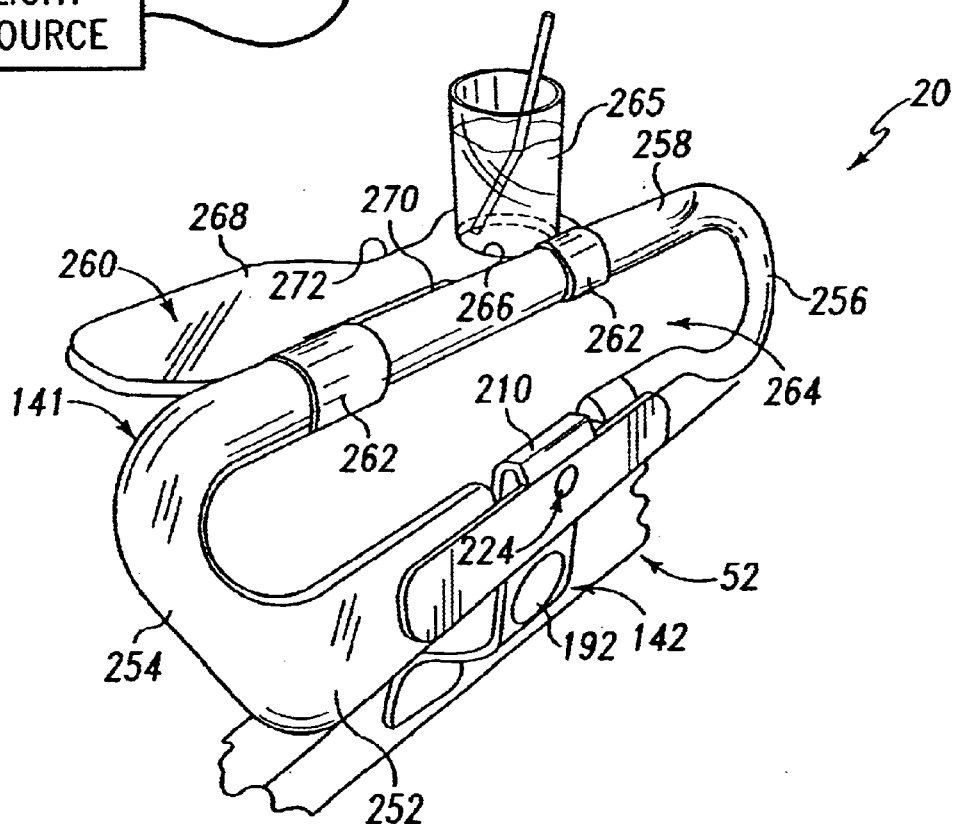
FIG. 33 is a view similar to FIG. 32 showing the armrest in a use position and having a cup or container holder supporting a cup therein.
Figure 34:
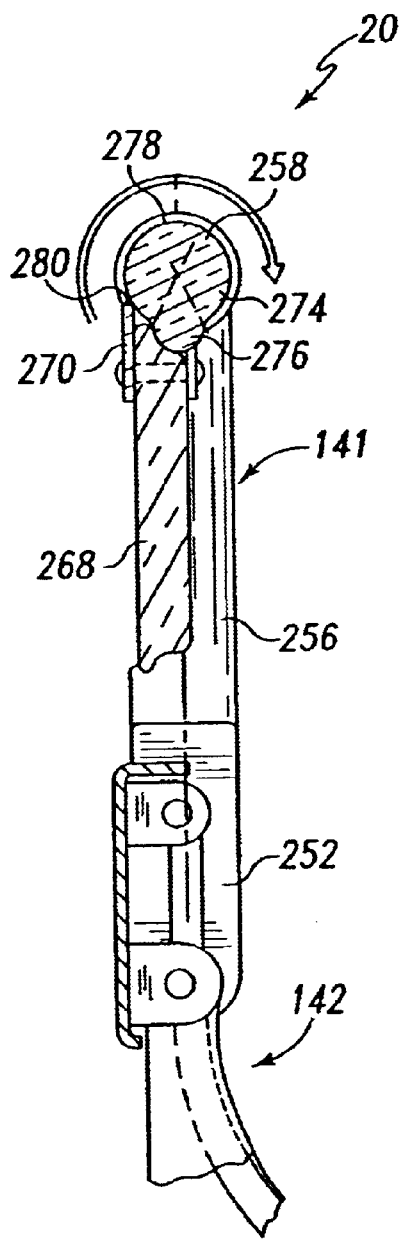
FIG. 34 is a cross-sectional view taken along line 34—34 of FIG. 32 showing the armrest in the storage position, the siderail further including a stop plate coupled to the armrest, a top rail portion of the rail member having a substantially circular lobe and a downwardly extending lobe coupled to the substantially circular lobe.

Each siderail 20 further includes a clear armrest 260 pivotably coupled to top rail portion 258 of rail member 141 by a pair of straps 262. Armrest 260 is movable between a storage position, as shown in FIG. 32, and a use position as shown in FIG. 33 so that armrest 260 is cantilevered from rail member 141. Bottom portion 252, top rail portion 258, angled end portion 254, and curved end portion 256 cooperate to define a pocket 264 in which armrest 260 is positioned while in the storage position as shown in FIGS. 32 and 34. To move armrest 258 to the use position, a patient or caregiver rotates armrest 270° to the position shown in FIGS. 33 and 35. While in the use position, a patient may rest their arm on armrest 258 or position a cup 265 in a recess 266 formed in armrest 258 defining a cup or container holder. According to alternative embodiments of the present disclosure, other configurations of container holders are provided such as an opening extending completely through the arm rest, an adjustable container holder configured to hold multiple sizes of containers, or other container or cup holder configurations known to those of ordinary skill in the art.

Armrest 260 includes a base portion 268 coupled to rail member 141 of siderail 20 by straps 262 and a stop plate 270 coupled to base portion 268 by an adhesive. Stop plate 270 is positioned to stop base portion 268 in the use position. Base portion 268 is formed to include a notch 272 sized to permit access to handle 210 so that a patient or a caregiver can access and pivot handle 210 when armrest 260 is in the storage position.

Figure 35:
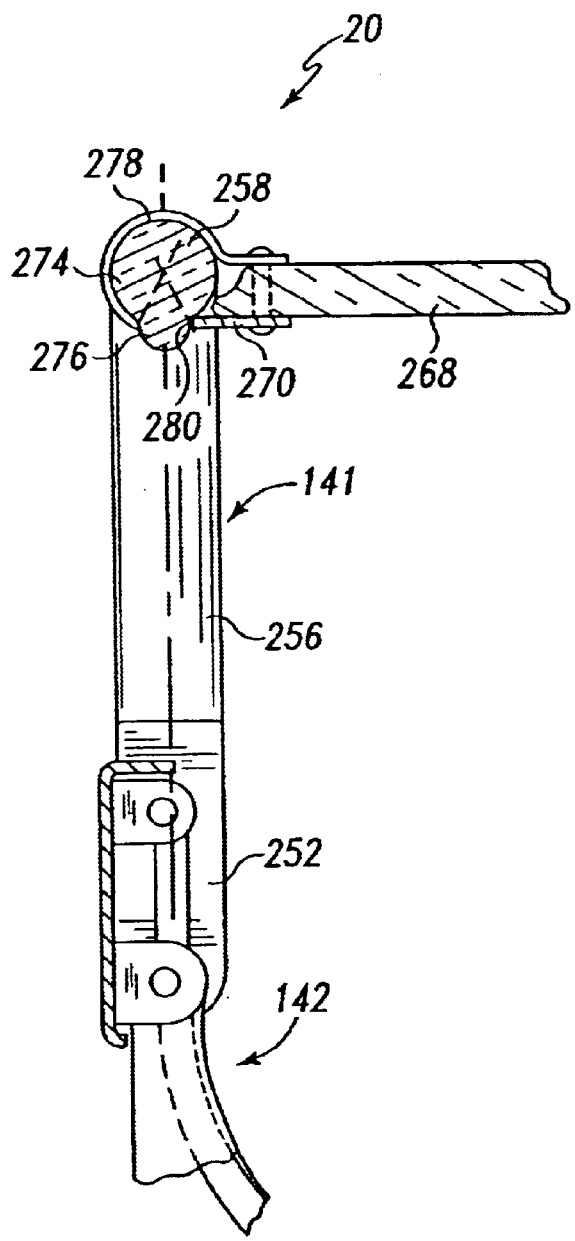
FIG. 35 is a cross-sectional view similar to FIG. 34 showing the armrest in the use position and the stop plate engaging the downwardly extending lobe so that further clockwise rotation of the armrest is prevented.

Top rail portion 258 of rail member 141 and stop plate 270 are configured to stop the rotation of armrest 260 when it reaches the use position. Top rail portion 258 has a dual-lobe cross section as shown in FIGS. 34 and 35. Top rail portion 258 has a circular base lobe 274 and a downwardly extending stop lobe 276 coupled to base lobe 274. Circular base lobe 274 has a circular outer surface 278 having a substantially uniform radius of curvature from the axis of rotation of armrest 260 so that an inner edge 280 of stop plate 270 does not engage outer surface 278 to impede the rotation of armrest 260 as it rotates from the storage position to the use position. Stop lobe 276 extends radially outwardly from outer surface 278 of base lobe 274 so that inner edge 280 of stop plate 270 engages stop lobe 276 after 270° of rotation. Thus, the rotation of armrest 260 is stopped at the use position as shown in FIG. 35. Stop lobes 276 and, optionally, base lobes 274 are formed to include grooves (not shown) that receive straps 262. Receipt of straps 262 in these grooves prevents longitudinal shifting of armrests 260 relative to top rail portions 258 of the respective rail member 141 while permitting rotation of armrests 260 relative to top rail portions 258. According to alternative embodiments, the inner edge engaging the stop lobe is integrally formed in the base of the armrest. According to alternative embodiments of the present disclosure, the arm rest is slidably, removably, or otherwise coupled to the rail member.

Figure 38:
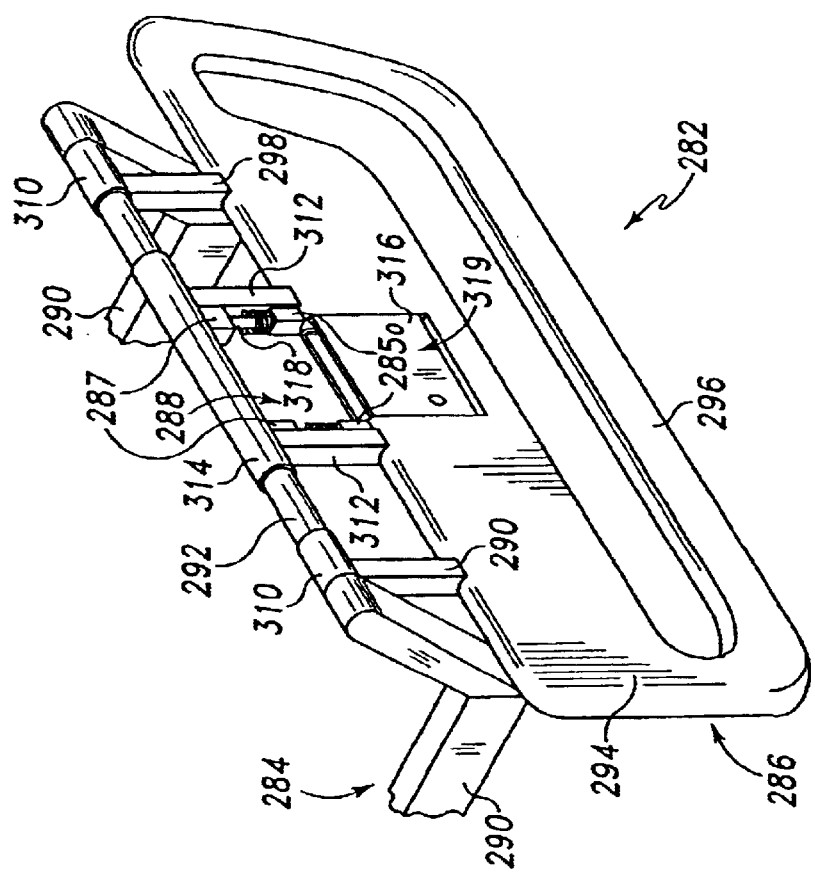
FIG. 38 is a perspective view similar to FIG. 36 showing the siderail in a lower position.

An alternative embodiment siderail 282 is shown in FIGS. 36–39. Siderail 282 includes a base frame 284 coupled to intermediate frame 52, a rail member 286 pivotably coupled to base frame 284, and a retainer 288 positioned on rail member 286 to hold rail member 286 in one of a plurality of positions. As shown in FIG. 36, siderail 282 is moveable to an upright use position to block the egress of a patient from the hospital bed, and a lowered storage position permitting the patient to exit the hospital bed as shown in FIG. 38.

Base frame 284 includes a pair of arms 290 rigidly coupled to intermediate frame 52 and a tubular support member 292 extending between arms 290 as shown in FIG. 36. Rail member 286 includes a base portion 294, a top rail portion 296 coupled to base portion 294, a first pair of posts 298 coupled to base portion 294, a pair of collars 310 coupled to the distal end of respective posts 298 to provide pivotal movement between base portion 294 and tubular support member 292, a second pair of posts 312 coupled to base portion 294, and a collar 314 coupled to the distal ends of second pair of posts 312 to provide pivotal movement between base portion 294 and tubular support member 292. Collars 310 engage arms 290 to prevent longitudinal shifting of rail member 286 relative to tubular support member 292.

As shown in FIG. 37, retainer 288 includes a pair of pins 318, springs 322 positioned around pins 318, and retention pins 324 coupled to pins 318. A release 319 is provided that includes a pair of flat handles 316 pivotably coupled to base portion 294 of rail member 286 and cables 320 coupling handles 316 to pins 318. Tubular support member 292 is formed to include first, second, and third apertures 326, 328, 330. Pins 318 are sized to slide into apertures 326, 328, 330 to hold siderail 282 into either an inner, vertical, or horizontal position. Rail member 286 includes a pair of first stabilizer blocks 285 appended to collar 314 adjacent to posts 312 and a pair of second stabilizer blocks 287 appended to base portion 294 adjacent to posts 312. Pins 318 extend through aligned bores 289, 291 formed in respective stabilizer blocks 285, 287 and through respective bores 293 formed in collar 314. Pins 318 are selectively received in apertures 326, 328, 330 when bores 289, 291, 293 are aligned with one of apertures 326, 328, 330 and handles 316 are released.

To move siderail 282 from one position to another, either of handles 316 are pivoted upwardly (shown in phantom in FIG. 37) so that one of cables 320 pulls pin 318 out of the respective aperture 326, 328, 330. When pins 318 are removed from apertures 326, 328, 330, siderail 282 is released to pivot about tubular support member 292. Pins 318 slide over tubular support member 292 until they slide into the next respective aperture 326, 328, 330 to hold siderail 282 into the next respective position.

When pins 318 are positioned in first apertures 326, siderail 282 is in the inner position so that rail member 286 is inclined inwardly toward the deck of the hospital bed and function as armrests for the patient. When pins 318 are positioned in second apertures 328, siderail 282 is in the substantially vertical upper position. When pins 318 are positioned in third apertures 330, siderail 282 is substantially horizontal so that a patient can be supported on siderail 282 during lateral patient transfer between the hospital bed and another patient-support device located adjacent to the hospital bed.

Figure 39:
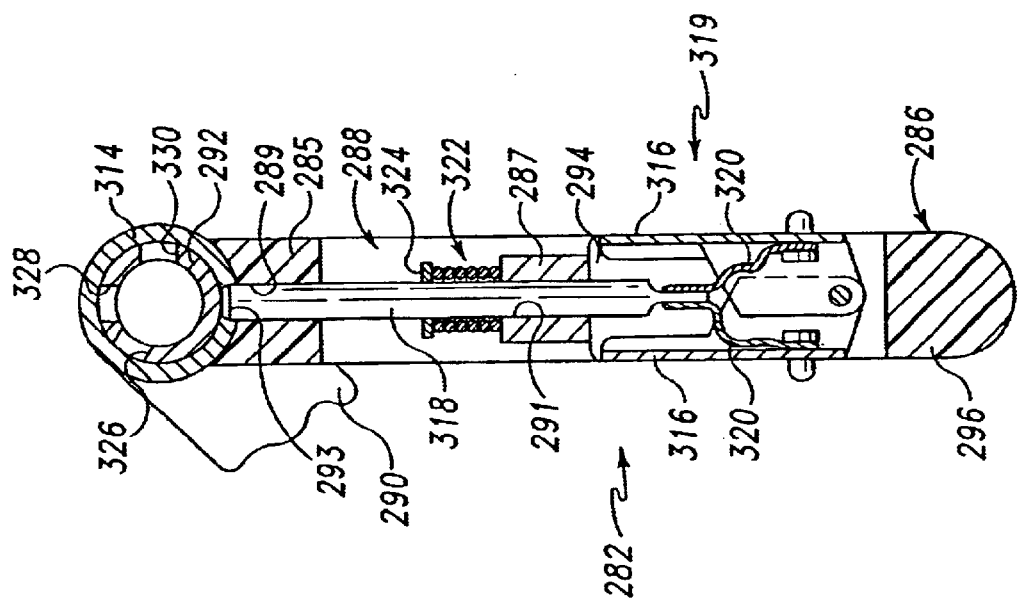
FIG. 39 is a cross-sectional view similar to FIG. 37 showing the siderail in the lower position with the pin disengaged from the apertures formed in the tubular support member.

When pins 328 are removed from apertures 326, 328, 330, springs 322 are compressed between retention pins 324 and second stabilizer block 287 as shown in FIG. 39. This compression urges pins 328 back to the retention position when they slide over one of apertures 326, 328, 330. As pins 328 move back to the retention position, cables 320 pull handles 316 back to the stored position shown in FIG. 37.

Deck 14 is configured to support mattress 13. As shown in FIGS. 40, 42, 43, and 44 each section 22, 24, 26, 28 of deck 14 includes angled side walls 358. Head and foot sections 22, 28 have substantially flat bottom floors or walls 360. Angled side walls 358 and floor 360 cooperate to define obtuse angles therebetween of approximately 135°. According to alternative embodiments of the present disclosure, the obtuse angles between the side walls and the floor may be range from slightly more than 90° to slightly less than 180°. According to other alternative embodiments of the present disclosure, the angles are right angles or acute angles.

As shown in FIGS. 28, 30, and 31, angled side walls 358 permit siderails 20, 21 to be coupled to intermediate frame 52 at a position inset from the outer perimeter of deck 14 and beneath said deck 14 to provide hospital bed 10 with a narrower overall width than beds without tucking siderails. When siderails 20, 21 are positioned in the lower position, top rail portions 258, 259 are positioned beneath the perimeter of mattress 13 so that rails 20, 21 do not extend beyond the width of mattress 13. Furthermore, by insetting siderails 20, 21, less room is necessary for siderails 20, 21 to swing between the upper and lower positions. In addition, when siderails 20, 21 are in their lowered positions, top edges of siderails 20, 21 are located adjacent to the angled side walls between the top and bottom surfaces of mattress 13 which increases the amount of clearance that exists between the bottom edges of siderails 20, 21 and the floor when intermediate frame 52 and deck 14 are in their lowered positions.

Figure 45:
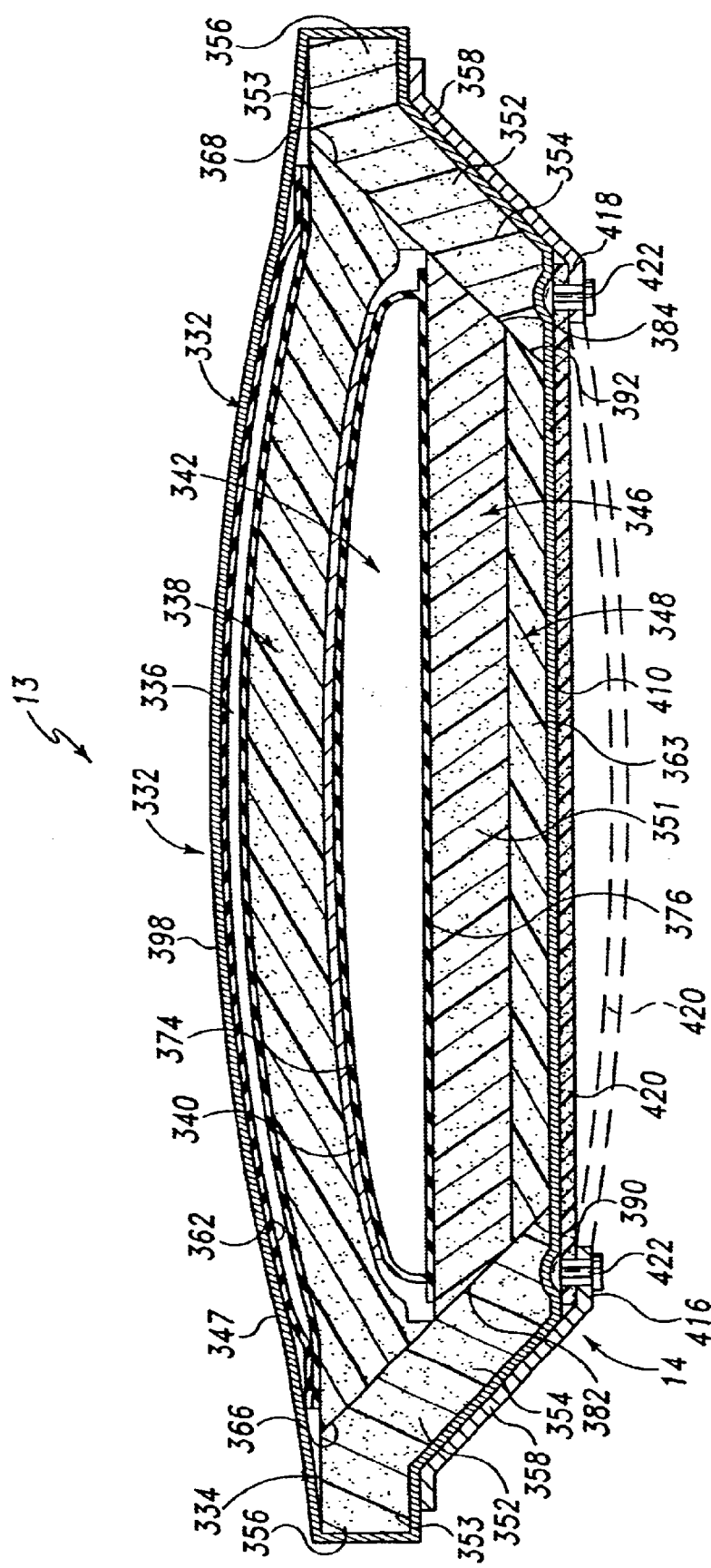
FIG. 45 is a cross-sectional view similar to FIG. 43 showing the crowning bladder in an inflated position to create a crown in the mattress.

Back and seat sections 24, 26 of deck 14 have flexible bottoms that flex due to a patient's weight to provide additional compliance to bed 10 that would otherwise require additional foam in mattress 13. Back and seat sections 24, 26 of deck 14 include angled side walls 358, respective horizontal flanges 416, 418 coupled to angled side walls 358, and a flexible panel or support member 420 coupled to horizontal flanges 416, 418 by fasteners 422 as shown in FIGS. 43–45. As shown in FIG. 44, each respective corner of flexible panels 420 is formed to include a slot 424 to receive one of fasteners 422. As weight is placed on flexible panels 420, they bend downwardly, as shown in phantom in FIGS. 43 and 45, and the outer edges of flexible panels 420 are pulled inwardly as slots 424 move relative to fasteners 422 as shown in phantom in FIG. 44. This movement permits panels 420 to deflect approximately 2 inches. Flexible panels 420 are made of compression molded glass mesh bonded by a hard thermoset resin. The preferred flexible panel is provided by Premix. According to alternative embodiments, flexible panels made of other materials are provided.

Flexible panel 420 is radiolucent to facilitate taking X-rays of a patient lying in hospital bed 10. Furthermore, flexible panel 420 has a substantially smooth surface to facilitate wiping or cleaning of deck 14. Thus, a flexible deck is provided that permits X-raying a patient positioned in hospital bed 10 and is also relatively easy to clean.

Foot section 28 of deck 14 is extendable and retractable. A full description of foot section 28 is disclosed in U.S. patent application Ser. No. 09/120,125, filed Jul. 22, 1998, the disclosure of which is expressly incorporated by reference herein.

Figure 40:
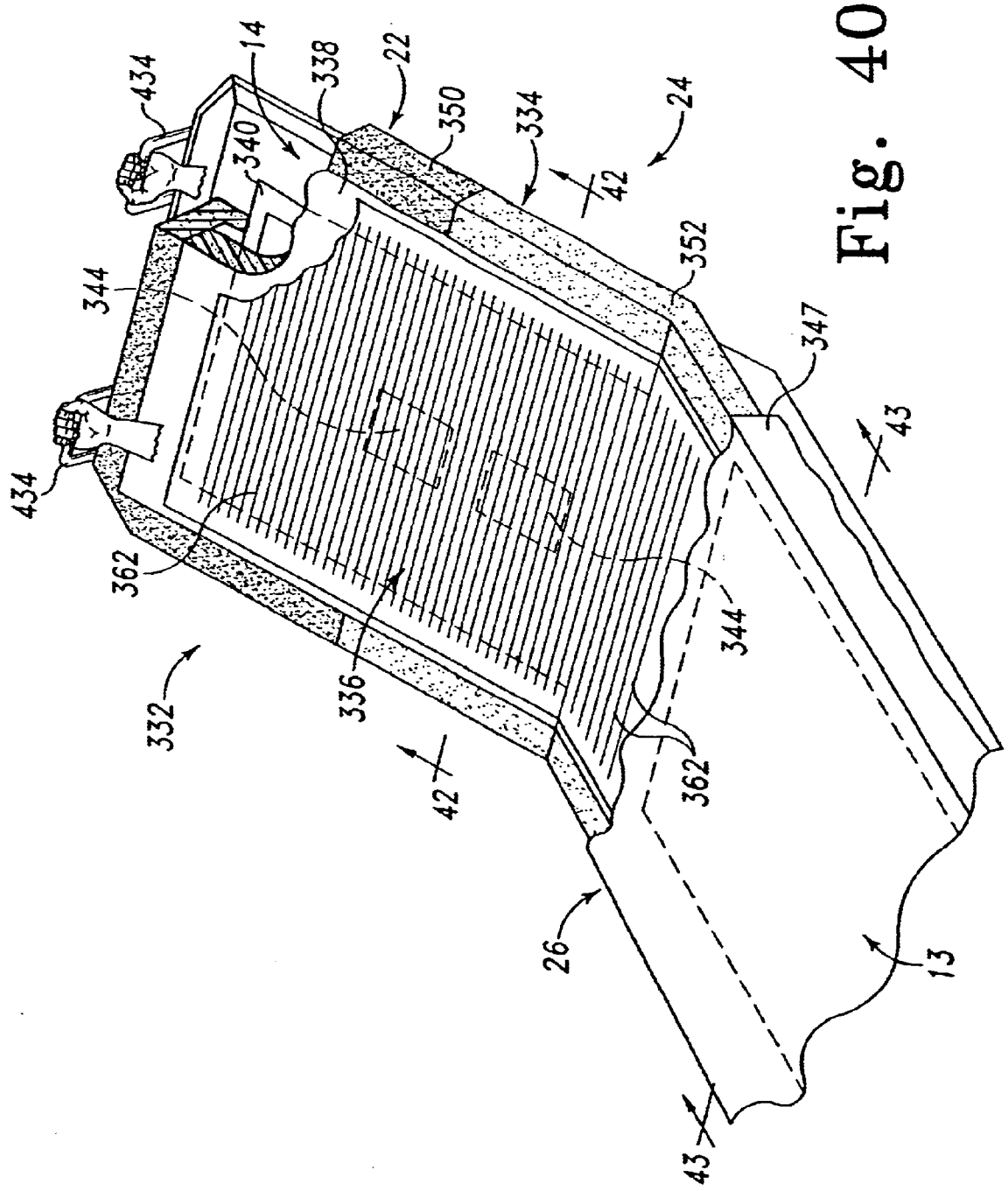
FIG. 40 is a perspective view of the hospital bed of FIG. 1 showing the deck and a mattress, with portions broken away, positioned on the deck.
Figure 53:
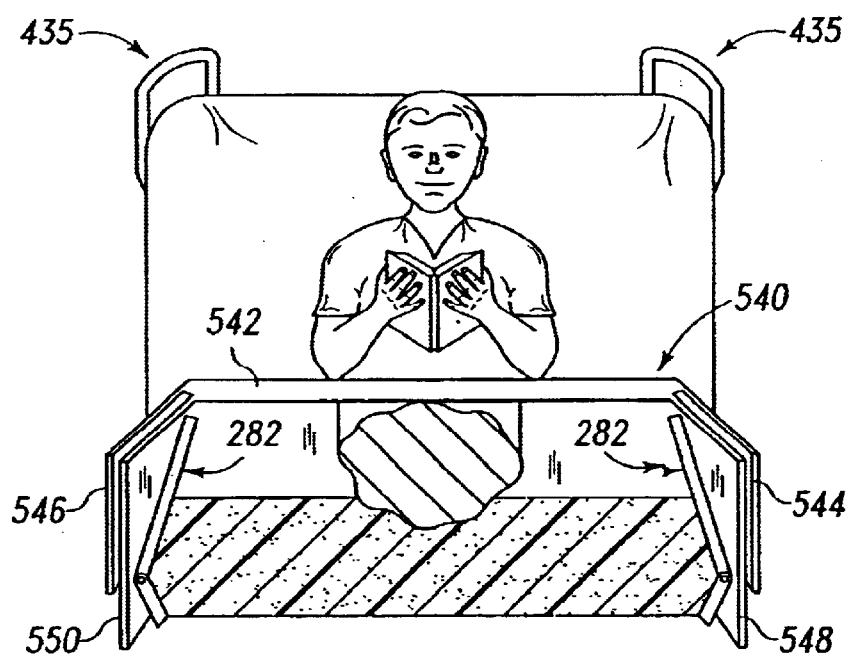
FIG. 53 is a cross-sectional view showing the footboard of FIG. 52 in the table position and positioned over the pair of siderails.

As shown in FIG. 40, deck 14 further includes a pair of grip handles 434 coupled to the upper end of head section 22 of deck 14. A patient positioned in hospital bed 10 may reposition themselves by grabbing grip handles 434 to lift their weight and shifting themselves to the right or left or pulling themselves closer to head end 53 of upper frame 52. An alternative embodiment pair of grip handles 435 is shown in FIG. 53. Grip handles 435 are coupled on the upper corner of the head section of the deck and aid in keeping the mattress properly positioned on the deck. It is known that when an upper body section of a hospital bed is raised, there is a tendency for a patient supported on the bed to slide toward the foot end of the bed and therefore, grip handles 434, 435 are especially useful for patients to reposition themselves when back and head sections 22, 24 are raised.

Figure 42:
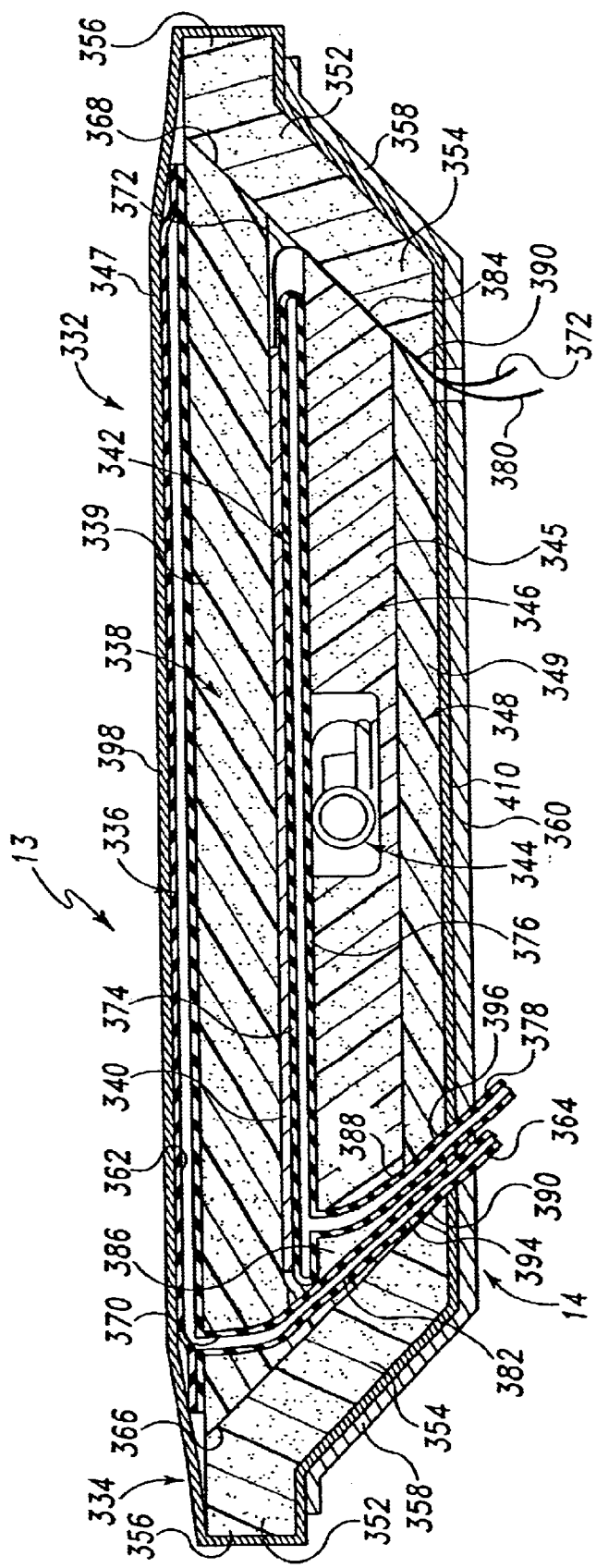
FIG. 42 is a cross-sectional view of the mattress of FIG. 40 taken along line 42—42 of FIG. 40 showing the mattress including a firming pad positioned near the top of the mattress, an upper foam layer positioned under the firming pad, a crowning bladder positioned under the upper foam layer, a massage motor positioned under the crowning bladder, and a pair of additional foam layers also positioned below the crowning bladder.

As shown in FIGS. 40 and 42, hospital bed 10 includes multi-component mattress 13. Mattress 13 includes a firm foam perimeter frame 334, a firming pad 336, an upper soft foam layer 338 positioned below firming pad 336, a heating layer 340 positioned below upper soft foam layer 338, a crowning bladder 342 positioned below heating layer 340, a plurality of massage motors 344 positioned below crowning bladder 342, a middle foam layer 346 positioned below crowning bladder 342, a lower foam layer 348 positioned below middle foam layer 346, and a layer of ticking 347 that covers the other components of mattress 13 as shown best in FIG. 42.

Firm foam perimeter frame 334 is made of foam material of greater firmness than soft foam layer 338 to provide mattress 13 with a structure that urges a patient away from the perimeter of mattress 13. Perimeter frame 334 includes a head portion or section 350, a body portion of section 352 made of a foam that is softer than head section 350, and a seat portion or section 353 made of a foam having a firmness equal to body section 352. Each section 350, 352, 353 of perimeter frame 334 has an angled base portion 354 and a flange portion 356 coupled to base portion 354. Angled base portions 354 conform to deck 14 and flange portions 356 extend out beyond deck 14 as shown in FIG. 42. The adjacent ends of sections 350, 352, 353 cooperate to define respective tapered gaps 355, 357 (as shown in FIG. 41) therebetween to facilitate tilting of head, back, and seat sections 22, 24, 26 of deck 14.

As shown in FIG. 40, firming pad 336 includes a plurality of transversely extending bladders 362. Firming pad 336 includes an inlet tube 364 that delivers pressured air to bladders 362. The pressurized air inflates bladders 362, as shown in FIG. 42, to stiffen mattress 13. By stiffening mattress 13, caregivers are better able to administer CPR and remove the patient from hospital bed 10. Furthermore, by stiffening mattress 13, a patient is better able to perform exercises while in hospital bed 10 than if mattress 13 was not stiffened. Hospital bed 10 further includes a dead head pump (not shown) to inflate bladders 362 and an exhaust port (not shown) for releasing the pressurized air from bladders 362 to return mattress 13 to the softer condition.

Figure 41:
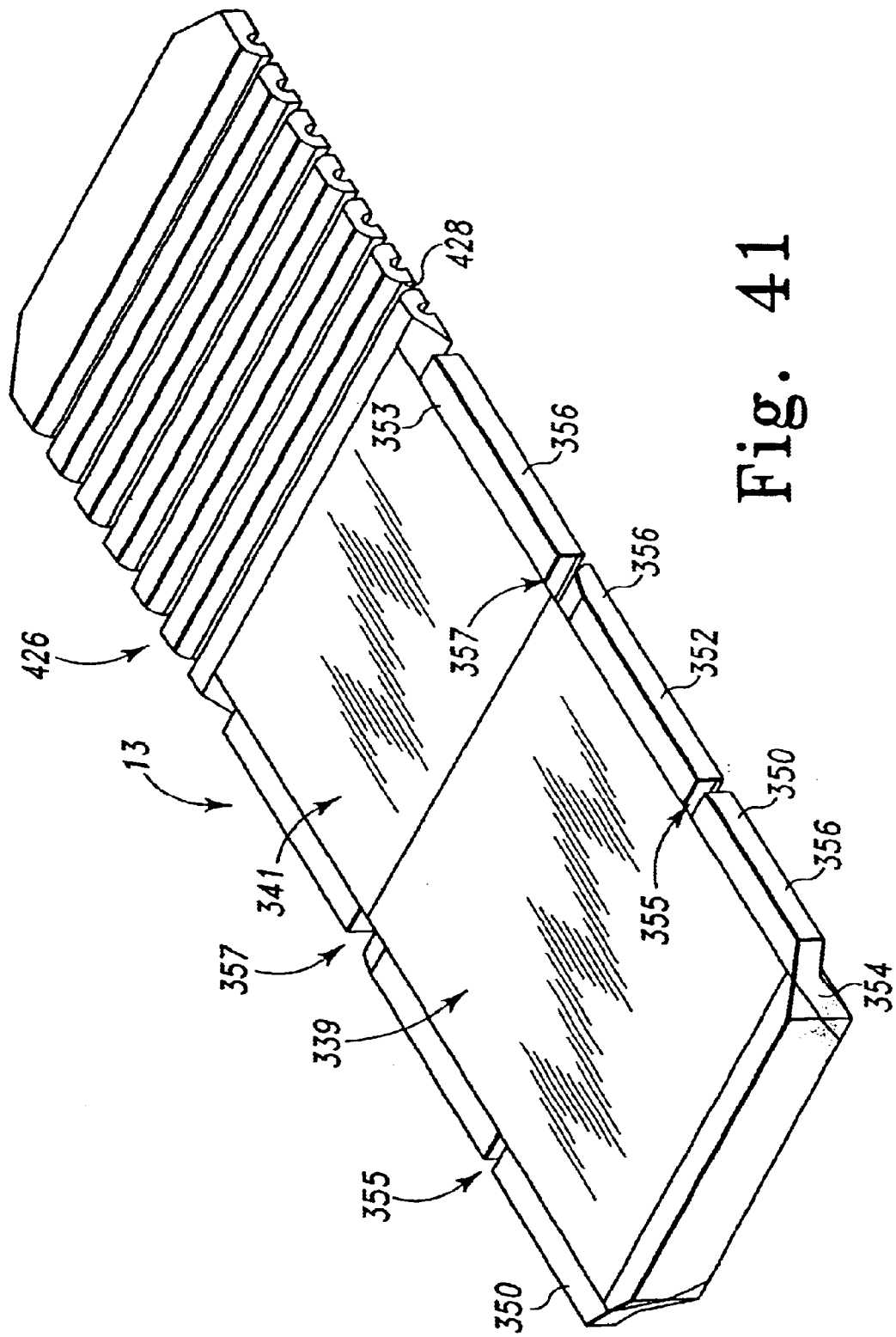
FIG. 41 is a perspective view of the mattress of FIG. 40 (with an outer layer of ticking removed)

As shown in FIG. 41, upper soft foam layer 338 includes a head and back portion of section 339 and a separate seat portion or section 341. As shown in FIG. 42, each portion or section 339, 341 includes a pair of tapered side surfaces or walls 366, 368 configured to mate with base portion 354 of perimeter frame 334. An aperture 370 is formed in upper foam layer 338 to receive inlet tube 364. As previously mentioned, upper soft foam layer 338 is made of softer foam to provide a soft structure on which the patient may rest.

Heating layer 340 is positioned under upper soft foam layer 338 to be near the surface of mattress 13. Heating layer 340 is preferably made of a resistive heating material, such as Gorix. A cable 372 is coupled to heating layer 340 and a heating control portion of control unit 692 that regulates the temperature and timing of the heating. According to an alternative embodiment, a heating layer is provided with zones to heat different areas of the mattress at different temperature or durations of time. For example, the foot end of the mattress could be heated to provide heating of the foot extremities while the body section is heated at a lower temperature.

Crowning bladder 342 is moveable between a deflated position, as shown in FIG. 43, wherein mattress 13 is substantially flat and an inflated position wherein mattress 13 is crowned, as shown in FIG. 45, to facilitate lateral patient transfer from bed 10 to another patient-support device adjacent bed 10 by creating an inclined surface which provides a slight amount of gravity assistance when the caregiver is moving the patient toward the side of mattress 13. It is preferred that firming pad 336 and crowning bladder 342 are both inflated during patient transfer, although it is not necessary.

As shown in FIG. 42, crowning bladder 342 includes a top layer 374, a bottom layer 376 coupled to top layer 374, and an inlet tube 378 coupled to bottom layer 376. Inlet tube 378 is coupled to a pump (not shown) that provides pressurized air to inflate the area between top and bottom layers 374, 376. An exhaust port (not shown) is coupled to crowning bladder 342 to release the pressurized air to return mattress 13 to the flat position.

Massage motors 344 are positioned in mattress 13 to permit a caregiver to give a patient vibration therapy for comfort and to prevent pulmonary complications. Each massage motor is a D.C. "slot" motor that is substantially thin. A cable 380 is coupled to each massage motor 344 and coupled to control unit 692 that regulates the timing and intensity of the vibrations. Each massage motor 344 may be operated independently or simultaneously.

Middle foam layer 346 is made of a viscoelastic foam that is stiffer than upper soft foam layer 338. Similar to upper foam layer 338, middle foam layer 346 includes a head and back portion or section 345 and a separate seat portion or section 351. As shown in FIG. 42, each section of middle foam layer 346 includes a pair of tapered side walls 382, 384 configured to mate with base portion 354 of perimeter frame 334. A pair of apertures 386, 388 are formed in middle foam layer 346 to receive inlet tubes 364, 378.

Figure 46:
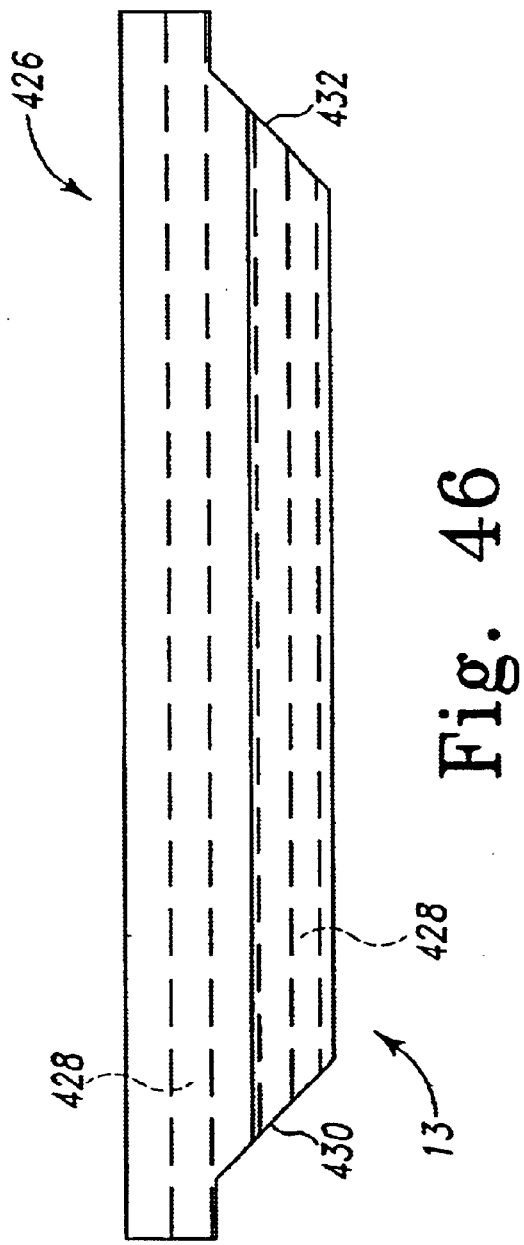
FIG. 46 is an end view of the foot section of the mattress of FIG. 41 showing the foot section of the mattress formed to include angled sides to conform to the deck.
Figure 47:
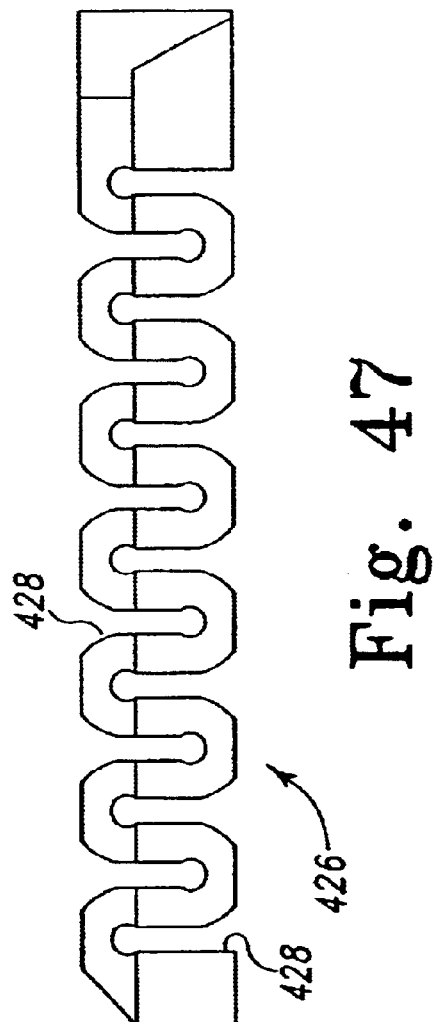
FIG. 47 is a side elevation view of the foot section of the mattress of FIG. 41 showing the foot section formed to include slots permitting the foot section to extend and retract.

Lower foam layer 348 is made of a stiffer material than middle foam layer 346. In alternative embodiments, lower foam layer 348 is formed integrally with and is comprised of foam having the same density as either head section 350 or body section 352 of perimeter frame 334. Thus, bed 10 is provided with a mattress 13 having a stiffness gradient in which the stiffness increases with the depth of mattress 13. Similar to upper and middle foam layers 338, 346, lower foam layer 348 includes a head and back portion or section 349 and a separate seat portion or section 363. As shown in FIG. 42, lower foam layer 348 includes a pair of tapered side walls 390, 392 configured to mate with base portion 354 of perimeter frame 334. A pair of apertures 394, 396 are formed in lower foam layer 348 to receive inlet tubes 364, 378. Cables 372, 380 are positioned between right base portion 354 and respective side walls 384, 392 of middle and lower foam layers 346, 348. Mattress 13 includes foot portion or section 426 that extends and retracts with the movement of foot section 28. As shown in FIGS. 41, 46, and 47, foot section 426 is formed to include a plurality of transverse slots 428. As foot section 28 of deck 14 extends, each of the transverse slots 428 widens to compensate for the extension. As foot section 28 retracts, slots 428 narrow. As shown in FIG. 46, foot section 426 includes a pair of angled side surfaces or walls 430, 432 configured to conform to the angled side walls of foot section 28 of deck 14.

As shown in FIG. 42, ticking 347 is provided to protect the other components of mattress 13 from contamination. Ticking 347 includes an upper portion 398 and a lower portion 410 configured to conform to deck 14 that is coupled to upper portion 398 by a zipper. Lower portion 410 of ticking 347 is provided with magnets that "stick" to deck 14 to prevent mattress 13 from sliding. Ticking 347 includes a fire-resistant acrylic knit having fiberglass yarn that provides a fire barrier. Ticking 347 also provides a vapor barrier to prevent contamination of the other mattress components. According to alternative embodiments, the upper and lower portions are sewn together or configured from a sleeve. According to another alternative embodiment of the present disclosure, a fire barrier layer separate from the ticking is provided.

Figure 48:
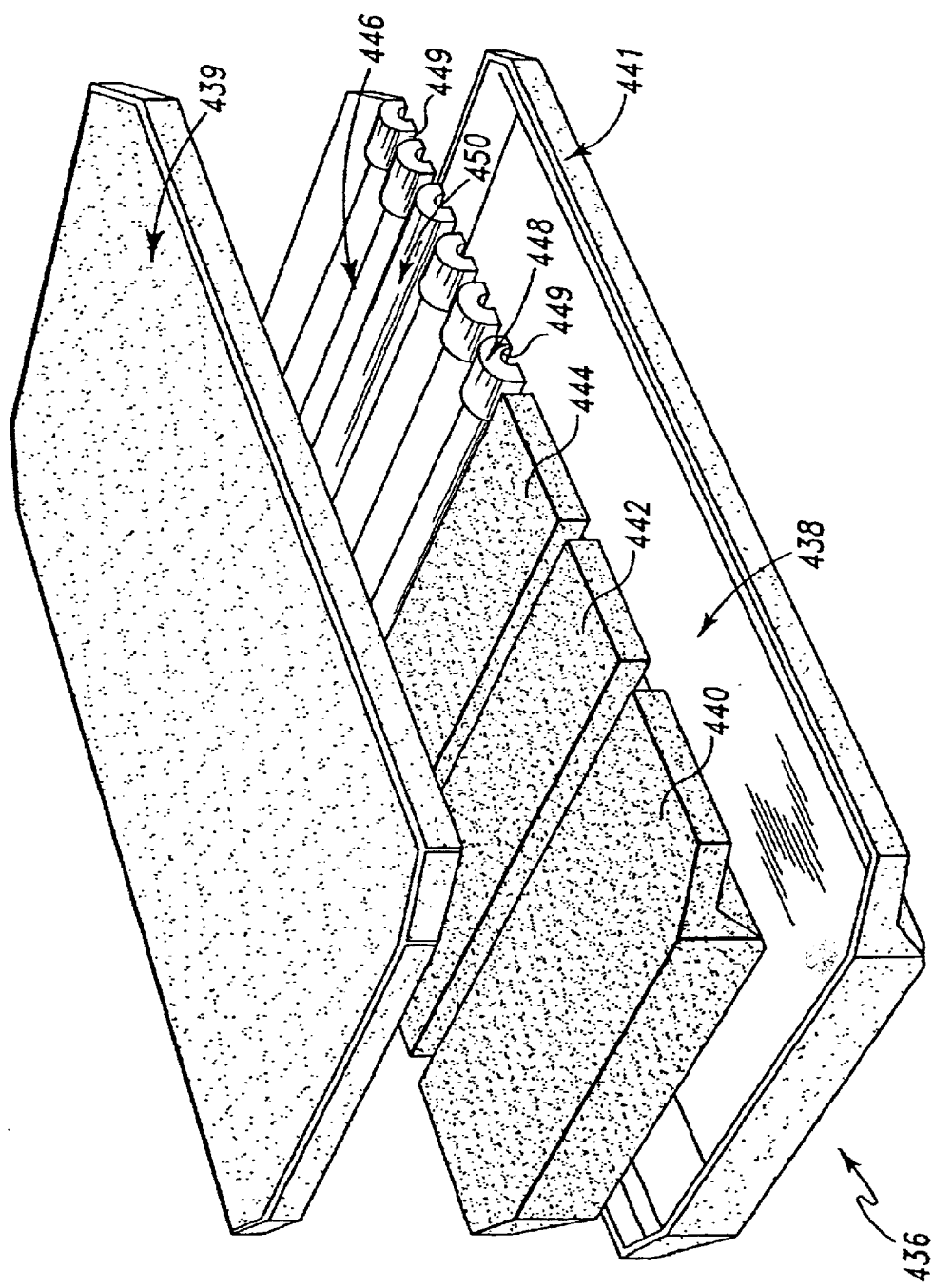
FIG. 48 is an exploded view of an alternative embodiment mattress.

An alternative embodiment mattress 436 is shown in FIG. 48. Mattress 436 includes a foam core 438 and sealed upper and lower ticking 439, 441. Core 438 is positioned between upper and lower ticking 439, 441 and includes head, back, and seat portions or sections 440, 442, 444 made of a medium stiffness foam and a foot portion or section 446 made of a viscoelastic foam that is expandable and retractable for use with foot section 28 of deck 14. Head, back, seat, and foot sections 440, 442, 444 each include angled side walls configured to conform to the angled walls of deck 14. Thus, mattress 436 includes portions or sections 440, 442, 444, 446 that are each one-piece blocks of foam which minimizes the cost of mattress 436 yet still permits mattress 436 to articulate with deck 14 of bed 10 and still permits deck 14 to extend and retract in length.

Foot section 446 is formed to include top and bottom transverse slots 449 similar to slots 428 of mattress 13 to permit foot section 446 to expand and retract. Foot section 446 is configured to prevent a patient's foot from migration over the edge of mattress 436. Foot section 446 includes a raised perimeter 448 that provides a boundary or fence to block a patient's foot from reaching the outer edge of mattress 436. Foot section 446 is also configured to reduce the level of interface pressure between the patient's foot and mattress 436. Foot section 446 includes a raised calf portion 450 positioned to rest under a patient's calf. Calf portion 450 supports a portion of the patient's weight that would otherwise be support by the patient's heel and thus reduces the overall interface pressure between the patient's heel and mattress 436. According to the preferred embodiment, calf portion 450 is made of a stiffer foam than the remainder of foot section 446. Slots 449 formed in foot section 446 create corrugations therein. The corrugation associated with calf portion 450 has a consistent height across foot section 446 whereas each of the other corrugations have recessed central portions located between the associated raised perimeters 448.

Figure 49:
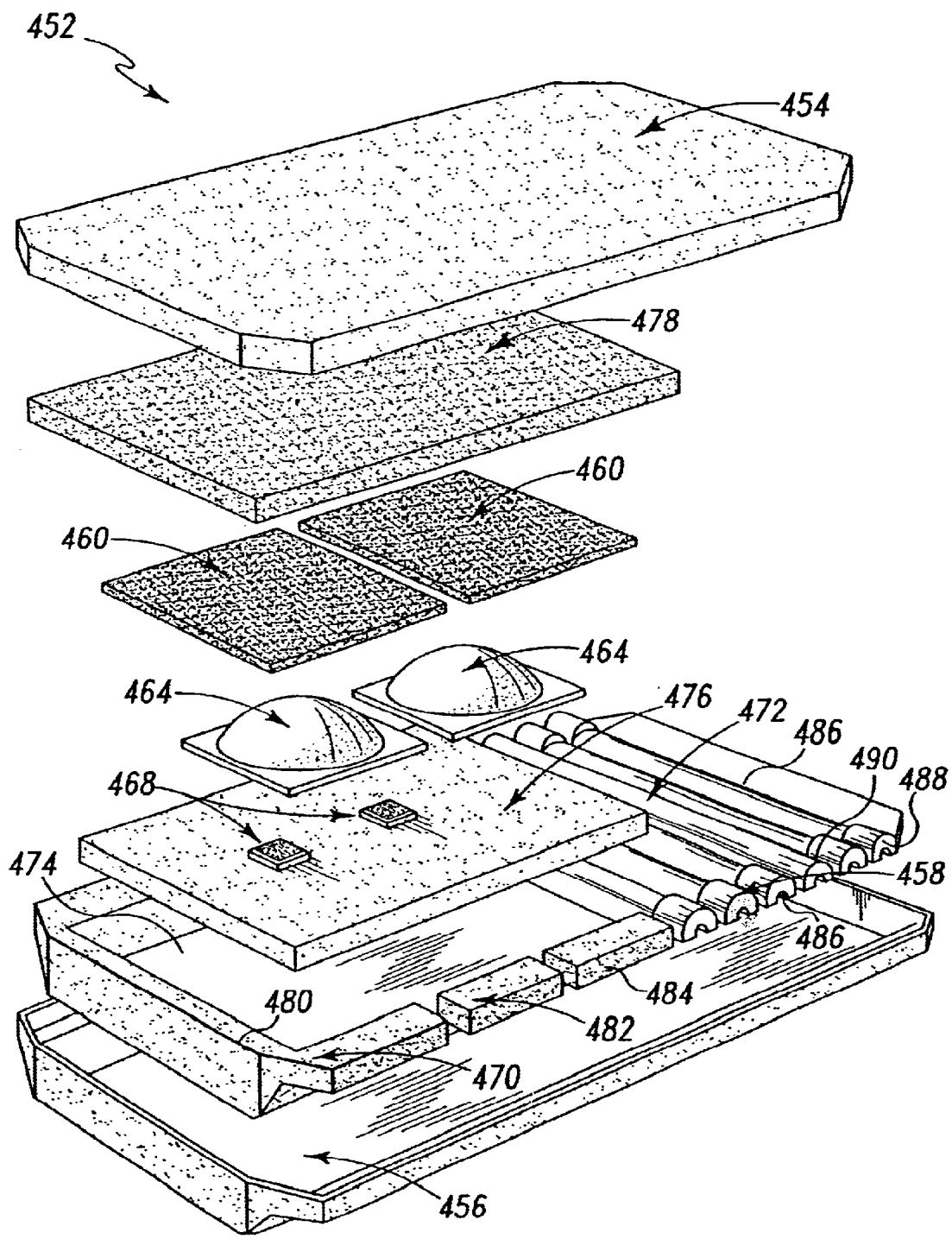
FIG. 49 is an exploded view of another alternative embodiment mattress.

Another alternative embodiment mattress 452 is provided in FIG. 49. Mattress 452 includes upper and lower sealed ticking 454, 456, a foam core 458, a pair of heating pads 460, a pair of crowning bladders 464, and a pair of vibration mechanisms 468. Core 458 is positioned between upper and lower ticking 454, 456 and includes a perimeter frame 470, a foot portion or section 472, a lower foam layer 474 positioned within perimeter frame 470, a middle foam layer 476 positioned above lower foam layer 474, and an upper foam layer 478 positioned directly below upper ticking 454. Upper foam layer 478 is made of a low ILD foam material that includes wax impregnation cooling. Middle foam layer 476 is made of viscoelastic foam.

Perimeter frame 470 includes a head portion or section 480, a back portion or section 482, and a seat portion or section 484. Head section 480 is made of a high ILD foam and back section 482 is made of a medium ILD foam. Head, back, and seat sections 480, 482, 484 and foot section 472 include angled side walls configured to conform to the angled walls of deck 14. Lower foam layer 474 optionally may be either formed integrally with head section 480 out of high ILD foam or formed integrally with back and seat sections out of medium ILD foam.

Foot section 472 is formed to include top and bottom transverse slots 486 similar to slots 428 of mattress 13 to permit foot section 472 to expand and retract. Foot section 472 is configured to prevent a patient's foot from migrating over the edge of mattress 452. Foot section 472 includes a raised perimeter 488 that provides a boundary or fence to block a patient's foot from reaching the outer edge of mattress 452. Foot section 472 is also configured to reduce the level of interface pressure between the patient's foot and mattress 452. Foot section 472 includes a raised calf portion 490 positioned to rest under a patient's calf. According to a preferred embodiment, calf portion 490 supports a portion of the patient's weight that would otherwise be support by the patient's heel and thus reduces the overall interface pressure between the patient's heel and mattress 452. Calf portion 490 is made of a stiffer foam than the remainder of foot section 472.

Figure 50:
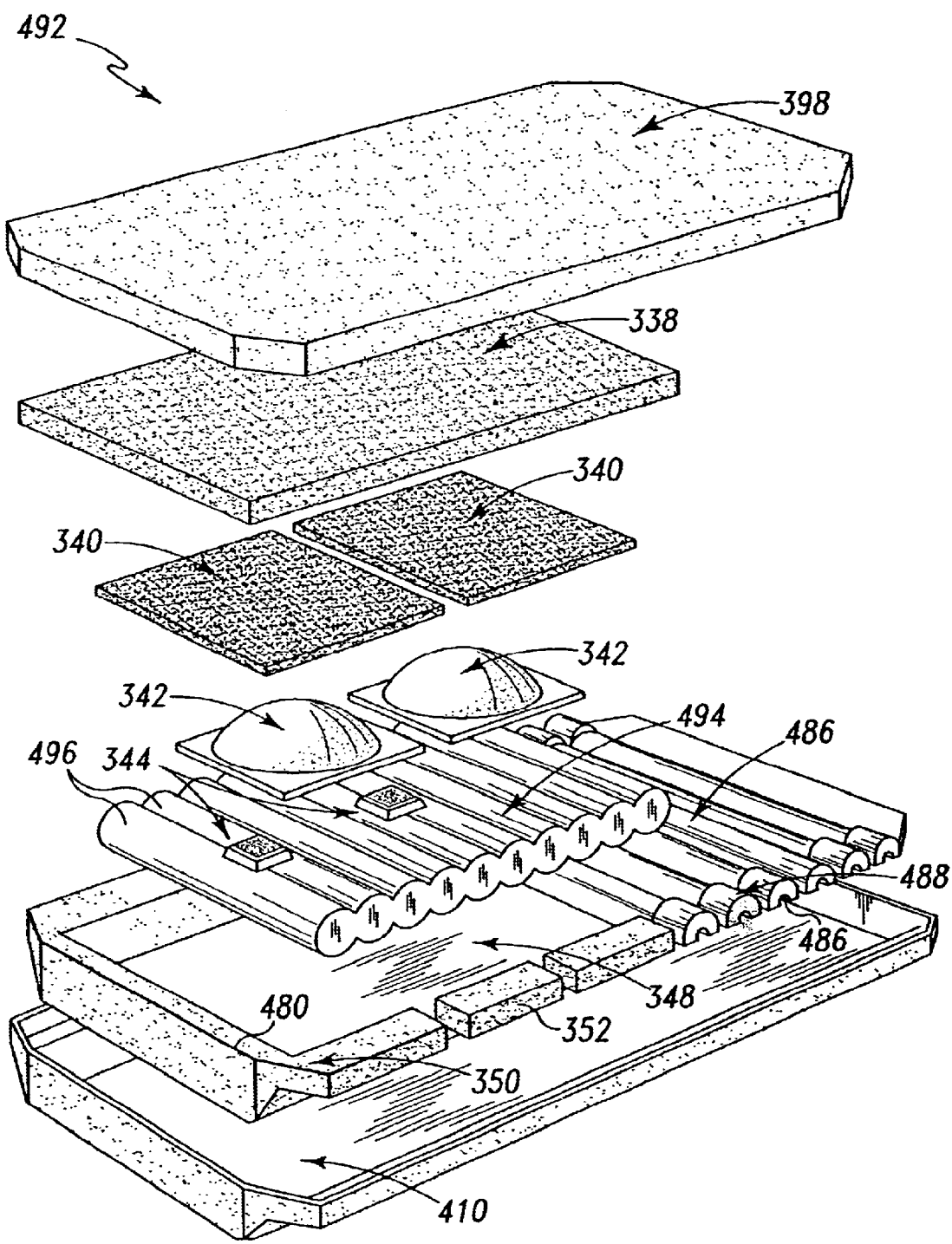
FIG. 50 is an exploded view of yet another alternative embodiment mattress including an air bladder having a plurality of cylinders.

Another alternative embodiment mattress 492 is provided in FIG. 50. Mattress 492 is substantially similar to mattress 452 of FIG. 49. Mattress 492 includes an air bladder 494 comprising a plurality of transverse cylinders 496 coupled side-by-side. Illustrative transverse cylinders 496 are in fluid communication with one another such that air bladder 494 is a single bladder zone that is inflated as a unit. However, it is within the scope of the disclosure as presently perceived for multiple air bladder zones to be provided in mattress 492 in lieu of air bladder 494 and for the level of inflation in each of these separate zones to be controlled individually.

Figure 51:
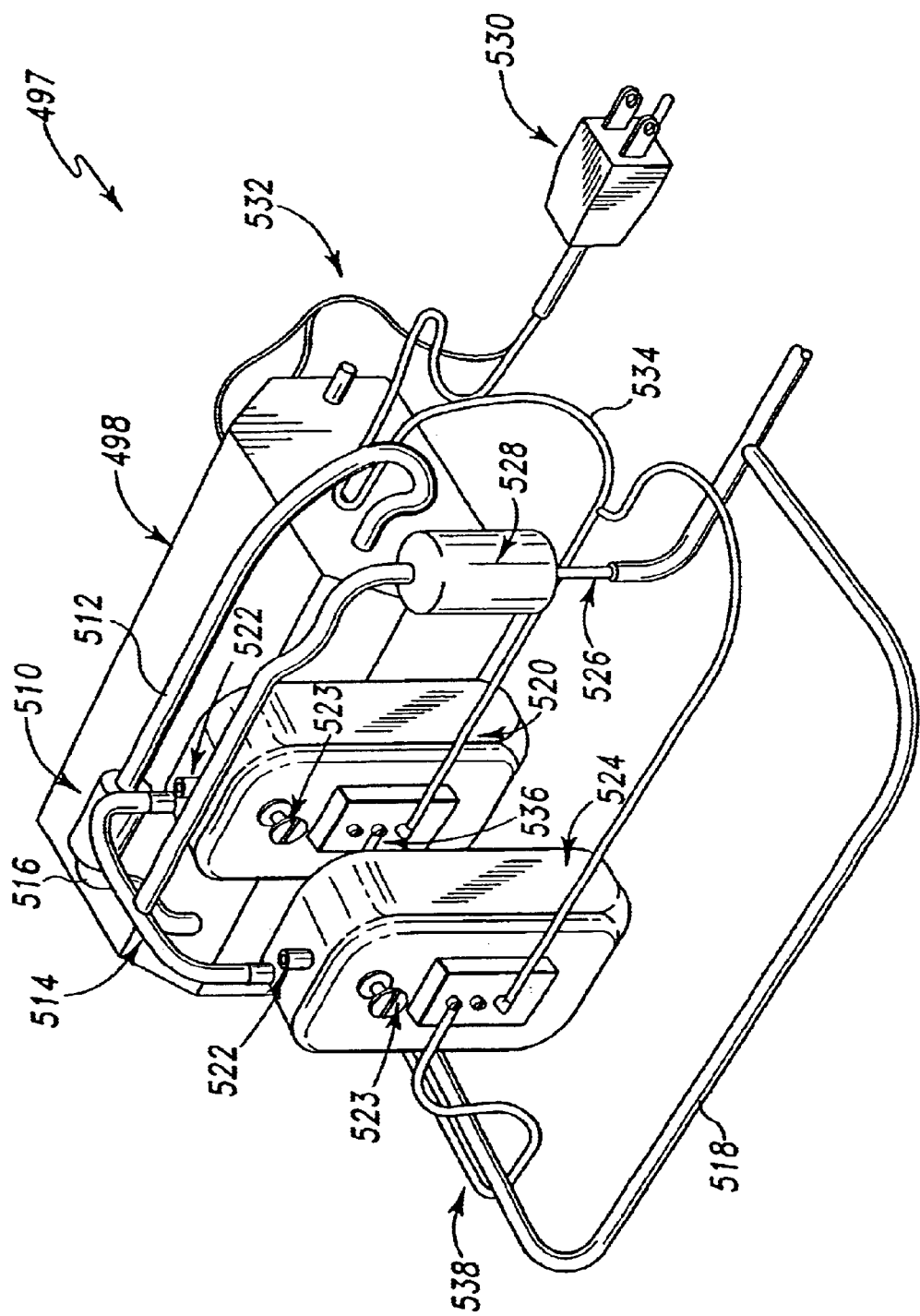
FIG. 51 is a perspective view of an air system for controlling the pressure level in the air bladder of FIG. 50.

The air pressure in air bladder 494 is controlled by an air system 497 shown in FIG. 51. Air system 497 includes a pump 498 (preferably a Thomas Model 6025SE air pump), a check valve 510 coupled to pump 498 by a first conduit 512, a dump valve 514 coupled to check valve 510 by a second conduit 516 and to air bladder 494 by a third conduit 518, a valve switch 520 coupled to third conduit 518 by a fourth conduit 522, a pump switch 524 coupled to fourth conduit 522, a pneumatic resistor 526 positioned within fourth conduit 522, and a pneumatic capacitor 528 also positioned in fourth conduit 520. Air system 497 also includes an electric plug 530 including a common wire 532 coupled to pump 498 and dump valve 514 and a hot wire 534 coupled to valve and pump switches 520, 524. Air system 497 further includes a first wire 536 coupled to dump valve 514 and valve switch 520 and a second wire 538 coupled to pump 498 and pump switch 524.

Hot wire 534 is coupled to valve switch 520 so that valve switch 520 is normally in the closed position completing the electrical circuit to run pump 498. When valve switch 520 senses a pressure greater than 10 inches of water, it switches to the open position opening the electrical circuit to turn pump 498 off. Hot wire 534 is coupled to pump switch 524 so that valve switch 520 is normally in the opened position so that dump valve 514 is normally closed. When pump switch 524 senses a pressure greater than 12 inches of water, it switches to the closed position completing the electrical circuit to open valve 514. Each switch 520, 524 includes an adjustment screw 523 to adjust the switching pressure at which pump 498 and dump value 514 are activated and deactivated.

Air system 497 provides air bladder 494 with a range of air pressures between the predetermined high and low limits (preferably between 0.3–0.4 psi). If the pressure of air bladder 494 is between predetermined high and low levels, pump 494 does not run and dump valve 514 is not open to bleed air. Valve and pump switches 520, 524 cooperate to regulate the air pressure level in air bladder 494 by monitoring the air pressure in air bladder 494, turning pump 498 on when the air pressure in air bladder 494 is below the predetermined lower limit, and opening dump valve 514 when the air pressure in air bladder 494 is above the predetermined high limit.

To inflate air bladder 494, plug 530 is inserted into an outlet (not shown) or air system 497 is otherwise turned on. Valve and pump switches 520, 524 measure the pressure level in air bladder 494 through third and fourth conduits 518, 522. If the pressure is below the lower limit, pump switch 524 moves to a position closing a circuit between hot wire 534 and second wire 538 to provide pump 498 with electricity to run pump 498. Pump 498 responds by pumping pressurized air through first conduit 512, dump valve 514, second conduit 516, check valve 510, and third conduit 518 to air bladder 494. Check valve 510 permits air to flow from pump 498 through first conduit 512, but prevents air from flowing to pump 498 through first conduit 512.

The gradual introduction of air into air bladder 494 increases the pressure therein. As the pressure in air bladder 494 surpasses the predetermined lower limit, pump switch 524 moves from the normally closed position to the open position so that the electrical circuit to pump 498 is broken and pump 498 stops. If the pressure level in air bladder 494 dips below the predetermined lower limit, pump switch 524 moves back to the normally closed position so that the electrical circuit to pump 498 is complete and pump 498 again pumps air into air bladder 494.

As a patient enters the hospital bed including mattress 492, the overall pressure in air bladder 494 increases. If this pressure rises above the predetermined high limit, valve switch 520 moves from the normally open position, with dump valve 514 deactivated and in the closed position, to the closed position. This completes the electrical circuit to dump valve 514 to activate and open dump valve 514. When dump valve 514 is open, air flows from air bladder 494 to third conduit 518 and out of dump valve 514. As air is bled out of air bladder 494, the air pressure in air bladder 494 gradually decreases until the air pressure is below the predetermined high limit as which point dump valve 514 closes. Thus, air is introduced and removed from air bladder 494 through a single port (third conduit 518) and fewer couplers are required to connect air system 397 to air bladder 494.

Pneumatic resistor 526 and pneumatic capacitor 528 cooperate to define a simple and inexpensive pneumatic damper that prevents momentary spikes in the air bladder pressure from reaching pump and valve switches 524, 520. By damping the air pressure "seen" by pump and valve switches 524, 520, they do not switch on and off for minor momentary changes in air bladder air pressure so that excessive switching of pump 498 and dump valve 514 does not occur. Such momentary changes in the air pressure in the air pressure of air bladder 494 may occur when a patient shifts in the hospital bed or when pump 498 and dump valve 514 are activated and deactivated.

Pneumatic resistor 526 is a restriction having an inside diameter less than the inside diameter of third and fourth conduits 518, 522. Pneumatic capacitor 528 is a tube having an inside diameter that is greater than the inside diameter of third and fourth conduits 518, 522. The tube is packed with foam. According to the presently preferred embodiment, the inside diameter of pneumatic resistor 526 is 0.125 inches and the inside diameter of pneumatic capacitor 528 is 0.5 inches. Thus, air system 497 is a simple, inexpensive air system that maintains the level of inflation in air bladder 494 within a predetermined range of pressures, without the need for expensive electrical circuit components such as microprocessors or micro-controllers. According to an alternative embodiment of the present disclosure, the air system includes microprocessors and/or micro-controllers.

Figure 52:
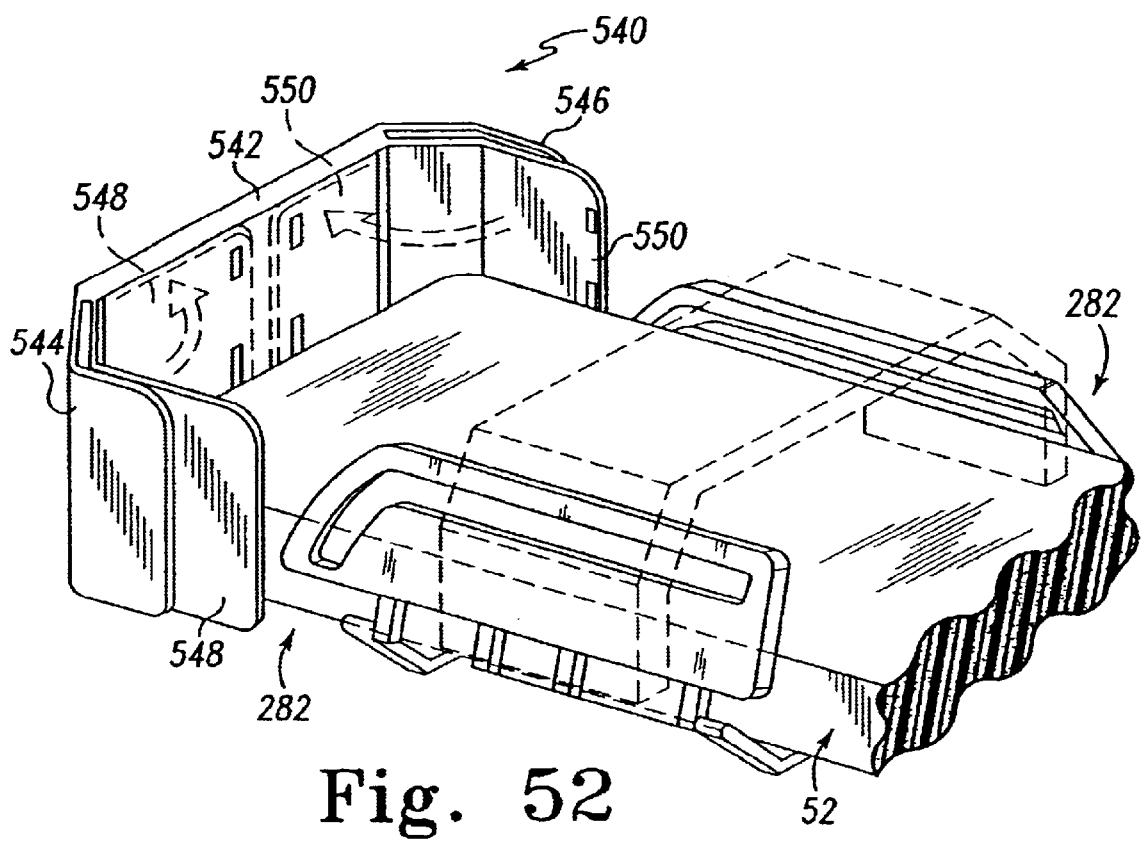
FIG. 52 is a perspective view of an alternative embodiment footboard releasably coupled to the deck to permit the footboard to be removed from the deck and positioned over the siderails to provide a table (in phantom) for a patient.

An alternative embodiment footboard 540 is shown in FIG. 52. Footboard 540 includes a base 542, a pair of side portions 544, 546 rigidly coupled to base 542, and a pair of flaps 548, 550 pivotably coupled to base 542. As shown in FIG. 52, flaps 548, 550 extend beyond side portions 544, 546 toward siderails 282. This extension reduces the gap between siderails 282 and footboard 540 so that a patient is prevented from exiting the hospital bed through said gap. As shown in phantom in FIG. 52, flaps 548, 550 may be moved to a storage position positioned adjacent to base 542. Each flap 548, 550 is configured so that they will not fold out past siderails 282 to prevent a patient supported by the hospital bed from pushing flaps 548, 550 outwardly in an effort to exit the bed.

According to an alternative embodiment footboard, a base and a pair of flaps are provided. The base is coupled to the intermediate frame and extends along the lower end of the mattress and each flap is pivotably coupled to the base to swing outwardly to a storage position adjacent an outer surface of the base. To move the flap to a use position, the siderails are lowered and the flap are swung to a position adjacent to the respective sides of the mattress. The siderails are then raised to trap the respective flaps between the respective sides of the mattress and the respective siderails. This trapping prevents a patient positioned in the bed from swinging the flaps to the storage position in an effort to exit the bed. Thus, no gap exits between the siderails and the base through which a patient may exit the bed.

Footboard 540 is removable from the hospital bed and forms a table when positioned over siderails 282 slanted to the inner position as shown in FIG. 53. While positioned over siderails 282, base 542 is substantially horizontal providing a surface for placing various items such as food trays, beverage containers, books, or other items. Base 542 is formed to include recesses for holding cups or other objects or to define a lip to prevent objects from rolling off of base 542. Side portions 544, 546 restrain transverse movement of footboard 540. Flaps 548, 550 may remain positioned to extend down below side portions 544, 546 or may be tucked in the storage position while footboard 540 is being used as a table.

Figure 54:
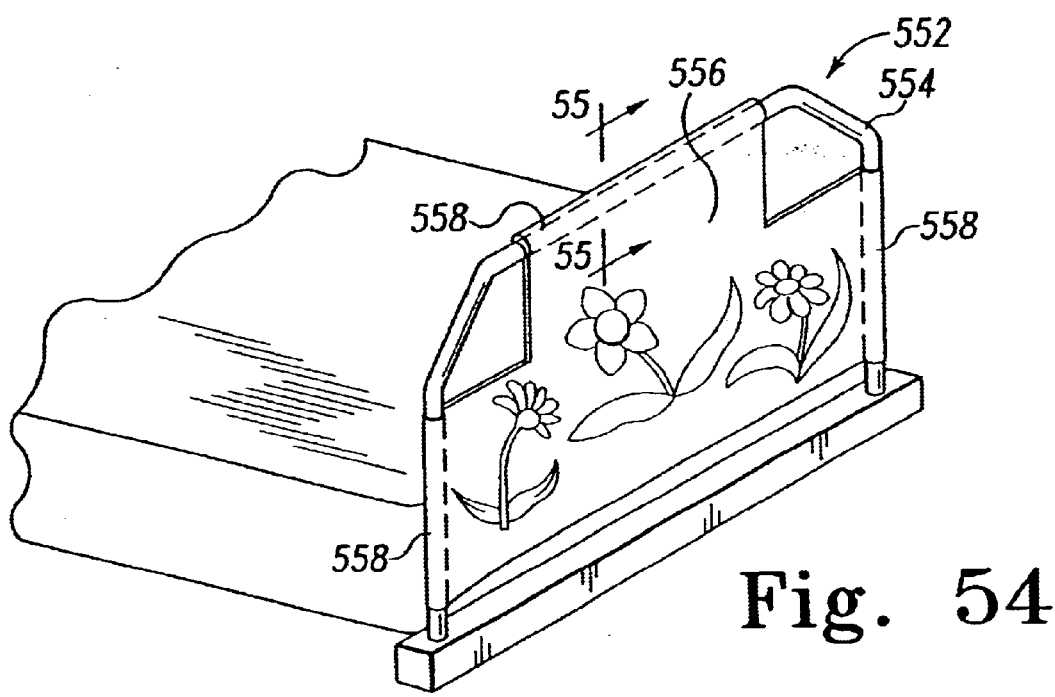
FIG. 54 is a perspective view of alternative headboard showing the headboard including a tubular frame removably coupled to the deck and a fabric screen coupled to the tubular frame.
Figure 55:
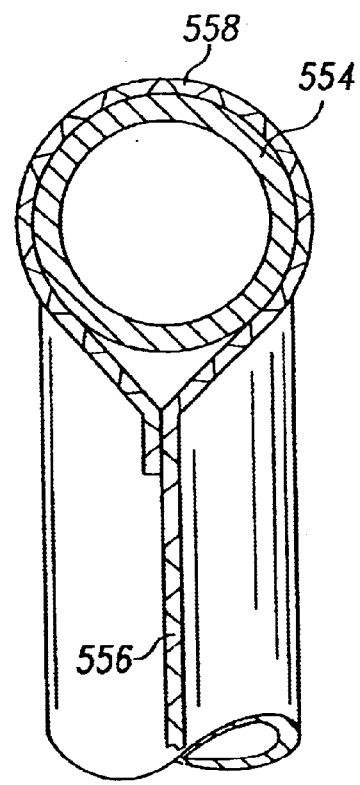
FIG. 55 is a cross-sectional view taken along lines 55—55 of FIG. 54 showing the fabric screen coupled to the tubular frame.

An alternative removable headboard 552 is shown in FIG. 54. Headboard 552 includes a tubular frame 554 removably coupled to the deck and a fabric screen 556 slidably coupled to tubular frame 554. As shown in FIG. 55, fabric screen 556 is sewn together near the perimeter to form a sleeve 558 in which portions of tubular frame 554 are positioned. To clean or replace screen 556 with another fabric pattern that "matches" the decor of the hospital room (such as the curtain fabric, furniture upholstery, comforter, sheets, or other items in the hospital room), tubular frame 554 is pulled upwardly and removed from the deck. Screen 556 is slid along tubular frame 554 until completely removed therefrom. Screen 556 is then laundered. To put screen 556 back on tubular frame 554, an end of tubular frame 556 is fed into each sleeve 558 and screen 556 is slid around tubular frame 556 until it surrounds tubular frame 556 as shown in FIG. 54. The respective ends of tubular frame 556 are then inserted back into the deck to reinstall headboard 552 to the hospital bed. According to an alternative embodiment of the present disclosure, a footboard is provided having a removable fabric screen.

Figure 56:
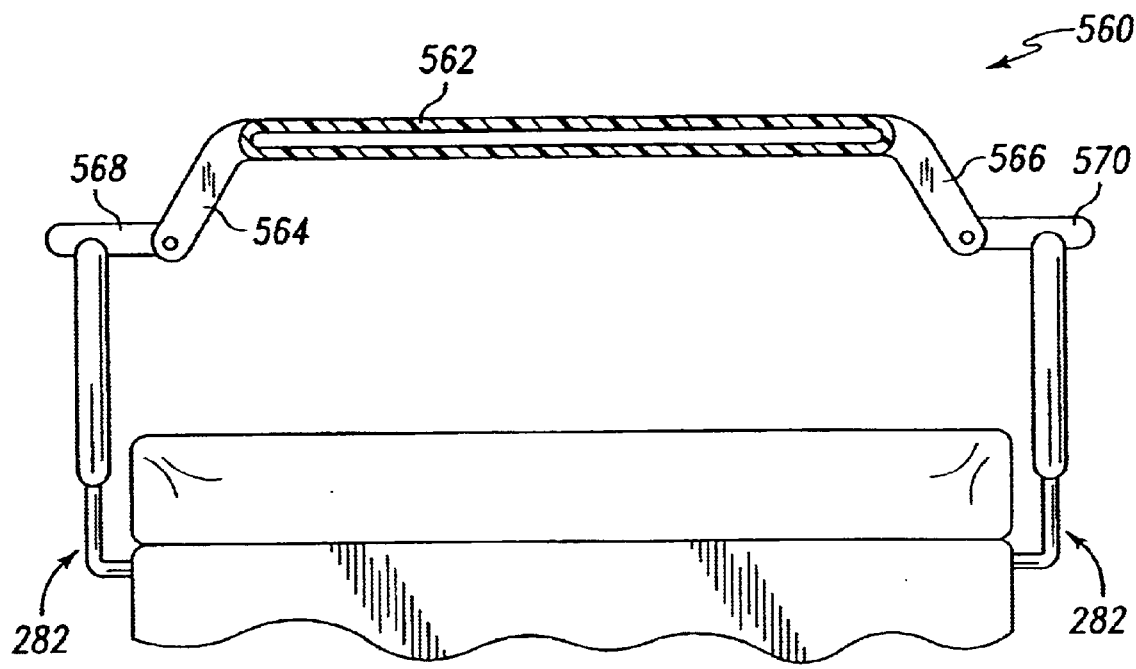
FIG. 56 is a cross-sectional view of yet another alternative embodiment footboard removed from the deck and having a base and pair of side flaps pivotably coupled to the base and positioned on the siderails to support the base.
Figure 57:
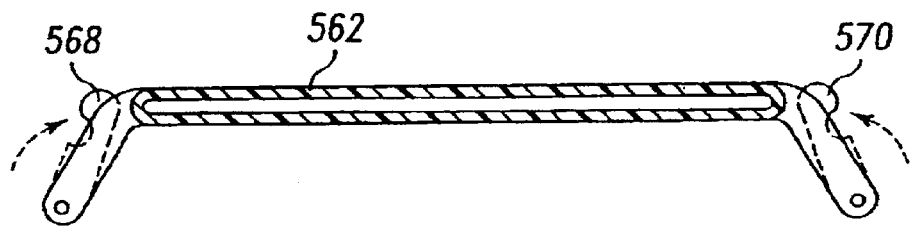
FIG. 57 is a view similar to FIG. 56 showing the side flaps in a storage position on the outside of the base.
Figure 58:
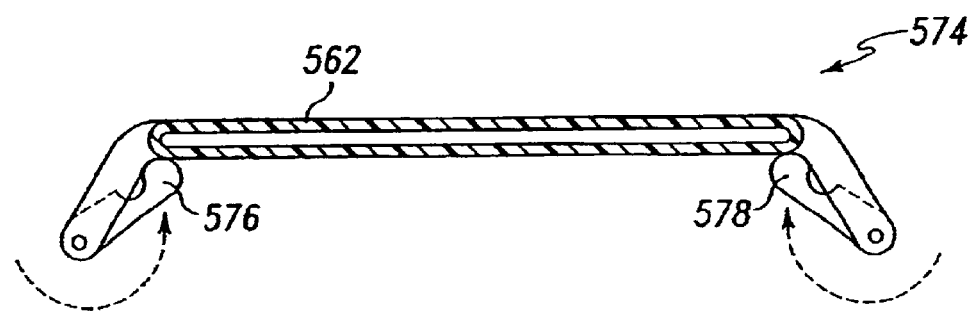
FIG. 58 is a view similar to FIG. 57 showing another alternative footboard having a base and a pair of side flaps positioned in a storage position on the inside of the base.

Yet another alternative removable footboard 560 is shown in FIG. 56. Footboard 560 is removable from the deck and includes a base 562, a pair of side portions 564, 566, and a pair of side flaps 568, 570 pivotably coupled to respective side portions 564, 566. Side flaps 568, 570 are movable between a use position as shown in FIG. 56 and function as extensions of side portions 564, 566 that engage a pair of siderails 282 coupled to the deck and a storage position tucked within an outer surface of side portions 564, 566 as shown in FIG. 57. Locks (not shown) are provided to secure side flaps 568, 570 in the use position. According to an alternative embodiment footboard 574, as shown in FIG. 58, side flaps 576, 578 tuck within an inner surface of side portions 580, 582. Stops (not shown) are provided to secure side flaps 568, 570 in the use position. Side flaps 568, 570, 576, 578 each include a notch positioned to secure the respective bases 562 to vertically-extending siderails 282.

Figure 59:
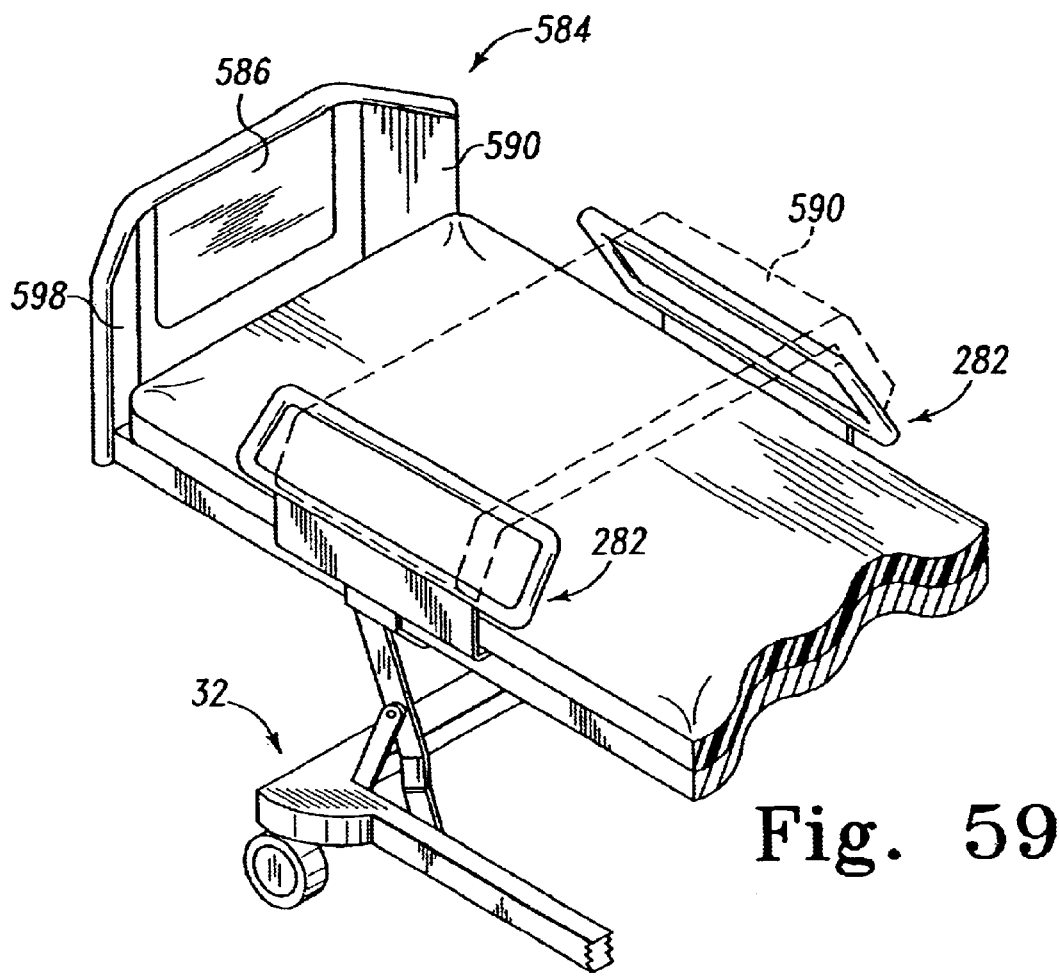
FIG. 59 is a perspective view of yet another alternative embodiment removable footboard positioned over a pair of siderails to provide a table.
Figure 60:
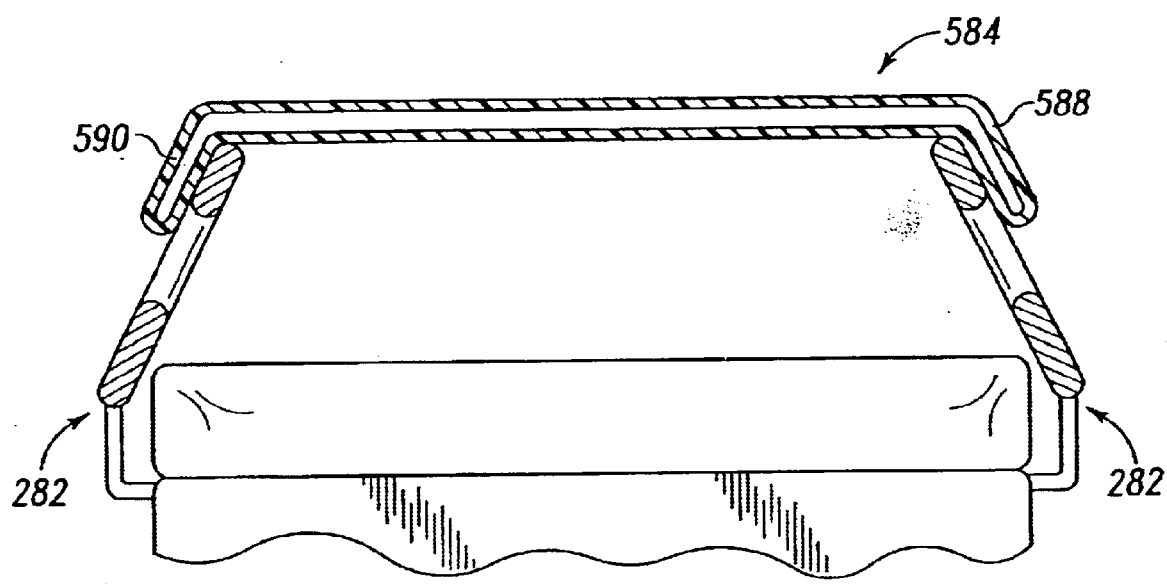
FIG. 60 is a cross-sectional view of the footboard of FIG. 59 showing the footboard positioned over the inwardly slanting siderails.

Yet another alternative embodiment removable footboard 584 is shown in FIGS. 59 and 60. Footboard 584 is a molded part and includes a base portion 586 formed to include a recess to retain object thereon and a pair of angled side portions 588, 590 positioned over a pair of siderails 592 that are inclined inwardly.

Figure 61:
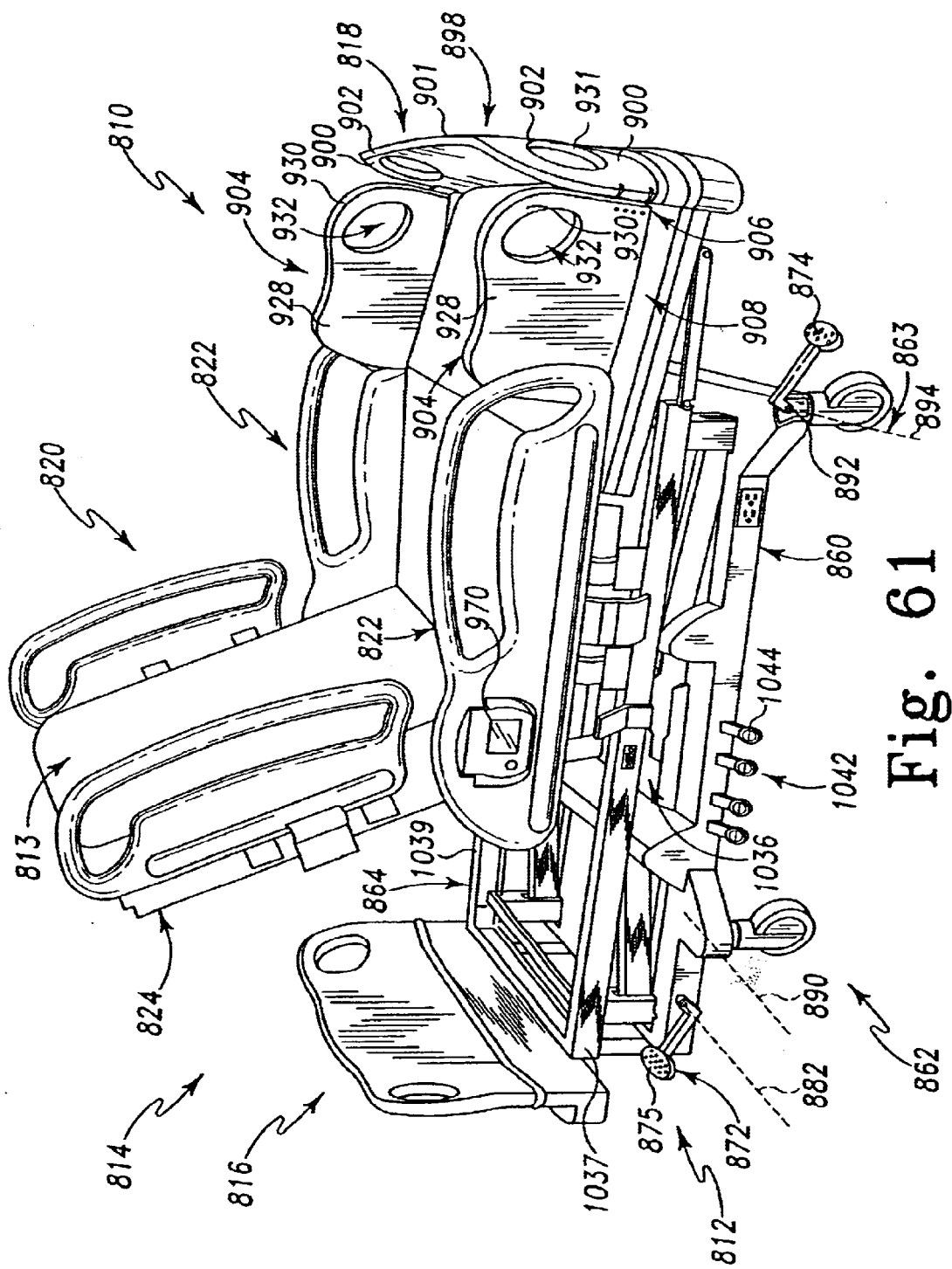
FIG. 61 is a perspective view of another alternative embodiment hospital bed showing the hospital bed including a frame, a deck coupled to and positioned above the frame with a head section of the deck tilted relative to an intermediate frame of the frame, a mattress supported by the deck, a headboard coupled to the frame, a footboard coupled to the deck, a pair of head end siderails coupled to the head section of the deck, a pair of foot end siderails coupled to the intermediate frame, and a pair of gap fillers coupled to the footboard and extending to the foot end siderails.

As shown in FIG. 61, another hospital bed 810 is provided including a frame 812, a deck 814 coupled to frame 812, a mattress 813 positioned on deck 814, a headboard 816 coupled to frame 812, a footboard 818 coupled to deck 814, a pair of head end siderails 820 coupled to deck 814, and a pair of foot end siderails 822 coupled to frame 812. Frame 812 is configured to raise and lower deck 814 relative to the floor and to move deck 814 to the Trendelenburg position and the Reverse Trendelenburg position.

Figure 62:
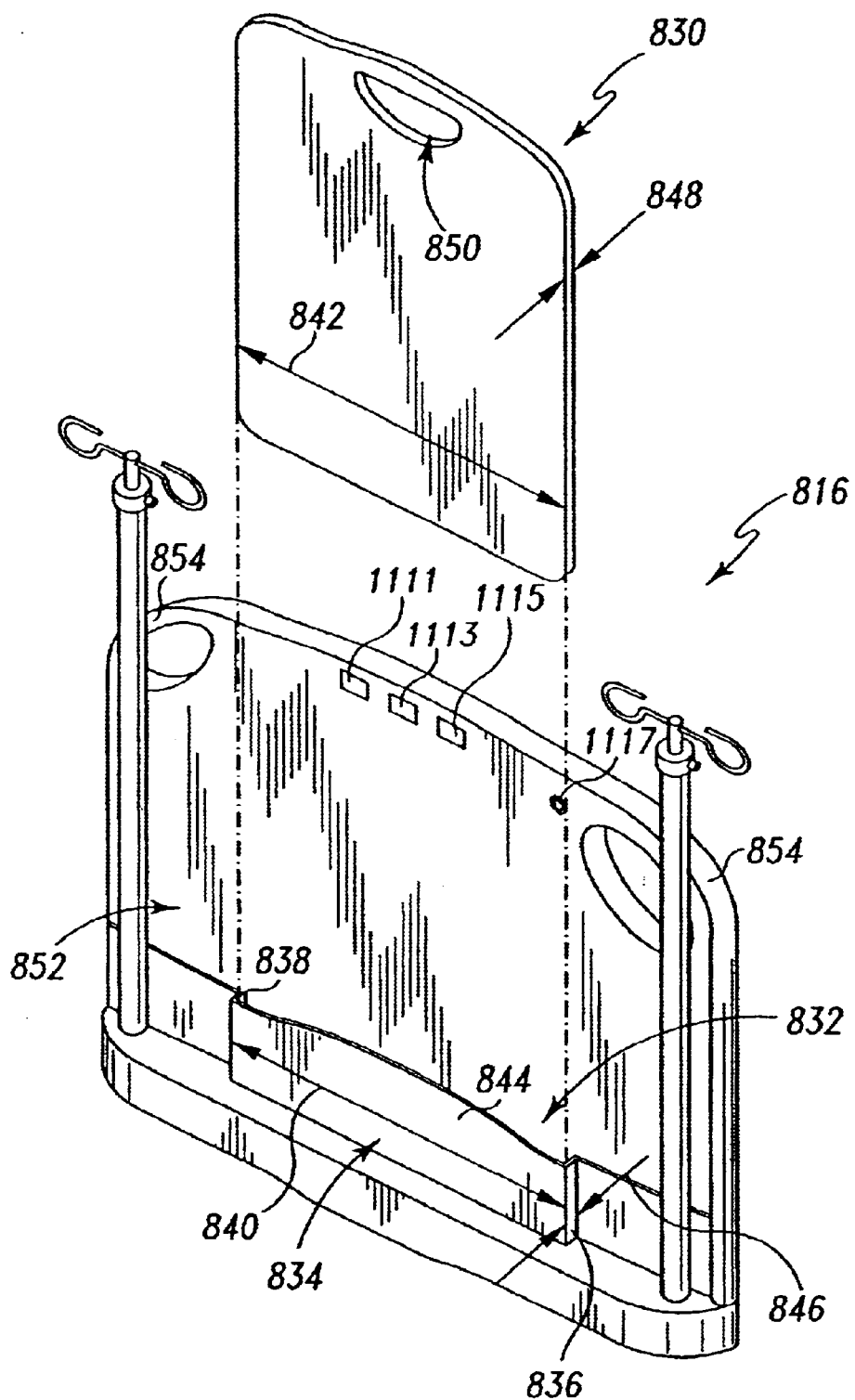
FIG. 62 is a perspective view of the headboard of FIG. 61 showing the headboard coupled to a portion of the intermediate frame, the bed including a pocket and a panel spaced apart from the headboard and aligned to fit within the pocket of the headboard.
Figure 64:
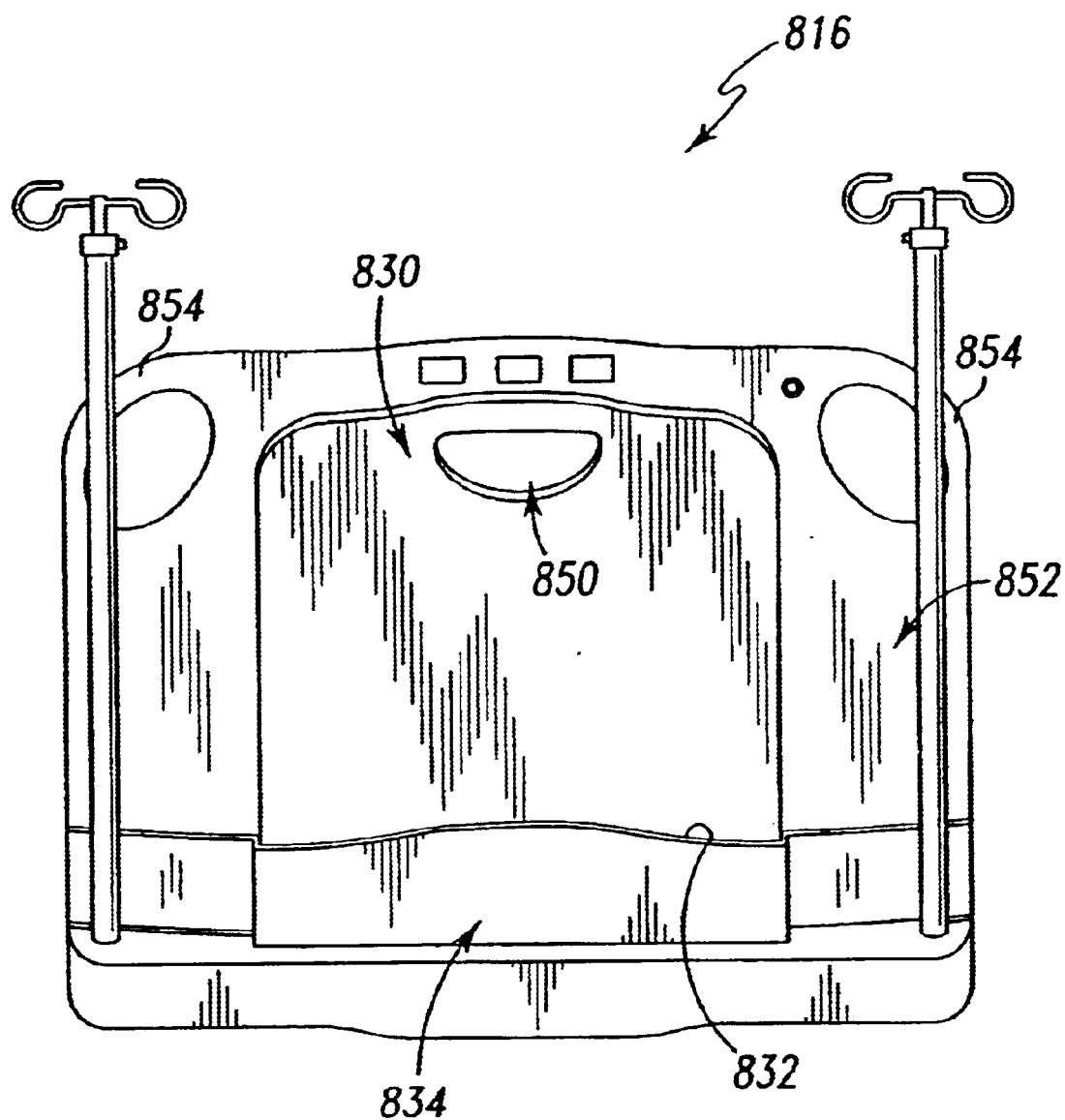
FIG. 64 is a view similar to FIG. 63 showing the panel positioned in the pocket of the headboard.

As shown in FIG. 62, bed 810 further includes a CPR crash board 830 and a pocket 832 sized to removably receive a board 830 as shown in FIG. 64. When necessary a caregiver can remove board 830 from pocket 832 and position board 830 under a patient's torso to assist the caregiver in administering CPR to the patient.

Bed 810 includes a CPR board retention member or strap 834 coupled to headboard 816 that defines pocket 832. Strap 834 is preferably made of steel or any other rigid material and includes first and second side walls 836, 838 spaced apart by a distance 840 slightly larger than a width 842 of board 830. Strap 834 also includes a third side wall 844 extending between first and second side walls 836, 838 and spaced apart from headboard 816 by a distance 846 slightly larger that a thickness 848 of board 830 so that board 830 can be removed from pocket 832 when necessary. As shown in FIG. 62, board 830 includes a handle opening 850 to facilitate such removal.

Figure 63:
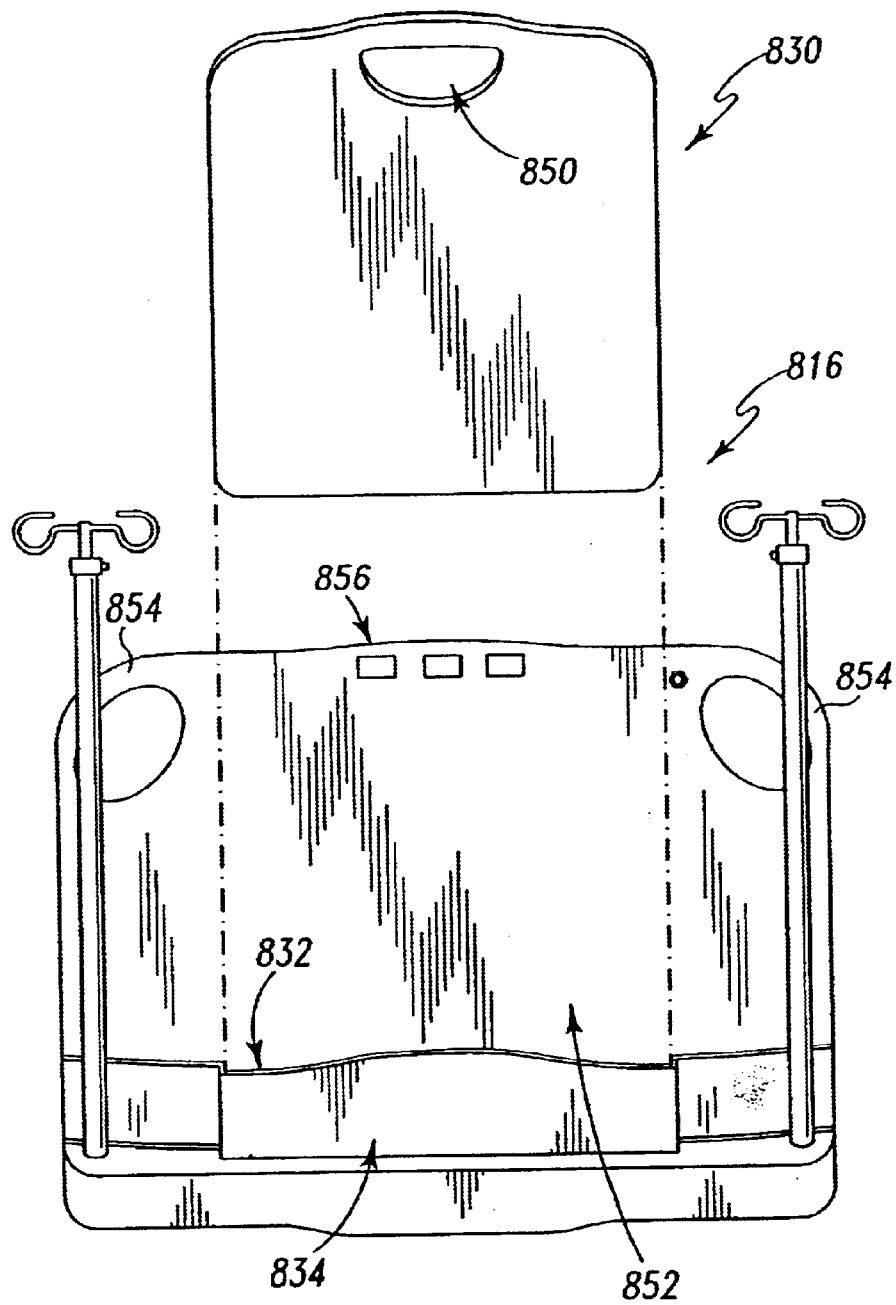
FIG. 63 is an end view of the headboard of FIG. 61 showing the panel spaced apart from the headboard.

As shown in FIG. 63, headboard 816 includes a base member 852 and a pair of handles 854 coupled thereto to facilitate pushing hospital bed 810 about a care facility. Headboard 816 further includes a plurality of control buttons 856 positioned above an upper edge of board 810. Control buttons 856 are provided to control a propulsion device 858 shown in FIGS. 85–87 and described in greater detail below.

Figure 65:
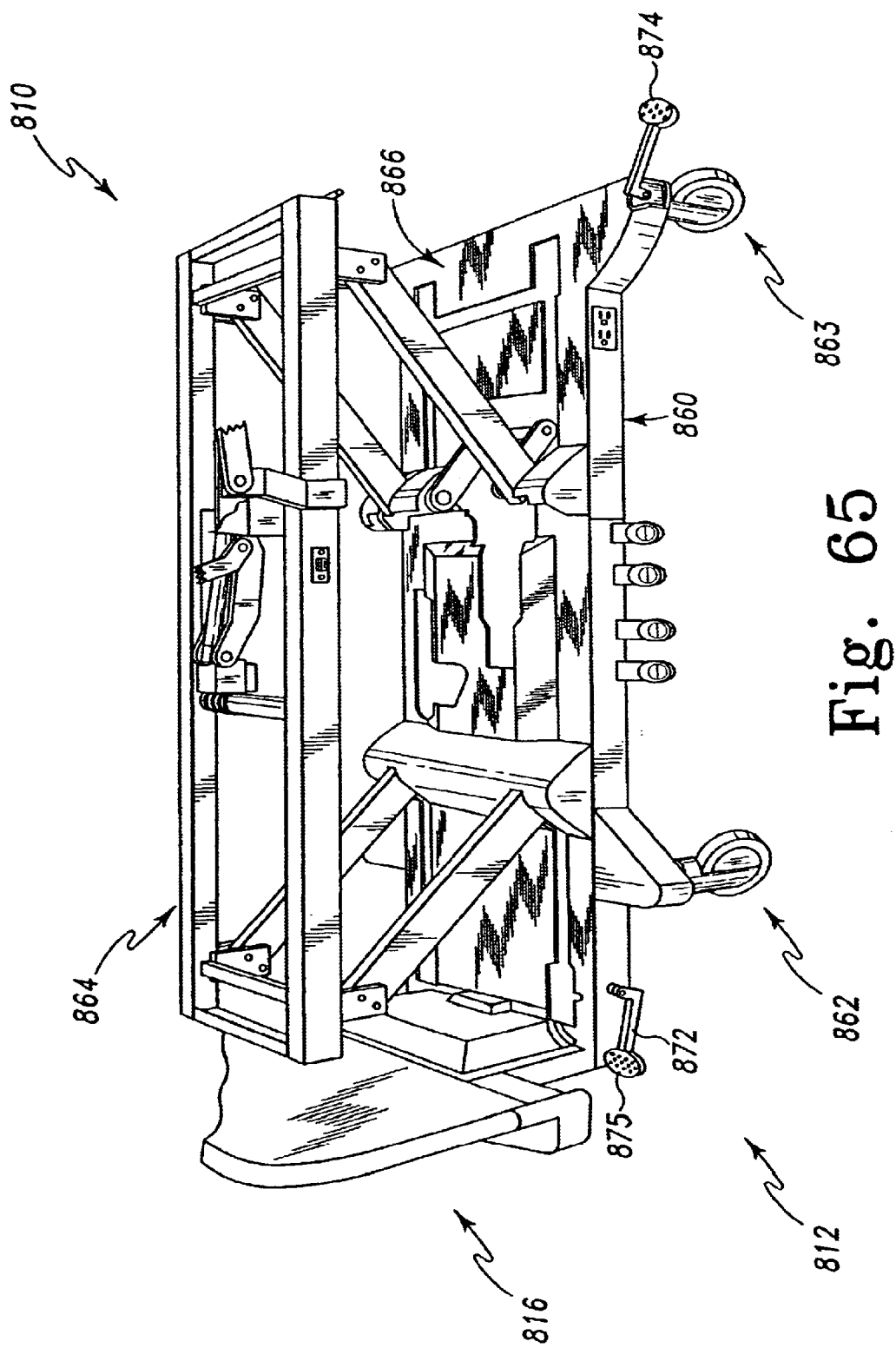
FIG. 65 is a perspective view of the bed of FIG. 61 with the deck, mattress, siderails, and headboard removed showing the frame including the intermediate frame, a shroud covering a base frame, and four linkage assemblies supporting the intermediate frame over the shroud.

As shown in FIG. 65, frame 812 includes a rectangular lower frame member or base frame 860, a pair of head end wheels or casters 862, a pair of foot end wheels or casters 863 coupled to base frame 860 to permit hospital bed 810 to be rolled about a care facility, a rectangular intermediate frame 864, a linkage system 866 coupled to intermediate and base frames 864, 860 to permit relative motion therebetween, and an actuator system (not shown) providing power to actuate linkage system 866 and move upper member 864 relative to base frame 860. Linkage system 866 and the actuator system are substantially similar to linkage system 654 and actuator system 656 shown in FIG. 8 and discussed above.

Figure 66:
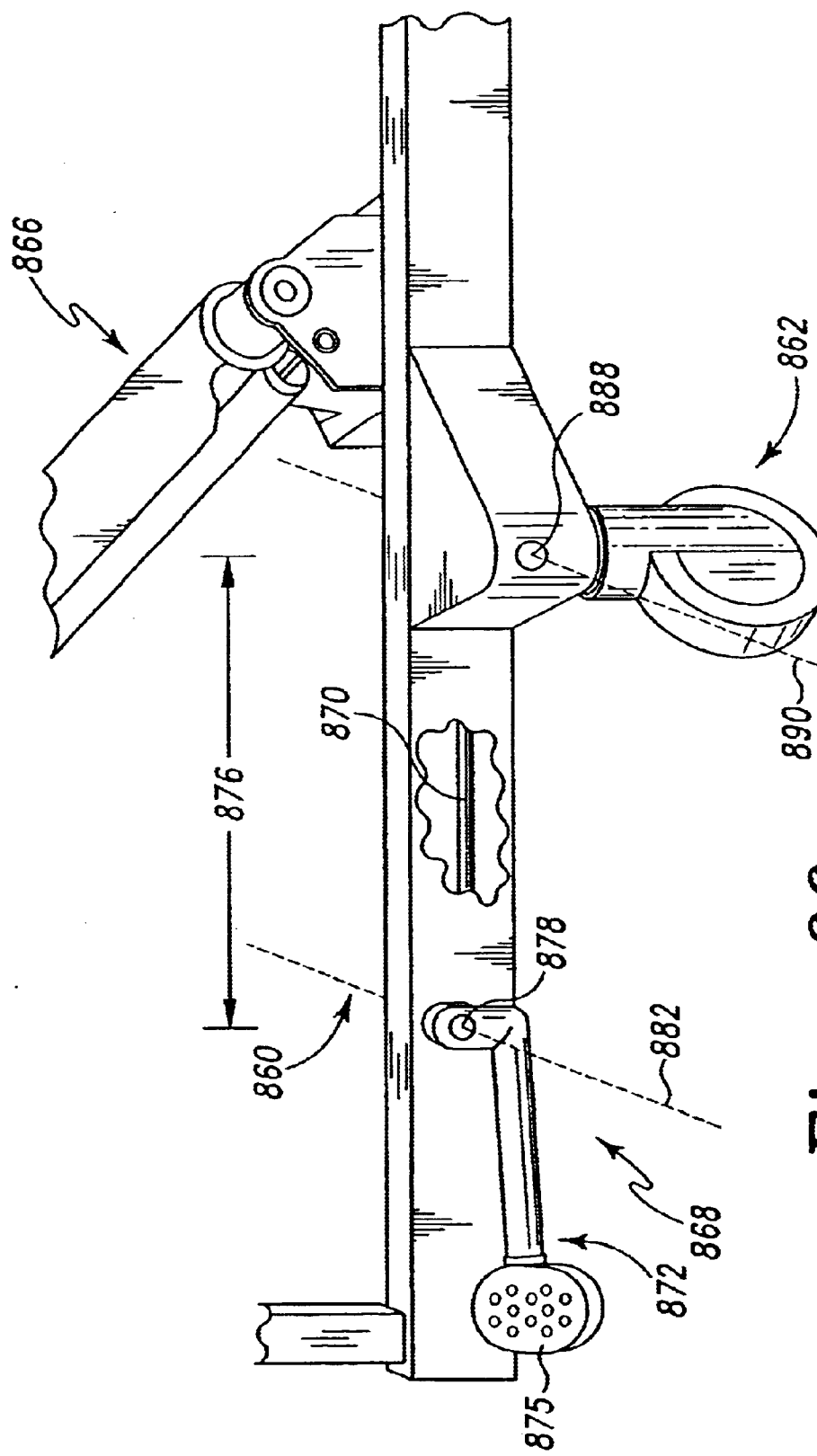
FIG. 66 is a perspective view of a portion of the base frame showing a caster brake pedal coupled to the base frame and spaced apart from a caster coupled to the base frame.
Figure 67:
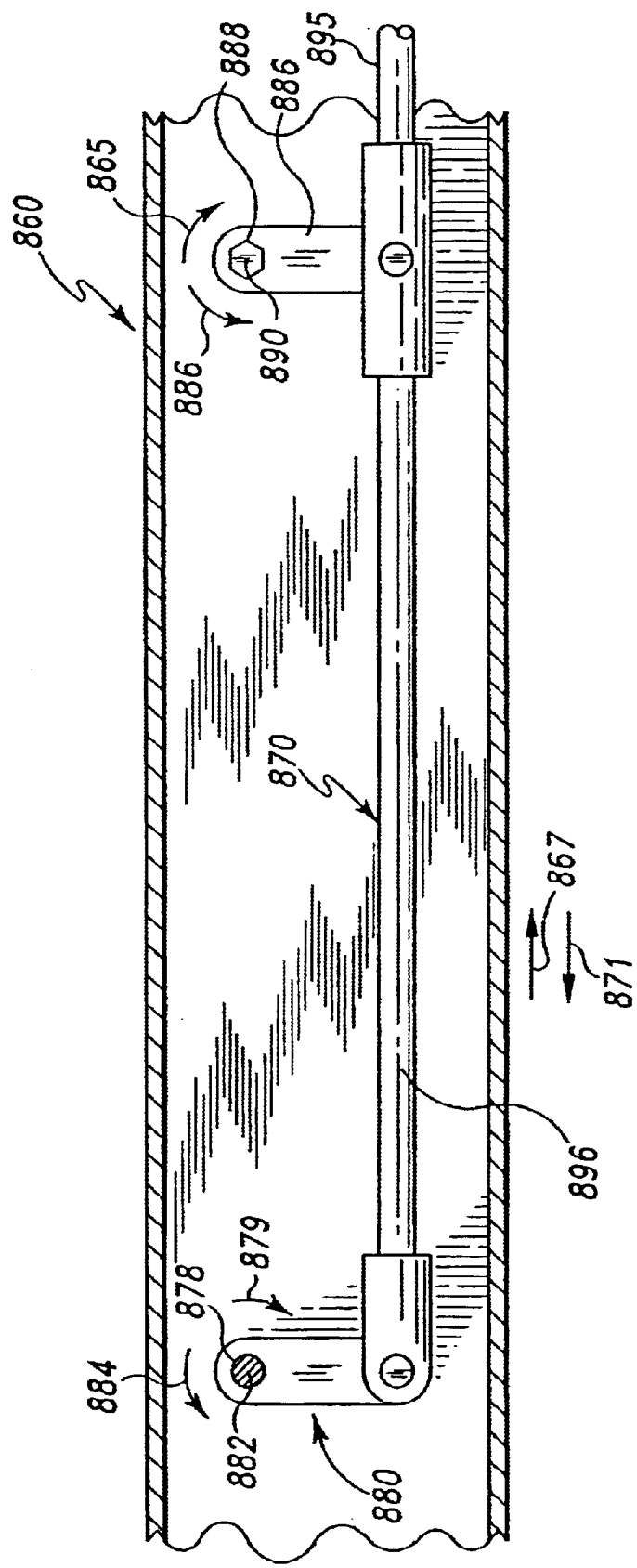
FIG. 67 is a cross-sectional view taken along line 67—67 of FIG. 66 showing a link extending from an arm of the caster brake pedal to an arm of a caster braking mechanism including a hexagonal rod.

Hospital bed 810 further includes a caster braking system 868 including a caster-brake link 870 extending through hollow base frame 860 as shown in FIGS. 66 and 67. The caster braking system 868 interconnects each caster 862, 863 to provide simultaneous braking of casters 862, 863. To simultaneously brake casters 862, 863, the caregiver steps on one of foot brake pedals 872, 874 and the caster braking system locks casters 862, 863 against rolling.

As shown in FIG. 66, foot brake pedal 872 is longitudinally spaced apart from caster 862 by a distance 876. Foot brake pedal 872 is coupled to base frame 860 by a rod 878 and pivotably coupled to caster-brake link 870 by an arm 880. According to the preferred embodiment, rod 878 is round. According to alternative embodiments, the rod is hexagonal.

During rotation of foot brake pedal 872 about axis 882 in direction 884, arm 880 transmits force to caster-brake link 870. Caster-brake link 870 moves in direction 871 to transmit this force to an arm 886 pivotably coupled to caster-brake link 870 and rigidly coupled to a hexagonal rod 888 of caster braking system 868. This rotation causes hexagonal rod 888 to rotate about an axis 890 in direction 886 causing caster 862 to lock.

According to the preferred embodiment of the present disclosure, caster-brake link 870 is positioned below rod 878 so that counterclockwise rotation of rod 878 by foot brake pedal 872 in direction 884 causes movement of caster-brake link 870 in direction 871. Similarly, rotation of rod 878 in clockwise direction 869 causes caster-brake link 870 to move in direction 867 and hexagonal rod 888 to rotate in clockwise direction 865 to unlock caster 868. According to an alternative embodiment of the present disclosure, the caster-brake link is positioned above the rod so that rotation of the rod in direction 882 causes the caster-brake link to move in direction 867 and movement of the rod in direction 869 causes the caster-brake link to move in direction 871.

Additional description of a caster braking system similar to the caster braking system of the present disclosure is provided in U.S. patent application Ser. No. 09/263,039, filed Mar. 5, 1999, to Mobley et al., entitled Caster and Braking System, which is expressly incorporated by reference herein. According to alternative embodiments of the present disclosure other configurations of caster braking and/or steering systems with or without simultaneous locking functions are provided for use with the foot brake pedal and caster-brake link of the present disclosure.

Caster-brake link 870 also transmits the rotation of foot brake pedal 872 to the other hexagonal rods 888, 892 associated with the other casters 862, 863 to simultaneously brake all four casters 862, 863. As shown in FIG. 67, link 870 includes a portion 895 that continues to extend through frame member 860 and coupled to hexagonal rod 892 in a manners similar to the coupling to hexagonal rod 888 shown in FIG. 67. Therefore, when hexagonal rods 888 of caster 862 rotate about axis of rotation 890, hexagonal rod 892 rotates about axis 894. To unlock casters 862, 863, foot brake pedal 872 is rotated in a direction opposite direction 884 to rotate hexagonal rod 888 in a direction opposite direction 890 to unlock caster 862. Caster-brake link 870 also transmits the rotation to the other hexagonal rods 888, 892 to simultaneously release all casters 862, 863.

A transversely extending rod (not shown) transmits the rotation of hexagonal rod 892 of one of foot end casters 863 to the other hexagonal rod 892 or the other foot-end caster 863. Another caster-brake link (not shown) that is identical to caster-brake link 870 extends through the opposite side of base frame 860 and couples hexagonal rods 888, 892 and rod 878 together so that rotation of the other head end pedal 872 is transferred to all four casters 862, 863 to provide simultaneous locking and unlocking of casters 862, 863.

Similarly, the caster-brake links 870 also transmit the rotation of foot brake pedals 874 to all four caster 862, 863. Foot brake pedals 874 are directly coupled to hexagonal rods 892 as shown in FIG. 61 and coupled to the caster-brake links 870 by an arm (not shown) similar to arm 886. Thus, if brake pedals 874 are rotated to lock or unlock either caster 863, the other casters 862, 863 are also locked or unlocked.

Brake pedal 872 is positioned so that a caregiver standing adjacent to headboard 816 can operate the caster braking system. As shown in FIG. 65, brake pedal 872 includes a foot pad 875 positioned adjacent to a head end of base frame 860. A caregiver positioned near headboard 816 can step on pad 875 to lock casters 862, 863 without having to move to the side of bed 810 to access brake pedal 872.

As shown in FIG. 66, because brake pedal 872 is longitudinally spaced apart from caster 862, axis of rotation 890 of hexagonal rod 888 is longitudinally positioned between axis of rotation 882 of rod 878 and axis of rotation 894 of hexagonal rod 892. Thus, the portion of caster-brake link 870 positioned between arms 880, 886 is an extension 896 that permits pedal 872 to be longitudinally spaced apart from caster 862. According to an alternative embodiment of the present disclosure, the foot end brake pedals are also spaced apart from the foot end casters in a manner similar to head end brake pedals.

As shown in FIG. 61, footboard 818 includes a body member 898 including a pair of curved end portions 900 and a substantially flat center portion 901 positioned between curved end portions 900. End portions 900 have handle portions 902 that facilitate pushing hospital bed 10 about a care facility. Bed 810 further includes a pair of gap fillers 904 pivotably coupled to curved end portions 900 of body member 898 by hinges 906.

Gap fillers 904 are provided to block movement of a patient into gaps 908 defined between foot end siderails 822 and footboard 818 so that a patient is prevented from exiting the hospital bed through gaps 902. As shown in FIG. 70, gap filler 904 can be pivoted in direction 914 to move each gap filler 904 from a use position to a storage position. To move gap filler 904 from the storage position to the use position, foot end siderail 822 must be lowered to the down storage position so that gap filler 904 is free to move in direction 905 to a position adjacent to mattress 813. Then, foot end siderail 822 is raised to trap gap filler 904 between mattress 813 and foot end siderail 822 as shown in FIG. 61.

Each gap filler 904 includes a body member 928 having a handle portion 930 defining openings 932, as shown in FIG. 61, that align with openings 931 defined by handle portions 902 of footboard 818 when gap fillers 904 are in the storage position. Each body member 928 includes a curved portion 903 and a substantially flat portion 905 coupled to curved portions 903 that complement curved end portions 900 and flat portion 901 of footboard 818 when in the storage position. To move gap fillers 904 to the storage position, the respective siderail 822 is lowered to permit the respective gap filler 904 to swing out in direction 914 to the storage position. When in the storage position, a first surface 907 of body member 928 is positioned adjacent to an outer surface 909 of footboard 818.

As shown in FIG. 69, footboard 818 further includes a first coupler 910 preferably made of hook-and-loop material and each gap filler 904 includes a second coupler 912 also preferably made of hook-and-loop material that is aligned with first coupler 910 to retain gap filler 904 in the storage position adjacent to outer surface 909 of footboard 818. When gap filler 904 is in the storage position, second coupler 912 couples to first coupler 910 to secure gap filler 904 in the storage position with first surface 906 of gap filler 904 adjacent to outer surface 908 of footboard 818. According to alternative embodiments of the present disclosure, other couplers are provided to coupled the gap fillers to the footboard when in the storage position. For example, according to alternative embodiments, snaps, ties, tabs, retainers, magnets, fasteners, and other couplers known to those of ordinary skill in the art are provided.

To move gap fillers 904 back to the use position, foot end siderails 822 are moved to the down storage position and second couplers 912 of gap fillers 904 are uncoupled from first couplers 910 of footboard 818. Gap fillers 904 are swung in direction 905 about hinges 906 so that distal ends 916 of gap fillers 904 are positioned adjacent to mattress 813 as shown in FIG. 70. Next, foot end siderails 822 are raised to trap each gap filler 904 between mattress 813 and the respective foot end siderail 822 as shown in FIGS. 61 and 70.

Figure 68:
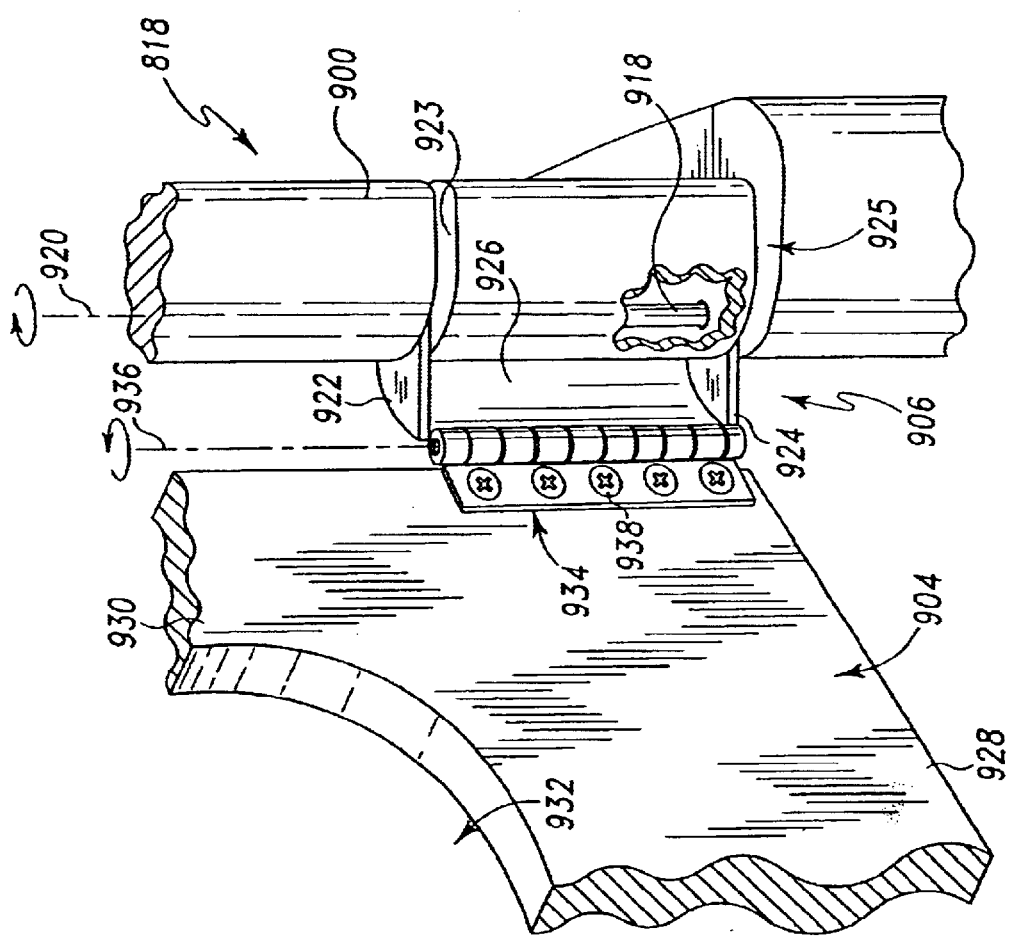
FIG. 68 is a perspective view showing a hinge coupling one of the gap fillers of FIG. 61 to the footboard.

As shown in FIG. 68, a hinge 906 is pivotably coupled to footboard 818 by a pin 918 so that hinges 906 rotate about a first vertical axis 920. Hinges 906 includes a pair of flanges 922, 924 through which pin 918 extends and a curved body portion 926 extending between flanges 922, 924. Footboard 818 includes a pair of slots 923, 925 that provide clearance for flanges 922, 924 to travel during rotation about first vertical axis 920.

Each gap filler 904 further includes a hinge plate 934 pivotably coupling each gap filler 904 to respective hinges 906 so that gap fillers 904 can rotate about a second vertical axis 936. Hinge plate 934 is coupled to body member 928 by fasteners 938. Thus, gap fillers 904 rotate about two spaced-apart vertical axises 920, 936 so that the respective gap fillers 904 can rest snugly against outer surface 908 of footboard 818 when in the storage position.

Figure 71:
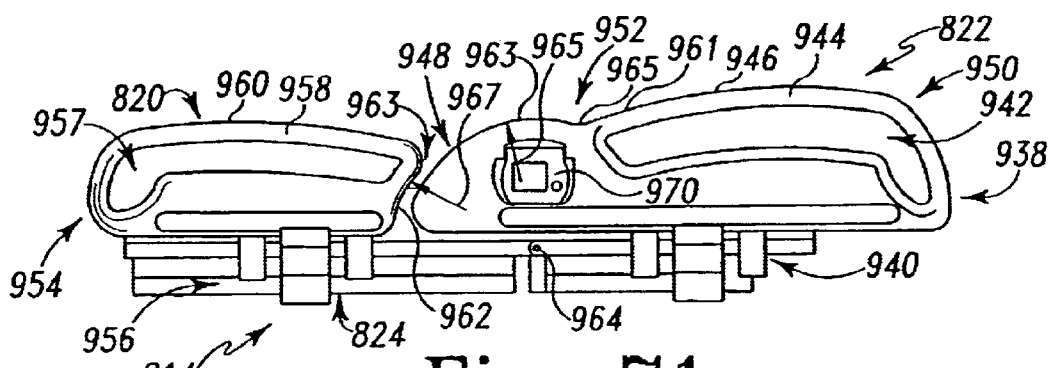
FIG. 71 is a side elevation view of the bed of FIG. 61 showing the deck in a bed position with the head section of the deck co-planar with a seat section of the deck.

As shown in FIG. 71, each foot end siderail 822 includes a rail member 938 coupled to deck 814 by a plurality of linkages 940. Rail member 938 includes an opening 942 positioned below a hand rail portion 944 of rail member 938. Rail member 938 includes an upper edge 946 including two convex end portions 948, 950 and a concave portion 952 positioned between convex end portions 948, 950. Suitable linkages for coupling the foot end and head end siderails to the deck and intermediate frame are discussed herein and in U.S. patent application 09/005,637, titled Bed Side Rails, filed Jan. 12, 1998, to Weismiller et al., the disclosure of which is expressly incorporated by reference herein.

Each head end siderail 820 includes a rail member 954 coupled to deck 814 by a plurality of linkages 956. Rail member 954 includes an opening 957 positioned below a hand rail portion 958 of rail member 954. Rail member 954 includes an upper edge 960 and a concave side edge 962 spaced apart from end portion 948 of foot end siderail 822 to define a gap 963 between foot and head end siderails 822, 820.

As shown in FIG. 71, end portion 948 of upper edge 946 and side edge 962 each have substantially uniform radii of curvature 965, 967 centered upon an axis of rotation 964 of a head portion or section 824 of deck 814. Because of this configuration, gap 963 remains substantially constant as head section 824 rotates in a clockwise direction 968 about axis of rotation 964 until it reaches the position shown in FIG. 73.

Concave portion 952 permits head section 824 to rotate further about axis of rotation 964 than if upper edge 946 were substantially flat. Concave portion 952 provides clearance for head end siderail 820 to travel as it approaches the position shown in FIG. 73. Thus, by providing concave portion 952, head section 824 and head end siderail 820 are permitted to rotate further about axis of rotation 964 before gap 963 would otherwise begin to close. According to the presently preferred embodiment of the present disclosure, head end siderail 820 does not rotate any further in clockwise direction 968 than shown in FIG. 73.

Figure 73:
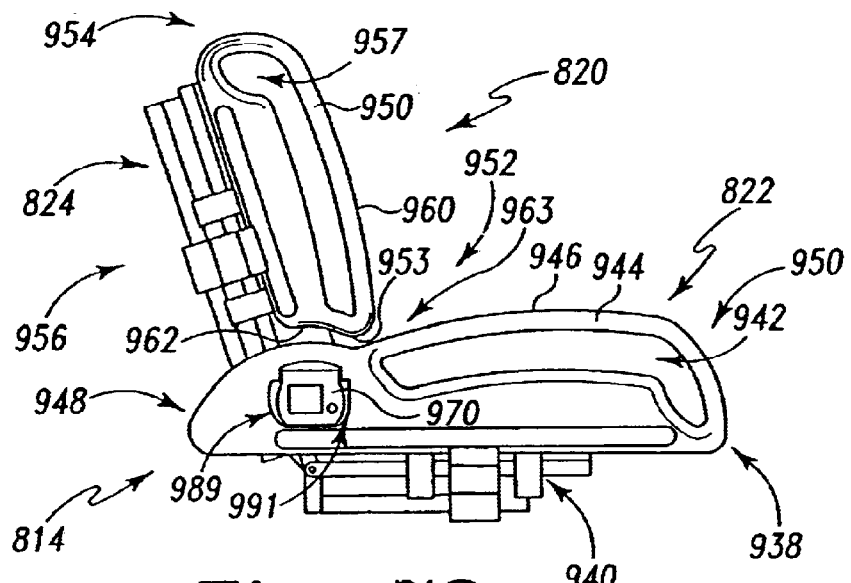
FIG. 73 is a view similar to FIG. 71 showing the head section of the deck tilted relative to the seat section of the bed and foot end of the head end siderail positioned adjacent to a notch formed in the foot end siderail.

Concave portion 952 compliments a convex corner 953 defined by the junction of upper edge 960 and a side edge 962 of rail member 954. When head end siderail 820 is positioned in its upper-most position, as shown in FIG. 73, corner 953 is substantially uniformly spaced apart from concave portion 952. Thus concave portion 952 and corner 953 define complementary formations assisting in the maintenance of a substantially uniform gap therebetween.

Concave portion 952 includes a pair of inclined portions 961, 963 portions and a curved portion 965 positioned between inclined portions 961, 963. According to alternative embodiments of the present disclosure, the concave portion is notched, more shallow, deeper, or any other concave shape known to those of ordinary skill in the art. According to another alternative embodiment of the present disclosure, the concave portion is positioned on the head end siderails to receive head end portions of the foot end siderails when in the raised position.

Figure 74:
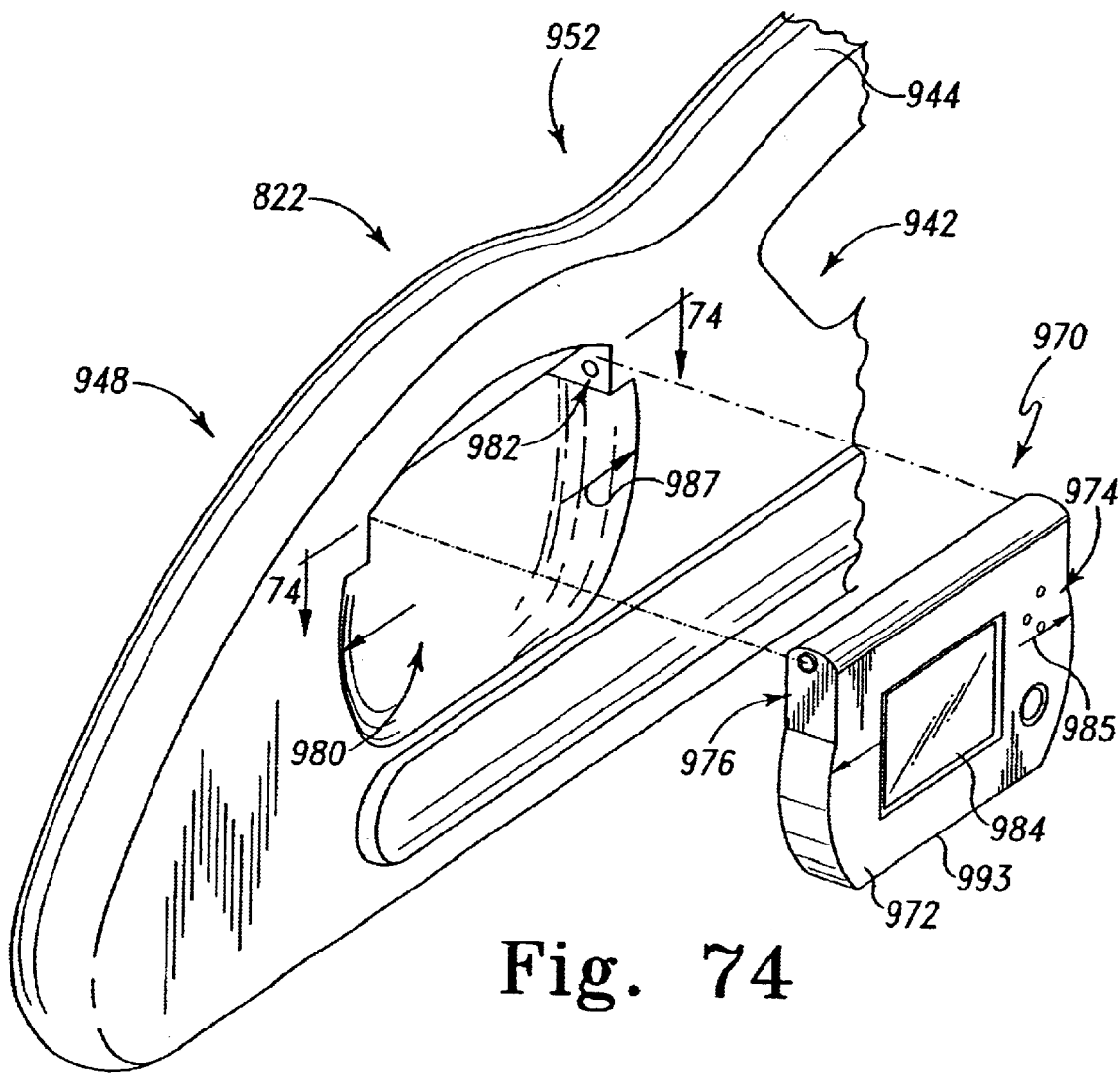
FIG. 74 is a partial perspective view of one of the foot end siderails of FIG. 61 showing the foot end siderail including a rail member having a pocket, the bed further including a controller positioned for insertion into the pocket.

Bed 810 further includes a control system configured to control various functions thereof. As shown in FIG. 74, the control system includes a controller 970 that is removably received by rail member 938 of foot end siderail 822 so that it can be removed from foot end siderail 822 and perform as a wireless remote control for controlling various functions of bed 810. For example, controller 970 is configured to control the raising and lowering of deck 814 and to control movement of head and seat sections 824, 826 of deck 814. Controller 970 is also configured to receive information from a caregiver related to a patient and to send and receive patient or bed-related data to a central computer for storage, tracking, and analysis.

According to alternative embodiments of the present disclosure, the controller is configured to control other features of the bed such as features of the mattress. Additional description of suitable electronics and other features of a controller is provided in U.S. Pat. No. 6,008,598, titled Hand-Held Controller For Bed and Mattress Assembly, filed Apr. 22, 1998, the disclosure of which is expressly incorporated herein by reference and U.S. Provisional Application Serial No. 60/202,284, titled Remote Control for a Hospital Bed, filed May 5, 2000, the disclosure of which is expressly incorporated by reference herein.

Figure 75:
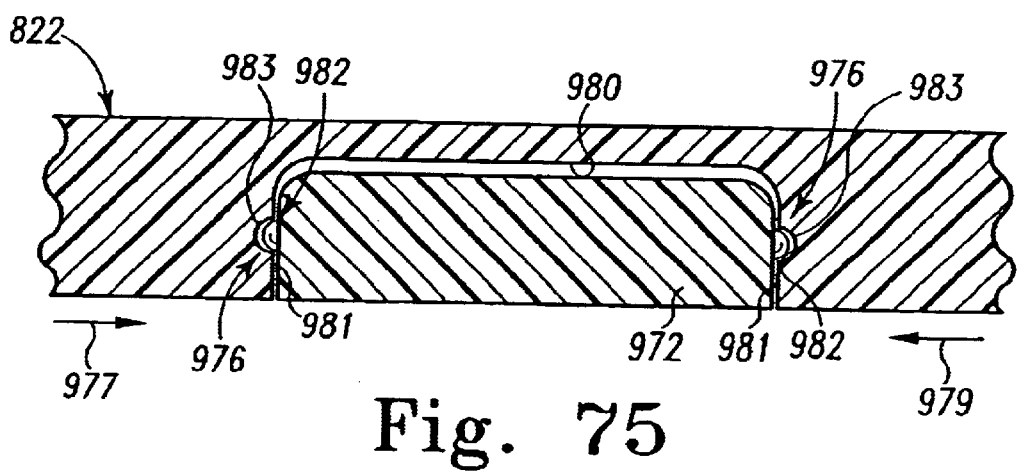
FIG. 75 is a cross-sectional view taken along line 75—75 of FIG. 74 showing the rail member including a pair of recesses and the controller including a pair of ball-detents aligned to fit within the recesses of the rail member to removably secure the controller in the pocket of the foot end siderail.

As shown in FIG. 74, controller 970 includes a housing 972, a speaker and microphone 974, and a pair of ball detents 976 coupled to side walls 978 of housing 972. Each rail member 938 of foot end siderails 822 includes a pocket 980 and a pair of recesses 982 configured to receive ball detents 976 as shown in FIGS. 74 and 75.

Ball detents 976 are spring biased outwardly to fit in recesses 982. To remove controller 970 from rail member 938, a user pulls on controller 970 and surfaces 983 defining recesses 982 force ball detents 976 inwardly in directions 977, 979 against the bias of the springs (not shown) to permit withdrawal of controller 970 from pocket 980. To couple controller 970 to either foot end siderail 822, ball detents 976 are aligned with recesses 982 and pushed into pocket 980 so that surfaces 981, 983 defining pocket 980 force ball detents 976 inwardly in directions 977, 979 against the bias of the springs until ball detents 976 are pushed into recesses 982 by the springs.

Ball detents 976 also pivotably couple housing 972 to each rail member 938. This coupling permits a user to read a touch control screen 984 of controller 970 and speak into microphone 974 better by titling a lower edge 993 of housing 972 upward. Control screen 984 is a touch screen configured to display information and receive touch commands from a user. According to alternative embodiments of the present disclosure, other configurations of couplers between the housing and the rail member are provided. For example, hooks, hook-and-loop type fasteners, snaps, a detachable hinge, or other devices known to those of ordinary skill in the art are provided to removably and/or pivotably couple the controller to the siderail. Additional description of a suitable touch control screen is provided in U.S. Pat. No. 5,715,548, entitled Chair Bed, to Weismiller et al., and U.S. patent application Ser. No. 09/187,825, entitled Controller For an Operating Room Table and Surface, to Borders, the disclosures of which are expressly incorporated by reference herein.

Housing 972 has a width 985 that is less than a width 987 of pocket 980 so that when controller 970 is positioned in pocket 980, controller 970 and surfaces 981, 983 cooperate to define hand holes 989, 991 as shown in FIG. 73. To tilt or remove controller 970, a caregiver inserts either of their hands or fingers into one of hand holes 989, 991 to grasp controller 970. Having grasped controller 970, the caregiver can then tilt controller 970 upward or pull on controller 970 to depress ball detents 976 and remove controller 970 from pocket 980. According to alternative embodiments of the present disclosure, the wireless remote controller is configured to couple to other barriers on the bed such as the head end siderails, headboard, or footboard.

Figure 76:
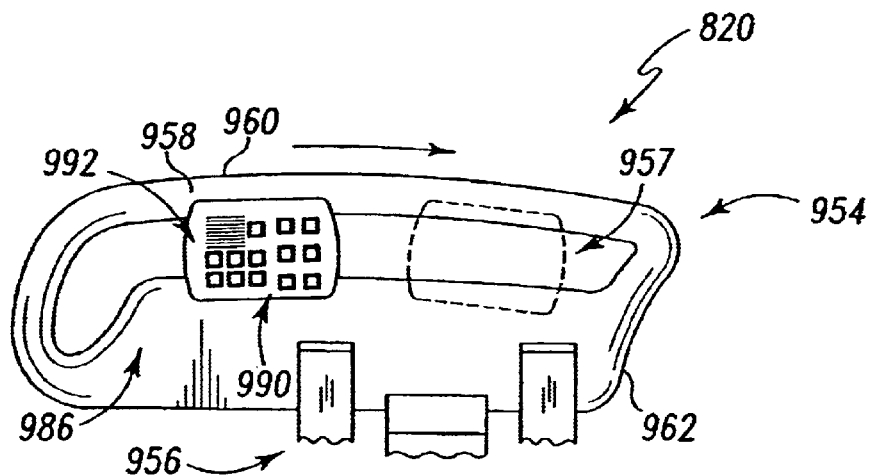
FIG. 76 is a side elevation view of one of the head end siderails showing the head end siderail including a longitudinal slot and the bed further including a controller positioned in the slot to slide along the length thereof.
Figure 78:
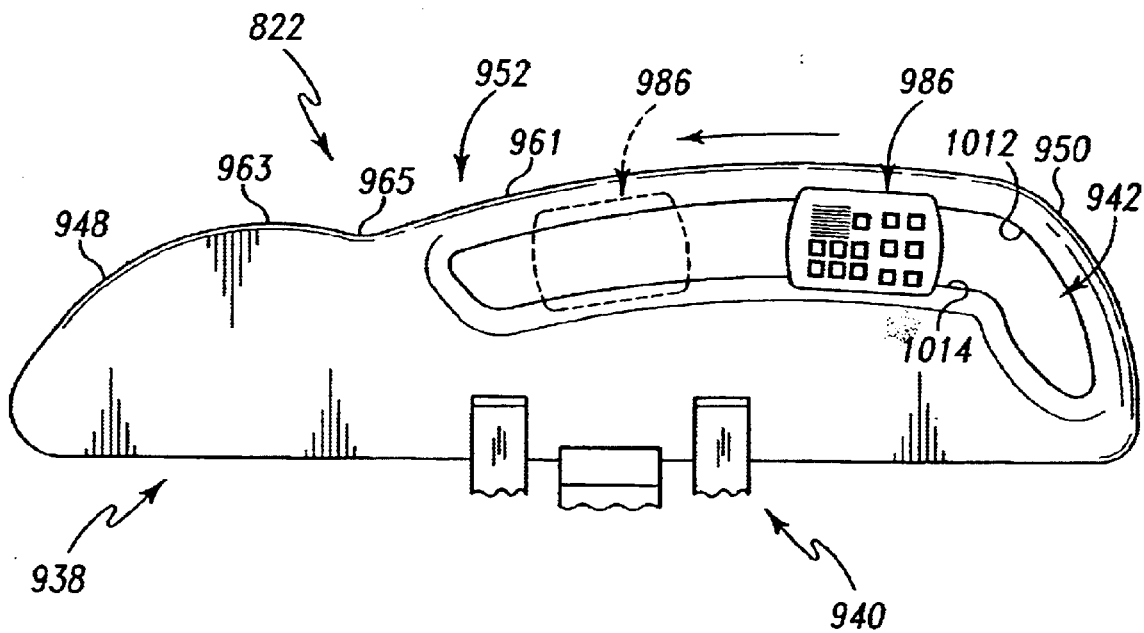
FIG. 78 is a side elevation view of one of the foot end siderails showing the foot end siderail including a longitudinal slot and the controller of FIG. 76 positioned in the slot to slide along the length thereof.
Figure 77:
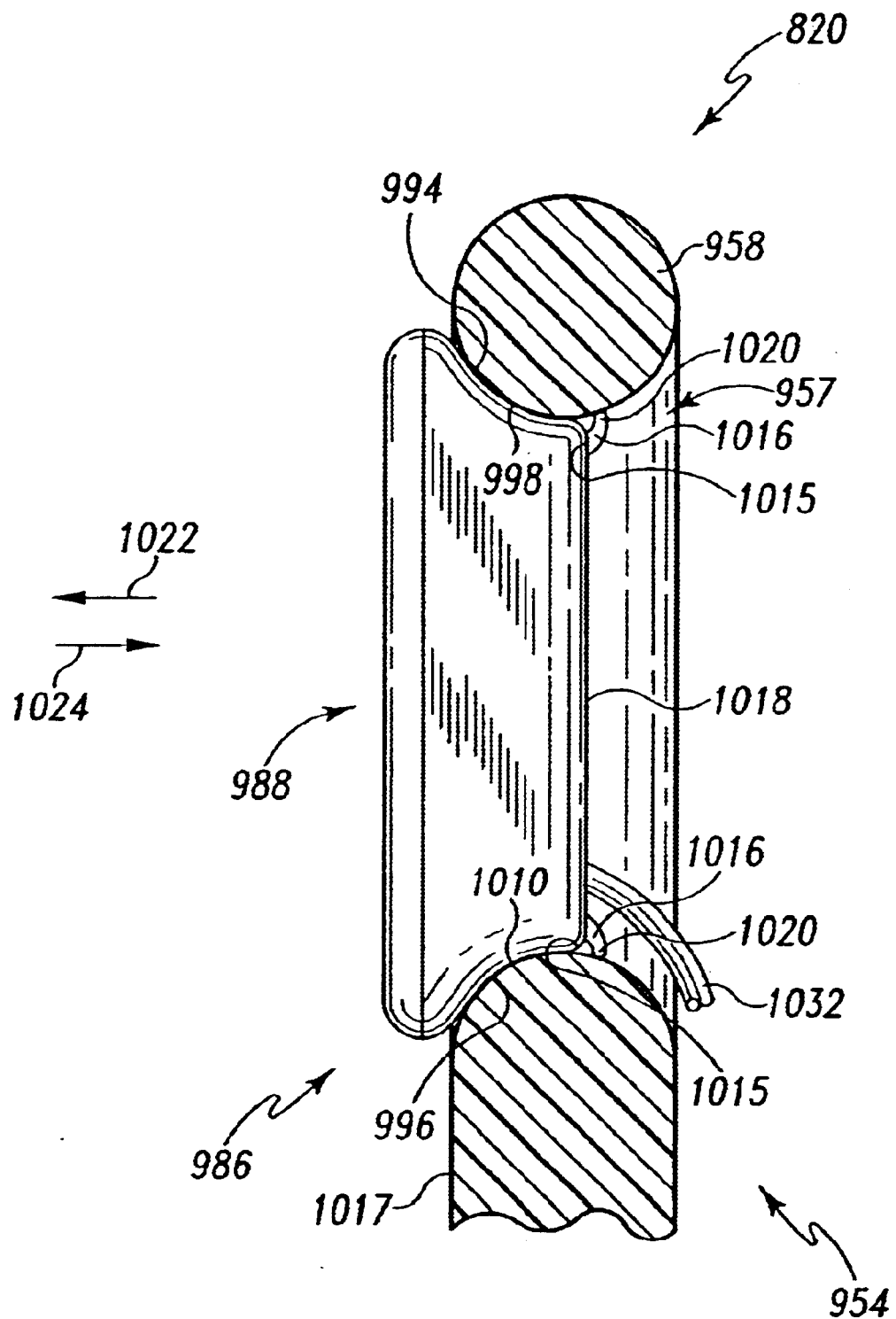
FIG. 77 is a cross-sectional view taken along line 77—77 of FIG. 76 showing the controller including a pair of tabs configured to removably and slidably couple the controller to the head end siderail.

As shown in FIGS. 76–78, the control system further includes a corded controller 986 configured to removably and slidably couple to head and foot end siderails 820, 822. Controller 986 includes a housing 988, a plurality of control buttons 990 for controlling various functions of bed 810, and a speaker 992 and microphone (not shown) for facilitating communication between a person positioned on bed 810 and a caregiver.

Controller 986 is configured to slide in either opening 957 of rail member 954 of head end siderail 820 or opening 942 of rail member 938 of foot end siderail 822. As shown in FIG. 76, controller 986 is configured to slide on rail member 954 between an infinite number of positions including a first position (shown in solid) and a second position (shown in phantom). Similarly, controller 986 is configured to slide on rail member 938 between an infinite number of positions including a first position (shown in solid in FIG. 78) and a second position (shown in phantom).

Because patients vary in size, one patient may find it more convenient to position controller 986 in one of the many available positions on either head or foot end siderails 820, 822 than another patient. Thus, various patients can position controller 986 in any of the infinite number of positions on any of head or foot end siderails 820, 822. Furthermore, a patient may decided to adjust the position of controller 986 if the configuration of deck 814 is changed. For example, if head section 824 of deck 814 is raised, a patient may desire to reposition controller 986.

As shown in FIG. 77, housing 988 of controller 986 includes a pair of spaced-apart concave surfaces 994, 996 that complement convex surfaces 998, 1010 of rail member 954 of head end siderail 820. Foot end siderail 822 also includes convex surfaces 1012, 1014 that are complemented by concave surfaces 994, 996. Thus, as shown in FIG. 77, a substantial portion of controller 986 is positioned within rail member 954 so that controller 986 maintains a relatively low profile compared to an inner surface 1017 of rail member 954 when positioned in rail member 954 to avoid interference with other components of bed 810 or other pieces of medical equipment. According to alternative embodiments of the present disclosure, the controller is positioned further in the opening formed in the rail member so that little or none of the controller extends beyond an inner surface of the rail member.

Controller 986 further includes four spaced-apart tabs or retainers 1016 configured to retain controller 986 in either opening 954, 957 (only two of the four tabs 1016 are visible in FIG. 77). Each tab 1016 is positioned near one of four corners 1015 of a back surface 1018 of housing 988 and has a distal end 1020 that contacts one of the convex surfaces 998, 1010, 1012, 1014.

Each tab 1016 is flexible so that when a patient pulls on controller 986 in direction 1022, tabs 1016 flex inwardly to permit distal ends 1020 to ride over the inner most portions of convex surfaces 998, 1010, 1012, 1014 so that tabs 1016 no longer retain controller 986 in the respective siderail 820, 822. To reposition controller 986 back in siderails 820, 822, the patient pushes controller in direction 1024 so that tabs 1016 ride back over the inner most portions of convex surfaces 998, 1010, 1012, 1014 so that tabs 1016 retain controller 986 in head and foot end siderails.

According to the presently preferred embodiment of the present disclosure, tabs 1016 are made of a flexible material such as rubber or plastic materials. According to alternative embodiments of the present disclosure, the tabs or retainers are pivotably coupled to the housing to provide movement of the distal ends of the tabs. According to another alternative embodiment of the present disclosure, ball detents are provided, such as those shown in FIG. 75, to removably retain the controller in the head and foot end siderails. According to other alternative embodiments of the disclosure, other retainers known to those of ordinary skill in the art are used to retain the controller in the siderails.

The respective pairs of convex surfaces 998, 1010, 1012, 1014 cooperate to define a rail or guide and concave surfaces 994, 996 and tabs 1016 cooperate to define a complementary formation configured to ride along the guide. According to alternative embodiments of the present disclosure, other configurations of guides and complementary formations are provided such as raised rails, channels, slots, or other configurations of guides and complementary formations known to those of ordinary skill in the art.

Figure 82:
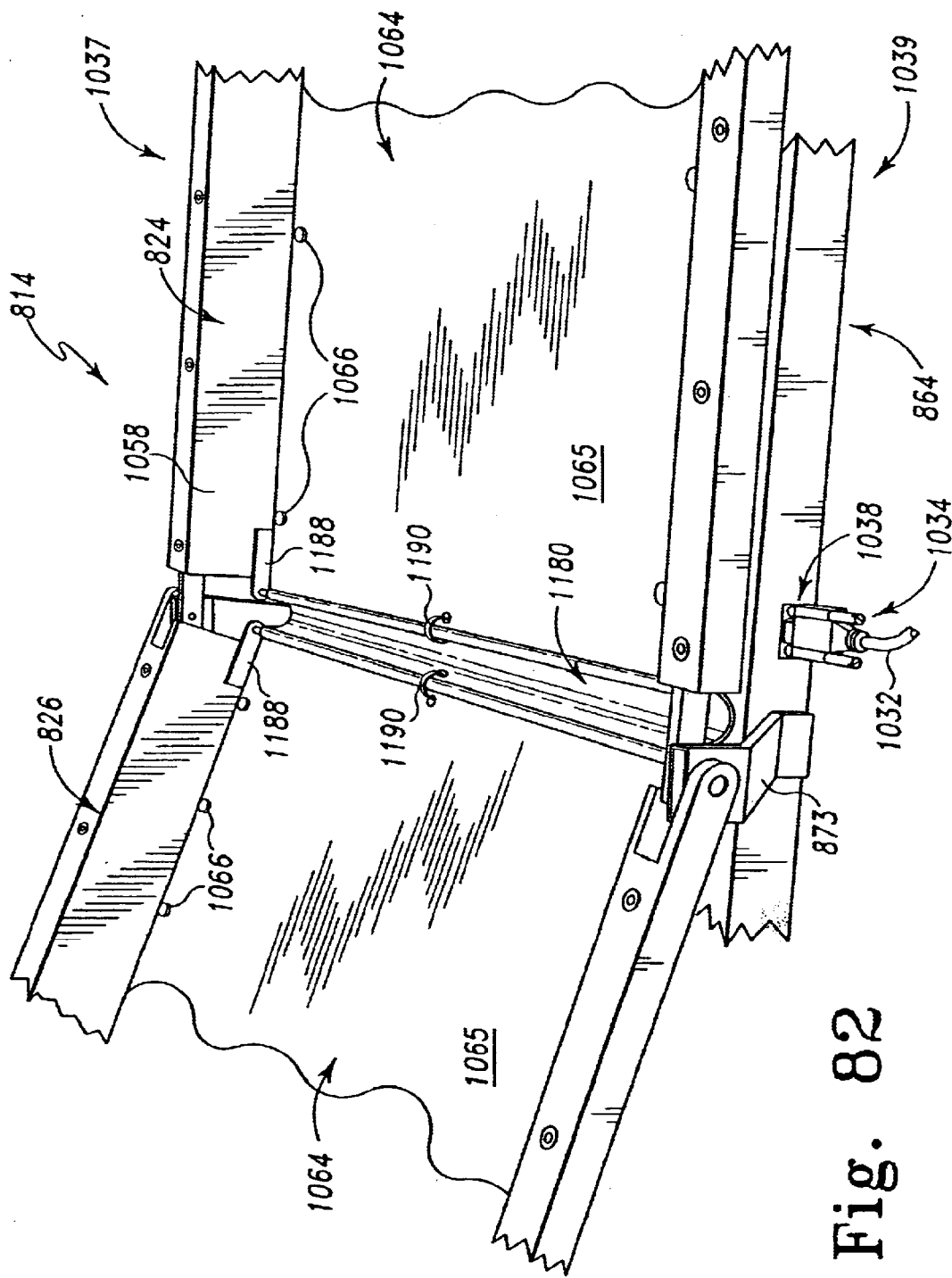
FIG. 82 is a perspective view of the deck and intermediate frame, with portions broken away, showing a spill guard positioned between the head section of the deck and the seat section of the deck.
Figure 84:
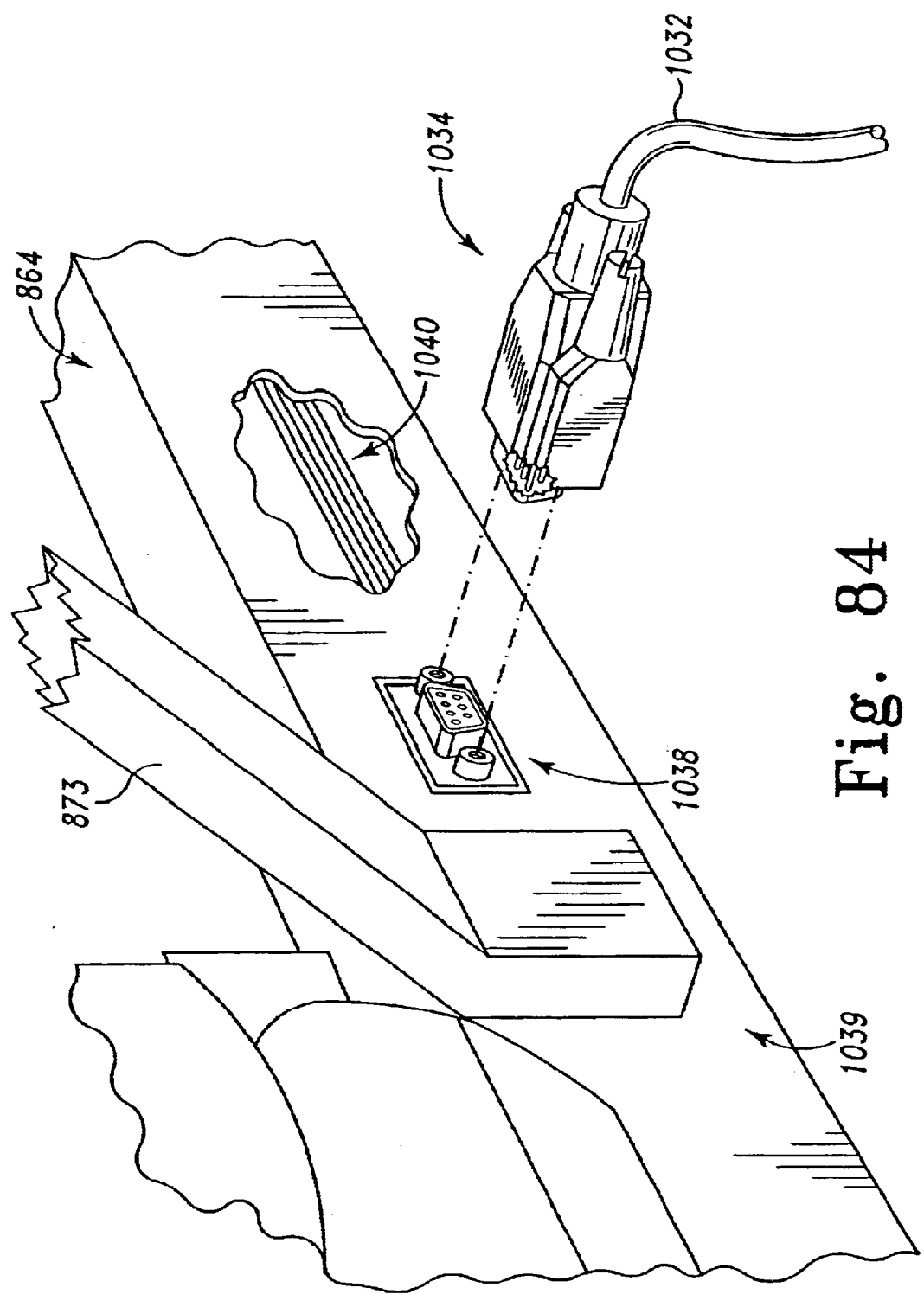
FIG. 84 is a perspective view of a portion of the intermediate frame showing the bed further including a male communications connector coupled to the intermediate frame and a female communications connector aligned to be coupled to the male communications connector.

As shown in FIG. 77, controller 986 further includes a cord 1032 that communicates electric signals to and from controller 986. As shown in FIGS. 82 and 84, cord 1032 includes a connector 1034 that couples to either of two connectors 1036, 1038 coupled to intermediate frame 864. According to the preferred embodiment of the disclosure, connector 1036 is coupled to a first side 1037 of bed 810 as shown in FIG. 61 and connector 1038 is coupled to an opposite second side 1039 of bed 810 as shown in FIGS. 82 and 84. A plurality of wires 1040 are coupled to each connector 1036, 1038 to communicate with the various electrically controlled devices of bed 810. Preferably, plurality of wires 1040 from each side 1037, 1039 meet at a junction (not shown) and then extend to the various electrically controlled devices.

Because two connectors 1036, 1038 are provided on opposite sides 1037, 1039 of bed 810, controller 986 can be plugged into either side 1037, 1039 of bed 810. Thus, if a patient or caregiver finds it more convenient to position controller 986 on the pair of head and foot end siderails 820, 822 on first side 1037 of bed 810, controller 986 can be plugged into connector 1036 without cord 1032 having to be strung over mattress 813. Similarly, if a patient or caregiver finds it more convenient to position controller 986 on the pair of head and foot end siderails 820, 822 on second side 1039 of bed 810, controller 986 can be plugged into connector 1038 without cord 1032 having to be strung over mattress 813. Thus, a corded controller is provided that can be removably coupled to either side of the bed without having to string the cord of the controller over the mattress of the bed.

As shown in FIG. 61, bed 810 further includes a plurality of pedals 1044 substantially similar to pedals 752. Pedals 1044 are provided to raise and lower deck 814 and to move deck 814, tilting and untilting head section 824 relative to intermediate frame 864, moving intermediate frame 864 between the Trendelenburg and Reverse Trendelenburg positions, and tilting and un-tilting seat section 826 relative to intermediate frame 864.

Figure 79:
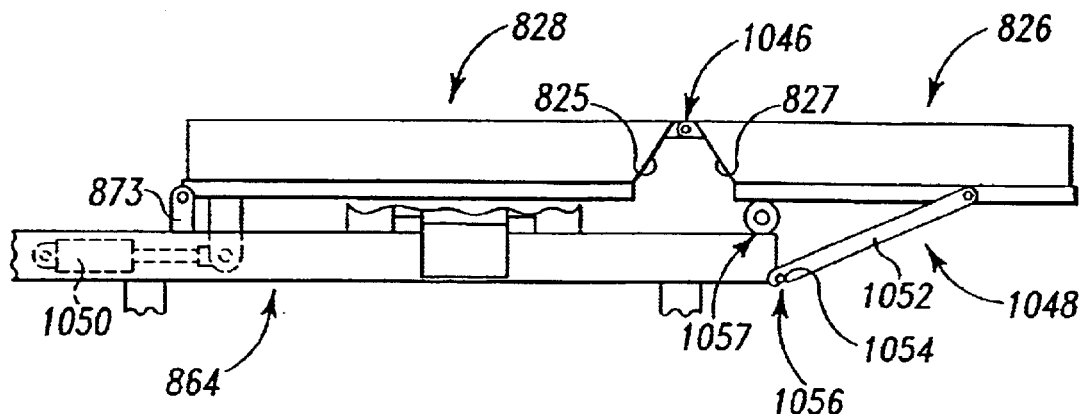
FIG. 79 is a side elevation view of a foot end of the hospital bed showing the deck including seat section pivotably coupled to the intermediate frame and a foot section pivotably coupled to the seat section, the bed further including an actuator coupled to the intermediate frame and the seat section, the foot section resting on a roller coupled to the intermediate frame, and a link coupled to the foot section and the intermediate frame.
Figure 80:
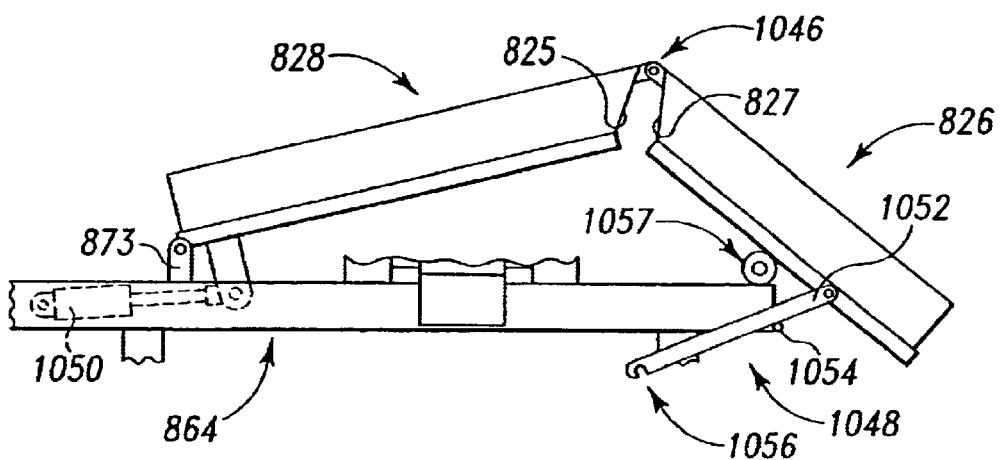
FIG. 80 is a view similar to FIG. 79 showing the actuator in an extended position tilting the seat section of the deck so that the foot section of the deck rolls on the roller and also assumes a tilted position.
Figure 81:
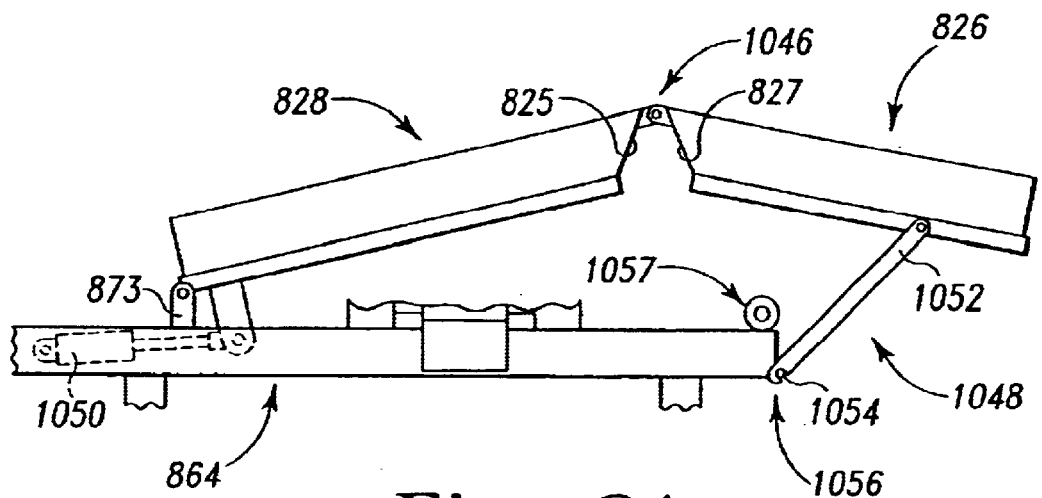
FIG. 81 is a view similar to FIG. 79 showing the actuator in the extended position and the seat section in the tilted position, the link being coupled to the intermediate frame to support the foot section is a raised position.

As previously mentioned, deck 814 includes several portions or sections 824, 828, 826, that can be tilted relative to intermediate frame 864. Head section 824 is positioned adjacent to headboard 816 and is pivotably coupled to upwardly extending flanges 873 of intermediate frame 864 as shown in FIG. 82. Seat section 826 is also pivotably coupled to upwardly extending flanges 873 of intermediate frame 864. Foot section 826 is pivotably coupled to seat section 826 by a hinge 1046 with footboard 818 to a foot end thereof as shown in FIGS. 79–81. Seat and foot sections 826, 828 have tapered ends portions 825, 827 providing clearance therebetween during titling of foot section 828 relative to seat section 826 as shown in FIG. 80. Thus, all sections 822, 826, 828 are pivotable relative to intermediate frame 864.

Hospital bed 810 further includes a tilt mechanism 1048 facilitating automatic tilting of seat and foot sections 826, 828 relative to intermediate frame 864 and foot section 828 relative to seat section 826. Tilt mechanism 1048 includes a tilt actuator 1050 coupled to intermediate frame 864 and seat section 826 and a link 1052 removably coupled to foot section 828 and pivotably coupled to intermediate frame 864. Intermediate frame 864 includes a pin 1054 received by a notch 1056 in link 1052 so that link 1052 is movable between a locked position, shown in FIGS. 79 and 81, and an unlocked position, shown in FIG. 80. These two positions provide two modes of titling between seat section 826 and foot section 828.

When in the locked position, link 1052 provides a rigid link between intermediate frame 864 and foot section 828. As tilt actuator 1050 is lengthened, seat section 826 pivots relative to intermediate frame 864 as shown in FIGS. 80 and 81. When link 1052 is in the locked position and tilt actuator 1050 is activated, foot section 828 moves upwardly relative to intermediate frame 864 as shown in FIG. 81 but, maintains a substantially horizontal orientation. According to alternative embodiments of the present disclosure, other orientations are provided.

When link 1052 is uncoupled from pin 1054 and tilt actuator 122 is activated, as shown in FIG. 80, foot section 828 rotates about a roller 1057 coupled to intermediate frame 864 so that a proximal end of foot section 828 is raised and a distal end of foot section 828 lowers. Thus, foot section 828 is movable relative to seat section 826 to maintain a substantially horizontal or other position, as shown in FIG. 81, when link 1052 is in the locked position and a tilted or other position, as shown in FIG. 81, relative to intermediate frame 864 when link 1052 is in the unlocked position.

According to alternative embodiments of the present disclosure, other configurations of linkage systems are provided to facilitate two modes of tilting the foot or other section of the deck relative to another section of the deck during movement of another section of the deck relative to the upper or other frame member. Such linkage systems include additional links, hinges, cables, brackets, flanges, or other members known to those of ordinary skill in the art.

Deck 814 is configured to support mattress 813. As shown in FIG. 82, sections 824, 826, 828 include angled side surfaces or walls 1058 similar to angled side walls 358 of deck 14. Head and seat sections 824, 826 of deck 814 include horizontal flanges 1060, 1062 coupled to respective angled side walls 1058.

Figure 83:
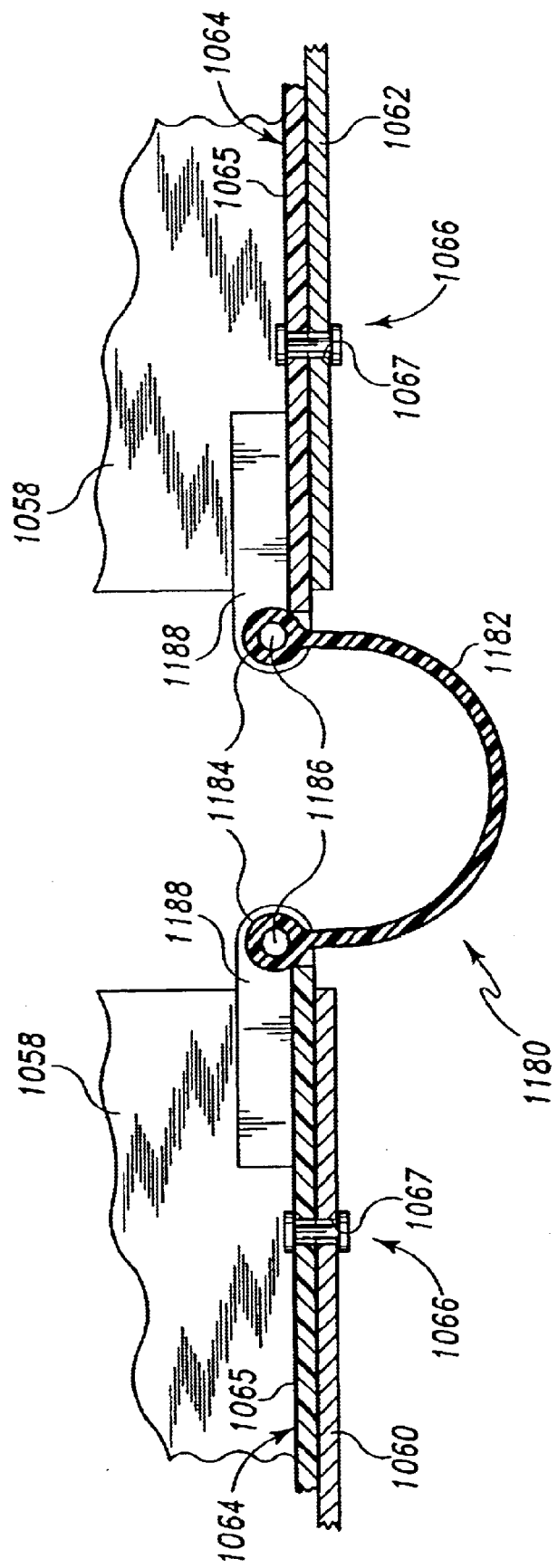
FIG. 83 is a cross-sectional view taken along line 83—83 of FIG. 82 showing the spill guard positioned between the head and seat sections of the deck.

Head and seat sections 824, 826 of deck 14 have flexible floors or bottoms that flex due to a patient's weight to provide additional compliance to bed 10 that would otherwise require additional foam in mattress 813. Each section 824, 826 includes a flexible panel 1064 coupled to horizontal flanges 1060, 1062 by fasteners 1066 as shown in FIGS. 82 and 83. Each fastener 1066 extends through a slot 1067 similar to slot 424 shown in FIG. 44. As weight is placed on flexible panels 1064, they bend downwardly and the outer edges of flexible panels 1064 are pulled inwardly. This movement permits panels 1064 to deflect approximately 2 inches. Flexible panels 1064 are made of compression molded glass mesh bonded by a hard thermoset resin. The preferred flexible panel is provided by Premix. According to alternative embodiments, flexible panels made of other materials are provided.

Flexible panel 1064 is radiolucent to facilitate taking X-rays of a patient lying in hospital bed 810. Furthermore, flexible panel 1064 has a substantially smooth wipeable surface 1065 to facilitate wiping or cleaning of deck 814. Thus, a smooth, flexible, and radiolucent deck is provided that permits X-raying a patient positioned in hospital bed 810 and is also relatively easy to clean. According to alternative embodiments of the present disclosure, the panel is rigid, rough, or non-radiolucent.

As shown in FIGS. 82 and 83, deck 814 includes a spill guard 1180 positioned between head and seat sections 824, 826. Spill guard 1180 is configured to capture bodily or other fluids that collect on head or seat sections 826, 824. During tilting of these sections 824, 826, these fluids run down panels 1064 and collect on spill guard 1180 to prevent contamination of bed components positioned thereunder.

Spill guard 1180 is made of a rubber material and includes a U-shaped body 1182 and a pair of rod-receiving sleeves 1184 coupled thereto as shown in FIG. 83. A pair of rods 1186 extend throughs sleeves 1186 and coupled to supports 1188 coupled to sidewalls 1058. A pair a ties 1190 are also provided to couple sleeves 1184 to respective panels 1064 as shown in FIG. 82.

Foot section 828 of deck 814 is extendable and retractable as shown in FIGS. 89 and 90 to move between first and second positions having first and second lengths 829, 831. A full description of foot section 828 is disclosed in U.S. patent application Ser. No. 09/120,125, filed Jul. 22, 1998, the disclosure of which is expressly incorporated by reference herein. According to alternative embodiments of the present disclosure other configurations of decks known to those of ordinary skill in the art are provided.

As shown in FIG. 88, hospital bed 810 includes multi-component mattress 813. Mattress 813 is similar to mattress 13 shown in FIGS. 40–42 except that foot section or portion 1068 includes a heel-pressure relief portion 1070. As shown in FIGS. 89–91, foot section 1068 includes an adjustable length or retractable foam portion 1072 having upwardly and downwardly facing surfaces 1075, 1077 including a plurality of longitudinally alternating transverse slots 1074 and a foam end portion 1076 coupled to the foot end of expandable portion 1072. As foot section 828 of deck 814 extends, each of the transverse slots 1074 widens to compensate for the extension. As foot section 828 retracts, slots 1074 narrow.

End portion 1076 is formed to include a cavity 1078 sized to receive cylindrical heel-pressure relief portion 1070. Preferably, heel-pressure relief portion 1070 includes an air bladder 1059 positioned in cavity 1078. An air supply 1080 including a valve 1082 is coupled to bladder 1059. According the preferred embodiment of the present disclosure, air supply 1080 is a compressor. According to alternative embodiments of the present disclosure, the air supply is a blower or other air supply known to those of ordinary skill in the art.

Heel-pressure relief portion 1070 is configured to relieve pressure under the heel of patient positioned on mattress 813. For example, during use, a patient's heel is positioned over portion 1070 as shown in FIGS. 89 and 90. Pressure-control valve 1082 is then moved from a first position to a second position to activate lowering of the pressure in bladder 1059 so that the patient's heel lowers until the patient's calves support more of the weight of the patient's lower legs. This transfer lowers the amount of pressure placed on the patient's heels to lower the potential for bed sores developing on the patient's heels. When heel-pressure relief is no longer required, valve 1082 is moved back to the first position to increase the pressure in bladder 1059 and raise the patient's heels to the normal position.

According to alternative embodiments of the present disclosure, other configurations of heel-pressure relief portions are provided. For example, according to one embodiment of the present disclosure, a substantially rectangular air bladder is provided. According to another embodiment, the cavity is left empty to provide a recess for the heel-pressure relief portions. According to another embodiment of the present disclosure, a foam member is provided in the cavity that has a lower ILD than the adjustable length foam portion to provide relief for the patient's heels.

As previously mentioned, foot section 828 of deck 814 is has an adjustable length so that it can be moved from a first position having a first length 1071 (as shown in FIG. 89) to a second position having a second length 1073 (as shown in FIG. 90). Preferably, the length of foot section 828 is adjusted depending upon the height of the patient positioned on mattress 813 so that the patient's foot is positioned adjacent to footboard 818. For example, as shown in FIG. 89, foot section 828 is extended to position the heels of a tall patient adjacent to footboard 818. Foot section 828 is retracted to position the heels of a shorter patient adjacent to footboard 818 as shown in FIG. 90. Thus, foot portion 1068 can be moved relative to the other portions of mattress 813 to position portion 1070 under the patient's heels.

Because the patient's heel is positioned adjacent to footboard 818, the patients heel is also positioned above heel-pressure relief portion 1070 to provide heel-pressure relief, if necessary. Thus, according to the present disclosure, a heel-pressure relief portion is provided that can be moved under the patient's heel to provided heel-pressure relief.

According to the preferred embodiment of the present disclosure, the length of foot section 828 and foot portion 1068 of mattress 813 corresponds to the position of head section 824 and the head portion of mattress 813. For example, if head section 824 is raised to the titled position as shown in FIG. 115, foot section 828 of deck 814 automatically extends by a distance 1079. If head section 824 is lowered, foot section 828 is automatically retracted to it's pre-extended position. By corresponding the extension and retraction of foot portion 1068 of mattress 813 with the movement of head section 824 of deck 814, the patient's foot is maintained above heel-pressure relief portion 1070. Furthermore, if footboard 818 is used as a foot prop, the patient's foot is maintained at a steady distance relative to footboard 818 during raising and lowering of head section 824.

According to the preferred embodiment of the present disclosure, distance 1079 is approximately 4.0 inches (10.16 centimeters) for all patients regardless of their height or weight. According to alternative embodiments of the present disclosure, the foot section is extended by more or less than this distance depending on specifics, such as height or weight, of a particular patient.

A controller 1081 is provided that corresponds the movement of the foot section 828 with movement of head section 824. When a patient or caregiver activates controller 1081 to raise head section 824, controller 1081 simultaneously moves foot section 826 to the extended position shown in FIG. 115 and raises head section 828 to the position shown in FIG. 115. When a patient or caregiver activates controller 1081 to lower head section 824, controller 1081 simultaneously lowers head section 824 and retracts foot section 828. According to alternative embodiments, correspondence of the movement of the foot section follows or proceeds movement of the head section.

According to a preferred embodiment of the present disclosure, controller 1081 is electrical and controls extension of actuators (electric, pneumatic, hydraulic, etc.) associated with the head and foot sections. According to an alternative embodiment of the present disclosure, the controller is mechanical and includes components such as links, cables, belts, or other components known to those of ordinary skill in the art for coordinating movement of components relative to one another.

According to the preferred embodiment of the present disclosure, controller 1081 includes a head section sensor 1083 configured to detect the position of head section 824 and a foot section sensor 1089 configured to detect the position of foot section 828. Controller 1081 uses the position information provided by sensors 1083, 1089 to determine when foot section 828 has moved far enough in response to movement of head section 824.

When foot section 828 is initially adjusted to position heel-pressure relief portion 1070 under the patient's heels, controller 1081 stores the positions of foot section 828 and head section 824 as detected by sensors 1083, 1089 as initial head and foot sections reference points. When head section 824 is raised or lowered, controller 1081 determines the degree of movement of head section 824 from the initial head section reference point and moves foot section 828 a proportional amount from the foot section reference point. When head section 824 is raised or lowered again, controller again determines the degree of movement from the initial head section reference point and moves the foot section a proportional amount from the initial foot section reference point. According to the preferred embodiment of the present disclosure, the sensors are potentiometers. According to alternative embodiments of the present disclosure, other sensors known to those of ordinary skill in the art are provided.

Preferably, the degree of automatic extension of foot section 826 is a function of the angle of head section 824. The further up head section 824 is raised from the initial head section reference point, the more foot section 826 is extended from the initial reference point so that heel-pressure relief portion is continuously positioned under the patient's heel throughout the range of motion of head section 824. The further down head section 824 is lowered from the initial head section reference point, the more foot section 826 is retracted from the initial foot section reference point so that heel-pressure relief portion 1070 is continuously positioned under the patient's heel throughout the range of motion of head section 824.

According to alternative embodiments of the present disclosure, other configurations of adjustable length portions of the foot portion of the mattress are provided with or without heel-pressure relief bladders, such as other configurations include combinations of foam, air bladders, fluidized bladders, or other configurations of mattress portions known to those of ordinary skill in the art.

Figure 85:
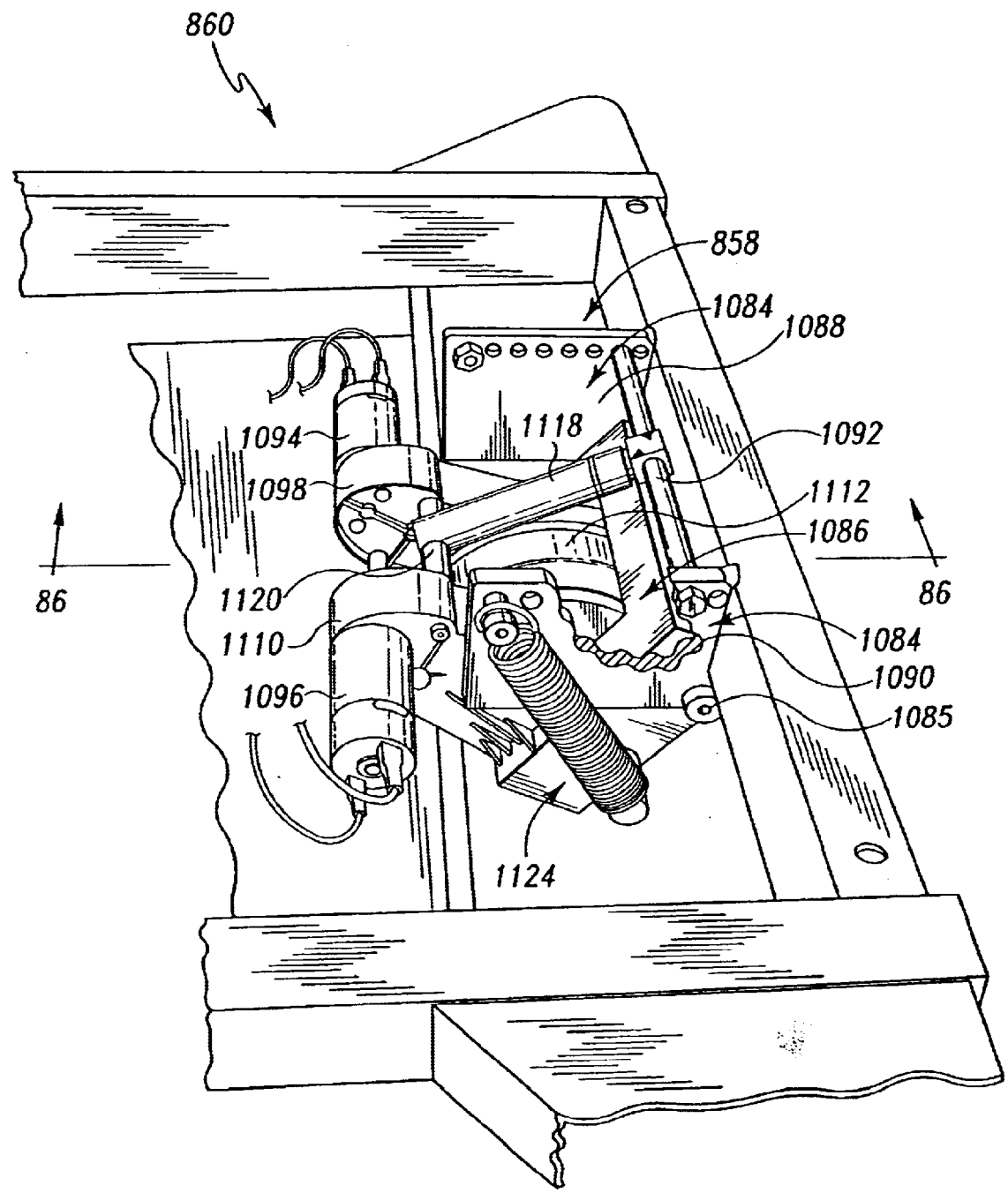
FIG. 85 is a perspective view of a propulsion device coupled to the base frame.
Figure 86:
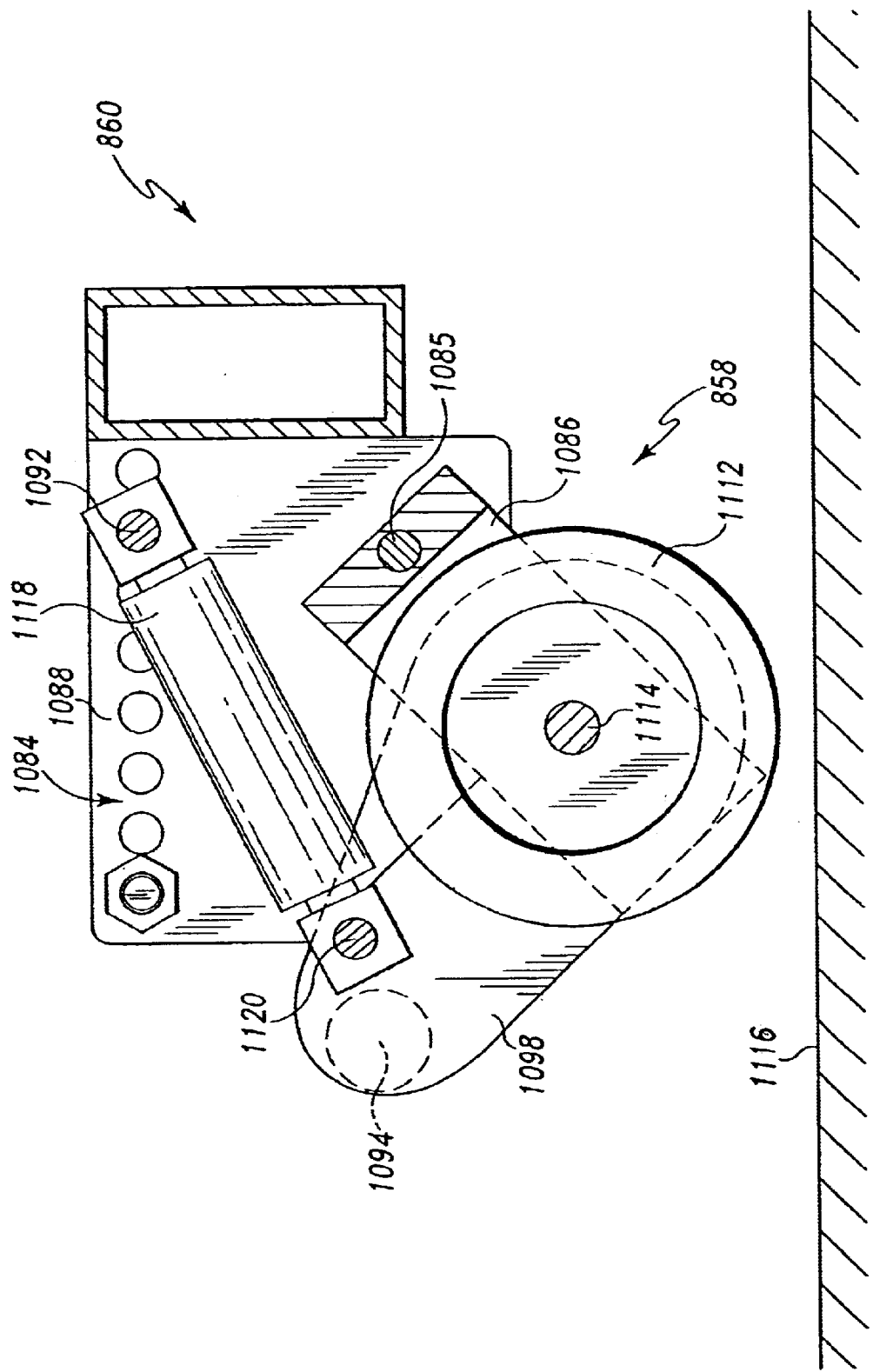
FIG. 86 is a cross-sectional view taken along line 86—86 of FIG. 85 showing the propulsion device including a wheel and an actuator in a retracted position supporting the wheel in a position spaced apart from the floor.
Figure 87:
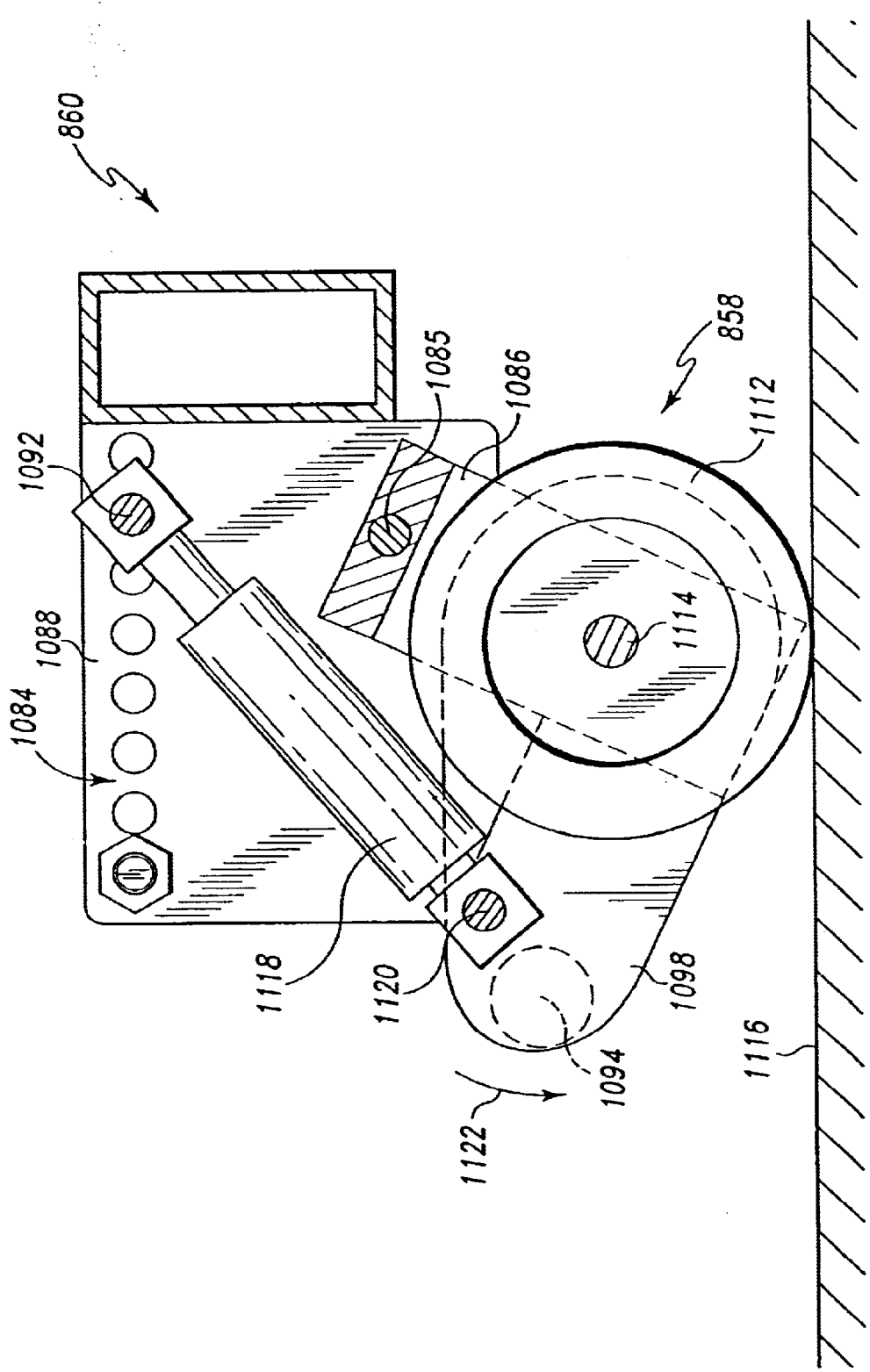
FIG. 87 is a view similar to FIG. 86 showing the actuator in an extended position so that the wheel contacts the floor.

Referring now to FIGS. 85–87, propulsion device 858 is provided to assist caregivers in moving bed 810 about a care facility. Propulsion device 828 includes stationary frame 1084 coupled to base frame 860 of bed frame 812 and a U-shaped rotatable frame 1086 rotatably coupled to stationary frame 1084 by shaft 1085. Stationary frame 1084 includes a pair of spaced apart plates 1088, 1090 and a pivot rod 1092 extending between plates 1088, 1090 as shown in FIG. 85.

Propulsion device 858 further includes a pair of motors 1094, 1096 coupled to U-shaped frame 1086 by a pair of gear boxes 1098, 1110 and a wheel 1112 rotatably coupled to U-shaped frame 1086 by a shaft 1114 as shown in FIG. 86. Gear boxes 1098, 1110 are coupled to shaft 1114 to transmit power thereto from motors 1094, 1096.

As shown in FIG. 86, when propulsion device 858 is not in use, wheel 1112 is spaced apart from floor 1116. Propulsion device 858 includes an actuator 1118 coupled to pivot rod 1092 and gear boxes 1098, 1110 by another pivot rod 1120. To move wheel 1112 into contact with floor 1116, actuator 1118 is extended, as shown in FIG. 87, to rotate gear boxes 1098, 1110, U-shaped frame 1086, and wheel 1112 in direction 1122 about shaft 1085. Once wheel 1112 is in contact with floor 1116, motors 1094, 1096 are activated to drive wheel 1112 through gear boxes 1098, 1110.

After the caregiver has positioned bed 810 in its desired location, wheel 1112 is raised by retracting actuator 1118. As shown in FIG. 85, propulsion device 858 further includes an extension spring 1124 coupled to U-shaped frame 1086 and stationary frame 1084. When wheel 1112 is lowered, spring 1124 is extended to add tension. This tension assists actuator 1118 in raising wheel 1112.

As shown in FIG. 62, control buttons 856 includes an a set of buttons 1111, 1113, 1115, 1117 configured to control operation of propulsion device 858. Button 1111 is an on/off button configured to enable and disable propulsion device 858. When button 1111 is moved to an on position, actuator 1118 is extended to lower wheel 1112. When button 1111 is moved to an off position, actuator 1118 is retracted to raise wheel 1112. Button 1113 is a forward/reverse button that controls the direction in which wheel 1112 rotates. When button 1113 is moved to a forward position, wheel 1112 is enabled to rotate in a direction pushing bed 810 in a first or forward direction. When button 1113 is moved to a reverse position, wheel 1112 is enabled to rotate in a direction pushing bed 810 in a second or reverse direction.

Button 1115 is a speed control button configured to regulate the speed of rotation of wheel 1112. When button 1115 is in a hi-speed position, wheel 1112 is enabled to rotate a first or high speed. When button 1115 is in a low-speed position, wheel 1112 is enabled to rotate a second or low speed. According to an alternative embodiment of the present disclosure, the speed control button is configured to have an infinite number of settings to provide infinite variability in the wheels operating speed.

Button 1117 is a go/no-go button that activates and deactivates rotation of wheel 1112. When button 1117 is moved to a go position, power is applied to motors 1094, 1096 and wheel 1112 rotates at the designated speed and in the designated direction. When button 1117 is moved to a no-go position, power is cut from motors 1094, 1096. If button 1111 is not moved to the on position, power will not be applied to motors 1094, 1096 regardless of the position of button 1117.

According to the preferred embodiment of the present disclosure, wires are provided that extend through headboard 816 from buttons 1111, 1113, 1115, 1117 to propulsion device 858. At a lower end of headboard 816, connectors (not shown) are provided on the wires to aid coupling and uncoupling of headboard 816 to frame 812. The connectors provide a coupling between portions of the wires in headboard 816 and the remainder of the wires positioned on frame 812 to facilitate quick uncoupling and re-coupling of these wires when headboard 816 is uncoupled and coupled to frame 812. Additional description of suitable connectors is provided in U.S. patent application Ser. No. 09/264,174, titled Patient Position Detection Apparatus For a Bed, filed Mar. 5, 1999, to Dixon et al., the disclosure of which is expressly incorporated by reference herein.

Figure 92:
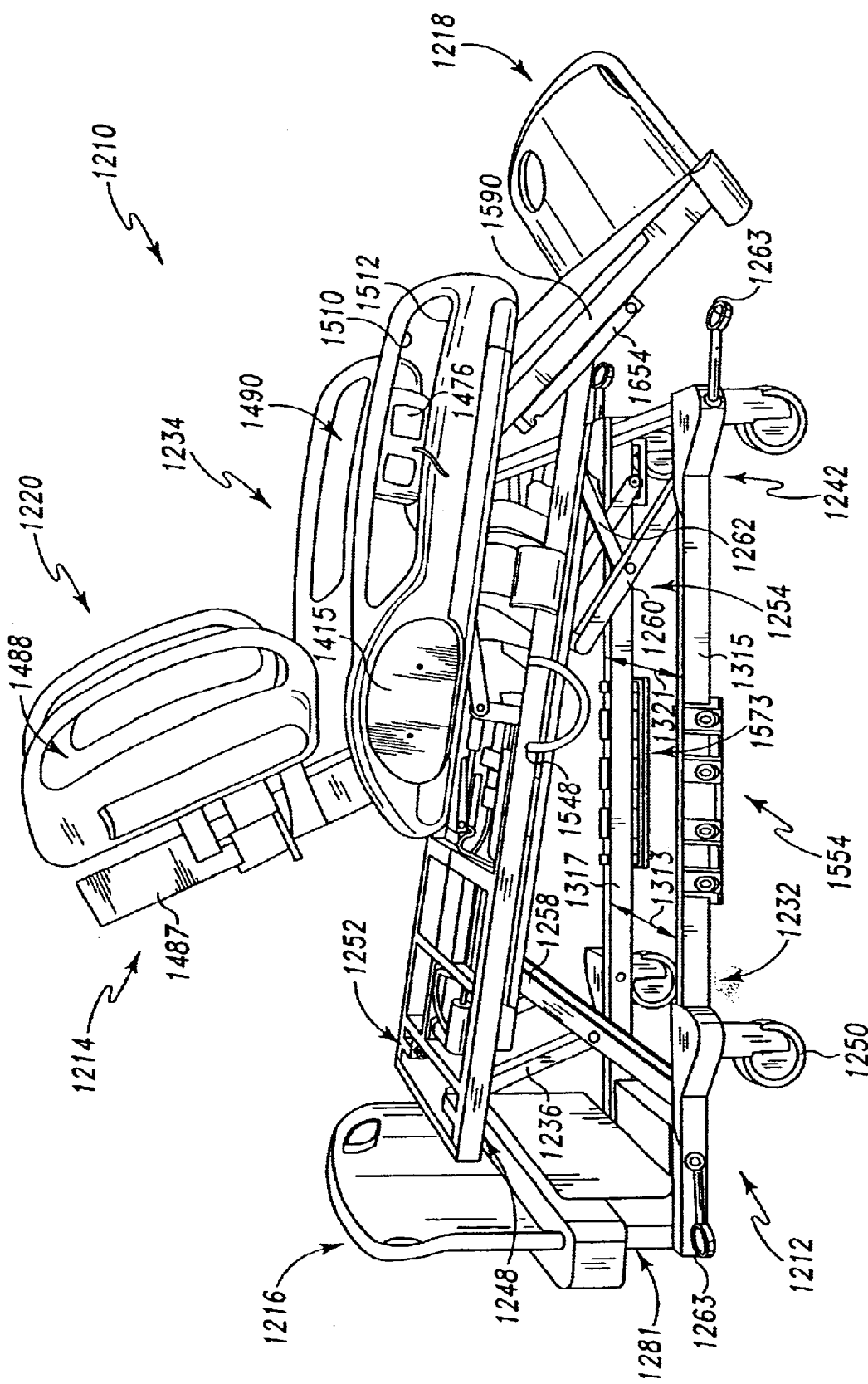
FIG. 92 is a perspective view of another alternative embodiment hospital bed showing the hospital bed including a frame having a base frame supported by a plurality of casters, a weigh frame, and a pair of support arms positioned between the weigh frame and the base frame, a headboard coupled to the base frame, a footboard coupled to the deck, and four foot pedal controls coupled to the base frame.

As shown in FIG. 92, another hospital bed 1210 is provided including a frame 1212 positioned on the floor, a deck 1214 coupled to frame 1212, a mattress 1230 positioned on deck 1214, a headboard 1216 coupled to frame 1212, a footboard 1218 coupled to deck 1214, a pair of head end siderails 1220 coupled to deck 1214, and a pair of foot end siderails 1234 coupled to frame 1212. Frame 1212 is configured to raise and lower deck 1214 relative to the floor and to move deck 1214 to the Trendelenburg position and the Reverse Trendelenburg position.

As shown in FIG. 92, frame 1212 includes a rectangular base frame 1232, an upper frame member or intermediate frame 1252, a linkage system 1254 coupled to intermediate and base frames 1252, 1232 to permit relative motion therebetween, and a rectangular weigh frame 1248 coupled to intermediate frame. Bed 1210 further includes a plurality of wheels or casters 1250 coupled to base frame 1232 to permit hospital bed 1210 to be rolled about a care facility and an actuator system 1256 providing power to actuate linkage system 1254 and move intermediate frame 1252 and weigh frame 1248 relative to base frame 1232.

Hospital bed 1210 further includes a caster braking system substantially similar to caster braking system 868 of hospital bed 810. The caster braking system includes a pair of caster-brake links 1251 extending through hollow base frame 1232. The caster braking system interconnects each caster 1250 to provide simultaneous braking of casters 1250. To simultaneously brake casters 1250, the caregiver steps on one of foot brake pedals 1263 and the caster braking system locks casters 1250 against rolling.

Linkage system 1254 includes a pair of head links 1258 pivotably coupled to a head end 1244 of base frame 1232 and slidably coupled to intermediate frame 1252, a pair of head end guide links 1236 pivotably coupled to respective head links 1258 and pivotably coupled to intermediate frame 1252 at a fixed pivot point, a pair of foot links 1260 slidably coupled to base frame 1232 and slidably coupled to intermediate frame 1252, and a pair of foot end guide links 1262 pivotably coupled to respective foot links 1260 and pivotably coupled to intermediate frame 1252 at a fixed pivot point.

Figure 94:
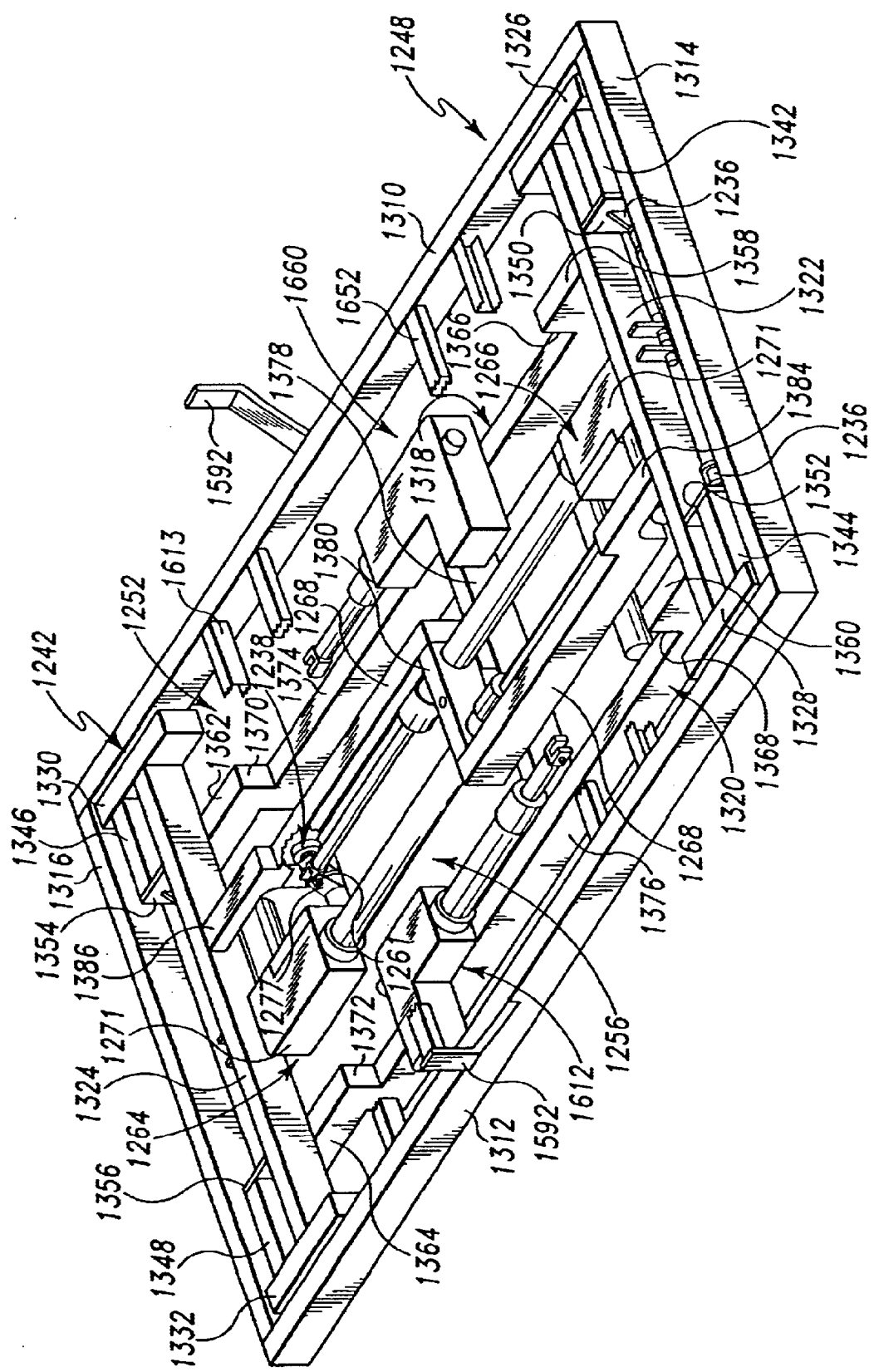
FIG. 94 is a perspective view of the weigh frame and intermediate frame.
Figure 95:
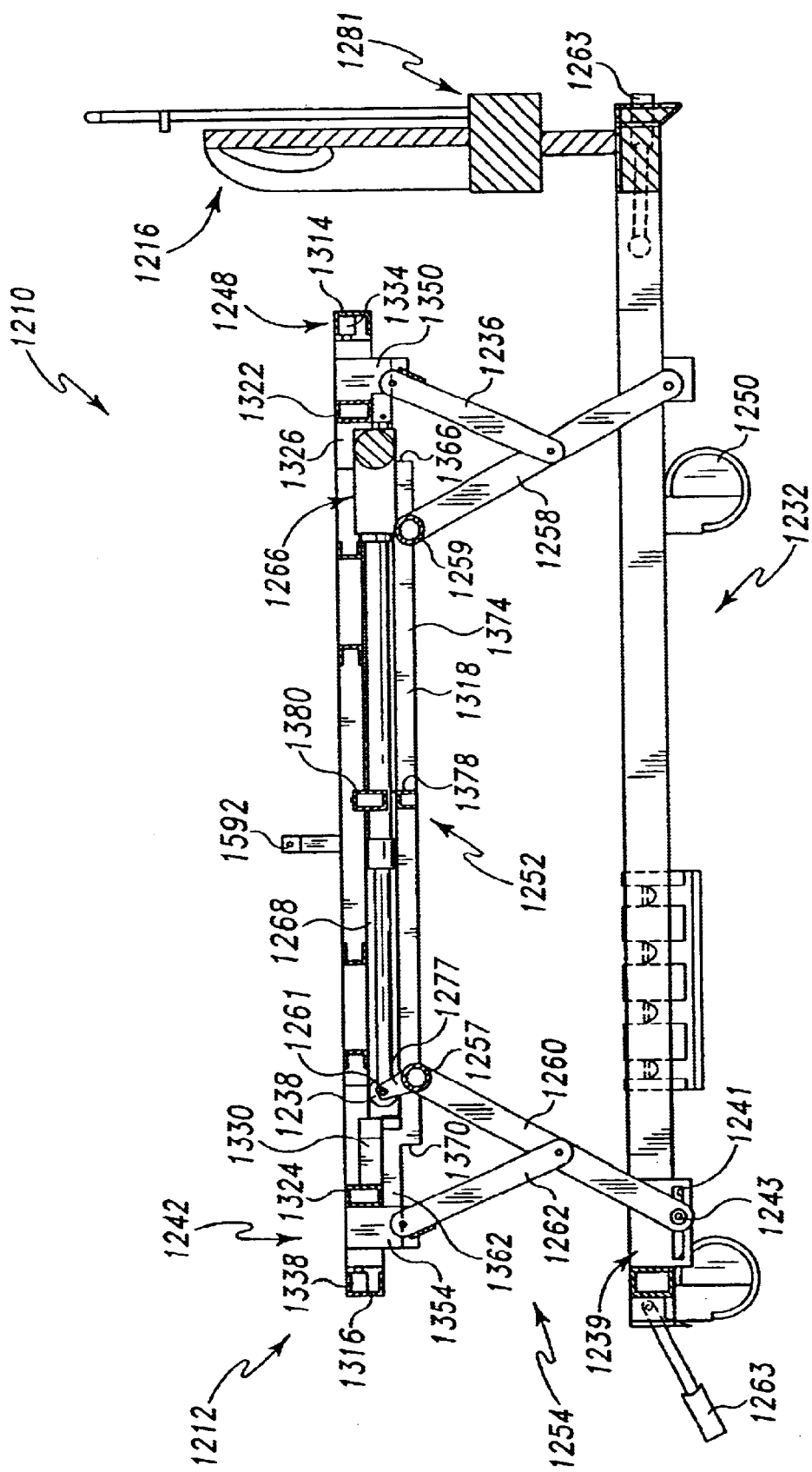
FIG. 95 is side elevation view the hospital bed of FIG. 92 taken along line 95—95 of FIG. 93 showing the weigh frame and intermediate frame supported by the lift arms in a raised position.

As shown in FIGS. 94 and 95, linkage system 1254 further includes rollers 1238 that ride on intermediate frame 1252 and pins 1261 coupling rollers 1238 to head and foot links 1258, 1260 to rotatably couple rollers 1238 to the upper ends of head and foot links 1258, 1260. Intermediate frame 1252 includes a pair of channel members 1268 sized to receive rollers 1238 to permit sliding of head and foot links 1258, 1260 along intermediate frame 1252 during raising and lowering of intermediate frame 1252 relative to base frame 1230.

Linkage system 1254 also includes a plate 1239 including a slot 1241 sized to receive a pin 1243 coupled to respective lower ends of foot end links 1260 as shown in FIG. 95. Pins 1243 slide in slots 1241 during movement of intermediate frame 1252 relative to base frame 1232 to provide an extra degree of freedom to help prevent binding of linkage system 1254.

Head end guide links 1236 restrict the motion of head links 1258 such that the pivot point between head links 1258 and intermediate frame 1252 is restrained to move vertically without moving horizontally. This restriction prevents horizontal movement of intermediate frame 1252 relative to base frame 1232 during raising and lowering of intermediate frame 1252. This restrained movement prevents intermediate frame 1252 from moving through an arch while moving between the upper and lower positions so that intermediate frame 1252 can be raised and lowered without requiring additional hospital room for clearance. Similarly, foot end guide links 1262 restrict the motion of foot links 1260 such that the pivot point between foot links 1260 and intermediate frame 1252 is restrained to move vertically without moving horizontally. Additional description of a similar motion can be found above for frame 12 of bed 10.

Actuator system 1256 provides the force and power necessary to raise and lower intermediate frame 1252. Actuator system 1256 includes a head link actuator 1264 coupled to head links 1258 and intermediate frame 1252 and a foot link actuator 1266 coupled to foot links 1260 and intermediate frame 1252. Actuator 1264 is coupled to head links 1258 through an extension link 1275 that is rigidly coupled to a cross strut 1259 which extends between and is rigidly coupled to each of head links 1258.

Similarly, actuator 1266 is coupled to foot links 1260 through an extension link 1277 that is rigidly coupled to a cross strut 1257 which extends between and which is rigidly coupled to each of foot links 1260. Cross struts 1259, 1257 coordinate the simultaneous movement of respective head and foot links 1258, 1260.

Pins 1261 are provided to pivotably couple actuators 1264, 1266 to extension links 1275, 1277. Rollers 1238 are also coupled to pins 1261 to guide movement of extension links 1275, 1277 and cross struts 1259, 1257 and head and foot links 1258, 1260 during actuation of actuators 1264, 1266.

Actuators 1264, 1266 have expandable lengths to adjust the angular position of head and foot links 1258, 1260 relative to intermediate frame 1252 so that head and foot ends 1253, 1255 of intermediate frame 1252 can be raised or lowered. Each of actuators 1264, 1266 is preferably an electric linear actuator having respective cylinder bodies 1267, cylinder rods 1269, and motors 1271 that operate to extend and retract cylinder rods 1269 relative to cylinder bodies 1267 from a fully extended position to a fully retracted position and an infinite number of positions therebetween. Cylinder rods 1269 are each pivotably coupled to respective extension links 1275, 1277 by pins 1261 and motors 1271 are each pivotably coupled to struts 1322, 1324 included in intermediate frame 1252 as shown, for example, in FIG. 94.

Each motor 1271 is electrically coupled to an electric power source 1281 coupled to base frame 1232. Power source 1281 includes a battery (not shown) and a plug (not shown). When bed 1210 is positioned in a location near a wall outlet, the plug is plugged into the wall outlet to provide power from operating motors 1271 and the other functions of bed 1210 and for recharging the batteries. When power source 1281 is unplugged from the wall outlet, the batteries provide the necessary operating power for bed 1210.

Actuators 1264, 1266 are available from LINAK U.S. Inc. of Louisville, Ky. Each actuator 1264 includes a power screw (not shown) that translates the rotational motion and power of motors 1271 into the linear motion and power of cylinder rods 1269. A screw nut (not shown) is provided that is coupled to cylinder rod 1269. The screw nut engages the power screw positioned in cylinder body 1267. Motor 1271 turns the power screw in one direction to push the screw nut away from motor 1271 and extend cylinder rod 1269 and turns the power screw in an opposite direction to pull the nut toward motor 1271 and retract cylinder rod 1269. According to alternative embodiments of the present disclosure, other configurations of actuators are provided such as pneumatic actuators with electrical or pneumatic controls, hydraulic actuators with electrical or hydraulic controls, motors with links, pulleys, or cables, or any other configurations of linear and non-linear actuators known to those of ordinary skill in the art.

When head and foot link actuators 1264, 1266 are actuated simultaneously, such that each actuator 1264, 1266 extends, intermediate frame 1252 raises away from base frame 1232. When head and foot link actuators 1264, 1266 are actuated simultaneously, such that each actuator 1264, 1266 retracts, intermediate frame 1252 lowers toward base frame 1232. When both actuators 1264, 1266 retract or extend at approximately the same rate, intermediate frame 1252 is maintained in a generally horizontal orientation and does not "swing" outwardly or inwardly relative to base frame 1232.

When head link actuator 1264 is activated and foot link actuator 1266 is maintained at a constant length, intermediate frame 1252 moves to the Trendelenburg position (not shown) similar to that shown for bed 10 in FIG. 5 so that head end 1253 of intermediate frame 1252 is lowered and foot end 1255 of intermediate frame 1252 is slightly raised. When the foot link actuator 1266 is activated and head link actuator 1264 is maintained at a constant length, intermediate frame 1252 moves to the Reverse Trendelenburg position so that foot end 1255 of intermediate frame 1252 lowers and head end 1253 of intermediate frame 1252 slightly raises.

Figure 96:
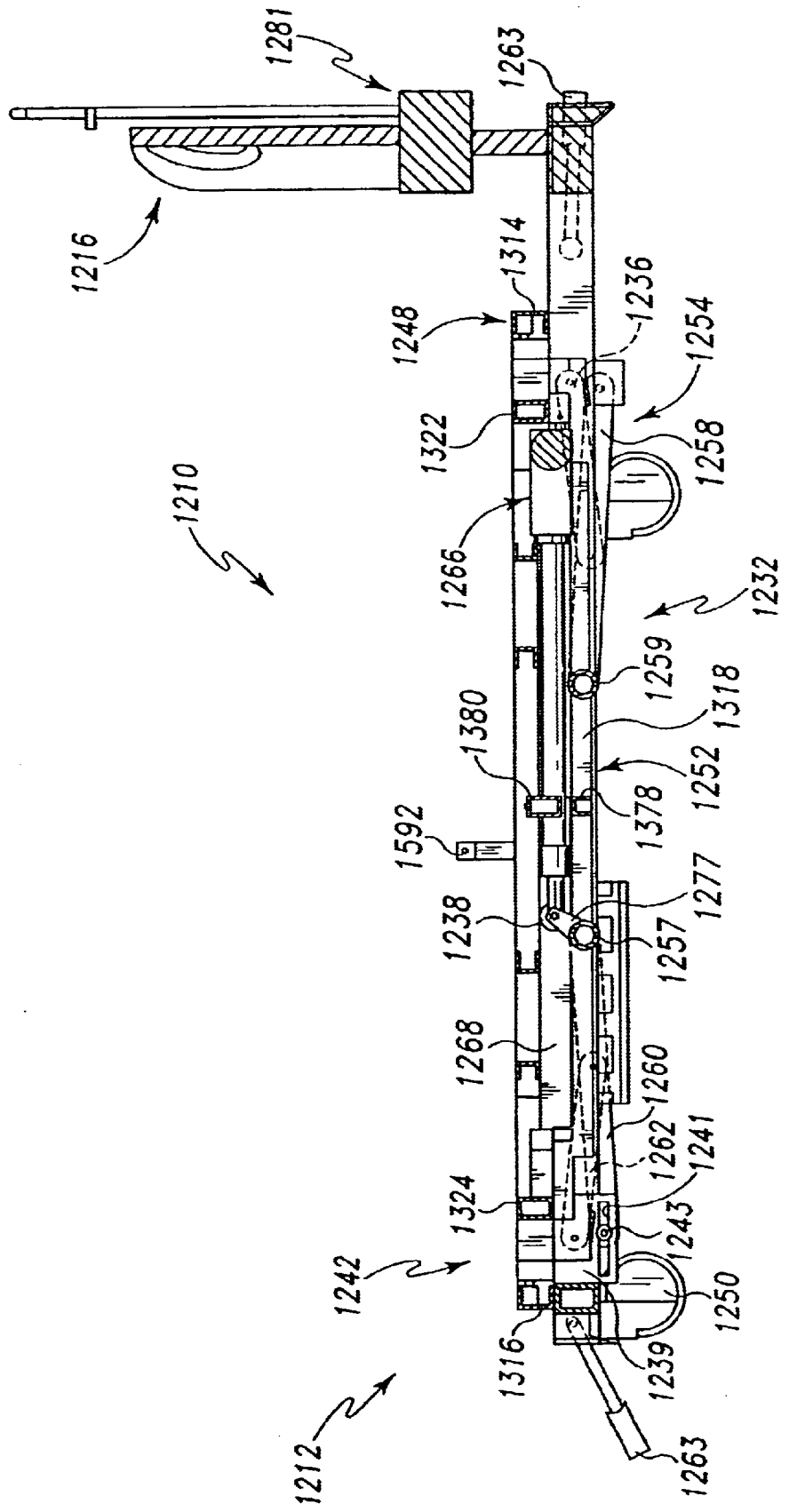
FIG. 96 is a view similar to FIG. 95 showing the lift arms supporting the weigh frame in a lowered position.

As shown in FIGS. 95 and 96, intermediate frame 1252 is lowered by activating both head and foot link actuators 1264, 1266. As the length of foot link actuator 1266 decreases, the angle between foot links 1260 and intermediate frame 1252 decreases and foot end 1255 of intermediate frame 1252 lowers. As the length of head link actuator 1264 decreases, the angle between head links 1258 and intermediate frame 1252 increases and head end 1253 of intermediate frame 1252 lowers.

As the length of head and foot link actuators 1264, 1266 continues to decrease, intermediate frame 1252 continues to lower from the upper position to a lower position as shown, for example, in FIG. 96. Because head and foot link actuators 1264, 1266 decrease their respective lengths at substantially the same rate, intermediate frame 1252 remains substantially horizontal while moving from the upper position, shown in FIG. 95, to the lower position shown in FIG. 96. To position upper frame 1252 back in the upper position, head and foot link actuators 1264, 1266 are simultaneously lengthened until each actuator 1264, 1266 returns to its original length as shown in FIG. 95.

Linkage system 1254 and actuator system 1256 also cooperate to move intermediate frame 1252 to the Trendelenburg position. To move intermediate frame 1252 to the Trendelenburg position, head link actuator 1264 decreases its length such that the angle between intermediate frame 1252 and head links 1258 increases. Head end 1253 of intermediate frame 1252 lowers and the length of foot link actuator 1266 remains substantially constant to provide a pivot point about which intermediate frame 1252 rotates. As intermediate frame 1252 rotates, foot end 1255 of intermediate frame 1252 is slightly raised. To reposition intermediate frame 1252 in the upper horizontal position, the length of head link actuator 1264 is increased until it returns to its previous length.

Actuator system 1256 and linkage system 1254 also cooperate to position intermediate frame 1252 in the Reverse Trendelenburg position as shown in FIG. 92. To move intermediate frame 1252 to the Reverse Trendelenburg position, the length of foot link actuator 1266 is decreased so that the angle between foot links 1260 and intermediate frame 1252 is decreased and foot end 1255 of intermediate frame 1252 lowers. The overall length of head link actuator 1264 remains substantially constant so that intermediate frame 1252 pivots about head links 1258. As intermediate frame 1252 pivots, head end 1253 of intermediate frame 1252 is slightly raised as foot end 1255 of intermediate frame 1252 lowers. To reposition intermediate frame 1252 in the upper horizontal position, the length of foot link actuator 1266 is increased until it returns to its previous length.

Figure 93:
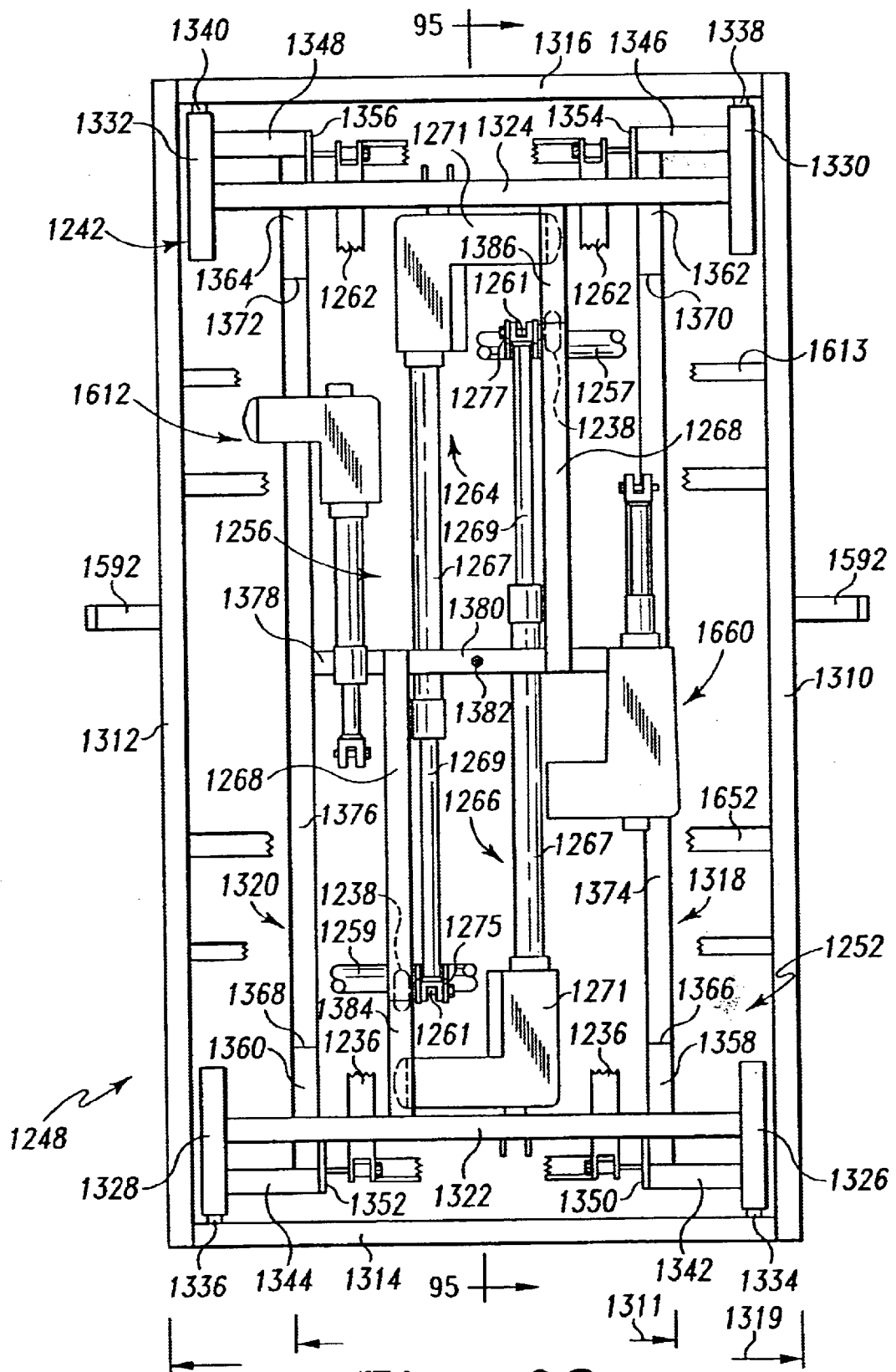
FIG. 93 is a top plan view of the frame showing the rectangular weigh frame and the frame further including an intermediate frame coupled to and positioned within the perimeter of the weigh frame.

As shown in FIG. 93, intermediate frame 1252 is surrounded by rectangular weigh frame 1248. Rectangular frame 1248 includes a pair of spaced apart longitudinally extending members 1310, 1312 and a pair of transversely extending members 1314, 1316 coupled to each longitudinally extending member 1310, 1312.

Intermediate frame 1252 includes a pair of longitudinally extending members 1318, 1320 and a pair of transversely extending members 1322, 1324 coupled to each longitudinally extending member 1318, 1320. Load cell members 1326, 1328, 1330, 1332 are coupled to each end of respective transversely extending member 1322, 1324 as shown in FIG. 93. A load cell 1334, 1336, 1338, 1340 is coupled to each respective load cell member 1326, 1328, 1330, 1332. Transversely extending members 1314, 1316 of weigh frame 1248 are supported by respective load cells 1334, 1336, 1338, 1340 as shown in FIGS. 93 and 95.

The weight of weigh frame 1248 and anything supported by weigh frame 1248, such as deck 1214, mattress 1230, and a patient, is transmitted to load cells 1334, 1336, 1338, 1340. This weight deflects or otherwise changes a characteristic of load cells 1334, 1336, 1338, 1340 which is detected to determine the total weight supported thereby. By subtracting a known weight of weigh frame 1248, deck 1214, mattress 1230 and any other bed components supported on weigh frame 1248, the weight of the patient positioned on bed 1210 can be determined. Additional description of load cells and methods for determining a patient's weight, position in the bed, and other indications provided by load cells is provided in U.S. patent application No. 09/669,707, filed Sep. 26, 2000, titled Load Cell Apparatus, to Mobley et al., the disclosure of which is expressly incorporated by reference herein. According to alternative embodiments of the present disclosure, other configurations and methods of using load cells or other devices to determine a patient's weight or other information related to the patient known to those of ordinary skill in the art are provided.

As shown in FIG. 93, intermediate frame 1252 further includes members 1342, 1344, 1346, 1348 coupled to load cell members 1326, 1328, 1330, 1332 and plate members 1350, 1352, 1354, 1356 coupled to respective transverse members 1322, 1324 and respective members 1342, 1344, 1346, 1348. As shown in FIG. 93, head and foot guide links 1236, 1262 are pivotably coupled to respective plate members 1350, 1352, 1354, 1356 to provided the pivotable coupling between head and foot guide links 1236, 1262 and intermediate frame 1252.

As shown in FIG. 94 longitudinally extending members 1318, 1320 of intermediate frame 1252 include respective upper portions 1358, 1360, 1362, 1364 coupled to the bottom sides of transversely extending members 1322, 1324 and to the outer side of plate members 1350, 1352, 1354, 1356, step portions 1366, 1368, 1370, 1372 coupled to respective upper portions 1358, 1360, 1362, 1364, and lower portions 1374, 1376 coupled to respective step portions 1366, 1368, 1370, 1372. As shown in FIG. 94, lower portions 1374, 1376 of longitudinally extending members 1318, 1320 are positioned at a lower elevation than longitudinally extending members 1310, 1312 of weigh frame 1248.

Intermediate frame 1252 further includes a transversely extending strut 1378 extending between lower portions 1374, 1376 and a yoke 1380 positioned over cylinder bodies 1269 of actuators 1264, 1266. Yoke 1380 is coupled to transversely extending strut 1378 by a fastener 1382 to sandwich cylinder bodies 1269 of actuators 1264, 1266 therebetween.

Intermediate frame 1252 also includes members 1384, 1386 coupled to transversely extending members 1322, 1324 and channel members 1268 as shown in FIG. 94. Channels 1268 are coupled to bottom side of members 1384, 1386 and to upper sides of transversely extending strut 1378 so that channel members 1268 are positioned at a lower elevation than longitudinally extending members 1310, 1312 of weigh frame 1248.

Motor 1271 of actuator 1264 is coupled to transversely extending member 1322 and motor 1271 of actuator 1266 is coupled to transversely extending member 1324 as shown in FIG. 93. As shown in FIG. 95, actuators 1264, 1266 are positioned below the elevation of the upper surface of weigh frame 1248.

As shown in FIG. 96, portions of intermediate frame 1252 nest within base frame 1232 when intermediate frame is in its lower-most position. As shown in FIG. 93, longitudinally-extending members 1318, 1320 of intermediate frame 1252 define an outer width 1311 that is less than an inner width 1313 between longitudinally extending members 1315, 1317 of base frame 1232. Weigh frame 1248 has an outer width 1319 defined by longitudinally extending members 1310, 1312 that is substantially equal to an outer width 1321 of base frame 1232. Because lower portions 1374, 1376 of longitudinally-extending members 1318, 1320 extend below weigh frame 1248 and are closer together than longitudinally extending members 1315, 1317 of base frame 1248, lower portions 1374, 1376 of intermediate frame 1252 are positioned within base frame 1248 when in the lower-most position.

Figure 97:
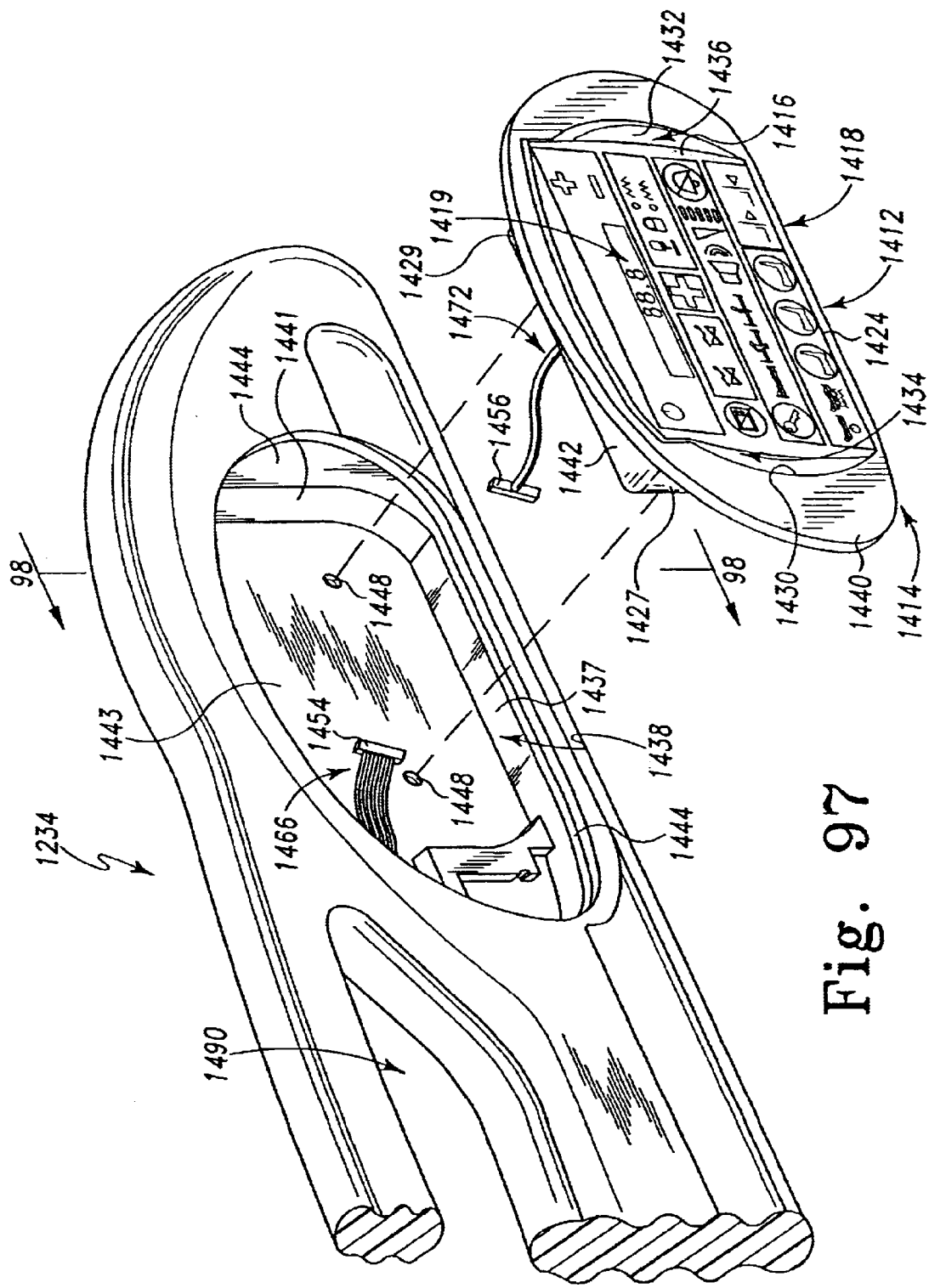
FIG. 97 is a partial perspective view of a first of the pair of foot end siderails showing the first foot end siderail including a rail member and a removable controller mount aligned for coupling to the rail member with a pair of screws, the removable controller mount having a pocket, and the bed further including a controller positioned in the pocket of the removable controller mount.

Bed 1210 further includes a control system configured to control actuators 1264, 1266 and other various components and functions of bed 1210. As shown in FIG. 97, the control system includes a controller 1412 that is removably received by foot end siderail 1234 so that it can be removed from one of foot end siderails 1234 and coupled to the other foot end siderail 1234 to control various functions of bed 1210. Controller 1412 is configured to control the raising and lowering of deck 1214 and to control movement of various portions or sections of deck 1214. Controller 1412 is also configured to receive information from a caregiver related to a patient and to send and receive patient or bed-related data to a central computer for storage, tracking, and analysis.

According to alternative embodiments of the present disclosure, the controller is configured to control other features of the bed such as features of the mattress. Additional description of suitable electronics and other features of a controller is provided in U.S. Pat. No. 5,715,548, titled Chair Bed, filed Aug. 4, 1995; U.S. Pat. No. 6,008,598, titled Hand-Held Controller For Bed and Mattress Assembly, filed Apr. 22, 1998; U.S. Pat. No. 6,131,868, titled Hospital Bed Communication and Control Device, filed Jan. 1, 1997; and U.S. Provisional Application Serial No. 60/202,284, titled Remote Control for a Hospital Bed, filed May 5, 2000, the disclosures of which are expressly incorporated by reference herein.

As shown in FIG. 97, bed 1210 includes a removable controller mount 1414 configured to removable couple controller 1412 to one of foot end siderails 1234. Bed 1210 further includes a removable cover 1415 configured to mount to the other foot end siderail 1234 as shown in FIG.

99. Removable controller mount 1414 with controller 1412 and removable cover 1415 are exchangeable. For example, to move controller 1412 from one side of bed 1210 to the other, removable controller mount 1414 with controller 1412 and cover 1415 are uncoupled from their respective foot end siderail 1234, switched between the opposite foot end siderails 1234, and re-coupled to opposite foot end siderail 1234 to complete the exchange. Thus, if the orientation of bed 1210 in a hospital or other room does not provide access to controller 1412, controller 1412 can be exchanged from one side of bed 1210 to the other to provide such access.

Figures 98, 100:
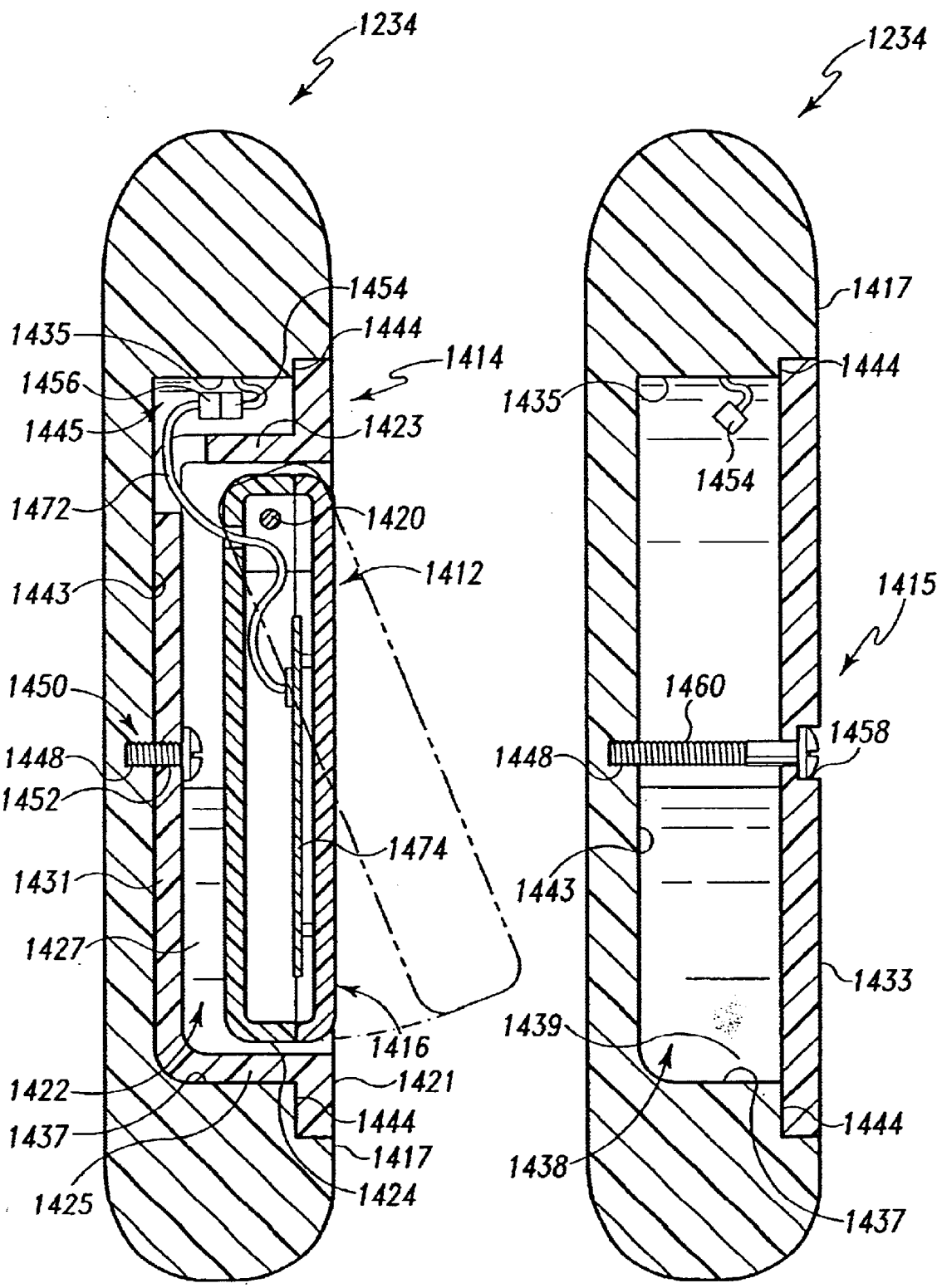
FIG. 98 is a cross-sectional view taken along line 98—98 of FIG. 97.
FIG. 100 is a cross-sectional view taken along line 100—100 of FIG. 99.
Figure 99:
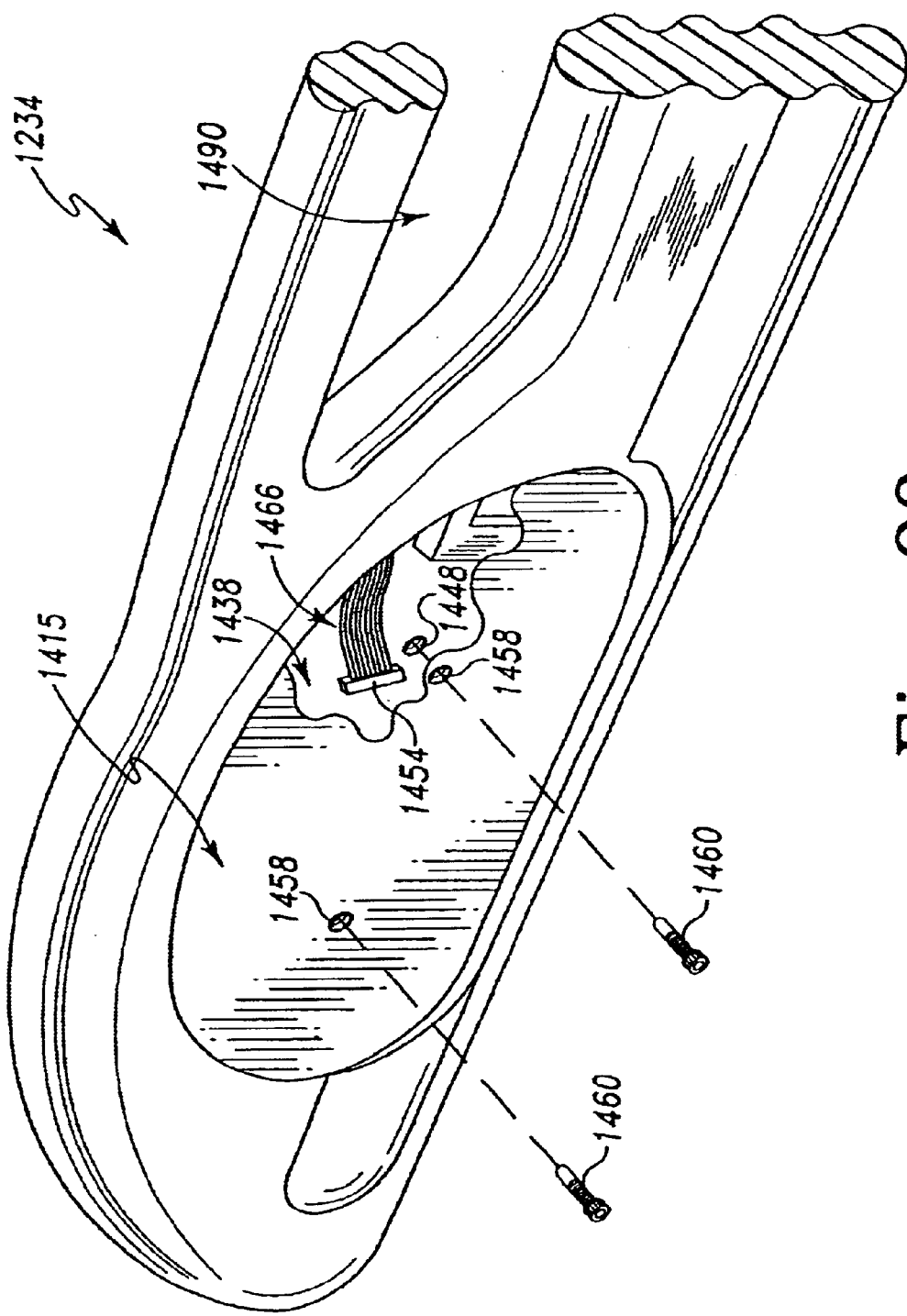
FIG. 99 is a partial perspective view of a second of the pair of foot end siderails showing the second foot end siderail including a rail member and a substantially flat removable panel, with portions broken away, coupled to the rail member.

Controller 1412 includes a housing 1416, a plurality of control buttons 1418, an LED display 1419, and a rod 1420 coupling housing 1416 to controller mount 1414. Controller mount 1412 includes a pocket 1422 configured to receive controller 1412 as shown in FIGS. 97 and 98. According to alternative embodiments of the present disclosure, the display is an LCD, plasma, or other display known to those of ordinary skill in the art.

Rod 1420 pivotably couples housing 1416 to controller mount 1414. This coupling permits a user to see control buttons 1418 better by titling a lower edge 1424 of housing 1416 upward. According to alternative embodiments of the present disclosure, other configurations of couplers between the housing and the controller mount are provided. For example, hooks, hook-and-loop type fasteners, snaps, a detachable hinge, or other devices known to those of ordinary skill in the art are provided to pivotably or otherwise couple the controller to the siderail.

Housing 1416 has a width that is less than a width of pocket 1422 so that when controller 1412 is positioned in pocket 1422, controller 1412 and surfaces 1430, 1432 cooperate to define hand holes 1434, 1436 as shown in FIG. 97. To tilt controller 1412, a caregiver inserts either of their hands or fingers into one of hand holes 1434, 1436 to grasp controller 1412. Having grasped controller 1412, the caregiver can then tilt controller 1412 upward.

Each foot end siderail 1234 includes a pocket 1438 sized to receive body 1142 of controller mount 1414 as shown in FIG. 97. Removable controller mount 1414 includes a perimeter flange 1440 and a body 1442 defining pocket 1422. Foot end siderail 1234 includes an edge or shoulder 1444 on which perimeter flange 1440 rests when controller mount 1414 is coupled to the respective foot end siderail 1234 so that an outer surface 1417 of siderail 1234 is flush with an outer surface 1421 of perimeter flange 1440.

As shown in FIG. 98, body 1422 includes a top wall 1423, a bottom wall 1425 spaced apart from top wall 1423, a pair of side walls 1427, 1429 extending between top and bottom walls 1423, 1425, and a back wall 1431 coupled to top, bottom, and side walls 1423, 1425, 1427, 1429. Top, bottom, side, bottom, and back walls 1423, 1425, 1427, 1429, 1431 cooperated to define pocket 1422. Perimeter flange 1440 is coupled to top, bottom, and side walls 1423, 1425, 1427, 1429.

Body 1442 and flange 1440 of controller mount 1414 and panel 1415 are configured to mount on either of the two foot end siderails 1234 so that controller 1412 can be initially mounted on one of foot end siderails 1234 and later moved to the other foot end siderail 1234 as discussed above. For example, flange 1440 and panel 1415 are symmetric about a vertical axis so that they can fit on either edge 1444 of foot end siderails 1234. When panel 1415 is coupled to the respective foot end siderail 1234 outer surface 1417 of siderail 1234 is flush with an outer surface 1433 of panel 1415 as shown in FIG. 100.

As shown in FIG. 100, siderail 1234 includes a top wall 1435, a bottom wall 1437 spaced apart from top wall 1435, a pair of side walls 1439, 1441 extending between top and bottom walls 1435, 1437, and a back wall 1443 coupled to top, bottom, and side walls 1435, 1437, 1439, 1441. Top, bottom, side, bottom, and back walls 1435, 1437, 1439, 1441, 1443 cooperated to define pocket 1438. Edge 1444 is positioned adjacent to top, bottom, and side walls 1435, 1437, 1439, 1441.

As shown in FIGS. 98 and 100, each foot end siderail 1234 further includes a pair of threaded fastener-receiving apertures 1448 configured to receive fasteners 1450 that extend through fastener-receiving apertures 1452 in back wall of 1431 of body 1442 of controller mount 1414 to removably couple controller mount 1414 to the respective foot end siderail 1234. Removable cover 1415 also includes counter-sunk fastener-receiving apertures 1458 configured to receive fasteners 1460 that extending into fastener-receiving apertures 1448 to removably couple cover 1415 to either foot end siderail 1234. According to alternative embodiments of the present disclosure, other configurations of fasteners are provided to removably or otherwise couple the controller mount to the siderail, such as snaps, tabs, latches, hooks, hook-and-loop type fasteners, screws, bolts, rivets, adhesives, or other configurations of couplings known to those of ordinary skill in the art.

Controller 1412 and each siderail 1234 are configured to facilitate electrical coupling and uncoupling of controller 1412 from either siderail 1234. Each foot end siderail 1234 includes an electrical coupler 1454 and controller 1412 also includes a complementary electrical coupler 1456 configured to coupled to either respective coupler 1454 of foot end siderails 1234. Electrical coupler 1454 is positioned in a space 1445 defined between top wall 1423 of controller mount 1414 and top wall 1435 of siderail 1234 when controller 1412 is coupled to the respective siderail 1234.

Electrical coupler 1454 is preferably a male plug connector that includes a body and a plurality of plugs. Each plug corresponds to one of a plurality of wires 1466 that extend through foot end siderail 1234 to a central controller or processor and various electrical components of bed 1210. Similarly, electrical coupler 1456 is preferably a female plug connector that includes a body and a plurality of sockets corresponding to one of a plurality of wires 1472 extending to and through controller housing 1416 to a circuit board 1474 configured to receive commands from buttons 1418 and to output data to display 1419. Each socket of coupler 1456 is sized to receive a corresponding plug of coupler 1454 to provide electrical coupling between wires 1466 of respective siderails 1234 and wires 1472 of controller 1412. Preferably, electrical couplers 1454, 1456 are indexed to insure correct orientation of the corresponding plugs and sockets.

To move controller 1412 from one foot end siderail 1234 to the other, controller 1412 is pivoted up to provide access to fasteners 1450. Fasteners 1450 are then removed to uncouple controller mount 1414 and thus controller 1412 from foot end siderail 1234. Electrical coupler 1456 of controller 1412 is uncoupled from electrical coupler 1454 of siderail 1234 so that controller 1412 is electrically uncoupled from siderail 1234. Similarly, fasteners 1460 are removed from the other foot end siderail 1234 to uncouple cover 1415 therefrom.

Controller mount 1414 and controller 1412 and cover 1415 are then moved to the opposite siderail 1234. Electrical coupler 1454 is then coupled to electrical coupler 1456 of the respective siderail 1234 and fasteners 1450 are threaded into fastener-receiving apertures 1448 to couple controller mount 1414 and controller 1412 to siderail 1234. Similarly, fasteners 1460 are threaded into fastener-receiving apertures 1448 of respective siderail 1234 to couple cover 1415 to siderail 1234.

According to alternative embodiments of the present disclosure, the controller mounts and controllers are configured to couple to other barriers on the bed such as the head end siderails, headboard, or footboard. According to another embodiment of the present disclosure, multiple controller mounts with controllers are provided on each bed.

Figure 101:
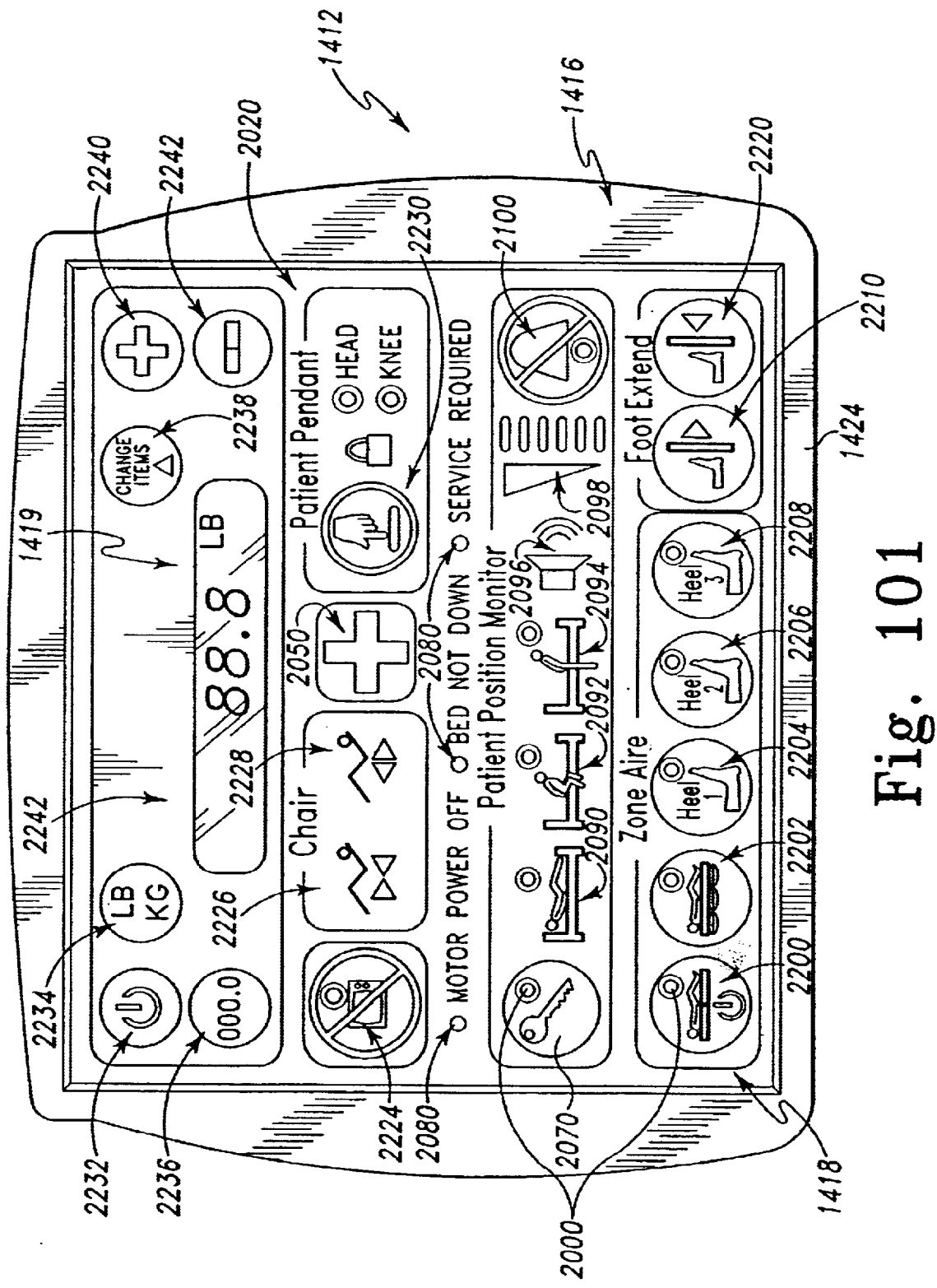
FIG. 101 is a side elevation view of the controller of FIG. 97.

Controller 1412 further includes an interface panel 2020, illustrated in FIG. 101. Interface panel 2020 includes a plurality of membrane input control buttons 1418 and a plurality of status indicators 2000 which are electrically coupled to circuit board 1474, allowing controller 1412 to be used by persons outside bed 1210 to control the operation of various features of bed 1210, including articulation of deck 1214, operation of the patient weighing function, enablement of a patient position monitoring system, lockout of a corded patient pendant controller 1476, sending a nurse call signal, and/or lockout of entertainment devices, such as television, radio, or the like. In a preferred embodiment, status indicators 2000 are an LED's electrically coupled to interface panel 2020. According to alternative embodiments of the present disclosure, other functions of the bed or remote equipment are controlled by the controller.

According to the preferred embodiment of the present disclosure, some of buttons 1418 are only operable after a key control button 2070 is first pressed. This helps prevent the accidental activation and deactivation of certain functions of bed 1210.

As shown in FIG. 101, patient position monitor buttons 2090, 2092, 2094 are provided that are only operable after key control button 2070 is first pressed. If a caregiver or patient presses any of buttons 2090, 2092, 2094 without first pressing key control button 2070, buttons 2090, 2092, 2094 will not respond to being pressed. According to alternative embodiments of the present disclosure, other buttons are also only operable after pressing the key control button.

Patient monitoring buttons 2090, 2092, 2094 control activation of patient position monitoring system, which notifies a caregiver when the patient changes position relative to bed 1210. When one of buttons 2090, 2092, 2094 is selected, the other respective buttons 2090, 2092, 2094 are automatically deselected.

Button 2094 controls activation of the position monitoring system to detect an "exit" condition when the patient has exited bed 1210. When button 2094 is pressed to activate monitoring of the exit condition, the respective indicator 2000 adjacent to button 2094 lights up. Otherwise the respective indicator 2000 adjacent to button 2094 is off. If the exit condition is detected, visual and audible alarms will activate notifying the caregiver that the patient has exited bed 1210.

Button 2092 controls activation of the position monitoring system to detect a "pre-exit" condition when the patient is bearing weight primarily on an edge of bed 1210, such as when the patient is sitting on the edge of bed 1210. When button 2092 is pressed to activate monitoring of the pre-exit condition, the respective indicator 2000 adjacent to button 2092 lights up. Otherwise the respective indicator 2000 adjacent to button 2092 is off. If the pre-exit condition is detected, the visual and audible alarms will activate notifying the caregiver that the patient has moved to the edge of bed 1210. Furthermore, the alarms will also activate if the exit condition is detected.

Button 2090 controls activation of the position monitoring system to detect a "patient up" condition when the patient's torso moves from being positioned over head section 1487 of deck 1226 to being positioned over another section of deck 1226. When button 2090 is pressed to activate monitoring of the patient up condition, the respective indicator 2000 adjacent to button 2090 lights up. Otherwise the respective indicator 2000 adjacent to button 2090 is off. If the patient up condition is detected, the visual and audible alarms will activate notifying the caregiver that the patient has moved to the up position. Furthermore, the alarms will also activate if the pre-exit and exit conditions are detected.

To turn any of the three patient position detection functions on or off, key control button 2070 must first be pressed. Once key control button 2070 is pressed, the caregiver has a predetermined time period in which to press the respective button 2090, 2092, 2094 to turn on or off the respective patient position monitoring function or to selection another patient position monitoring function. If the caregiver fails to turn a particular patient position monitoring function on or off or fails to select another patient position monitoring function within the predetermined time period, pressing buttons 2090, 2092, 2094 will have no effect and key control button 2070 must be pressed again. If the caregiver presses one of button 2090, 2092, 2094 within the predetermined time period, that respective button will toggle from on to off or off to on and the respective indicators 2000 lights up or turn off accordingly. According to the preferred embodiment of the present disclosure, the predetermined time period is 10 seconds.

Alarm control buttons 2096, 2100 and volume indicator 2098 are provided to a caregiver to control the volume of the audible alarm that sounds when the patient monitoring system detects one of the above-mentioned conditions. Alarm button 2096 controls the volume of the alarm. Volume indicator 2098 comprises a plurality of LED's that are lit according to the selected volume level, i.e., the higher the volume selected, the more LED's that are lit. If a user wants to turn the volume up, alarm button 2096 is pressed repeatedly until the desired volume is reached. To lower the volume, alarm button 2096 is pressed repeatedly until the peak volume is reached. After the peak volume is reached, continued pressing on alarm button 2096 will gradually reduce the volume of the alarm until the lowest volume is reached. After the lowest volume is reached, continued pressing on alarm button 2096 will gradually increase the volume. Alarm control button 2100 turns the audible alarm off.

Inflation system buttons 2200, 2202, 2204, 2206, 2208 are provided that control the function of the air pressure inflation system. On/off button 2200 turns the inflation system on or off. Maximum inflation button 2202 inflates the mattress zones to a predefined air pressure level to facilitate administration of CPR. Heel zone buttons 2204, 2206, 2208 enable inflation or deflation of the air bladders corresponding to the different heel zones of mattress 1230 for heel-pressure relief. When one of heel zone buttons 2204, 2206, 2208 is selected, a corresponding heel pressure relief bladder is deflated to provide heel-pressure relief. When the respective button 2204, 2206, 2208 is deselected, the pressure in the corresponding heel pressure relief bladder is inflated to is normal operating pressure. The respective indicators 2000 adjacent each button 2204, 2206, 2208 indicate which heel pressure relief bladder is current deflated.

Foot extend and retract buttons 2210, 2220 cause foot section 1590 to extend and retract which permits the position of footboard 1218 of bed 1210 to be adjusted relative to the position of the patient's foot. To extend foot section 1590, extend button 2210 is pressed until the desired position of footboard 1218 is reached. To retract foot section 1590, retract button 2220 is pressed until the desired position is reached.

Chair buttons 2226, 2228 are provided to control adjustment of the position of deck 1226 between the chair and bed positions. To move bed 1210 toward the chair position, chair button 2226 is pressed until the degree of the chair position is achieved. To move bed 1210 toward the bed position, chair button 2228 is pressed until the desired degree of the chair position is removed or until bed 1210 reaches the bed position.

TV button 2224 enables and disables (locks out) control of the television or other entertainment system. When nurse call button 2050 is pressed, a signal is sent to a nurse station or directly to predetermined caregivers that indicates that the patient needs attention.

Patient pendant button 2230 enables and disables (locks out) specific features of corded patient pendent controller 1476. By pressing button 2230, the control feature of controller 1476 that controls the head up and knee up functions are enabled and disabled. By pressing button 2230 once, the head up control provided by controller 1476 is disabled and the knee up control remains enabled. When the head up control of pendent 1476 is disabled, the respective indicator 2000 adjacent to the text "HEAD" is lit. When button 2230 is pressed a second time, the knee up control provided by controller 1476 is disabled and the head up control is enabled. When the knee up function of pendent 1476 is disabled, the respective indicator 2000 adjacent the text "KNEE" is lit. When button 2230 is pressed a third time, both the head up and knee up controls provided by controller 1476 are disabled. When the head up and knee up controls of pendent 1476 are disabled, both the respective indicators are lit. When button 2230 is pressed a fourth time, both the head up and knee up controls provided by controller 1476 are enabled and respective indicators are off. By enabling and disabling controller 1476 controls, a caregiver can prevent a patient having access to controller 1476 from accidentally articulating bed 1210 when such articulation may be undesirable.

Weigh system panel 2242 of interface panel 2020 includes a plurality of buttons and LED display 1419 which permit a caregiver to weigh the patient using the patient weighing function. Weighing system panel 2242 is enabled and disabled by on/off button 2232. Unit selection button 2234 enables the caregiver to choose between pounds and kilograms as the unit of weight measurement. LED display 1419 displays the patient's weight and selected unit of measurement.

Calibration button 2236, change item button 2238, add item button 2240, and subtract item button 2242 are provided to the caregiver to calibrate the system for weighing a patient. For example, before a patient is placed on bed 1210, calibration button 2236 is pressed to set the weight reading to 000.0 lbs/kg so that the initial weight of mattress 1230, deck 1226, and any other bed component or piece of medical equipment is negated from the weight reading. Thus, only the weight of the patient is indicated when the patient is on bed 1210.

If a bed component or piece of medical equipment is added to or removed from bed 1210 that may affect the weight reading, change item button 2238, add item button 2240, and subtract item button 2242 are used to take the additional or subtracted weight into account. For example, if a piece of medical equipment, such as an IV pole, is added to bed 1210, change item button 2238 and add item button 2240 are pressed while the piece of medical equipment is added and the additional weight detected by the weigh system is subtracted from the measured weight so that the additional weight of the IV pole is negated from the weight displayed on display 1419. Similarly, if a piece of medical equipment is removed from bed 1210, change item button 2238 and subtract item button 2242 are pressed while the piece of medical equipment is removed and the removed weight detected by the weigh system is added to the measured weight so that the loss of weight of the removed pieced of medical equipment is negated from the weight displayed on display 1419.

Light LED indicator 2080, which relate to various bed status functions, such as motor power, bed not down, or service required, are also included on interface panel 2020. The respective indicator 2080 adjacent to the text "Motor Power Off" is lit when the power to actuators 1266, 1268 is off. When the power to actuators 1266, 1268 is on, this respective indicator 2080 is off. The respective indicator 2080 adjacent to the text "Bed Not Down" is lit when intermediate frame 1252 is not in the lowermost position. When intermediate frame 1252 is in the lowermost position, this respective indicator 2080 is off. The respective indicator 2080 adjacent to the text "Service Required" is lit when bed 1210 detects that a component needs serviced. If bed 1210 does not detect that a component needs serviced, this respective indicator 2080 is off.

Figure 102:
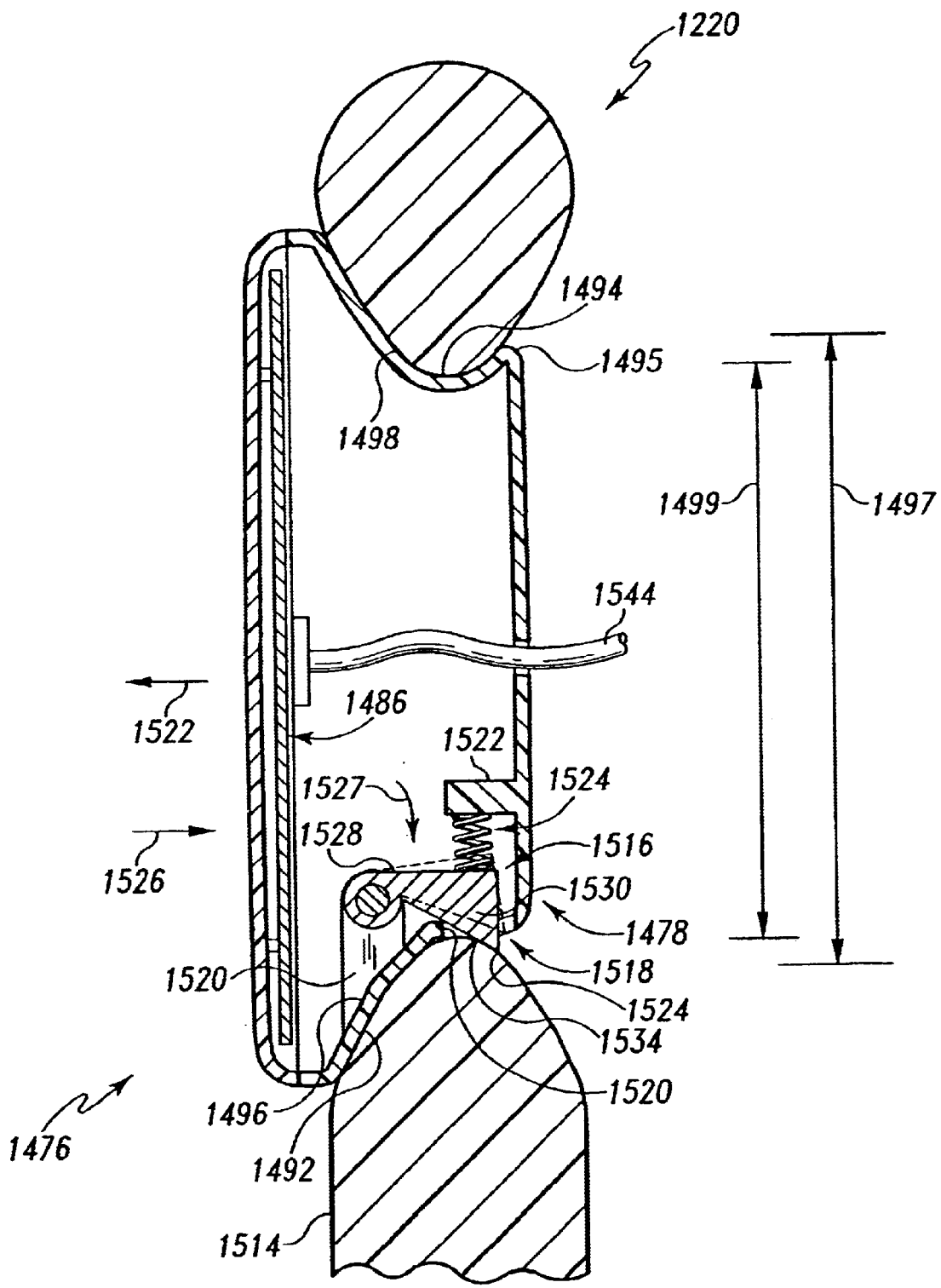
FIG. 102 is a cross-sectional view taken along line 102—102 of FIG. 104 showing another controller including a latch configured to removably and slidably couple the controller to one of the head and foot end siderails.

As shown in FIG. 102, the control system further includes corded pendant controller 1476 similar to controller 986 of bed 810 that is configured to removably and slidably couple to head and foot end siderails 1220, 1234. Controller 1476 includes a housing 1478, a plurality of control buttons (not shown) for controlling various functions of bed 1210, and a speaker and microphone (not shown) for facilitating communication between a person positioned on bed 1210 and a caregiver, and a circuit board 1486.

Controller 1476 is configured to slide in either opening 1488 of head end siderails 1220 or opening 1490 of foot end siderails 1234 between an infinite number of positions similar to the movement shown in FIGS. 76 and 78 for controller 986.

Because patients vary in size, one patient may find it more convenient to position controller 1476 in one of the many available positions on either head or foot end siderails 1220, 1234 than another patient. Thus, various patients can position controller 1476 in any of the infinite number of positions on any of head or foot end siderails 1220, 1234 depending on the preference of particular patient positioned on bed 1210. Furthermore, a patient may decided to adjust the position of controller 1476 if the configuration of deck 1214 is changed. For example, if a head portion or section 1487 of deck 1214 is raised, a patient may desire to reposition controller 1476 along the particular siderail 1220, 1234 or remove controller 1476 and place it on another siderail 1220,1234.

As shown in FIG. 102, housing 1478 of controller 1476 includes a first stepped concave surface 1492 and a second curved concave surface 1494 that complement convex surfaces 1496, 1498 of rail member 1506 of head end siderail 1220. Foot end siderail 1234 also includes convex surfaces 1510, 1512 that are complemented by concave surfaces 1492, 1494. As shown in FIG. 102, a substantial portion of controller 1476 is positioned within rail member 1506 so that controller 1476 maintains a relatively low profile compared to an inner surface 1514 of rail member 1506 when positioned in rail member 1506 to avoid interference with other components of bed 1210 or other pieces of medical equipment. According to alternative embodiments of the present disclosure, the controller is positioned further in the opening formed in the rail member so that little or none of the controller extends beyond an inner surface of the rail member.

The respective pairs of convex surfaces 1496, 1498, 1510, 1512 of siderails 1220, 1234 cooperate to define a top rail and a bottom rail that define a guide. Concave surfaces 1492, 1494 and retainer 1516 cooperate to define a complementary formation configured to ride along the top and bottom rails/guide. According to alternative embodiments of the present disclosure, other configurations of rails and guides and complementary formations are provided such as raised rails, channels, slots, or other configurations of guides and complementary formations known to those of ordinary skill in the art.

Controller 1476 further includes a retainer 1516 configured to retain controller 1476 in either opening 1490, 1488 to permit sliding of controller 1476 along siderails 1220, 1234 and to permit removal of controller 1476 from openings 1490, 1488. When controller 1476 is positioned in opening 1490 of foot end siderail 1234, retainer 1516 is positioned adjacent to concave surface 1496 of housing 1478.

Retainer 1516 includes a spring-biased retainer or latch member 1518 that extends through an aperture 1520 formed in housing 1478 so that when a patient pulls on controller 1476 in direction 1522, retainer member 1518 is pushed inwardly so that a distal end 1524 of retainer member 1518 rides over the inner most portion of convex surface 1496 so that retainer 1516 no longer retains controller 1476 in the respective siderail 1220, 1234.

To reposition controller 1476 back in siderails 1220, 1234, the patient positions second concave surface 1494 adjacent to convex surface 1498 of rail member 1506 of head end siderail 1220 so that a peaked tip 1495 of housing 1478 captures the respective rail member 1506. The lower end of controller 1476 is pushed in direction 1526 so that retainer member 1518 rides back over convex surface 1496. Peaked tip 1495 and retainer member 1518 then define a width 1497 that is greater than a width 1499 of opening 1488 so that controller 1476 is retained in either head end siderail 1220. An identical procedure is followed for placing and removing controller 1476 from opening 1490 in foot end siderails 1234. Furthermore, controller 1476 may also be coupled to rail member 1506 through the opposite side of opening 1488. According to an alternative embodiment of the present disclosure, the openings in the head and foot end siderails do not extend completely through the siderails.

Figure 103:
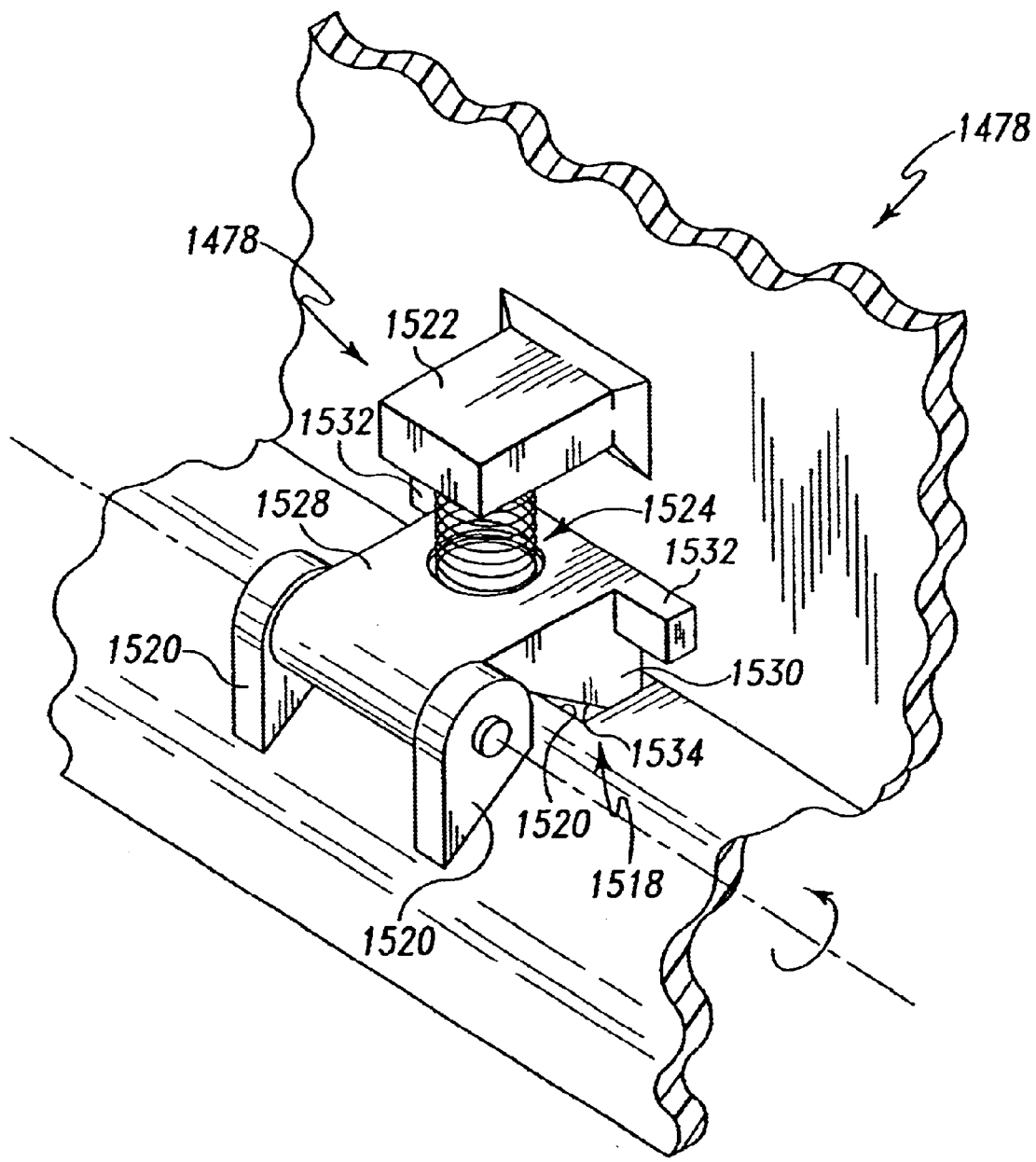
FIG. 103 is a partial perspective view of the latch configuration of FIG. 102.

As shown in FIGS. 102 and 103, housing 1478 including a pair of mounts 1520 on which retainer member 1518 is pivotably coupled. Housing 1478 further includes a spring mount 1522 and retainer 1516 further includes a biaser or spring 1524 positioned between spring mount 1522 and retainer member 1518. Spring 1524 biases retainer member 1518 in direction 1527 toward convex surface 1496 as shown in FIG. 102. According to alternative embodiments of the present disclosure, other biasers are provided, such as torsion springs, the retainer member being cantilevered and flexible, or other configurations of biasers known to those of ordinary skill in the art.

Retainer member 1518 includes a body portion 1528 pivotably coupled to mount 1520, a ramp-shaped latch portion 1530 positioned to extend through aperture 1520 of housing 1478, and a pair of stops or tabs 1532 as shown in FIG. 103. Ramp-shaped latch portion 1530 includes an inclined surface 1534 that rides over convex surface 1496. Tabs 1532 have an outer width that is greater than a width of aperture 1520 to prevent retainer member 1518 from rotating further than shown in FIGS. 102 and 103.

According to another alternative embodiment of the present disclosure, ball detent retainers are provided, such as those shown in FIG. 75, to removably retain the controller in the head and foot end siderails. According to other alternative embodiments of the disclosure, other retainers known to those of ordinary skill in the art are provided to retain the controller in the siderails such as tabs, clasps, catches, locks, other latches, clamps, pins, bolts, bars, hasp, hooks, or other retainers known to those of ordinary skill in the art.

Figure 104:
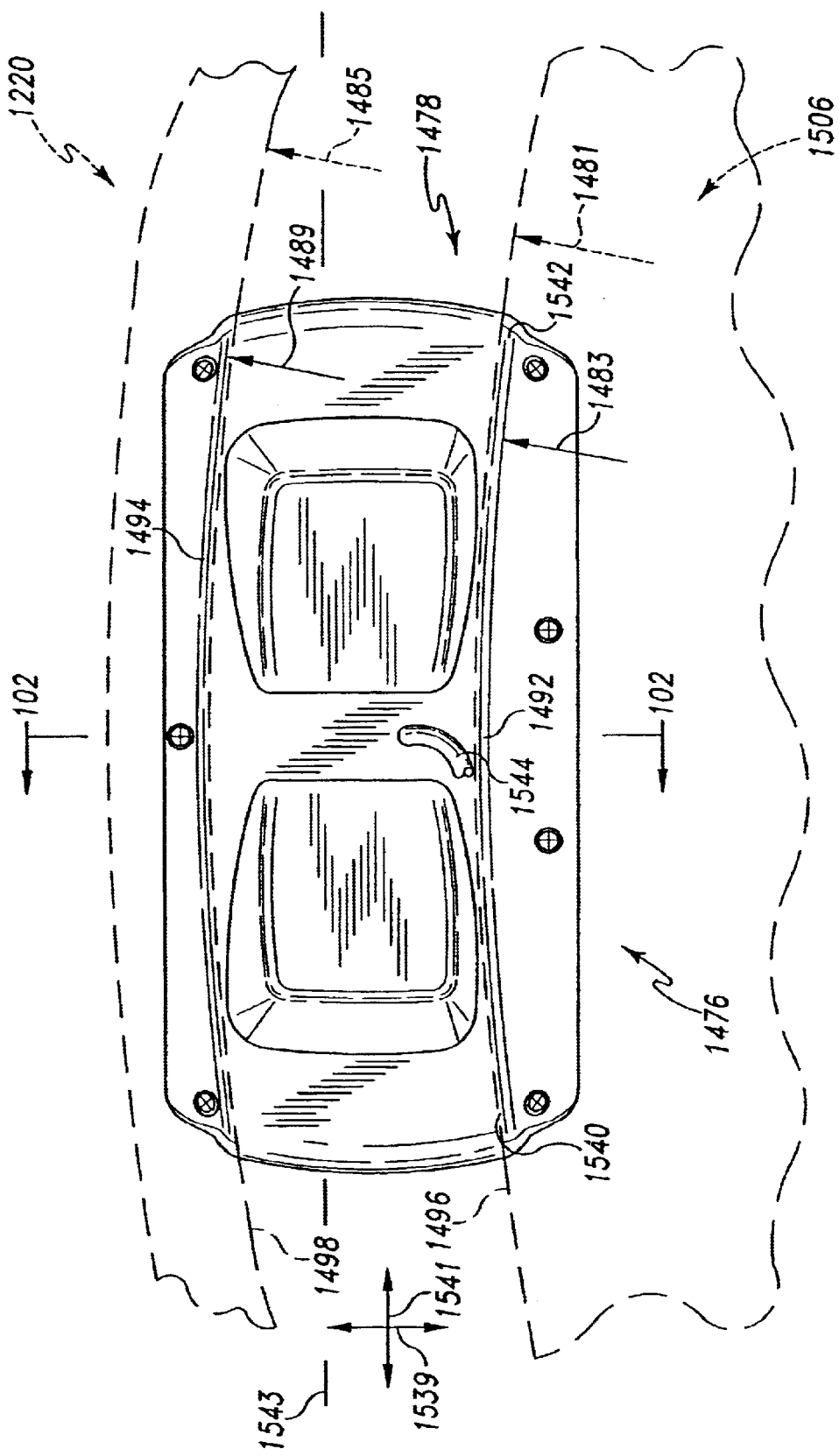
FIG. 104 is a side elevation view showing a back side of the controller of FIG. 102 showing the controller including a housing having a pair of spaced-apart surfaces defining curved channels to complement the contour of the siderails (shown in phantom)

As shown in FIG. 104, first and second concave surfaces 1492, 1494 are indexed to match convex surfaces 1496, 1498, 1510, 1512 of siderails 1220, 1234 to prevent insertion of controller 1476 in a upside-down orientation. Each surface 1492, 1494 is curved along its longitudinal length to substantially match the longitudinal contour of openings 1488, 1490 of head and foot end siderails 1220, 1234. For example, lower surface 1492 has a radius of curvature 1483 that matches a radius of curvature 1481 of lower surfaces 1496, 1510 of head and foot end rails 1220, 1234. Similarly, upper surface 1494 has a radius of curvature 1489 that matches a radius of curvature 1485 of upper surfaces 1498, 1512 of head and foot end rails 1220, 1234. If a patient or caregiver attempts to insert controller 1476 into either opening 1488, 1490 in an upside-down orientation, corners 1540, 1542 will block insertion of controller 1476 into opening 1488, 1490.

Because of the curvature of convex surfaces 1496, 1498, 1510, 1512 of siderails 1220, 1234, openings 1488, 1490 are also curved. As controller 1476 slides along these curved surfaces, they follow a path that has both longitudinal and transverse components 1539, 1541 relative to a longitudinal axis 1543 of the respective siderails 1220, 1234 as shown in FIG. 104.

Figure 109:
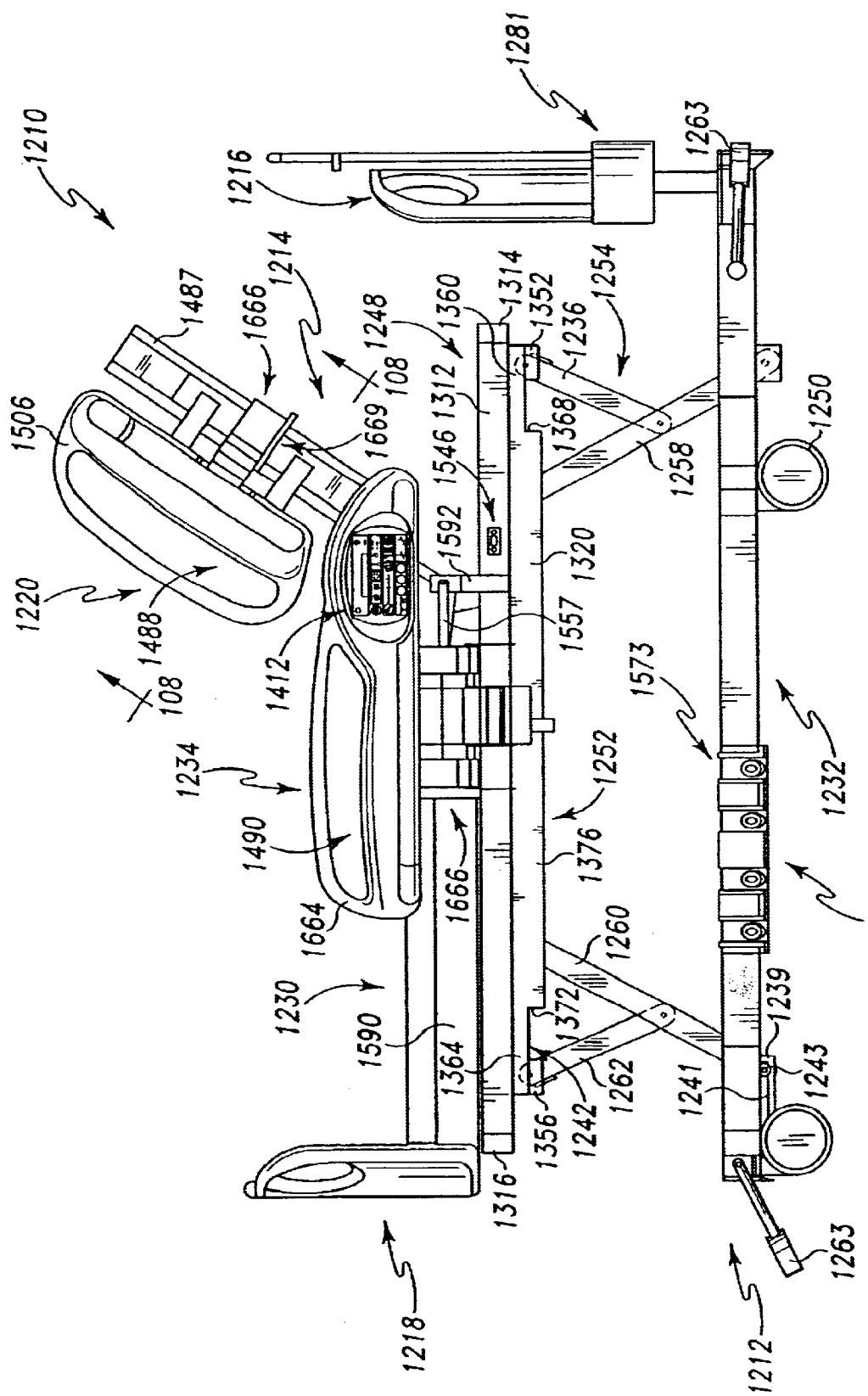
FIG. 109 is side elevation view of the bed of FIG. 92 showing the head section of the deck titled relative to the weigh frame and the head end siderail in an up position.

As shown in FIG. 102, controller 1476 further includes a cord 1544 that communicates electric signals to and from controller 1476. Cord 1544 includes a connector (not shown) similar to connector 1034 of bed 1210 that couples to either of two connectors 1546, 1548 on weigh frame 1248. According to the preferred embodiment of the disclosure, connector 1548 is coupled to a first side of bed 1210 as shown in FIG. 92 and connector 1546 is coupled to an opposite second side of bed 1210 as shown in FIG. 109. A plurality of wires (not shown) are coupled to each connector 1546, 1548 to communicate with the various electrically controlled devices of bed 1210. Preferably, the plurality of wires meet at a junction (not shown), such as a central controller or processor, and then extend to the various electrically controlled devices.

Because two connectors 1546, 1548 are provided on opposite sides of bed 1210, controller 1476 can be plugged into either side of bed 1210. Thus, if a patient or caregiver finds it more convenient to position controller 1476 on the pair of head and foot end siderails 1220, 1234 on the first side of bed 1210, controller 1476 can be plugged into connector 1546 without cord 1544 having to be strung over the mattress. Similarly, if a patient or caregiver finds it more convenient to position controller 1476 on the pair of head and foot end siderails 1220, 1234 on the second side of bed 1210, controller 1476 can be plugged into connector 1548 without cord 1544 having to be strung over the mattress. Thus, a corded controller is provided that can be removably coupled to either side of the bed without having to string the cord of the controller over the mattress of the bed.

Figure 105:
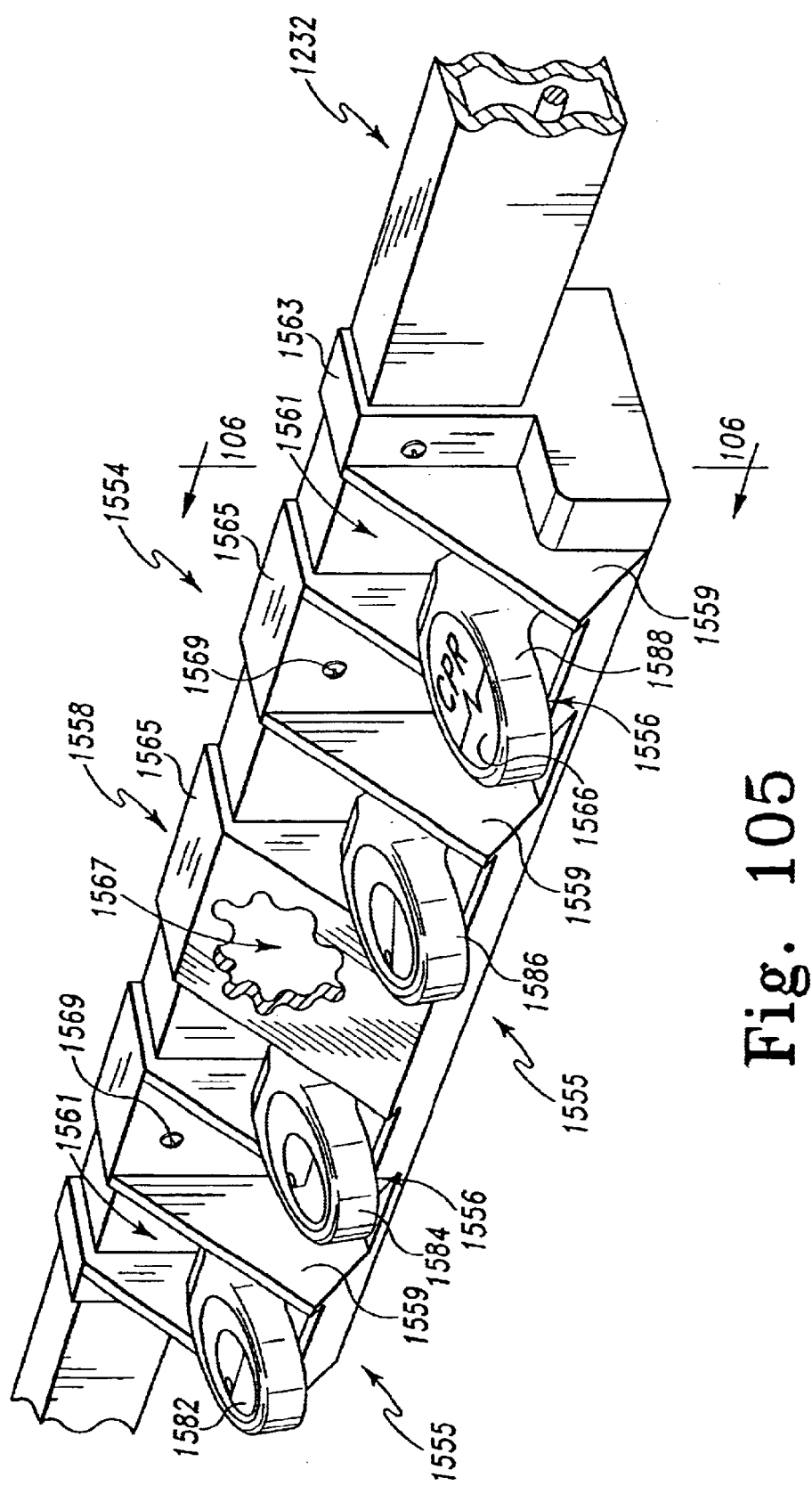
FIG. 105 is a perspective view showing a pedal housing coupled to a portion of the base frame and four pedals pivotably coupled to the pedal housing.

As shown in FIG. 105, the control system of bed 1210 further includes a foot-operated control assembly 1554 that includes a plurality of foot-operated controls 1555. Foot-operated controls 1555 are provided to control raising and lowering of deck 1214, raising and lowering head section 1487 relative to weigh frame 1248, and moving weigh frame 1248 between the Trendelenburg and Reverse Trendelenburg positions. Foot-operated controls 1555 are also provided to place bed 1210 in a CPR mode. When in the CPR mode, mattress 1230 is inflated to a predetermined maximum pressure to provide a firm surface for performing CPR, head section 1487 of deck 1226, if raised, is lowered to a flat position, and a seat section 1557 of deck 1226, if raised, is lowered to a flat position.

Each foot-operated control 1555 is associated with one of the above-mentioned functions and includes a pedal or control member 1556 appropriately labeled for the respective function. By stepping on any of pedals 1556 or raising any of pedals 1556 with the tip of one's foot, one of these functions of bed 1210 is activated. When pedals 1556 are released, they are automatically biased back to the neutral position and the function terminates.

Figure 106:
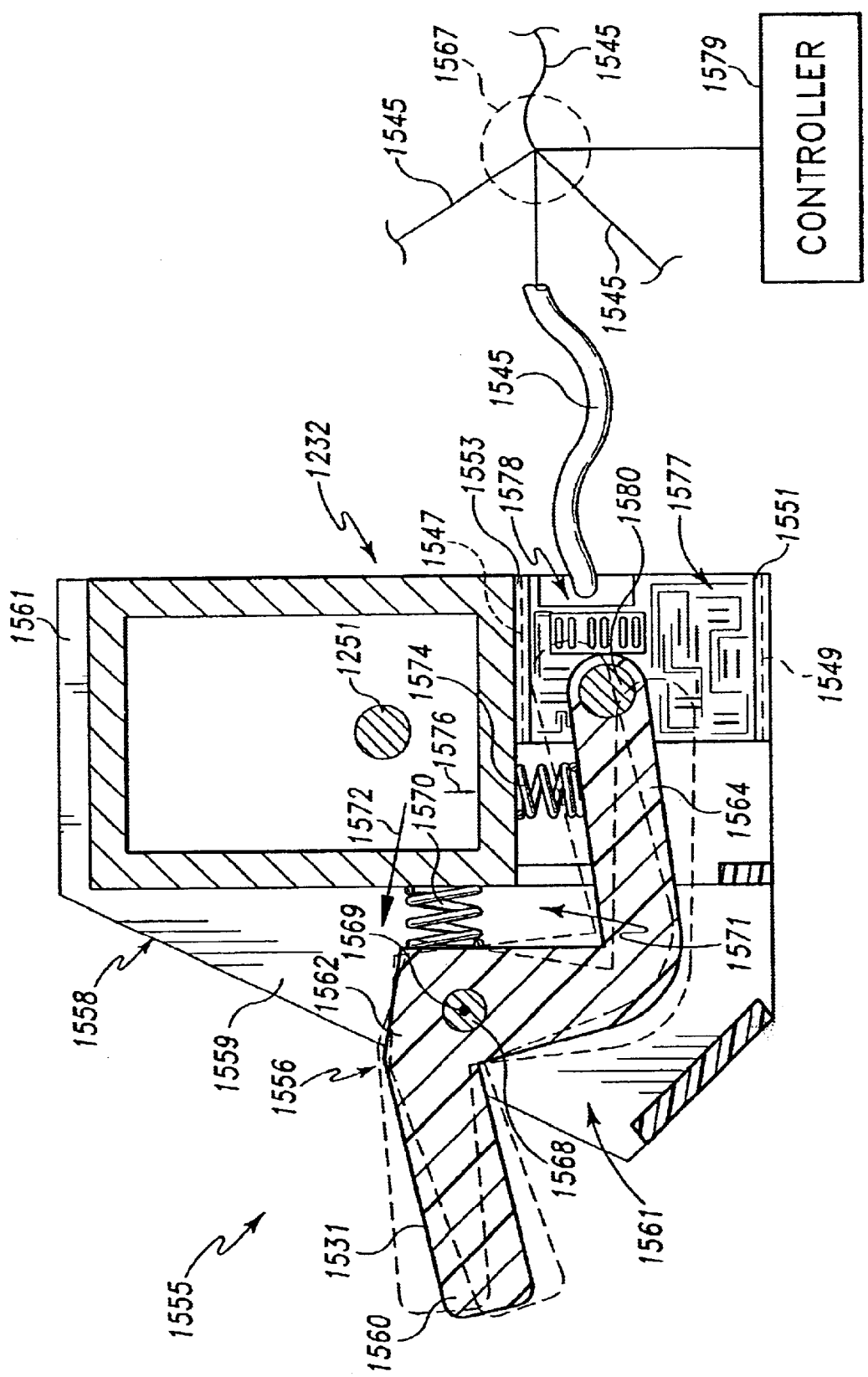
FIG. 106 is a cross-sectional view taken line 106—106 of FIG. 105 showing one of the foot pedals including a pedal pivotably coupled to the pedal housing, a first spring positioned between the base frame and the pedal to bias the pedal in a counterclockwise direction, a second spring positioned between the base frame and the pedal to bias the pedal in a clockwise direction, a magnet coupled to a distal end of the pedal, and a sensor arranged to detect the position of the magnet.

Pedals 1556 are pivotably coupled to a pedal housing 1558 that is fixedly coupled to base frame 1230 in a spaced-apart relationship with the floor. Pedal housing 1558 includes a plurality of walls 1559 that cooperated to define cavities 1561 that receive pedals 1556. Walls 1559 are coupled to a plurality of aligned rectangular collars 1563, 1565, 1567 that cooperate to receive base frame 1232 as shown in FIGS. 105 and 106. Collar 1565 is centrally located and defines an enclosed space 1567. Collars 1563, 1565 are coupled to base frame 1232 by a plurality of fasteners 1569.

As shown in FIG. 106, each pedal 1556 is pivotable between a first or up position (shown in phantom), a second or down position (shown in phantom), and a third or neutral position (shown in solid). Each pedal 1556 has a stepped profile and includes a pedal portion 1560, a pivot portion 1562, and a sensor portion 1564. Pedal portion 1560 extends beyond pedal housing 1558 to permit a caregiver to press down on pedal portion 1560 and lift up on pedal portion 1560. When in the neutral position, a top surface 1531 of pedal portion 1560 is at an angle of 15° from horizontal to help a caregiver's line of sight in viewing a decal or indicator 1566 positioned on each pedal portion 1560 that indicates what function of bed 1210 is controlled by the particular pedal 1556.

Pins 1568 are provided that extend through pivot portions 1562 and define a pivot axis 1569 about which pedals 1556 pivot on housing 1558. Each foot-operated control 1556 includes a biaser 1571 including a first spring 1570 positioned between base frame 1232 and pivot portion 1562 to bias pedal 1556 in a clockwise direction 1572, as shown in FIG. 106, and a second spring 1574 positioned between base frame 1232 and pivot portion 1562 to bias pedal 1556 in an opposite counterclockwise direction 1576. According to the preferred embodiment of the present disclosure, first and second springs 1570, 1574 are balanced to urge pedal 1556 to the neutral position shown in solid in FIG. 106. According to alternative embodiments of the present disclosure, the pedals and/or the base frame include spring mounts or counter-bores to secure the springs. According to another alternative embodiment of the present disclosure, the springs are adhered to the pedal and/or base frame.

If pedal portion 1560 is pushed down to move pedal 1556 to the down position, first spring 1570 compresses and second spring 1574 expands. This compression and expansion creates an imbalance that biases pedal 1556 back to the neutral position when released. Similarly, if pedal portion 1562 is raised up to move pedal to the up position, second spring 1574 compresses and first spring 1572 expands. This compression and expansion creates an imbalance that biases pedal 1556 back to the neutral position when released.

The position of each pedal 1556 is detected by a sensor 1578. If sensor 1578 detects that the respective pedal 1556 has moved to a predetermined up position, one function of bed 1210 is activated. When sensor 1578 detects that the respective pedal 1556 has moved to a predetermined down position, another, typically opposite, function is activated. When sensor 1578 detects that the respective pedal 1556 is in a predetermined neutral position, the respective functions are terminated. Thus, each foot-operated control 1555 is configured to activate a function of bed 1210 when moved into either the up or down position.

Sensor 1578 is preferably mounted on a circuit board 1577. Pedal housing 1558 includes a pair of transversely extending lips 1551, 1553 defining slots 1549, 1547 sized to receive opposite edges of circuit board 1577. To position sensor 1578 on housing 1558, the edges of circuit board 1577 are slid into slots 1549, 1547 and secured with a fastener, such as a screw, adhesive, locking tab, or any other fastener known to those of ordinary skill in the art. A cable 1545 is coupled to each sensor 1578 to send signals indicative of the position of pedal 1556 detected by sensor 1578. Cables 1545 extend into enclosed space 1567 of centrally located collar 1565. Each cable 1545 is coupled to a circuit board (not shown) or other junction positioned in enclosed space 1567 and a single cable 1581 extends to a central controller or processor 1579 to control the various actuators and mattress components.

According to the preferred embodiment of the present disclosure, sensor 1578 is a Hall effect field sensor that detects change in the characteristics of a magnetic field generated by pedal 1556. A magnet 1580 is positioned on sensor portion 1564 of each pedal 1556 in a position spaced apart from sensor 1578. Sensor 1578 detects the change in position of magnet 1580 during movement of the respective pedal 1556 by detecting the change in magnetic field. Based on this change in magnetic field, sensor 1578 sends a signal indicative of the up, down, or neutral positions of the respective pedal 1556 to controller 1579. Controller 1579 then initiates the application of power to motors 1271 of actuators 1264, 1266, 1612, 1660 from power source 1281 to control and power the function of the respective components of bed 1210.

According to alternative embodiments of the present disclosure, other sensors are provided to detect the position of the pedals and to control the respective functions of the bed, such as other proximity switches, a three-position mechanical switch, other mechanical switches, other electrical switches, other field sensors that detect changes in an electric field due to changes in capacitance or inductance, other field sensors known to those of ordinary skill in the art, or any other sensor known to those of ordinary skill in the art.

As shown in FIG. 105, four pedals 1556 are provided to control various functions of bed 1210 when raised up or pushed down. For example, a first pedal 1582 is provided that when pivoted upwardly, raises weigh frame 1248 and when stepped on, lowers weigh frame 1248. A second pedal 1584 is provided for raising and lowering head section 1487 relative to weigh frame 1248 when lifted and stepped on. Series of pedals 1556 also includes a third pedal 1586 for moving weigh frame 1248 between the Trendelenburg and Reverse Trendelenburg positions.

A fourth pedal 1588 is provided for quickly putting bed 1210 in the CPR mode. When pedal 1558 is moved to the raised or lowered position, mattress 1230 is inflated to the predetermined maximum pressure, head section 1487 of deck 1226, if raised, is lowered to the flat position, and seat section 1557, if raised, is lowered to the flat position to facilitate administration of CPR. According to the preferred embodiment of the present disclosure, mattress 1230 automatically returns to normal pressure thirty minutes after the CPR mode is initiated. If desired, the caregiver uses controller 1412 to override the CPR mode to return mattress 1230 to normal pressure. According to alternative embodiments of the present disclosure, the CPR pedal is not provided. According to an alternative embodiment the plurality of pedals also includes a pedal for extending and retracting a foot section of the hospital bed or for activating any other feature of the bed.

Pedals 1582, 1584, 1586, therefore, are operated in an intuitive manner to control the various functions of the hospital bed. That is, pedals 1582, 1584, 1586 are stepped on to perform a "down" function and are lifted upwardly with the top of a user's foot to perform an "up" function.

As shown in FIG. 92, a second pedal housing 1573 and second set of foot-operated controls 1575 are supported on base frame 1232 on the opposite side of bed 1210. Pedal housing 1573 is identical to pedal housing 1558 and foot-operated controls 1575 are identical to foot-operated controls 1555.

Deck 1214 is substantially similar to deck 814 of bed 810 and includes several portions or sections 1487, 1557, 1590 that can be tilted relative to intermediate frame 1252. Head section 1487 is positioned adjacent to headboard 1216 and is pivotably coupled to a pair of deck flanges 1592 coupled to weigh frame 1248 as shown in FIG. 92. Seat section 1557 is also pivotably coupled to upwardly extending flanges 1592 of weigh frame 1248. Foot section 1590 is pivotably coupled to seat section 1557 by a hinge 1594 and is coupled adjacent to footboard 1218.

Similar to deck sections 22, 24, 26, 28 of deck 14 of bed 10, each section 1487, 1557, 1590 of deck 1214 includes angled side walls 1622. Each section 1487, 1557, 1590 further includes substantially flat and rigid bottom walls 1624 preferably made of steel.

Foot section 1590 of deck 1214 is extendable and retractable. A full description of an extendable and retractable foot section is disclosed in U.S. patent application Ser. No. 09/120,125, filed Jul. 22, 1998, the disclosure of which is expressly incorporated by reference herein.

Figure 107:
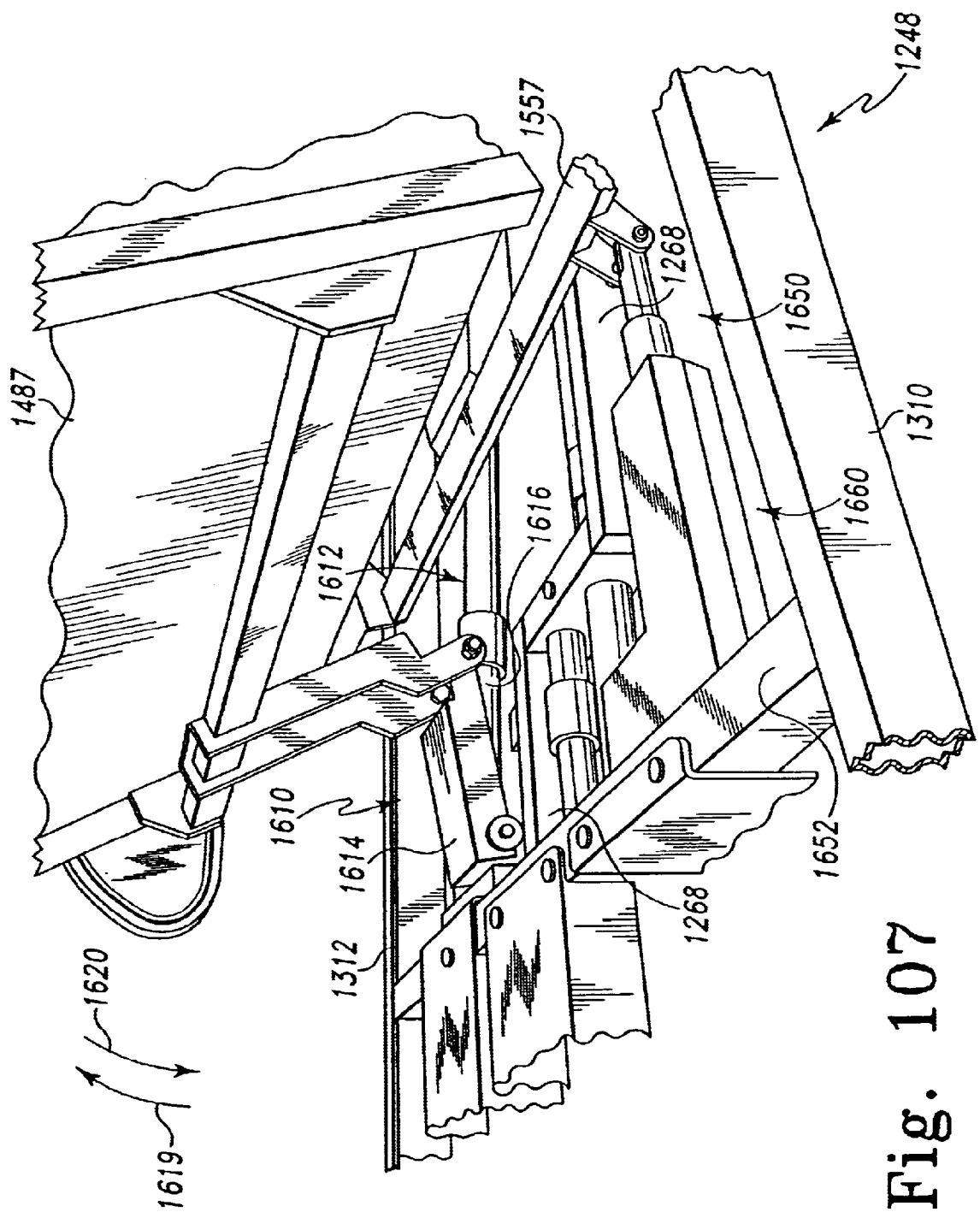
FIG. 107 is a partial perspective view showing the head section of the deck titled relative to the weigh frame.

Hospital bed 1210 includes a tilt assembly 1610 that enables head section 1487 to be moved automatically relative to weigh frame 1248. As shown in FIG. 107, tilt assembly 1610 includes a tilt actuator 1612 coupled to a transversely extending strut 1613 of weigh frame 1248 and a transfer link 1614 pivotably coupled to tilt actuator 1612 and head section 1487.

To raise or tilt head section 1487, a rod 1616 of actuator 1612 is extended so that transfer link 1614 pushes head section 1487 in a clockwise direction 1619 as shown in FIG. 107. To lower head section 1487, rod 1616 is retracted so that transfer link 1614 pulls head section 1487 in a counterclockwise direction 1620 as shown in FIG. 107.

Hospital bed 1210 further includes a tilt assembly 1650 facilitating automatic tilting of foot and seat sections 1590, 1557 relative to weigh frame 1248 and foot section 1590 relative to seat section 1557. Tilt assembly 1650 is substantially similar to tilt assembly 1048 of bed 810. Tilt assembly 1650 includes a tilt actuator 1660 coupled to a transversely extending strut 1652 of weigh frame 1248 and seat section 1557 and a link 1654 pivotably coupled to foot section 1590 and removably and pivotably coupled to weigh frame 1248. Weigh frame 1248 includes a pin received by a notch in link 1654 so that link 1654 is movable between a locked position (see, for example, FIGS. 79 and 81 showing link 1052 of tilt assembly 1048 of bed 810), and an unlocked position (see, for example, FIG. 80 showing link 1052 of bed 810). These two positions provide two modes of titling between seat section 1557 and foot section 1590 (see, for example, FIGS. 79–81 for bed 810).

When in the locked position, link 1654 provides a rigid link between weigh frame 1248 and foot section 1590. As tilt actuator 1660 is lengthened, seat section 1557 pivots relative to weigh frame 1248 (as shown in FIGS. 80 and 81 for bed 810). When link 1654 is in the locked position and tilt actuator 1660 is activated, foot section 1590 moves upwardly relative to weigh frame 1248 (as shown in FIG. 81 for bed 810) but, maintains a substantially horizontal orientation. According to alternative embodiments of the present disclosure, other orientations are provided.

When link 1654 is uncoupled from the pin and tilt actuator 1660 is activated (as shown in FIG. 80 for bed 810), foot section 1590 rotates about a roller coupled to weigh frame 1248 so that a proximal end of foot section 1590 is raised and a distal end of foot section 1590 lowers. Thus, foot section 1590 is movable relative to seat section 1557 to maintain a substantially horizontal or other position (as shown in FIG. 81 for bed 810) when link 1654 is in the locked position and a tilted or other position (as shown in FIG. 81 for bed 810) relative to weigh frame 1248 when link 1654 is in the unlocked position.

According to alternative embodiments of the present disclosure, other configurations of linkage systems are provided to facilitate two modes of tilting the foot or other section of the deck relative to another section of the deck during movement of another section of the deck relative to the upper or other frame member. Such linkage systems include additional links, hinges, cables, brackets, flanges, or other members known to those of ordinary skill in the art.

Figure 110:
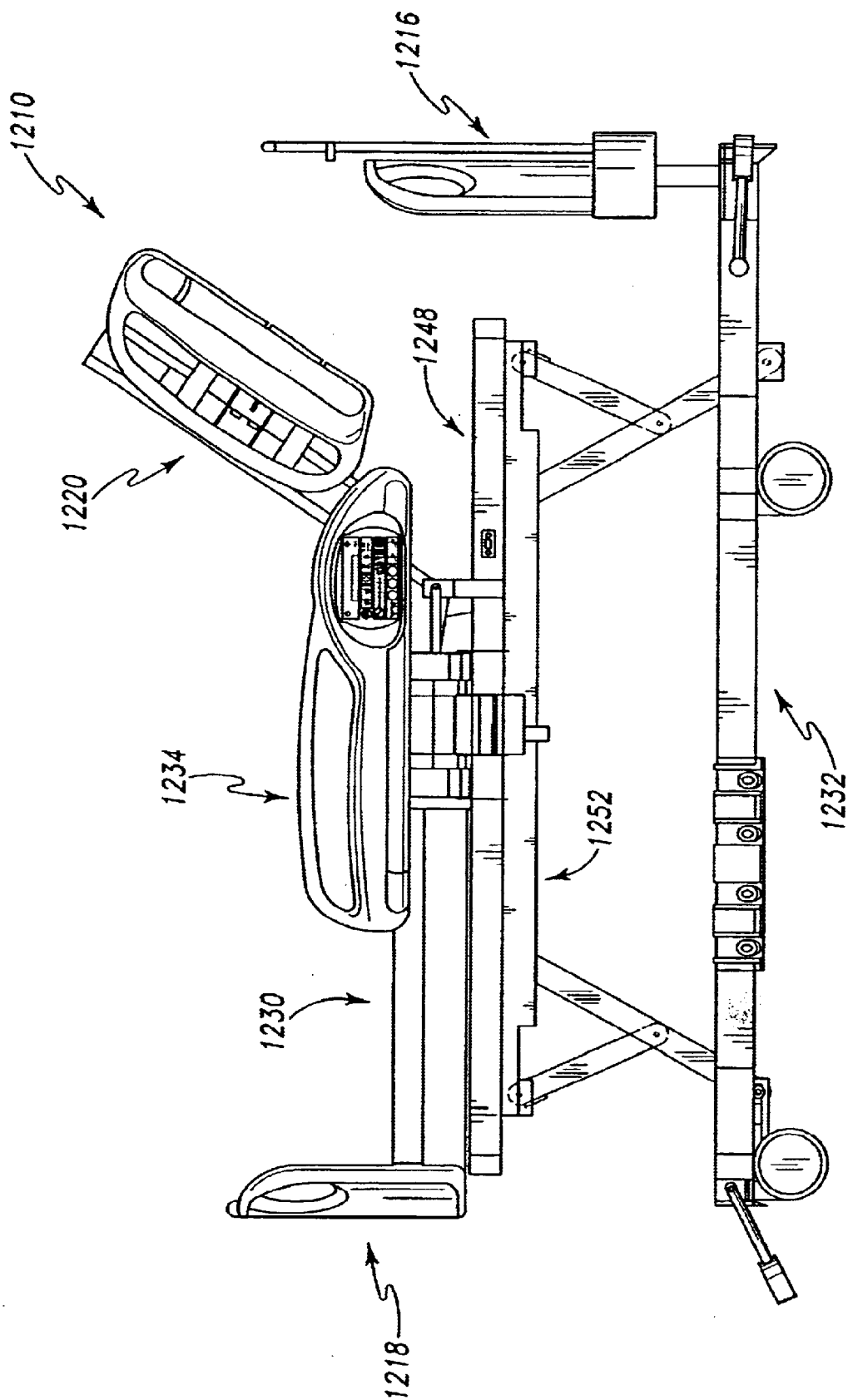
FIG. 110 is a view similar to FIG. 109 showing the head end siderail in a lowered position.

Split siderails 1220, 1234 are pivotably coupled to respective head section 1487 of deck 1214 and weigh frame 1248. Each siderail 1220, 1234 is configured to move between up positions, as shown in FIG. 109, and down positions, as shown in FIG. 110, to permit entry and egress of patients into and out of hospital bed 1210. Each siderail 1220, 1234 includes a respective rail member 1506, 1664 and a linkage assembly 1666, 1667 coupled between respective rail members 1506, 1664 and respective head section 1487 of deck 1214 and weigh frame 1248 that permit rail members 1506, 1664 to be moved between upper and lower positions.

Linkage assembly 1666 includes a first link 1668 rigidly coupled to respective head section 1487 of deck 1214 and weigh frame 1248, a pair of curved second links 1670 pivotably coupled to first link 1668, a third link 1672 pivotably coupled to second links 1670, and a curved fourth link 1674 pivotably coupled to third and first links 1668, 1672. Linkage assemblies 1666, 1667 are substantially similar to linkage assembly 142 of bed 10.

Figure 111:
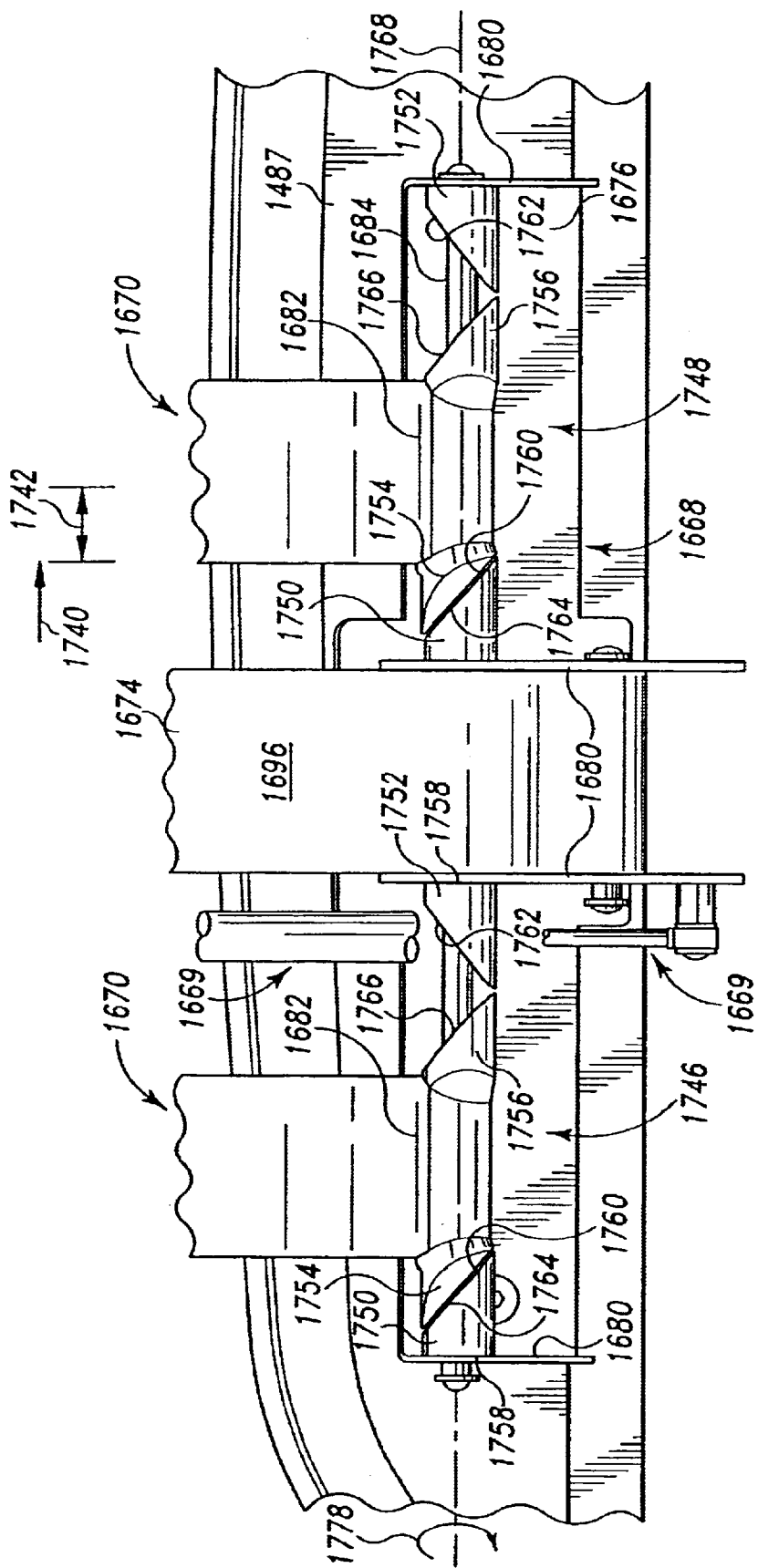
FIG. 111 is side elevation view of a portion of the head end siderail in the raised position showing the siderail including a pair of spaced-apart links pivotably coupled to a longitudinally extended rod, the rod including two pairs of cylindrical cams, and each link including a pair of spaced-apart cylindrical cams positioned to contact the cylindrical cams of the rod.

First link 1668 includes a base 1676 coupled to intermediate weigh frame 1248 and four upwardly extending flanges 1680 rigidly coupled to base 1676 as shown in FIG. 111. Each second link 1670 includes a first end 1682 pivotably coupled to flanges 1680 by a rod 1684 and a looped second end 1686 pivotably coupled to third link 1672 by a rod 1688 as shown in FIG. 108.

Figure 108:
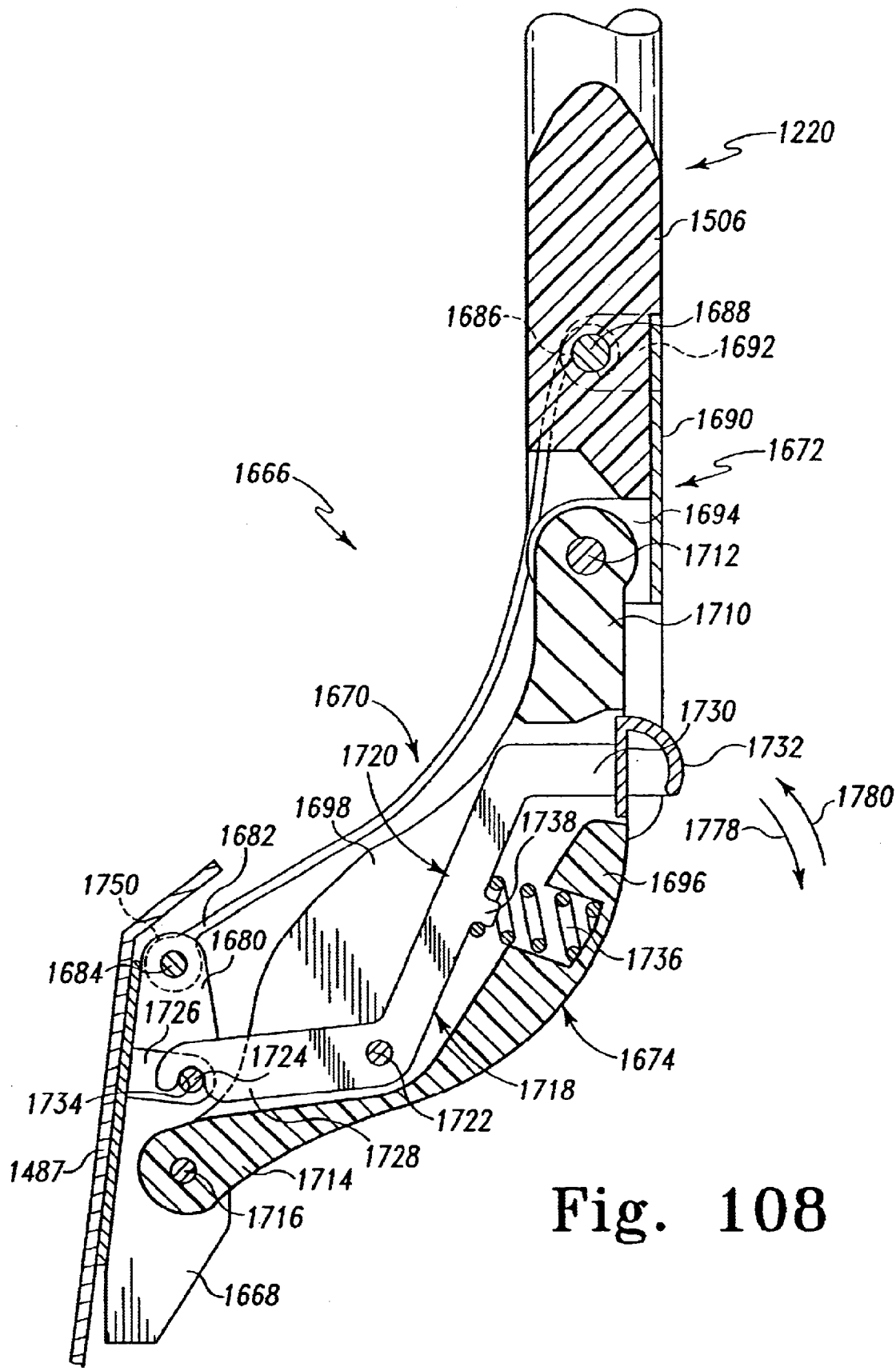
FIG. 108 is a cross-sectional view of the head end siderail taken along line 108—108 of FIG. 109.

Third link 1672 includes a base 1690, a first pair of inwardly extending flanges 1692 coupled to base 1690, and a second pair of inwardly extending flanges 1694 also coupled to base 1690 as shown in FIG. 108. Rod 1688 extends between flanges 1692 and through second ends 1686 of second link 1670 to provide the pivotable connection therebetween.

As shown in FIG. 108, fourth link 1674 includes a base 1696 and a latch-receiving slot 1698 formed in base 1696. A first end 1710 of base is slidably and pivotably coupled to second pair of flanges 1694 of third link 1672 by a rod 1712. A second end 1714 of base 1696 is pivotably coupled to the lower ends of flanges 1680 of first link 1668 by a rod 1716. Thus, linkage assembly 1666 provides a four bar linkage permitting siderails 1220 to swing between the up and down positions.

Figure 112:
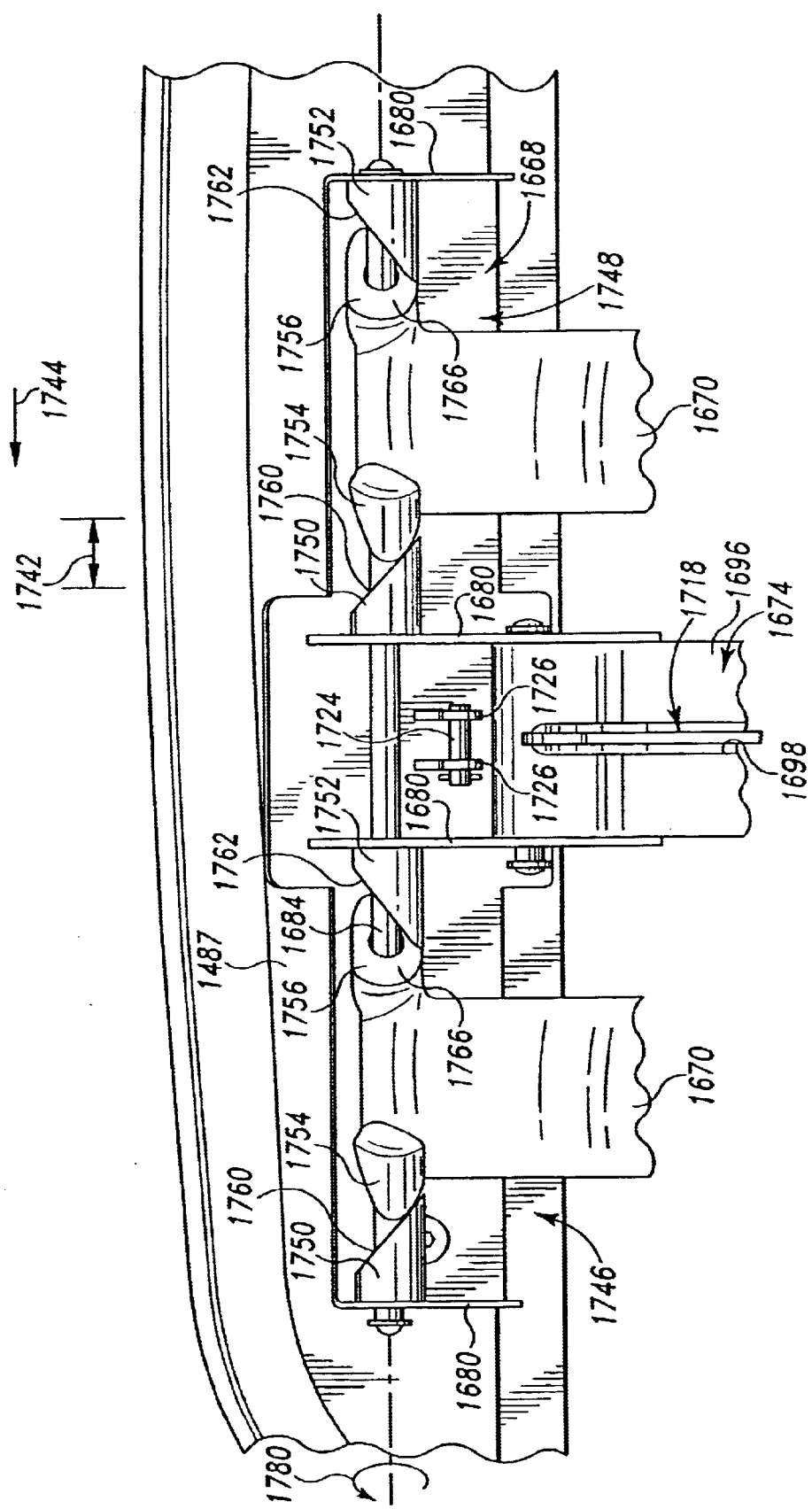
FIG. 112 is a view similar to FIG. 111 showing the siderail translated to the right when in the lowered position.

Each siderail 1220 further includes a retainer 1718 configured to "bind" the four bar linkage to prevent siderails 1220 from moving from the up position to the down position. As shown in FIG. 108, retainer 1718 includes a Z-shaped latch member 1720 positioned in latch-receiving slot 1698 and pivotably coupled to fourth link 1674 by rod 1722 to move between a latched position, as shown in FIG. 108, and an unlatched position and a catch rod 1724 coupled to first link 1668 by a pair of flanges 1726. Rod 1724 extends between flanges 1726 as shown in FIG. 112. Latch member 1720 includes a first end 1728 that engages catch rod 1724 and a second end 1730. A handle 1732 is provided that is coupled to second end 1730. First end 1728 includes a notch 1734 configured to receive catch rod 1724 therein to secure latch member 1720 in the latched position as shown in FIG. 108.

When first end 1728 is latched onto catch rod 1724, a three bar linkage is established between first link 1668, latch member 1720, and fourth link 1674. This arrangement of linkages binds first link 1668 relative to fourth link 1674 so that linkage assembly 1666 is also bound from moving while latch member 1720 is in the latched position to prevent siderails 1220 from swinging to the lower position.

To unbind linkage assembly 1666 and permit siderails 1220 to swing to the down position, latch member 1720 must be moved from the latched position to the unlatched position. A caregiver can unlatch latch member 1720 by pulling downwardly and outwardly on handle 1732 to pivot latch member 1720 in the clockwise direction. This movement pulls first end 1728 of latch member 1720 away from catch rod 1724 so that latch member 1720 no longer binds first and fourth links 1668, 1674.

As shown in FIG. 111, assembly 1666 further includes a gas spring or dashpot 1669 coupled to first link 1668 and third link 1672. Gas spring 1669 is compressed when siderail 1220 is lowered to dampen the movement and prevent rapid lowering of rail member 1506.

Because first and fourth links 1668, 1674 are free to pivot relative to one another, linkage assembly 1666 is also unbound and free to permit siderails 1220 to swing between the upper and lower positions. A spring 1736 is provided between a middle portion of fourth link 1674 and a spring mount 1738 coupled to a middle portion of latch member 1720 to bias latch member 1720 toward the latched position. According to alternative embodiments of the present disclosure, other retainers are provided to hold the siderails in the upper position such as clasps, catches, locks, other latches, clamps, pins, bolts, bars, hasp, hooks, or other retainers known to those of ordinary skill in the art.

Head end siderails 1220 are configured to move longitudinally when raised and lowered. When lowered, head end siderail 1220 moves in a first direction 1740, shown in FIG. 111, by a distance 1742 toward a head end of head section 1487 of deck 1214. When raised, head end siderails 1220 moves in a second direction 1744, shown in FIG. 112, by distance 1742 back toward a foot end of head section 1487.

By moving head end siderails 1220 when lowering, additional clearance is provided between head end siderail 1220 and foot end siderail 1234. Thus, when head section 1487 of deck 1214 is in the raised position (as shown in FIG. 110), foot end siderail 1234 is in the raised position (as shown in FIG. 110), and head end siderail 1220 is lowered from the up position, rail member 1506 of head end siderail 1220 is pushed in direction 1742 to that contact with foot end siderail 1234 is avoided.

As shown in FIGS. 111 and 112, linkage assembly 1666 of head end siderails 1220 includes a first set of cams 1746 and a second set of cams 1748. Each set of cams 1746, 1748 includes a pair of stationary cam members 1750, 1752 rigidly coupled to flanges 1680 of first links 1668 and a pair of rotary cam members 1754, 1756 rigidly coupled to first ends 1682 of second links 1670. As shown in FIGS. 111 and 112, rod 1684 extends through rotary cam members 1754, 1756 to pivotably couple second links 1670 to first links 1668. According to an alternative embodiment of the present disclosure, only one set of cams are provided.

As shown in FIG. 111, each stationary cam member 1750, 1752 is a truncated cylinder that has a first substantially flat end surface 1758 coupled to flanges 1680. Each respective stationary and rotary cam member 1750, 1752, 1754, 1756 further includes an inclined cam surface 1760, 1762, 1764, 1766 that cooperates with a longitudinal axis of rotation 1768 of rod 1684 to define respective angles therebetween of approximately 45°.

As shown in FIG. 111, cam surfaces 1760 of stationary cam members 1750 are substantially parallel with and slightly spaced-apart from cam surfaces 1764 of rotary cam members 1754 when head end siderail 1220 is in the fully raised position. Cam surfaces 1762 of stationary cam members 1752 are spaced-apart from cam surfaces 1766 of rotary cam members 1756 and define an angle of approximately 90° therebetween.

When handle 1732 is pulled, head end siderail 1220 moves towards the lowered position. During this movement, rail member 1506, second links 1670, and rotary cam members 1754 rotate in a clockwise direction 1778, as shown in FIG. 1778, so that cam surfaces 1764 of rotary cam members 1754 move into contact with cam surfaces 1760 of stationary cam members 1750. As shown in FIG. 112, continued rotation of rotary cam members 1754 create forces between rotary cam members 1754 and stationary cam members 1750. These forces push rotary cam members 1754, second links 1670, and rail member 1506 of head end siderail 1220 in direction 1740. When head end siderail 1220 is moved to the lowered position, rail member 1506 is pushed toward the head end of head section 1487 by distance 1742, as shown in FIG. 112.

As previously mentioned, third link 1672 is slidably coupled to fourth link 1674 by rod 1712. During movement of rail member 1506 of head end siderail 1220 in direction 1740, fourth link 1674 does not move longitudinally so that third link 1672 and rail member 1506 slides relative to fourth link 1674.

When head end siderail 1220 is initial moved toward the raised position, cam surfaces 1762 of stationary cam members 1752 are slightly spaced-apart from cam surfaces 1766 of rotary cam members 1756. Cam surfaces 1760 of stationary cam members 1750 are slightly spaced-apart from cam surfaces 1764 of rotary cam members 1754.

As head end siderail 1220 is moved further toward the raised position, rail member 1506, second links 1670, and rotary cam members 1754 rotate in a counterclockwise direction 1780, as shown in FIG. 112, so that cam surfaces 1762 of stationary cam members 1752 move into contact with cam surfaces 1766 of rotary cam members 1756. Continued rotation of rotary cam members 1754 create forces between rotary cam members 1756 and stationary cam members 1752. These forces push rotary cam members 1756, second links 1670, and rail member 1506 of head end siderail 1220 in direction 1744. During this movement, third link 1672 and rail member 1506 slides relative to fourth link 1674 in direction 1744.

As shown in FIG. 111, cam surfaces 1760 of stationary cam members 1750 are substantially parallel with and slightly spaced-apart from cam surfaces 1764 of rotary cam members 1754 when head end siderail 1220 is back to the fully raised position. Cam surfaces 1762 of stationary cam members 1752 are spaced-apart from contact cam surfaces 1766 of rotary cam members 1756 and define an angle of approximately 90° therebetween.

According to alternative embodiments of the present disclosure, other configurations of siderails that move in a longitudinal direction during raising and lowering are provided. These alternative embodiments includes other configurations of cams, links, belts, cable, pulleys, or other mechanisms known to those of ordinary skill in the art for creating movement of a member in one direction based on movement of the same or another member in another direction.

The linkage assembly of foot end siderails 1234 are substantially similar to linkage assembly 1666 of head end siderails 1220. However, the linkage assembly of foot end siderails 1234 are not configured to move rail member 1664 longitudinally when moved between the raised and lowered position. Therefore, the linkage assembly of foot end siderail 1234 does not includes cam members and the third link is not configured to slide relative to the fourth link.

Figure 113:
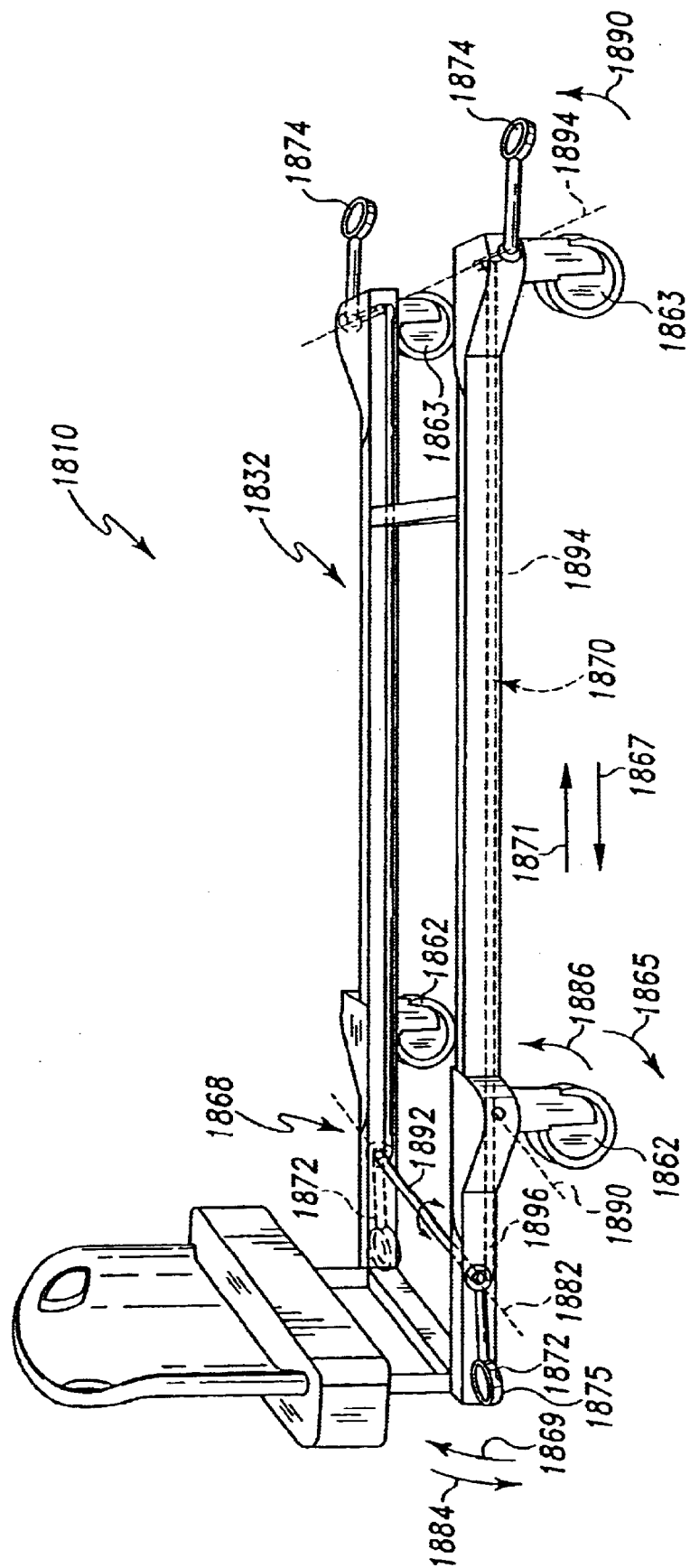
FIG. 113 is a perspective view of a base frame of another alternative embodiment bed showing four casters coupled to the base frame, a first pair of foot pedals coupled to two of the casters, a second pair of foot pedals longitudinally spaced apart from the other two casters, a transverse link coupling the second pair of foot pedals together, and a pair of spaced-apart longitudinally extending links coupling the first and second pair of foot pedals together so that all four casters are linked to move simultaneously.

A base frame 1832 of another alternative embodiment hospital bed 1810 is shown in FIG. 113. Bed 1810 includes a caster braking system 1868 including a caster-brake link 1870 extending through hollow base frame 1832 as shown in FIG. 113. Caster braking system 1868 interconnects each caster 1862, 1863 to provide simultaneous braking of casters 1862, 1863. To simultaneously brake casters 1862, 1863, the caregiver steps on one of foot brake pedals 1872, 1874 and caster braking system 1868 locks casters 1862 against rolling. Caster braking system 1868 further includes a transversely extending rod 1892 that is offset from casters 1862, 1863 that facilitates coordination of the locking and unlocking of casters 1862, 1863 located on opposite sides of bed frame 1832.

As shown in FIG. 113, foot brake pedal 1872 is longitudinally spaced apart from caster 1862 by a distance 1876. Foot brake pedal 1872 is coupled to base frame 1832 by a rod (not shown) similar to rod 878 of bed 810 and pivotably coupled to caster-brake link 1870 by an arm (not shown) similar to arm 880 of bed 810. During rotation of foot brake pedal 1872 about axis 1882 in direction 1884, the arm transmits force to caster-brake link 1870. Caster-brake link 1870 moves in direction 1871 to transmits this force to an arm (not shown) similar to arm 886 of bed 810 pivotably coupled to caster-brake link 1870 and rigidly coupled to a hexagonal rod (not shown) similar to rod 888 of bed 810 of caster braking system 868. This rotation causes the hexagonal rod to rotate about an axis 1890 in direction 1886 causing caster 1862 to lock.

According to the preferred embodiment of the present disclosure, caster-brake link 1870 is positioned below rod 1878 so that counterclockwise rotation of rod 1878 by foot brake pedal 1872 in direction 1884 causes movement of caster-brake link 1870 in direction 1871. Similarly, rotation of pedal 1872 in clockwise direction 1869 causes caster-brake link 1870 to move in direction 1867 and the hexagonal rod to rotate in clockwise direction 1865 to unlock caster 1862. According to an alternative embodiment of the present disclosure, the caster-brake link is positioned above the rod so that rotation of the pedal in direction 1884 causes the caster-brake link to move in direction 1867 and movement of the pedal in direction 1869 causes the caster-brake link to move in direction 1871.

Additional description of a caster braking system similar to the caster braking system of the present disclosure is provided in U.S. patent application Ser. No. 09/263,039, filed Mar. 5, 1999, to Mobley et al., entitled Caster and Braking System, the disclosure of which is expressly incorporated by reference herein. According to alternative embodiments of the present disclosure other configurations of caster braking and/or steering systems with or without simultaneous locking functions are provided for use with the foot brake pedal and caster-brake link of the present disclosure.

Caster-brake link 1870 also transmits the rotation of foot brake pedal 1872 to the other hexagonal rods (not shown) similar to 888, 892 of bed 810 associated with the other casters 1862, 1863 to simultaneously brake all four casters 1862, 1863. As shown in FIG. 113, link 1870 includes a portion 1894 that continues to extend through frame member 1832 and couples to the hexagonal rod of caster 1863 in a manner similar to the coupling to hexagonal rod 888 shown in FIG. 67. Therefore, when the hexagonal rods of caster 1862 rotate about axis of rotation 1890, the hexagonal rod of caster 1863 rotates about axis 1894. To unlock casters 1862, 1863, foot brake pedal 1872 is rotated in a direction opposite direction 1884 to rotate the hexagonal rod of caster 1863 in a direction opposite direction 1890 to unlock caster 1862. Caster-brake link 1870 also transmits the rotation to the other hexagonal rods of the other casters 1862, 1863 to simultaneously release all casters 1862, 1863.

Transversely extending rod 1892 transmits the rotation of pedal 1872 to the other hexagonal rods. Another caster-brake link 1894 that is identical to caster-brake link 1870 extends through the opposite side of base frame 1832 and couples the hexagonal rods of the other casters 1862, 1863 together so that rotation of the other head end pedal 1872 is transferred to all four casters 1862, 1863 to provide simultaneous locking and unlocking of casters 1862, 1863.

Similarly, the caster-brake links 1870, 1894 also transmit the rotation of foot brake pedals 1874 to all four caster 1862, 1863. Foot brake pedals 1874 are directly coupled to the hexagonal rods and coupled to the caster-brake links 1870 by an arm (not shown) similar to arm 886 of bed 810. Thus, if brake pedals 1874 are rotated to lock or unlock either caster 1863, the other casters 1862, 1863 are also locked or unlocked.

Brake pedal 1872 is positioned so that a caregiver standing adjacent to headboard 1816 can operate the caster braking system. As shown in FIG. 113, brake pedal 1872 includes a foot pad 1875 positioned adjacent to a head end of base frame 1832. A caregiver positioned near headboard 1816 can step on pad 1875 to lock casters 1862, 1863 without having to move to the side of bed 1810 to access brake pedal 1872.

As shown in FIG. 113, because brake pedal 1872 is longitudinally spaced apart from caster 1862, axis of rotation 1890 of the hexagonal rod is longitudinally positioned between axis of rotation 1882 of rod 1878 and axis of rotation 1894 of the opposite hexagonal rod. Thus, the portion of caster-brake link 1870 positioned between arms 1880, 1886 is an extension 1896 that permits pedal 1872 to be longitudinally spaced apart from caster 1862. According to an alternative embodiment of the present disclosure, the foot end brake pedals are also spaced apart from the foot end casters in a manner similar to head end brake pedals.

According to the present disclosure, a patient support is provided. The patient support includes a frame, a mattress supported by the frame, a barrier positioned to block egress of a patient from the mattress, and a controller. The barrier includes first and second spaced-apart rails and the controller is positioned to slide along the first and second rails. For example, see illustrative preferred embodiments in FIGS. 76–78, 92, and 102–104.

According to another embodiment of the present disclosure, a patient support is provided that includes a frame, a mattress supported by the frame, a barrier positioned to block egress of a patient from the mattress, and a controller. The barrier includes upper and lower surfaces that cooperate to define an opening. The controller is positioned to slide along the lower surface defining the opening in the barrier. For example, see illustrative preferred embodiments in FIGS. 76–78, 92, and 102–104.

According to another embodiment of the present disclosure, a patient support is provided that includes a frame, a mattress supported by the frame, a barrier positioned to block egress of a patient from the mattress, and a controller. The barrier includes a curved opening and the controller is positioned in the curved opening to move along the barrier. For example, see illustrative preferred embodiments in FIGS. 76–78, 92, and 102–104.

According to another embodiment of the present disclosure, a patient support is provided that includes a frame, a mattress supported by the frame, a barrier positioned to block egress of a patient from the mattress, and a controller. The barrier includes a surface defining an opening in the barrier. The controller includes a housing and a retainer coupled to the housing. The retainer is configured to contact the surface of the barrier to removable couple the housing to the barrier. For example, see illustrative preferred embodiments in FIGS. 76–78, 92, and 102–104.

According to another embodiment of the present disclosure, a patient support is provided that includes a frame, a mattress supported by the frame, a barrier positioned to block egress of a patient from the mattress, and a controller. The controller is removably coupled to the barrier and is movable from a first position spaced apart from the barrier to a second position coupled to the barrier. The controller is movable along a path having a horizontal component from the first position to the second position to couple the controller to the barrier. The controller is movable along the barrier when in the second position. For example, see illustrative preferred embodiments in FIGS. 76–78, 92, and 102–104.

According to another embodiment of the present disclosure, a patient support is provided that includes a frame and a mattress supported by the frame. The mattress has a first side and a second side transversely spaced-apart from the first side. The patient support further includes a first barrier positioned to block egress of a patient from the first side of the mattress, a second barrier positioned to block egress of a patient from the second side of the mattress, and a controller. The first barrier includes a first opening formed therein and the second barrier includes a second opening formed therein. The controller is configured to be removably received in the first opening of the first barrier and removably received in the second opening of the second barrier. For example, see illustrative preferred embodiments in FIGS. 76–78, 92, and 102–104.

According to another embodiment of the present disclosure, a patient support is provided that includes a frame, a mattress supported by the frame, a barrier positioned to block egress of a patient from the mattress, and a controller. The barrier has a longitudinal axis. The barrier includes a guide configured to direct movement of the controller along the barrier in a path having longitudinal and transverse components. For example, see illustrative preferred embodiments in FIGS. 76–78, 92, and 102–104.

According to another embodiment of the present disclosure, a patient support is provided that includes a frame, a mattress supported by the frame, a pair of spaced-apart barriers positioned to block egress of a patient from the mattress, and a controller removably coupled to the barrier. The controller includes a housing, a cord coupled to the housing, and a first connector coupled to the cord. The patient support further includes a second connector supported by the frame. The first connector is configured to couple to the second connector to provide communication for the controller through the first and second connectors when the first connector is coupled to the second connector. The patient support further includes a third connector supported by the frame. The first connector is configured to couple to the third connector to provide communication for the controller through the first and third connectors when the first connector is coupled to the third connector. For example, see illustrative preferred embodiments in FIGS. 76–78, 82, 84, 92, and 102–104.

According to another embodiment of the present disclosure, a patient support is provided that includes a frame having a base frame and an intermediate frame configured to move relative to the base frame between first and second positions, a deck coupled to the intermediate frame, and a mattress supported by the deck. The deck includes at least one deck section configured to move relative to the intermediate frame between first and second positions. The patient support further includes a plurality of actuators configured to move between first and second positions to move the intermediate frame relative to the base frame and deck section relative to the intermediate frame and a plurality of electrical foot-operated controls supported by the frame. Each of the plurality of foot-operated controls is movable to a first position to control movement of at least one of the plurality of actuators to the first position and a second position to control movement of at least one of the plurality of actuators to the second position. For example, see illustrative preferred embodiments in FIGS. 15, 16, 92, 105, and 106.

According to another embodiment of the present disclosure, a patient support is provided that includes a frame, a deck supported by the frame, a mattress supported by the deck, and an actuator configured to move between first and second positions to move at least one of a portion of the frame and a portion of the deck. The patient support further includes an electrical foot-operated control movable to a first position activating movement of the actuator to the first position and a second position activating movement of the actuator to the second position. For example, see illustrative preferred embodiments in FIGS. 15, 16, 92, 105, and 106.

According to another embodiment of the present disclosure, a patient support is provided that includes a frame, a deck supported by the frame, a mattress supported by the deck, and an actuator configured to move at least one of a portion of the frame and a portion of the deck. The patient support further includes a control configured to control movement of the actuator. The control including a control member and a field sensor configured to detect a change in a field caused by a change in position of the control member to control operation of the actuator based upon the change in position of the control member. For example, see an illustrative preferred embodiment in FIGS. 92, 105, and 106.

According to another embodiment of the present disclosure, a patient support is provided that includes a frame, a deck supported by the frame, a mattress supported by the deck, a first actuator configured to move between first and second positions to move at least one of a portion of the frame and a portion of the deck, and a second actuator configured to move between first and second positions to move at least one of a portion of the frame and a portion of the deck. The patient support further includes a foot-operated control movable to a first position to control movement of the first and second actuators to the first positions and a second position to control movement of the first and second actuators to the second positions. For example, see illustrative preferred embodiments in FIGS. 15, 16, 92, 105, and 106.

According to another embodiment of the present disclosure, a patient support is provided that includes a frame, a plurality of wheels configured to support the frame and facilitate movement of the frame on the floor, a deck supported by the frame, a mattress supported by the deck, and an actuator configured to move at least one of a portion of the frame and a portion of the deck. The patient support further includes an electrical foot-operated control configured to control movement of the actuator. For example, see illustrative preferred embodiments in FIGS. 15, 16, 92, 105, and 106.

According to another embodiment of the present disclosure, a patient support is provided that includes a frame, a deck supported by the frame, a mattress supported by the deck, and an actuator configured to move at least one of a portion of the frame and a portion of the deck. The patient support further includes an electrical foot-operated control supported by the frame and configured to control movement of the actuator. For example, see illustrative preferred embodiments in FIGS. 15, 16, 92, 105, and 106.

According to another embodiment of the present disclosure, a patient support is provided that includes a frame, a deck supported by the frame, a mattress supported by the deck, an actuator configured to move between first and second positions to move at least one of the frame and a portion of the deck, and a power source configured to apply power to the actuator to move between the first and second positions. The patient support further includes a foot-operated control movable to a first position initiating application of power from the power source to the actuator to move the actuator to the first position and a second position initiating application of power from the power source to the actuator to move the actuator to the second position. For example, see illustrative preferred embodiments in FIGS. 15, 16, 92, 105, and 106.

According to another embodiment of the present disclosure, a patient support is provided that includes a frame, a deck supported by the frame, and a mattress supported by the deck. The mattress includes a retractable foot portion configured to have an adjustable length. The retractable foot portion includes a foam portion and a heel-pressure relief portion. For example, see an illustrative preferred embodiment in FIGS. 88–91, 114, and 115.

According to another embodiment of the present disclosure, a mattress is provided. The mattress includes a head portion, a seat portion, and a retractable foot portion. The head, seat, and foot portions cooperate to define a patient rest surface. The retractable foot portion has an adjustable length, a main body, and a heel-pressure relief portion. The main body has a cavity sized to received the heel-pressure relief portion. For example, see an illustrative preferred embodiment in FIGS. 88–91, 114, and 115.

According to another embodiment of the present disclosure, a mattress is provided. The mattress includes a head portion, a seat portion, and a foot portion. The foot portion has an adjustable length. The head, seat, and foot portions cooperate to define a patient rest surface having an adjustable length. The foot portion includes an adjustable length foam portion and a heel-pressure relief portion having a stiffness less than the stiffness of the foam portion. For example, see an illustrative preferred embodiment in FIGS. 88–91, 114, and 115.

According to another embodiment of the present disclosure, a method of supporting a patient is provided. The method includes the step of providing a patient support. The patient support has an adjustable length, a foam calf support, and a heel-pressure relief portion that has a stiffness less than the stiffness of the foam calf support. The method further includes the step of adjusting the length of the patient support to position the foam calf support under a patient's calves and the heel-pressure relief portion under a patient's heels. For example, see an illustrative preferred embodiment in FIGS. 88–91, 114, and 115.

According to another embodiment of the present disclosure, a patient support is provided that includes a frame, a deck supported by the frame, a mattress supported by the deck, and a controller. The deck includes a head section configured to move relative to the frame and a foot section having an adjustable length. The controller is configured to change the length of the foot section to correspond to the position of the head section of the deck. The foot section of the deck remains substantially horizontal during the change of the length of the foot section. For example, see an illustrative preferred embodiment in FIGS. 88–91, 114, and 115.

According to another embodiment of the present disclosure, a patient support is provided that includes a frame, a deck supported by the frame, and a mattress supported by the deck. The deck includes a head section and a foot section. The head section is configured to raise and lower relative to the frame. The mattress has a head portion positioned over the head section of the deck and an adjustable length foot portion positioned over the foot section of the deck. The length of the foot portion of the mattress is configured to increase in length to correspond to raising of the head section of the deck. For example, see an illustrative preferred embodiment in FIGS. 88–91, 114, and 115.

According to another embodiment of the present disclosure, a patient support is provided that includes a frame, a deck supported by the frame, and a mattress supported by the deck. The deck includes a head section, a seat section, and a foot section. The head section is configured to raise and lower relative to the frame. The mattress has a head portion positioned over the head section of the deck and a foot portion having a heel-pressure relief portion. The position of the heel-pressure relief portion corresponds to the position of the head section relative to the frame. For example, see an illustrative preferred embodiment in FIGS. 88–91, 114, and 115.

According to another embodiment of the present disclosure, a method of maintaining heel-pressure relief of a patient is provided. The method includes the step of providing a patient support. The patient support includes a frame, a deck supported by the frame and having a foot section and a head section movable between first and second positions relative to the frame, and a mattress having a foot portion positioned over the foot section of the deck and a head section positioned over the head section of the deck. The foot portion has a heel-pressure relief portion configured to reduce the surface pressure on a patient's heel. The method further comprises the step of corresponding the position of the heel-pressure relief portion of the mattress with the position of the head section of deck to maintain the position of the heel-pressure relief portion under the patient's heel. For example, see an illustrative preferred embodiment in FIGS. 88–91, 114, and 115.

According to another embodiment of the present disclosure, another patient support is provided. The patient support includes a frame, a mattress positioned over the frame, and a barrier positioned to block egress of a person from the mattress. The barrier is made of a non-opaque material. For example, see an illustrative preferred embodiment in FIG. 32.

According to another embodiment of the present disclosure, another patient support is provided. The patient support includes a frame, a mattress positioned over the frame, and a barrier positioned to block egress of a person from the mattress. The barrier is made of a non-opaque material. The patient support further includes a light source positioned to introduce light into the barrier made of non-opaque material to illuminate the barrier. For example, see an illustrative preferred embodiment in FIG. 32.

According to another embodiment of the present disclosure, another patient support is provided. The patient support includes a frame, a mattress positioned over the frame, and a siderail positioned to block egress of a person from the mattress. The siderail is made of a non-opaque material. For example, see an illustrative preferred embodiment in FIG. 32.

According to another embodiment of the present disclosure, another patient support is provided. The patient support includes a frame, a mattress positioned over the frame, and at least one headboard and footboard positioned to block egress of a person from the mattress. The at least one headboard and foot board is made of a non-opaque material. For example, see an illustrative preferred embodiment in FIG. 1.

According to another embodiment of the present disclosure, another patient support is provided. The patient support includes a frame, a mattress positioned over the frame, and a siderail. The siderail includes a rail member configured to move from a first position to a second position. The rail member has an inner side facing the mattress and an outer side facing away from the mattress. The siderail further includes a retainer configured to hold the rail member in the first position and a patient-accessible release configured to permit movement of the siderail from the first position. The patient-accessible release is accessible to a person normally positioned on the mattress. For example, see illustrative preferred embodiments in FIGS. 27–33 and 36–39.

According to another embodiment of the present disclosure, another patient support is provided. The patient support includes a frame, a mattress positioned over the frame, and a siderail. The siderail includes a rail member configured to move from a first position to a second position, a retainer configured to hold the rail member in the first position, a release configured to permit movement of the rail member from the first position, and a lock configured to prevent the release from permitting movement of the rail member from the first position. For example, see an illustrative preferred embodiment in FIGS. 27–33.

According to another embodiment of the present disclosure, another patient support is provided. The patient support includes a frame, a mattress positioned over the frame, and a siderail including a rail member configured to move from a first position to a second position. The patient support further includes a retainer configured to hold the rail member in the first position, a first release configured to permit movement of the siderail from the first position, and second release configured to permit movement of the siderail from the first position. For example, see illustrative preferred embodiments in FIGS. 27–33 and 36–39.

According to another embodiment of the present disclosure, another patient support is provided. The patient support includes a frame, a mattress positioned over the frame, and a siderail. The siderail includes a rail member configured to move from a first position blocking egress of a person positioned on the mattress to a second position and an armrest arranged to support an arm of the person positioned on the mattress. For example, see an illustrative preferred embodiment in FIGS. 32–35.

According to another embodiment of the present disclosure, another patient support is provided. The patient support includes a frame, a mattress positioned over the frame, and a siderail. The siderail includes a rail member configured to move from a first position blocking egress of a person positioned on the mattress to a second position and a container holder configured to support a container. For example, see an illustrative preferred embodiment in FIGS. 32–35.

According to another embodiment of the present disclosure, another patient support is provided. The patient support includes a frame, a mattress positioned over the frame, and a barrier positioned to block egress of a patient from the mattress, a wireless controller configured to couple to the barrier. The wireless controller is configured to control a function of the patient support. For example, see an illustrative preferred embodiment in FIGS. 74 and 75.

Figure 72:
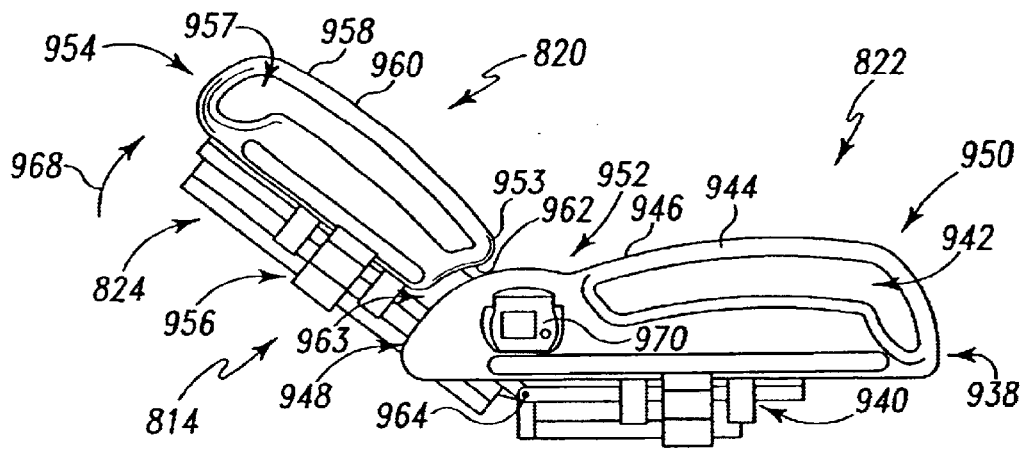
FIG. 72 is a view similar to FIG. 71 showing the head section of the deck tilted relative to the seat section of the deck.

According to another embodiment of the present disclosure, another patient support is provided. The patient support includes a frame, a mattress positioned over the frame, a first siderail positioned to block egress of a patient from the mattress. The first siderail includes a first end and a second end spaced apart from the first end. The patient support further includes a second siderail positioned to block egress of a patient from the mattress. The first siderail is configured to move between first and second positions relative to the second siderail. The second siderail includes an upper edge having a concave portion arranged to receive the first end of the first siderail when in the second position. For example, see an illustrative preferred embodiment in FIGS. 71–73.

According to another embodiment of the present disclosure, another patient support is provided. The patient support includes a frame, a mattress positioned over the frame, a first siderail, and a second siderail. The mattress defines a substantially horizontal plane. The first siderail is positioned to block egress of a patient from a first side of the mattress. The first siderail is configured to tilt inward toward the mattress to define an acute angle with the horizontal plane defined by the mattress. The second siderail is positioned to block egress of a patient from a second side of the mattress. The second siderail is configured to tilt inward toward the mattress to define an angle with the horizontal plane defined by the mattress. For example, see an illustrative preferred embodiment in FIGS. 52–53.

According to another embodiment of the present disclosure, another patient support is provided. The patient support includes a frame, a mattress positioned over the frame, a barrier positioned to block egress of a patient positioned on the mattress, and a CPR panel configured to be positionable under a patient positioned on the mattress to facilitate administering CPR on the patient. The patient support further includes a CPR panel retention member arranged to retain lower corners of the CPR panel adjacent to the barrier. For example, see an illustrative preferred embodiment in FIGS. 62–64.

According to another embodiment of the present disclosure, another patient support is provided. The patient support includes a frame, a mattress positioned over the frame, and a barrier positioned to block egress of a patient positioned on the mattress. The barrier includes a perimeter frame member and a screen coupled to the perimeter frame member. The perimeter frame member defines an opening. The screen includes a tubular sleeve defining a passage sized to slidably receive the perimeter frame member and a panel coupled to the sleeve to extend across the opening defined by the perimeter frame member. For example, see an illustrative preferred embodiment in FIGS. 54 and 55.

According to another embodiment of the present disclosure, another patient support is provided. The patient support includes a frame, a mattress supported by the frame, a footboard supported by the frame, a headboard supported by the frame, and a controller pivotably coupled to at least one of the headboard and footboard. For example, see an illustrative preferred embodiment in FIG. 14.

According to another embodiment of the present disclosure, another patient support is provided. The patient support includes a frame, a mattress supported by the frame, a footboard supported by the frame, and a headboard supported by the frame. At least one of the headboard and footboard is removable from a normally vertical blocking position blocking egress of a patient from the mattress and a horizontal table position positioned over the mattress. For example, see illustrative preferred embodiments in FIGS. 52, 53, and 56–60.

According to another embodiment of the present disclosure, another patient support is provided. The patient support includes a frame, a mattress supported by the frame, a footboard supported by the frame, and a headboard supported by the frame, a siderail supported by the frame. The patient support further includes a gap filler coupled to at least one of the footboard and headboard to block egress of a patient through a gap defined between said at least one of the footboard and headboard and the siderail. For example, see an illustrative preferred embodiment in FIGS. 61 and 68–70.

According to another embodiment of the present disclosure, another patient support is provided. The patient support includes a frame, a deck supported by the frame, and a mattress supported by the deck. The deck including an upper deck portion, a lower deck portion coupled to the upper deck portion by a slanted deck side wall so that the lower deck portion is spaced apart from the upper deck to define a central, longitudinal recess in the deck. The lower deck portion extends across the deck to provide a lower deck support surface. For example, see illustrative preferred embodiments in FIGS. 40, 42–45, and 82.

According to another embodiment of the present disclosure, another patient support is provided. The patient support includes a frame and a deck supported by the frame. The deck includes a foot section, a back section pivotably coupled to the frame to move between first and second positions relative to the frame, and a head section pivotably coupled the back section to move between first and second positions. The patient support further includes a mechanism configured to control movement of the back and head sections. The mechanism is configured to move between a first position wherein the head section remains substantially horizontal with the back section when the back section is moved from the first position to the second position and a second position wherein the head section tilts relative to the back section when the back section is moved from the first position to the second position. For example, see an illustrative preferred embodiment in FIGS. 17–21.

According to another embodiment of the present disclosure, another patient support is provided. The patient support includes a frame and a deck supported by the frame. The deck includes a seat section pivotably coupled to the frame to move between first and second positions and a foot section pivotably coupled to the seat section to move between first and second positions. The patient support further includes a mechanism configured to control movement of the foot section relative to the seat section. The mechanism is configured to move between a first position wherein the foot section remains substantially horizontal when the seat section moves from the first position to the second position and a second position wherein the foot section deviates from being substantially horizontal when the seat section moves from the first position to the second position. For example, see illustrative preferred embodiments in FIGS. 22–26, 79–81, and 92.

According to another embodiment of the present disclosure, another patient support is provided. The patient support includes a frame, a deck supported by the frame, and a mattress supported by the support member of the deck. The deck includes a pair of spaced-apart sidewalls and a support member extending between the side walls. The support member is configured to move relative to at least one of the side walls to permit deflection thereof when a patient is positioned on the mattress. For example, see illustrative preferred embodiments in FIGS. 43–45 and 82–83.

According to another embodiment of the present disclosure, another patient support is provided. The patient support includes a frame, a deck supported by the frame, and a mattress supported by the deck. The deck includes a head end and a foot end spaced apart from the head end. The patient support further includes at least one hand grip coupled to the head end of the deck. For example, see illustrative preferred embodiments in FIGS. 40 and 53.

According to another embodiment of the present disclosure, another patient support is provided. The patient support includes a frame and a deck supported by the frame. The deck includes a plurality of deck sections configured to move relative to the frame. The patient support further includes a spill guard positioned in a gap defined between at least two of the plurality of deck sections. For example, see an illustrative preferred embodiment in FIGS. 82 and 83.

According to another embodiment of the present disclosure, another patient support is provided. The patient support includes a frame including a base frame, an intermediate frame, and a plurality of lift arms configured to support the intermediate frame on the base frame. The plurality of lift arms are slidably coupled to the base frame by a plurality of roller positioned in the base frame. The patient support further includes a plurality of wheels coupled to the base frame to facilitate movement of the base frame and a wheel control link positioned in the base frame to facilitate simultaneous control of the plurality of wheels. For example, see an illustrative preferred embodiment in FIGS. 3 and 4.

According to another embodiment of the present disclosure, another patient support is provided. The patient support includes a frame including a base frame, an intermediate frame, and a plurality of lift arms configured to move the intermediate frame relative to the base frame. The patient support further includes a deck supported by the intermediate frame, a headboard coupled to the base frame, and a footboard supported by the intermediate frame. For example, see illustrative preferred embodiments in FIGS. 1, 9, 61, and 92.

According to another embodiment of the present disclosure, another patient support is provided. The patient support includes a frame including a base frame, an intermediate frame, and a plurality of lift arms configured to move the intermediate frame relative to the base frame. The patient support further includes a deck supported by the intermediate frame, a headboard coupled to the base frame, and a footboard coupled to the deck. For example, see illustrative preferred embodiments in FIGS. 1, 9, 61, and 92.

According to another embodiment of the present disclosure, another patient support is provided. The patient support includes a frame having a longitudinal axis, a deck supported by the frame, a mattress supported by the deck, a first wheel positioned to support a head end of the frame at a first longitudinal location, a second wheel positioned to support a foot end of the patient support at a second longitudinal location, and a pedal supported by the frame at a third longitudinal location. The pedal is configured to control at least one of the first and second wheels. The first longitudinal location is positioned between the second and third longitudinal locations. For example, see illustrative preferred embodiments in FIGS. 61, 92, and 113.

According to another embodiment of the present disclosure, another patient support is provided. The patient support includes a frame having a base frame, an intermediate frame, and a plurality of lift arms configured to support the intermediate frame on the base frame and to permit movement of the intermediate frame between first and second positions relative to the base frame, and a deck supported by the intermediate frame. The patient support further includes a shroud supported by the base frame. The shroud includes at least one opening therein configured to permit movement of at least one other component of the patient support in the opening when the intermediate frame moves between the first and second positions. For example, see an illustrative preferred embodiment in FIGS. 61 and 65.

According to another embodiment of the present disclosure, another patient support is provided. The patient support includes a frame, a mattress supported by the frame, and a barrier supported by the frame. The barrier is configured to move between a raised position blocking egress of a patient positioned on the mattress and a lowered position. The barrier is configured to move along a longitudinal axis when moved between the raised and lowered positions. For example, see an illustrative preferred embodiment in FIGS. 109–112.

According to another embodiment of the present disclosure, another patient support is provided. The patient support includes a frame, a mattress supported by the frame, a first barrier positioned to block egress of a patient from the mattress, and a second barrier positioned to block egress of a patient from the mattress. The first barrier includes a first pocket formed therein. The second barrier includes a second pocket formed therein. The patient support further includes a controller configured to be removably received in the first pocket of the first barrier and removably received in the second pocket of the second barrier. For example, see illustrative preferred embodiments in FIGS. 74–75 and 97–101.

According to another embodiment of the present disclosure, another patient support is provided. The patient support includes a frame, a mattress supported by the frame, a first barrier positioned to block egress of a patient from the mattress, and a second barrier positioned to block egress of a patient from the mattress. The first barrier includes a first pocket formed therein. The second barrier includes a second pocket formed therein. The patient support further includes a controller configured to be removably received in the first pocket of the first barrier and removably received in the second pocket of the second barrier. The patient support further includes a controller mount configured to be removably received in the first and second pockets and the controller is coupled to the controller mount. For example, see an illustrative preferred embodiment in FIGS. 97–101.

According to another embodiment of the present disclosure, another patient support is provided. The patient support includes a frame, a mattress supported by the frame and a controller. The controller includes a key control button and a plurality of input control buttons. Each of the plurality of input control buttons is configured to receive commands from a user to control a function of the patient support. The key control button is configured to enable and disable the plurality of input control buttons to control the functions of the patient support. For example, see an illustrative preferred embodiment in FIG. 101.

According to another embodiment of the present disclosure, another patient support is provided. The patient support includes a frame having a longitudinal axis, a deck supported by the frame, a mattress supported by the deck, a first pair of wheels positioned to support a head end of the frame at a first longitudinal location, and a second pair of wheels positioned to support a foot end of the patient support at a second longitudinal location. Each of the first and second pairs of wheels includes a blocking devices configured to block at least one of the rotation or pivoting of the first and second wheels. The patient support further includes a plurality of transfer links configured to coordinate operation of the blocking devices of the first and second pairs of wheels and a rod positioned at a third longitudinal location longitudinally spaced apart from the first and second longitudinal locations. The rod extends transversely between at least two of the plurality of transfer links to coordinate movement thereof. For example, see an illustrative preferred embodiment in FIG. 113.

According to the present disclosure, a mattress for use with a patient support is provided. The mattress includes a patient support surface having a longitudinal axis. The mattress further includes a crowning bladder configured to move between a first position wherein the patient support surface is substantially flat and a second position creating a crown in patient support surface positioned on the longitudinal axis thereof. For example, see illustrative preferred embodiments in FIGS. 45, 49, and 50.

According to another embodiment of the present disclosure, another mattress for use with a patient support is provided. The mattress includes a patient support surface. The mattress further includes a firming bladder including a plurality of cells configured to move between a first position having a first firmness and a second position having a second firmness greater than the first firmness to provide substantially firm support for the patient support surface. For example, see an illustrative preferred embodiment in FIGS. 40 and 42–45.

According to another embodiment of the present disclosure, another mattress for use with a patient support is provided. The mattress includes a cover defining a patient support surface and an interior region. The mattress further includes a vibration motor positioned in the cover to provide vibrations to the patient support surface. For example, see illustrative preferred embodiments in FIGS. 42, 49, and 50.

According to another embodiment of the present disclosure, another mattress for use with a patient support is provided. The mattress includes a head section, a seat section, and a foot section. The head, seat, and foot sections cooperate to define a patient support surface. At least on of the head, seat, and foot sections includes a fence configured to block movement of the patient off of the patient support surface. For example, see illustrative preferred embodiments in FIGS. 48–50.

According to another embodiment of the present disclosure, another mattress for use with a patient support is provided. The mattress includes a head section, a seat section, and a foot section. The head, seat, and foot sections cooperate to define a patient support surface. At least on of the head, seat, and foot sections include a fence configured to block movement of the patient off of the patient support surface. The patient support further includes a cover defining an interior region and the head, seat, and foot sections are positioned in the interior region. For example, see illustrative preferred embodiments in FIGS. 48–50.

According to another embodiment of the present disclosure, another mattress for use with a patient support is provided. The mattress includes a head section, a seat section, and a foot section. The head, seat, and foot sections cooperate to define a patient support surface. The foot section includes a fence configured to block movement of the patient off of the patient support surface. For example, see illustrative preferred embodiments in FIGS. 48–50.

According to the present disclosure, a pressure system for use with a mattress of a patient support is provided. The mattress includes a bladder. The pressure system includes a pressure source and a pressure regulator configured to maintain a pressure of fluid in the bladder of the mattress within a predetermined range. The pressure system further includes a conduit configured to deliver fluid to the bladder from the pressure source when the pressure of the fluid in the bladder is below the predetermined range and remove fluid from the bladder when the pressure of the fluid is above the predetermined range. For example, see an illustrative preferred embodiment in FIG. 51.

According to the present disclosure, a frame for a patient support is provided. The frame includes a base frame, an intermediate frame, and at least three lift arms configured to support the intermediate frame on the base frame and to permit movement of the intermediate frame between first and second positions relative to the base frame. Each of the lift arms includes a first link coupled to the base frame, a second link coupled to the intermediate frame, a third link pivotably coupled to the first and second links, and a fourth link pivotably coupled to the first and second links. For example, see illustrative preferred embodiments in FIGS. 8–13 and 65.

According to another embodiment of the present disclosure, another frame for a patient support is provided. The frame includes a base frame, an intermediate frame, and a plurality of lift arms configured to support the intermediate frame on the base frame and to permit movement of the intermediate frame between first and second positions relative to the base frame. Each of the lift arms includes first and second links, the first link being pivotably coupled to the base frame and pivotably coupled to the intermediate frame. The second link is pivotably coupled to the first link and pivotably coupled to at least one of the base frame and intermediate frame. For example, see illustrative preferred embodiments in FIGS. 1, 2–7, and 92–96.

According to another embodiment of the present disclosure, another frame for a patient support is provided. The frame includes a base frame, an intermediate frame, and at least one lift arm configured to support the intermediate frame on the base frame and to permit movement of the intermediate frame between first and second positions relative to the base frame. At least one of the base and intermediate frames is configured to nest within the other of the at least one of the base and intermediate frames. For example, see an illustrative preferred embodiment in FIGS. 92–96.

According to the present disclosure, the various features of the bedframes, decks, mattresses, headboards, footboards, siderails, controllers, and other components of the various embodiment beds of the present disclosure may be exchanged or used in combination with the features of the other beds disclosed herein or beds known to those of ordinary skill in the art.

The features of the present disclosure have been described with respect to beds, but they can also be used on examination tables, stretchers, gurneys, wheel chairs, chair beds, or any other patient support devices for supporting a person during rest, treatment, or recuperation.

Although the invention has been described in detail with reference to certain illustrated embodiments, variations and modifications exist within the scope and spirit of the present invention as described and defined in the following claims.

What is claimed is:

1. A patient support comprising
   a frame,
   a mattress supported by the frame,
   a barrier positioned to block egress of a patient from the mattress, the barrier including first and second spaced-apart rails, and a controller positioned to slide along the first and second rails simultaneously.

2. The patient support of claim 1, wherein the first and second rails cooperate to define an opening in the harder and the controller is positioned in the opening.

3. The patient support of claim 2, wherein the opening is curved.

4. The patient support of claim 1, wherein at least one of the rails includes a convex surface and the controller includes a concave surface positioned adjacent to the convex surface of the rail.

5. The patient support of claim 1, wherein first rail includes a first convex surface, the second rail includes a second convex surface, and the controller includes a first concave surface positioned adjacent to the first convex surface of the first rail and a second concave surface positioned adjacent to the second convex surface of the second rail.

6. The patient support of claim 1, wherein the controller is removably coupled to the barrier.

7. The patient support of claim 6, wherein the controller includes a housing and a retainer coupled to the housing to removably couple the housing to the barrier.

8. The patient support of claim 7, wherein the retainer contacts one of the first and second rails when the controller is coupled to the barrier.

9. The patient support of claim 6, wherein the controller is supported by the first and second rails.

10. A patient support comprising
a frame,
a mattress supported by the frame,
a barrier positioned to block caress of a patient from the mattress, the barrier including first and second spaced-apart rails, the first and second rails cooperate to define an opening in the barrier, the first rail including a first surface, the second rail including a second surface, the first and second surfaces cooperating to define the opening, and
a controller positioned to slide along the first and second rails, the controller being positioned in the opening, the controller contacting the first and second surfaces when positioned to slide on the first and second rails.

11. The patient support of claim 10, wherein the controller further includes a housing and a retainer coupled to the housing to removably couple the housing to the barrier.

12. The patient support of claim 11, wherein the retainer contacts one of the first and second rails when the controller is coupled to the barrier.

13. The patient support of claim 10, wherein the opening is curved.

14. The patient support of claim 10, wherein at least one of the rails includes a convex surface and the controller includes a concave surface positioned adjacent to the convex surface of the rail.

15. The patient support of claim 10, wherein the rails are vertically spaced apart by a distance and the controller has a maximum vertical height that is greater than the distance.

16. The patient support of claim 10, wherein the controller is indexed to inhibit improper placement of the controller in the opening.

17. A patient support comprising
a frame,
a mattress supported by the frame,
a barrier positioned to block egress of a patient from the mattress, the barrier including upper and lower surfaces that cooperate to define an opening, and
a controller positioned to slide along the lower surface defining the opening in the barrier.

18. The patient support of claim 17, wherein the controller is removably coupled to the barrier.

19. The patient support of claim 17, wherein the controller is coupled to the barrier to slide along the upper edge defining the opening in the barrier.

20. The patient support of claim 17, wherein the upper and lower edges are convex and the controller includes upper and lower edges that are concave to complement the upper and lower edges of the barrier.

21. The patient support of claim 17, wherein the controller includes a housing and a retainer configured to couple the housing to the barrier.

22. The patient support of claim 21, wherein the retainer is a latch.

23. The patient support of claim 22, wherein the latch is biased into contract with the barrier.

24. The patient support of claim 21, wherein the retainer is a flexible tab.

25. The patient support of claim 24, wherein the controller includes another retainer configured to couple the housing to the upper edge defining the opening in the barrier.

26. A patient support comprising
a frame,
a mattress supported by the frame,
a barrier positioned to block egress of a patient from the mattress, the barrier including a curved opening, and
a controller positioned in the curved opening to move along the barrier.

27. The patient support of claim 26, wherein the barrier includes a longitudinally-extending first curved surface and a spaced-apart longitudinally extending second curved surface that cooperates with the longitudinally extending first curved surface to define the curved opening.

28. The patient support of claim 27, wherein the first curved surface has a first radius of curvature, the second curved surface has a second radius of curvature, the controller has a first curved surface having a radius of curvature generally equal to the first radius or curvature of the first curved surface and a second curved surface having a radius of curvature generally equal to the second radius of curvature of the second curved surface.

29. The patient support of claim 26, wherein the barrier includes a first curved surface cooperating to define the curved opening and the controller includes a first curved channel positioned adjacent to the first curved surface of the barrier.

30. The patient support of claim 29, wherein the barrier includes second curved surface spaced apart from the first curved surface that cooperates to define the curved opening and the controller includes a second curved channel positioned adjacent to the second surface of the barrier.

31. The patient support of claim 26, wherein the barrier includes a pair of rails cooperating to define the curved opening and at least one of the rails is curved.

32. The patient support of claim 31, wherein the controller includes a curved channel sized to receive a portion of the curved rail.

33. The patient support of claim 26, wherein the controller is configured to slide along the length of the barrier.

34. The patient support of claim 26, wherein controller is configured to slide along the barrier.

35. The patient support of claim 26, wherein the controller is removably received in the curved opening.

36. A patient support comprising
a frame,
a mattress supported by the frame,
a barrier positioned to block egress of a patient from the mattress, the barrier including an outer perimeter surface defining a perimeter of the barrier and an inner surface defining an opening in the barrier, and
a controller having a housing and a retainer coupled to the housing, spaced apart from the outer perimeter surface of the barrier, and configured to contact the inner surface of the barrier to couple the housing to the barrier to permit selective removal of the housing from the barrier.

37. The patient support of claim 36, wherein the retainer includes a latch positioned to removably couple the housing to the barrier.

38. The patient support of claim 37, wherein the latch is movable between a first position coupling the housing to the barrier and a second position permitting removal of the housing from the barrier.

39. The patient support of claim 37, wherein the latch is biased into contact with the inner surface of the barrier.

40. The patient support of claim 37, wherein the housing includes an opening and the latch is positioned to extend through the opening.

41. The patient support of claim 40, wherein the latch includes a stop configured to limit movement of the latch through the opening.

42. The patient support of claim 37, wherein the latch is pivotably coupled to the housing.

43. The patient support of claim 36, wherein the controller includes a corner edge and the retainer is positioned along the corner edge.

44. The patient support of claim 36, wherein the retainer and the housing cooperate to define a first width of the controller when the retainer is in a first position relative to the housing and a second width of the controller when the retainer is in a second position relative to the housing, the first width is less than a width of the opening and the second width is greater than the width of the opening.

45. A patient support comprising
a frame,
a mattress supported by the frame,
a barrier positioned to block egress of a patient from the mattress, the barrier including an outer perimeter surface defining a perimeter of the harder and an inner surface defining an opening in the barrier, and
a controller having a housing and a retainer coupled to the housing, spaced apart from the outer perimeter surface of the barrier, and configured to contact the inner surface of the barrier to removable couple the housing to the barrier, the retainer including a latch positioned to removably couple the housing to the barrier, the latch including a ramp portion configured to ride over the inner surface of the barrier during removal of the controller from the barrier.

46. The patient support of claim 45, wherein the controller further includes a biaser positioned to urge the latch into contact with the inner surface of the barrier.

47. The patient support of claim 45, wherein the opening in the barrier is curved.

48. The patient support of claim 45, wherein the controller follows a horizontal path during removal from the barrier.

49. The patient support of claim 45, wherein the latch is pivotably coupled to the housing.

50. The patient support of claim 45, wherein the latch is longitudinally centered on the housing.

51. A patient support comprising
a frame,
a mattress supported by the frame,
a barrier positioned to block egress of a patient from the mattress, and
a controller removably coupled to the barrier, the controller being movable from a first position spaced apart from the barrier to a second position coupled to the barrier, the controller being movable along a substantially horizontal path from the first position to the second position to couple the controller to the barrier, the controller being movable along the barrier when the second position.

52. The patient support of claim 51, wherein the controller includes a housing and a retainer configured to removably couple the housing to the barrier.

53. The patient support of claim 52, wherein the barrier includes an opening and the controller is positioned in the opening.

54. The patient support of claim 53, wherein the controller is movable along the horizontal path to position the controller in the opening.

55. The patient support of claim 53, wherein the housing and the retainer cooperate to define a first width when the retainer is in a first position relative to the housing and a second width when the retainer is in a second position relative to the housing and the opening has a width that is greater than the first width and less than the second width.

56. The patient support of claim 52, wherein the path is completely horizontal.

57. The patient support of claim 52, wherein the bonier includes a side defining a substantially vertical plane and the controller is inserted through the vertical plane when coupled to the barrier.

58. The patient support of claim 57, wherein the barrier includes an opening and the controller is positioned in the opening.

59. The patient support of claim 58, wherein the opening extends completely through the barrier.

60. A patient support comprising
a frame,
a mattress supported by the frame, the mattress having a first side and a second side transversely spaced-apart from the first side,
a first barrier positioned to block egress of a patient from the first side of the mattress, the first barrier including a first opening formed therein,
a second bonier positioned to block egress of a patient from the first side of the mattress, the second barrier including a second opening formed therein, and
a controller configured to be removably received in the first opening of the first barrier and removably received in the second opening of the second barrier.

61. The patient support of claim 60, wherein the controller is configured to move along the first barrier when received in first opening.

62. The patient support of claim 61, wherein the controller is configured to move along the second barrier when received in the second opening.

63. The patient support of claim 62, wherein the controller is slidably coupled to the first and second siderails when received in either of the first and second openings.

64. The patient support of claim 60, wherein the first and second openings are curved.

65. The patient support of claim 64, wherein the controller includes a housing have a curved portion that complements the curvature of the first and second openings.

66. The patient support of claim 60, wherein the controller includes a housing and a retainer configured to couple the housing to the first and second barriers.

67. A patient support comprising
   a frame,
   a mattress supported by the frame,
   a barrier positioned to block egress of a patient from the mattress, the barrier having a longitudinal axis, and
   a controller, the barrier including a guide configured to direct movement of the controller along the barrier in a path having longitudinal and transverse components.

68. The patient support of claim 67, wherein the guide includes first and second spaced-apart longitudinally and transversely-extending curved surface that cooperate to guide controller along the path.

69. The patient support of claim 68, wherein the first curved surface has a first radius of curvature, the second curved surface has a second radius of curvature, the controller has a first curved surface having a radius of curvature generally equal to the first radius of curvature of the first curved surface and a second curved surface having a radius of curvature generally equal to the second radius of curvature of the second curved surface.

70. The patient support of claim 67, wherein the harder includes a first curved surface and the controller includes a first curved channel positioned adjacent to the first curved surface of the barrier.

71. The patient support of claim 70, wherein the harder includes second curved surface spaced apart from the first curved surface and the controller includes a second curved cannel positioned adjacent to the second ace of the barrier.

72. The patient support of claim 71, wherein the guide includes a pair of rails cooperating to guide the controller.

73. The patient support of claim 72, wherein at least one of the rails is curved.

74. The patient support of claim 73, wherein the controller includes a curved channel sized to receive a portion of the curved rail.

75. The patient support of claim 67, wherein be guide includes an opening and the controller is positioned in the opening.

76. The patient support of claim 67, wherein controller is configured to slide along the barrier.

77. The patient support of claim 67, wherein the controller is removably coupled to the guide.

78. A patient support comprising
   a frame,
   a mattress supported by the frame,
   a pair of spaced-apart barriers positioned to block egress of a patient from the mattress,
   a controller removably coupled to the barrier, the controller including a housing, a cord coupled to the housing, and a first connector coupled to the cord,
   a second connector supported by the frame, the first connector being configured to couple to the second connector to provide communication for the controller through the first and second connectors when the first connector is coupled to the second connector, and
   a third connector supported by the frame in a location spaced apart from the second connector, the first connector being configured to couple to the third connector to provide communication for the controller through the first and third connectors when the first connector is coupled to the third connector.

79. The patient support of claim 78, wherein the second and third connectors are coupled to the frame.

80. The patient support of claim 78, wherein the frame includes a first frame supported by the floor and a second frame supported above the second frame and configured to be raised and lowered relative to the first frame, the mattress is supported by the second frame, and the second and third connectors are coupled to the second frame.

81. The patient support of claim 78, wherein the first, seconds and third connectors are plug connectors.

82. The patient support of claim 81, wherein the first connector includes at least one of a plurality of plugs and a plurality of sockets and the second and third connectors includes at least one of a plurality of sockets and a plurality of plugs.

83. The patient support of claim 78, wherein the frame includes a first side and a second opposite side, the second connector is supported by the frame on the first side, and the third connector is supported by the frame on the second side.

84. The patient support of claim 83, wherein the second connector is coupled to the first side of the frame and the third connector is coupled to the second side of the frame.

85. The patient support of claims 78, wherein the second connector is coupled to a first plurality of wires, the third connector is coupled to a second plurality of wires, and first and second plurality of wires meet at a junction.

* * * * *